US009315833B2

(12) United States Patent
McBride et al.

(10) Patent No.: US 9,315,833 B2
(45) Date of Patent: Apr. 19, 2016

(54) YEAST CELLS EXPRESSING AN EXOGENOUS CELLULOSOME AND METHODS OF USING THE SAME

(75) Inventors: John McBride, Lyme, NH (US); Mark Mellon, Grantham, NH (US); Vineet Rajgarhia, Dublin, CA (US); Elena E. Brevnova, Lebanon, NH (US); Erin Wiswall, Danbury, NH (US); David A. Hogsett, Grantham, NH (US); Danie LaGrange, Durbanville (ZA); Shaunita Rose, Strand (ZA); Emile Van Zyl, Stellenbosch (ZA)

(73) Assignees: Lallemand Hungary Liquidity Management LLC, Budapest (HU); Stellenbosch University, Stellenbosch (ZA)

( * ) Notice: Subject to any disclaimer, the term of this patent is extended or adjusted under 35 U.S.C. 154(b) by 655 days.

(21) Appl. No.: 13/201,257

(22) PCT Filed: Feb. 18, 2010

(86) PCT No.: PCT/US2010/024592
§ 371 (c)(1),
(2), (4) Date: Feb. 23, 2012

(87) PCT Pub. No.: WO2010/096562
PCT Pub. Date: Aug. 26, 2010

(65) Prior Publication Data
US 2012/0142046 A1 Jun. 7, 2012

Related U.S. Application Data

(60) Provisional application No. 61/202,352, filed on Feb. 20, 2009.

(51) Int. Cl.
C12P 7/10 (2006.01)
C07K 14/33 (2006.01)
(Continued)

(52) U.S. Cl.
CPC . *C12P 7/10* (2013.01); *C07K 14/33* (2013.01); *C12N 9/2402* (2013.01); *C12N 9/248* (2013.01);
(Continued)

(58) Field of Classification Search
None
See application file for complete search history.

(56) References Cited

U.S. PATENT DOCUMENTS

| | | | |
|---|---|---|---|
| 8,361,752 B2 * | 1/2013 | Kohda et al. | 435/71.1 |
| 2009/0035811 A1 * | 2/2009 | Kohda et al. | 435/41 |
| 2011/0097769 A1 | 4/2011 | Del Cardayre et al. | |

FOREIGN PATENT DOCUMENTS

| | | | |
|---|---|---|---|
| EP | WO 01/70998 | * | 9/2001 |
| WO | WO 2008/100251 | * | 8/2008 |
| WO | WO 2009/093118 A1 | | 7/2009 |

OTHER PUBLICATIONS

Fierobe et al., Cellulosome from Clostridium cellulolyticum: Molecular Study of the Dockerin/Cohesin Interaction., Biochemistry (1999), vol. 38, pp. 12822-12832.*

(Continued)

*Primary Examiner* — Alexander Kim
(74) *Attorney, Agent, or Firm* — Nutter McClennen & Fish LLP

(57) ABSTRACT

The present invention relates to the engineering and expression of heterologous cellulosomes in microorganisms in order to facilitate the conversion of biomass to useful products. In some embodiments, the invention relates to the expression of scaffoldin proteins which form the nucleus of a cellulosome. Cellulases or other biomass-degrading enzymes can be non-covalently linked to the scaffoldin protein by virtue of a dockerin domain-cohesin domain interaction.

51 Claims, 11 Drawing Sheets

(51) Int. Cl.
*C12N 15/81* (2006.01)
*C12N 9/24* (2006.01)
*C12N 9/42* (2006.01)

(52) U.S. Cl.
CPC ............ *C12N 9/2437* (2013.01); *C12N 9/2445* (2013.01); *C12N 15/81* (2013.01); *C12Y 302/01004* (2013.01); *C12Y 302/01008* (2013.01); *C12Y 302/01021* (2013.01); *C12Y 302/01037* (2013.01); *C12Y 302/01091* (2013.01); *C07K 2319/035* (2013.01); *C07K 2319/70* (2013.01); *Y02E 50/16* (2013.01); *Y02P 20/52* (2015.11)

(56) References Cited

OTHER PUBLICATIONS

Perret et al., Production of Heterologous and Chimeric Scaffoldins by Clostridium acetobutylicum ATCC 824., J Bacteriol. (Jan. 2004), vol. 186(1), pp. 253-257.*
Bayer et al., The potential of cellulases and cellulosomes for cellulosic waste management., Current Opinion in Biotechnology vol. 18, Issue 3, Jun. 2007, pp. 237-245.*
Gusakov et al., Design of Highly Efficient Cellulase Mixtures for Enzymatic Hydrolysis of Cellulose., Biotechnology and Bioengineering (2007), vol. 97, pp. 1028-1038.*
Desvaux et al., The cellulosome of Clostridium cellulolyticum., Enzyhme and Micribial Technology (2007), vol. 97, pp. 1028-1038.*
Ito et al. Improvement of cellulose-degrading ability of a yeast strain displaying Trichoderma reesei endoglucanase II by recombination of cellulose-binding domains., Biotechnol Prog. (2004), vol. 20(3), pp. 688-691.*
ExPASy last viewed on Feb. 13, 2015.*
Kondo et al., Yeast cell-surface display—applications of molecular display., Applied Microbiology and Biotechnology (Mar. 2004), vol. 64, Issue 1, pp. 28-40.*
Beguin, P., "Detection of Cellulase Activity in Polyacrylamide Gels Using Congo Red-Staiined Agar Replicas," *Anal. Biochem.* 131(2):333-336, Academic Press, United States (1983).
Bowie, J.U., et al., "Deciphering the Message in Protein Sequences: Tolerance to Amino Acid Substitutions," *Science* 247:1306-1310, AAAS, United States (1990).
Casey, G.P., et al., "A Convenient Dominant Selection Marker for Gene Transfer in Industrial Strains of *Saccharomyces cerevisiae*: SMRI Encoded Resistance to the Herbicide Sulfometuron Methyl," *J. Inst. Brew* 94(2):93-97 (1988).
Caspi, J., et al., "Conversion of *Thermobifida fusca* free exoglucanases into cellulosornal components: comparative impact on cellulose-degrading activity," *J. Biotechnol.* 135(4):351-357, American Society for Microbiology, United States (2008).
Cunningham. B.C, and Wells, J.A., "High-Resolution Epitope Mapping of hGH-Receptor Interactions by Alanine-Scanning Mutagenesis," *Science* 241:1081-1085, American Society for the Advancement of Science, United States (1989).
Den Haan, R., et al., "Functional expression of cellobiohydrolases in *Saccharomyces cerevisiae* towards one-step conversion of cellulose to ethanol," *Enzyme. Microb. Technol.* 40(5):1291-1299, Elsevier, Inc., United States (2007).
Dijkerman, R., et al., "The role of the cellulolytic high molecular mass (HMM) complex of the anaerobic fungus *Piromyces* sp. strain E2 in the hydrolysis of microcrystalline cellulose," *Arch. Microbiol.* 167(2-3):137-142, Springer-Verlag, Germany (1997).
Dijkerman, R., et al., "Adsorption Characteristics of Cellulolytic Enzymes from the Anaerobic Fungus *Piromyces* sp. strain E2 on Microcrystalline Cellulose," *Appl. Environ. Microbiol.* 62(I):20-5, American Society for Microbiology, United States (1996).

Fierobe, H.P., et al., "Action of Designer Cellulosomes on Homogeneous Versus Complex Substrates," *J. Biol. Chem.* 280(16):16325-16334, American Society for Biochemistry and Molecular Biology, United States (2005).
Gal, L., et al., "CelG from *Clostridium cellulolyticum*: A Multidomain Endoglucanase Acting Efficiently on Crystalline Cellulose," *J. Bacteriol.* 179(21):6595-6601, American Society for Microbiology, United States (1997).
Hahn-Hägerdal, B., et al., "Metabolic Engineering of *Saccharomyces cerevisiae* for Xylose Utilization," *Adv. Biochem. Eng. Biotecnol.* 73:53-84, Springer-Verlag, Germany (2001).
Ito, J., et al., "Regulation of the Display Ratio of Enzymes on the *Saccharomyces cerevisiae* Cell Surface by the Immunoglobulin G and Cellulosomal Enzyme Binding Domains," *Appl. Environ. Microbiol.* 75(12):4149-4154, American Society for Microbiolgy, United States (2009).
Lamed, R., et al., "Characterization of a Cellulose-Binding, Cellulase-Containing Complex in *Clostridium thermocellum*," *J. Bacteriol.* 156(2):282-836, American Society for Microbiology, United States (1983).
Levasseur, A., et al., "Design and Production in *Aspergillus niger* of a Chimeric Protein Associating a Fungal Feruloyl Esterase and a Clostridial Dockerin Domain," *Appl. Environ. Mircobiol.* 70(12):6984-6991, American Society for Microbiology, United States (2004).
Lynd, L.R., et al., "Microbial Cellulose Utilization: Fundamentals and Biotechnology," *Microbiol. Mol. Biol. Rev.* 66(3):506-577, American Society for Microbiology, United States (2002).
Ma, H., et al., "Plasmid Contruction by Homologous Recombination in Yeast," *Gene* 58(2-3):201-216, Elsevier B.V., Netherlands (1987).
McBride, J.E., et al., "Utilization of cellobiose by recombinant β-glucosidase-expressing strains of *Saccharomyces cerevisiae*: characterization and evaluation of the sufficiency of expression," *Enzyme. Microb. Technol.* 37(1):93-101, Elsevier, Inc., United States (2005).
Nagy, T., et al., "Characterization of a double dockerin from the cellulosome of the anaerobic fungus *Piromyces equi*," *J. Mol. Biol.* 373(3):612-622, Elsevier, Ltd., England (2007).
Nakamura, Y., et al.,"Codon Usage tabulated rom the international DNA sequence databases: status for the year 2000," *Nuleic Acids Res.* 28(1):292 , Oxford University Press, England (2000).
Raghothama, S., et al., "Characterization of a cellulosome dockerin domain from the anaerobic fungus *Piromyces equi*," *Nat. Struc. Biol.* 8(9):775-779, Nature Publishing Group, United States (2001).
Tsai, S.L., et al., "Functional Assembly of Minicellulosomes on the *Saccharomyces cerevisiae* Cell Surface for Cellulose Hydrolysis and Ethanol Production," *Appl. Environ. Mircobiol.* 75(19):6087-6093, American Society for Microbiology, United States (2009).
Van Der Vaart, J.M., et al., "Comparison of Cell Wall Proteins of *Saccharomyces cerevisiae* as Anchors for Cell Surface Expression of Heterologous Proteins," *Appl. Environ. Mircobiol.* 63(2):615-620, American Society for Microbiology, United States (1997).
Van Rensburg, P., et al., "Engineering Yeast for Efficient Cellulose Degredation," *Yeast* 14:67-76, John Wiley & Sons, Ltd., England (1998).
Van Rooyen, R., et al., "Construction of cellobiose-growing and fermenting *Saccharomyces cerevisiae* strains," *J. Biotech.* 120:284-295, Elsevier B.V., Netherlands (2005).
Van Zyl, W.H., et al., "Consolidated Bioprocessing for Bioethanol Production Unsing *Saccharomyces cerevisiae*," *Adv. Biochem. Engin./Biotechnol.* 108:205-235, Springer-Verlag, Germany (2007).
Wilson, C.A. and Wood, T.M., "The anaerobic fungus *Neocallimastix frontalis*: Isolation and properties of a cellulosome-type enzyme fraction with the capacity to solubilize hydrogen-bond-ordered cellulose," *Appl. Microbiol. Biotechnol.* 37(1):125-129, Springer-Verlag, Germany (1992).
International Search Report for International Application No. PCT/US2010/024592, European Patent Office, Netherlands, mailed on Aug. 20, 2010.

* cited by examiner

```
                    SEQUENCE LISTING

<160> NUMBER OF SEQ ID NOS: 70

<210> SEQ ID NO 1
<211> LENGTH: 25
<212> TYPE: DNA
<213> ORGANISM: Unknown
<220> FEATURE:
<223> OTHER INFORMATION: Oligonucleotide X03900

<400> SEQUENCE: 1
gtaccactct tgacgacacg gctta                                             25

<210> SEQ ID NO 2
<211> LENGTH: 23
<212> TYPE: DNA
<213> ORGANISM: Unknown
<220> FEATURE:
<223> OTHER INFORMATION: Oligonucleotide X03901

<400> SEQUENCE: 2
atgctcatgt agagcgcctg ctc                                               23

<210> SEQ ID NO 3
<211> LENGTH: 26
<212> TYPE: DNA
<213> ORGANISM: Unknown
<220> FEATURE:
<223> OTHER INFORMATION: Oligonucleotide X03902

<400> SEQUENCE: 3
taatagacag agtggttccc atggac                                            26

<210> SEQ ID NO 4
<211> LENGTH: 25
<212> TYPE: DNA
<213> ORGANISM: Unknown
<220> FEATURE:
<223> OTHER INFORMATION: Oligonucleotide X03905

<400> SEQUENCE: 4
aggtgtatag aggtggggaa tgatc                                             25

<210> SEQ ID NO 5
<211> LENGTH: 1960
<212> TYPE: DNA
<213> ORGANISM: Clostridium cellulolyticum

<400> SEQUENCE: 5
```

-continued

```
gcggccgcgc tattttccat aaaaaaccaa gcaactgctt atcaacacac ttaattaaaa      60
acaaaatggt ttctttcacc tccttgttgg ctggtgttgc tgcaatctcc ggtgtcttgg     120
ctgctccagc tgccgaagtc gaaccagttg ctgtcgaaaa gagagaagcc gaagctgaag     180
ccattaactc tcaagatatg gtcaagaaga tgggtatcgg tatgaacttg ggtaacacct     240
tcgatgctcc aactgaaggt tcttggtcca aggctgccca agaatactac ttcgatgact     300
tcaagcaagc tggtttcaag cacgttagga ttcccattcg ttgggaccaa cacaccttgg     360
ctaactctcc atacactgtt gactctaact tcttgaaccg tattgaaact gttattgact     420
ggtctttgtc tcgtggtttc gtcactgtca tcaactctca ccgacacc tggttgatgg      480
acaactactc tcaaaacatc ggtagatttg aaaagatttg gaacaaatc gcccaaagat      540
tcaaaggtaa gtctgaaaac ttggtcttcg aaatcttgaa cgaaccacac ggtaacatca     600
ccgactctca aatcaacgat atgaataaga gattttgaa cattattaga aagaccaacc      660
caactcgtaa cgtcatcatc ggtgctggtt actggaactc ttacaactct ttatctcaat     720
tggaaatccc aaacgaccca acttgattg ctaccttcca ctactacgac ccatactctt      780
tcacacacca atggcaaggt acctggggta ccaagaacga catggacgcc atcgctatgg     840
ttttcaacca cgttaagaag tggtccgata agaataacat tccagtctat ttgggtgaat     900
acggtgtcat gggtcactct gacagaacct cagctgtcaa atggttcgac ttcgtctccg     960
atcaagccat ctcccatggt ttctcttgcg gtgcttggga caacggtgtc ttcggttctg    1020
ttgacaacga catggccttc tacaacagag ataccagaca atttgacaaa gaaattttga    1080
atgccatctt gactactggt accacctacg actggacccc accaaccgaa accaacccag    1140
acccaccaag aactccagcc accccagctt acggtgaaca attgattgaa gatttcgaag    1200
gtgccatgca atgggctgcc tactctggtg ttgacgctac cgcttcctgt aagatctctt    1260
ccggtaagtc caacaacggt ttggaaatta cctacgctgg ttcttctaac ggttactggg    1320
gtgttgttga caacgagcac agaaaccaag attgggaaaa gtggcaaaag atctcttttg    1380
acattaagtc ttcaaacact aacgaagtta gattgttaat cgctgaacaa tctaagattg    1440
aaggtgaaga cggtgaacac tggacctacg ttatcaagcc atctacttcc tggactacca    1500
ttgaaattcc attctcttct ttcactaaga gaatggatta ccaaccacca gctcaagacg    1560
gttctgaaac cttcgacttg tacaaggtcg gttcattgca cttcatgtac tctaactcca    1620
actccggtac tttaaacatt gacaacatta aattgatcgg tttgccagaa gaacaaatcg    1680
gtggtaaaat tggtgatgtt aacgaagatg gtaacatcga cgctattgac tttgctttat    1740
tgaagaagta cttgttagac tcctctatct ctatcaacaa ggttaacgcc gacattaatt    1800
tggacggtga tatcaacgct atcgacttcg ctaagttgaa gatgatgttg ttgggtgacg    1860
gtggtggttc tggtggtggc tctcatcatc accaccacca ctaaggcgcg ccgcttttga    1920
ttaagccttc tagtccaaaa aacacgtttt ttgcggccgc                          1960
```

<210> SEQ ID NO 6
<211> LENGTH: 612
<212> TYPE: PRT
<213> ORGANISM: Clostridium cellulolyticum

<400> SEQUENCE: 6

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys

```
                20                  25                  30
Arg Glu Ala Glu Ala Ala Ile Asn Ser Gln Asp Met Val Lys Lys
             35                  40                  45
Met Gly Ile Gly Met Asn Leu Gly Asn Thr Phe Asp Ala Pro Thr Glu
             50                  55                  60
Gly Ser Trp Ser Lys Ala Ala Gln Glu Tyr Tyr Phe Asp Asp Phe Lys
 65                  70                  75                  80
Gln Ala Gly Phe Lys His Val Arg Ile Pro Ile Arg Trp Asp Gln His
                 85                  90                  95
Thr Leu Ala Asn Ser Pro Tyr Thr Val Asp Ser Asn Phe Leu Asn Arg
                100                 105                 110
Ile Glu Thr Val Ile Asp Trp Ser Leu Ser Arg Gly Phe Val Thr Val
                115                 120                 125
Ile Asn Ser His His Asp Thr Trp Leu Met Asp Asn Tyr Ser Gln Asn
                130                 135                 140
Ile Gly Arg Phe Glu Lys Ile Trp Glu Gln Ile Ala Gln Arg Phe Lys
145                 150                 155                 160
Gly Lys Ser Glu Asn Leu Val Phe Glu Ile Leu Asn Glu Pro His Gly
                165                 170                 175
Asn Ile Thr Asp Ser Gln Ile Asn Asp Met Asn Lys Arg Ile Leu Asn
                180                 185                 190
Ile Ile Arg Lys Thr Asn Pro Thr Arg Asn Val Ile Ile Gly Ala Gly
                195                 200                 205
Tyr Trp Asn Ser Tyr Asn Ser Leu Ser Gln Leu Glu Ile Pro Asn Asp
                210                 215                 220
Pro Asn Leu Ile Ala Thr Phe His Tyr Tyr Asp Pro Tyr Ser Phe Thr
225                 230                 235                 240
His Gln Trp Gln Gly Thr Trp Gly Thr Lys Asn Asp Met Asp Ala Ile
                245                 250                 255
Ala Met Val Phe Asn His Val Lys Lys Trp Ser Asp Lys Asn Asn Ile
                260                 265                 270
Pro Val Tyr Leu Gly Glu Tyr Gly Val Met Gly His Ser Asp Arg Thr
                275                 280                 285
Ser Ala Val Lys Trp Phe Asp Phe Val Ser Asp Gln Ala Ile Ser His
                290                 295                 300
Gly Phe Ser Cys Gly Ala Trp Asp Asn Gly Val Phe Gly Ser Val Asp
305                 310                 315                 320
Asn Asp Met Ala Phe Tyr Asn Arg Asp Thr Arg Gln Phe Asp Lys Glu
                325                 330                 335
Ile Leu Asn Ala Ile Leu Thr Thr Gly Thr Thr Tyr Asp Trp Thr Pro
                340                 345                 350
Pro Thr Glu Thr Asn Pro Asp Pro Arg Thr Pro Ala Thr Pro Ala
                355                 360                 365
Tyr Gly Glu Gln Leu Ile Glu Asp Phe Glu Gly Ala Met Gln Trp Ala
                370                 375                 380
Ala Tyr Ser Gly Val Asp Ala Thr Ala Ser Cys Lys Ile Ser Ser Gly
385                 390                 395                 400
Lys Ser Asn Asn Gly Leu Glu Ile Thr Tyr Ala Gly Ser Ser Asn Gly
                405                 410                 415
Tyr Trp Gly Val Val Asp Asn Glu His Arg Asn Gln Asp Trp Glu Lys
                420                 425                 430
Trp Gln Lys Ile Ser Phe Asp Ile Lys Ser Ser Asn Thr Asn Glu Val
                435                 440                 445
```

-continued

```
Arg Leu Leu Ile Ala Glu Gln Ser Lys Ile Glu Gly Glu Asp Gly Glu
    450                 455                 460

His Trp Thr Tyr Val Ile Lys Pro Ser Thr Ser Trp Thr Thr Ile Glu
465                 470                 475                 480

Ile Pro Phe Ser Ser Phe Thr Lys Arg Met Asp Tyr Gln Pro Pro Ala
                485                 490                 495

Gln Asp Gly Ser Glu Thr Phe Asp Leu Tyr Lys Val Gly Ser Leu His
            500                 505                 510

Phe Met Tyr Ser Asn Ser Asn Ser Gly Thr Leu Asn Ile Asp Asn Ile
        515                 520                 525

Lys Leu Ile Gly Leu Pro Glu Glu Gln Ile Gly Gly Lys Ile Gly Asp
    530                 535                 540

Val Asn Glu Asp Gly Asn Ile Asp Ala Ile Asp Phe Ala Leu Leu Lys
545                 550                 555                 560

Lys Tyr Leu Leu Asp Ser Ser Ile Ser Ile Asn Lys Val Asn Ala Asp
                565                 570                 575

Ile Asn Leu Asp Gly Asp Ile Asn Ala Ile Asp Phe Ala Lys Leu Lys
            580                 585                 590

Met Met Leu Leu Gly Asp Gly Gly Gly Ser Gly Gly Gly Ser His His
        595                 600                 605

His His His His
    610
```

<210> SEQ ID NO 7
<211> LENGTH: 2353
<212> TYPE: DNA
<213> ORGANISM: Clostridium cellulolyticum

<400> SEQUENCE: 7

```
gcggccgcgc tatttttcat aaaaaaccaa gcaactgctt atcaacacac ttaattaaaa     60
acaaaatggt ttcattcact tccttgttag ctggtgtcgc tgctatctcc ggtgttttag    120
ctgctccagc tgctgaagtt gaaccagtcg cagttgaaaa gagagaagct gaagctgaag    180
ctgctggtac ttacaattac ggtgaagctt tgcaaaagtc tatcatgttc tacgaatttc    240
aaagatctgg tgacttgcca gccgacaaga gagacaactg gagagacgat tccggtatga    300
aggatggttc tgacgttggt gtcgatttga ctggtggttg gtacgacgcc ggtgaccacg    360
tcaaattcaa cttgccaatg tcttacacct cagccatgct agcttggtct ttgtatgaag    420
acaaggacgc ctacgacaag tcaggtcaaa ccaagtacat tatggacggt atcaaatggg    480
ctaacgatta cttcattaaa tgtaacccaa ctccaggtgt ttactactac caagtcggtg    540
atggtggtaa ggaccattcc tggtggggtc cagctgaagt catgcaaatg gaaagaccat    600
ccttcaaggt cgacgcttct aagccaggtt cagctgtttg cgcttcaacc gctgcctctt    660
tggcttctgc tgccgtcgtt ttcaagtctt ctgacccaac ctacgccgaa aagtgtatct    720
ctcatgctaa gaacttgttc gatatggctg acaaggctaa gtctgatgct ggttacactg    780
ccgcttctgg ttactactct agctcctctt tctacgacga tttgtcttgg gctgctgttt    840
ggttgtactt ggctaccaac gattctactt acttggataa ggctgaatct tacgttccaa    900
actggggtaa ggaacaacaa accgacatca tcgcttacaa atggggtcaa tgttgggacg    960
acgttcacta cggtgccgaa ctattgttgg ctaagttgac caacaagcaa ttgtacaagg   1020
actccatcga aatgaaccta gacttttgga ccaccggtgt caacggtact agagtttctt   1080
acaccccaaa gggtttggct tggttgtttc aatggggttc tttgagacat gctaccaccc   1140
```

-continued

```
aagctttctt ggctggtgtt tacgctgaat gggaaggttg tacccatct aaggtctccg    1200
tttacaagga cttcttgaag tcccaaatcg actacgcttt gggttctacc ggtagatctc    1260
ttgtcgttgg ttacggtgtt aacccaccac aacacccaca ccatagaacc gctcacggtt    1320
cttggactga ccaaatgact tctccaactt accacagaca caccatctac ggtgccttgg    1380
tcggtggtcc agacaacgct gacggttaca ccgacgaaat caacaactac gttaacaacg    1440
agatcgcttg cgattacaac gctggtttta ctggtgcttt ggctaagatg tacaagcact    1500
ccggtggtga tccaattcca aacttcaagg ccatcgaaaa gatcaccaac gatgaagtca    1560
ttatcaaggc tggtttgaac tccactggtc aaactacac cgaaatcaaa gccgttgttt    1620
acaaccaaac cggttggcca gctagagtca ccgataagat ctctttcaag tacttcatgg    1680
acttgtctga aattgtcgct gccggtattg acccttgtc cttggttact tcctctaact    1740
actccgaagg taagaacacc aaagtctctg gtgttttgcc atgggacgtc tccaacaacg    1800
tctactacgt caacgttgac ttgaccggtg aaaacattta cccaggtggt caatctgctt    1860
gtagaagaga agttcaattc cgtatcgctg ctccacaagg tagaagatac tggaacccaa    1920
agaacgattt ctcttacgat ggtctaccaa ccacctctac tgttaatacc gttaccaaca    1980
ttccagttta tgacaacggt gttaaggtct tcggtaacga accagccggt ggttctgaaa    2040
acccagatcc agaaattttg tacggtgacg tcaactctga caagaacgtc gacgctttag    2100
atttcgccgc cttgaagaag tacttgttgg gtggcacttc ctctattgat gttaaggctg    2160
ctgatactta caaggacggt aatatcgacg ccattgacat ggctaccttg aagaagtacc    2220
tattgggtac catcactcaa ttgccacaag gtggtggcgg ttctggtggc ggttctcacc    2280
accatcatca ccactaaggc gcgccgcttt tgattaagcc ttctagtcca aaaaacacgt    2340
tttttgcggc cgc                                                       2353
```

<210> SEQ ID NO 8
<211> LENGTH: 743
<212> TYPE: PRT
<213> ORGANISM: Clostridium cellulolyticum

<400> SEQUENCE: 8

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala Gly Thr Tyr Asn Tyr Gly Glu Ala
        35                  40                  45

Leu Gln Lys Ser Ile Met Phe Tyr Glu Phe Gln Arg Ser Gly Asp Leu
    50                  55                  60

Pro Ala Asp Lys Arg Asp Asn Trp Arg Asp Asp Ser Gly Met Lys Asp
65                  70                  75                  80

Gly Ser Asp Val Gly Val Asp Leu Thr Gly Gly Trp Tyr Asp Ala Gly
                85                  90                  95

Asp His Val Lys Phe Asn Leu Pro Met Ser Tyr Thr Ser Ala Met Leu
            100                 105                 110

Ala Trp Ser Leu Tyr Glu Asp Lys Asp Ala Tyr Asp Lys Ser Gly Gln
        115                 120                 125

Thr Lys Tyr Ile Met Asp Gly Ile Lys Trp Ala Asn Asp Tyr Phe Ile
    130                 135                 140

Lys Cys Asn Pro Thr Pro Gly Val Tyr Tyr Tyr Gln Val Gly Asp Gly
```

```
145                 150                 155                 160
Gly Lys Asp His Ser Trp Trp Gly Pro Ala Glu Val Met Gln Met Glu
                165                 170                 175
Arg Pro Ser Phe Lys Val Asp Ala Ser Lys Pro Gly Ser Ala Val Cys
                180                 185                 190
Ala Ser Thr Ala Ala Ser Leu Ala Ser Ala Ala Val Val Phe Lys Ser
                195                 200                 205
Ser Asp Pro Thr Tyr Ala Glu Lys Cys Ile Ser His Ala Lys Asn Leu
    210                 215                 220
Phe Asp Met Ala Asp Lys Ala Lys Ser Asp Ala Gly Tyr Thr Ala Ala
225                 230                 235                 240
Ser Gly Tyr Tyr Ser Ser Ser Phe Tyr Asp Asp Leu Ser Trp Ala
                245                 250                 255
Ala Val Trp Leu Tyr Leu Ala Thr Asn Asp Ser Thr Tyr Leu Asp Lys
            260                 265                 270
Ala Glu Ser Tyr Val Pro Asn Trp Gly Lys Glu Gln Gln Thr Asp Ile
            275                 280                 285
Ile Ala Tyr Lys Trp Gly Gln Cys Trp Asp Asp Val His Tyr Gly Ala
        290                 295                 300
Glu Leu Leu Leu Ala Lys Leu Thr Asn Lys Gln Leu Tyr Lys Asp Ser
305                 310                 315                 320
Ile Glu Met Asn Leu Asp Phe Trp Thr Thr Gly Val Asn Gly Thr Arg
                325                 330                 335
Val Ser Tyr Thr Pro Lys Gly Leu Ala Trp Leu Phe Gln Trp Gly Ser
                340                 345                 350
Leu Arg His Ala Thr Thr Gln Ala Phe Leu Ala Gly Val Tyr Ala Glu
                355                 360                 365
Trp Glu Gly Cys Thr Pro Ser Lys Val Ser Val Tyr Lys Asp Phe Leu
                370                 375                 380
Lys Ser Gln Ile Asp Tyr Ala Leu Gly Ser Thr Gly Arg Ser Phe Val
385                 390                 395                 400
Val Gly Tyr Gly Val Asn Pro Pro Gln His Pro His His Arg Thr Ala
                405                 410                 415
His Gly Ser Trp Thr Asp Gln Met Thr Ser Pro Thr Tyr His Arg His
                420                 425                 430
Thr Ile Tyr Gly Ala Leu Val Gly Gly Pro Asp Asn Ala Asp Gly Tyr
                435                 440                 445
Thr Asp Glu Ile Asn Asn Tyr Val Asn Asn Glu Ile Ala Cys Asp Tyr
    450                 455                 460
Asn Ala Gly Phe Thr Gly Ala Leu Ala Lys Met Tyr Lys His Ser Gly
465                 470                 475                 480
Gly Asp Pro Ile Pro Asn Phe Lys Ala Ile Glu Lys Ile Thr Asn Asp
                485                 490                 495
Glu Val Ile Ile Lys Ala Gly Leu Asn Ser Thr Gly Pro Asn Tyr Thr
                500                 505                 510
Glu Ile Lys Ala Val Val Tyr Asn Gln Thr Gly Trp Pro Ala Arg Val
            515                 520                 525
Thr Asp Lys Ile Ser Phe Lys Tyr Phe Met Asp Leu Ser Glu Ile Val
            530                 535                 540
Ala Ala Gly Ile Asp Pro Leu Ser Leu Val Thr Ser Ser Asn Tyr Ser
545                 550                 555                 560
Glu Gly Lys Asn Thr Lys Val Ser Gly Val Leu Pro Trp Asp Val Ser
                565                 570                 575
```

```
Asn Asn Val Tyr Tyr Val Asn Val Asp Leu Thr Gly Glu Asn Ile Tyr
            580                 585                 590

Pro Gly Gly Gln Ser Ala Cys Arg Arg Glu Val Gln Phe Arg Ile Ala
        595                 600                 605

Ala Pro Gln Gly Arg Arg Tyr Trp Asn Pro Lys Asn Asp Phe Ser Tyr
    610                 615                 620

Asp Gly Leu Pro Thr Thr Ser Thr Val Asn Thr Val Thr Asn Ile Pro
625                 630                 635                 640

Val Tyr Asp Asn Gly Val Lys Val Phe Gly Asn Glu Pro Ala Gly Gly
                645                 650                 655

Ser Glu Asn Pro Asp Pro Glu Ile Leu Tyr Gly Asp Val Asn Ser Asp
            660                 665                 670

Lys Asn Val Asp Ala Leu Asp Phe Ala Ala Leu Lys Lys Tyr Leu Leu
        675                 680                 685

Gly Gly Thr Ser Ser Ile Asp Val Lys Ala Ala Asp Thr Tyr Lys Asp
    690                 695                 700

Gly Asn Ile Asp Ala Ile Asp Met Ala Thr Leu Lys Lys Tyr Leu Leu
705                 710                 715                 720

Gly Thr Ile Thr Gln Leu Pro Gln Gly Gly Gly Gly Ser Gly Gly Gly
                725                 730                 735

Ser His His His His His His
            740

<210> SEQ ID NO 9
<211> LENGTH: 2854
<212> TYPE: DNA
<213> ORGANISM: Clostridium cellulolyticum

<400> SEQUENCE: 9
gcggccgcgc tattttcat  aaaaaaccaa gcaactgctt atcaacacac ttaattaaaa      60
acaaaatggt ctctttcact tctttgttgg ctggtgttgc tgctatctcc ggtgtgttgg     120
ctgccccagc cgccgaagtc gaaccagtcg ccgtcgaaaa gagagaagct gaagctgaag     180
ctttggttgg tgctggtgac ttgattagaa atcatacttt cgacaacaga gtcggtttac     240
cttggcacgt tgttgaatcc tacccagcta aggcttcctt cgaaatcacc tccgacggta     300
agtacaagat caccgctcaa aagattggtg aagctggtaa gggtgaaaga tgggacattc     360
aattcagaca cagaggtttg gctctacaac aaggtcatac ctacaccgtc aagttcactg     420
ttaccgcatc tagagcttgt aagatctacc caaagattgg tgatcaaggt gatccatacg     480
acgaatactg gaacatgaac caacaatgga acttcttgga attgcaagct aacacccccaa     540
agaccgttac ccaaactttc actcaaacta gggtgataa  gaagaacgtt gaatttgctt     600
tcaccttgc  tccagataag actacctctg aagctcaaaa cccagcctct ttccaaccaa     660
ttacttacac ttttgacgaa atctacatcc aagatccaca gttcgccggt tacaccgaag     720
atccaccaga accaactaac gttgtcagat tgaatcaagt tggtttctac ccaaacgctg     780
acaagattgc taccgttgct acctcctcta ctaccccaat taactggcaa cttgtcaact     840
ccaccggcgc tgccgttttg accggtaagt ctaccgttaa gggtgctgat agagcttccg     900
gtgacaacgt tcacatcatt gatttctctt cttacactac tccaggtacc gattacaaga     960
tcgttaccga cgtctctgtc actaaggctg tgacaacga  atccatgaag ttcaacatcg    1020
gtgacgactt gttcacccaa atgaagtacg attccatgaa gtacttctac cacaacagat    1080
ctgctatccc aattcaaatg ccatactgtg accaatccca atgggctaga ccagccggtc    1140
```

```
acaccaccga catttggct  ccagacccaa ccaaggacta caaggccaac tacaccttgg    1200
acgttaccgg tggttggtac gacgccggtg accacggtaa gtatgttgtg aacggtggta    1260
tcgctacctg gaccgtcatg aacgcttacg aacgtgcttt gcacatgggt ggtgacacct    1320
ccgtcgctcc attcaaagat ggttctttga acattccaga atccggtaac ggttacccag    1380
atatcttaga tgaagctaga tacaacatga agactttgtt gaacatgcaa gtcccagccg    1440
gtaacgaatt ggctggtatg gctcaccaca aggctcacga cgagagatgg accgctttgg    1500
ctgtccgtcc agaccaagat accatgaaga gatggttaca accaccatct accgctgcta    1560
cttttgaactt ggccgctatc gccgcccagt cttctcgttt gtggaagcaa ttcgactctg    1620
ccttcgctac caagtgcttg actgccgctg aaactgcctg ggacgctgcc gtcgcccacc    1680
cagaaattta cgctaccatg gaacaaggtg ctggtggtgg tgcttacggt gacaactacg    1740
ttttggatga tttctactgg gctgcttgcg aattgtacgc tactactggt tccgacaagt    1800
acttgaacta tatcaagtct tctaagcact acttggaaat gccaactgaa ttgactggtg    1860
gtgaaaacac cggtattact ggtgctttcg actggggttg tactgccggt atgggtacta    1920
tcactttggc tttagttcca actaagctac cagccgctga cgttgctacc gccaaggcta    1980
acattcaagc tgccgctgac aagttcatct ctatttcaaa ggcccaaggt tacggtgtcc    2040
cattggaaga aaaggtcatt tcttccccat tcgatgcttc cgttgtcaag ggttttcaat    2100
ggggttctaa ctccttcgtc attaacgaag ctatcgtcat gtcttacgct tacgagttct    2160
ccgatgtcaa cggtactaag aacaacaagt acatcaacgg tgctttgact gctatggact    2220
acttgttggg tagaaaccca acattcaat  cctatatcac cggttacggt gataacccat    2280
tggaaaaccc acaccacaga ttctgggctt accaagctga caatactttc ccaaagccac    2340
ctccaggttg tttgtccggt ggtccaaact ctggtttaca agatccttgg gtcaagggtt    2400
ctggttggca accaggtgaa agaccagccg aaaagtgttt catggacaac atcgaatctt    2460
ggtctactaa cgaaattacc atcaactgga acgctccatt ggtttggatt tcagcctact    2520
tggacgaaaa gggtccagaa atcggtggtt ctgtcactcc accaaccaac ttgggtgacg    2580
ttaacggtga cggtaacaag gacgctttgg acttcgctgc tttgaagaag gctttgttgt    2640
ctcaagacac ttccaccatc aacgttgcta cgctgatat  caacaaggac ggttccatcg    2700
acgctgttga cttcgctcta ttgaagtctt tcttgttagg taagatcact ttgggtggtg    2760
gttctggtgg tggttcccac caccatcacc accactaagg cgcgccgctt tgattaagc    2820
cttctagtcc aaaaaacacg ttttttgcgg ccgc                                2854
```

<210> SEQ ID NO 10
<211> LENGTH: 910
<212> TYPE: PRT
<213> ORGANISM: Clostridium cellulolyticum

<400> SEQUENCE: 10

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala Leu Val Gly Ala Gly Asp Leu Ile Arg
        35                  40                  45

Asn His Thr Phe Asp Asn Arg Val Gly Leu Pro Trp His Val Val Glu
    50                  55                  60

-continued

```
Ser Tyr Pro Ala Lys Ala Ser Phe Glu Ile Thr Ser Asp Gly Lys Tyr
 65                  70                  75                  80

Lys Ile Thr Ala Gln Lys Ile Gly Glu Ala Gly Lys Gly Glu Arg Trp
                 85                  90                  95

Asp Ile Gln Phe Arg His Arg Gly Leu Ala Leu Gln Gln Gly His Thr
            100                 105                 110

Tyr Thr Val Lys Phe Thr Val Thr Ala Ser Arg Ala Cys Lys Ile Tyr
        115                 120                 125

Pro Lys Ile Gly Asp Gln Gly Asp Pro Tyr Asp Tyr Trp Asn Met
130                 135                 140

Asn Gln Gln Trp Asn Phe Leu Glu Leu Gln Ala Asn Thr Pro Lys Thr
145                 150                 155                 160

Val Thr Gln Thr Phe Thr Gln Thr Lys Gly Asp Lys Lys Asn Val Glu
                165                 170                 175

Phe Ala Phe His Leu Ala Pro Asp Lys Thr Thr Ser Glu Ala Gln Asn
            180                 185                 190

Pro Ala Ser Phe Gln Pro Ile Thr Tyr Thr Phe Asp Glu Ile Tyr Ile
        195                 200                 205

Gln Asp Pro Gln Phe Ala Gly Tyr Thr Glu Asp Pro Pro Glu Pro Thr
210                 215                 220

Asn Val Val Arg Leu Asn Gln Val Gly Phe Tyr Pro Asn Ala Asp Lys
225                 230                 235                 240

Ile Ala Thr Val Ala Thr Ser Ser Thr Thr Pro Ile Asn Trp Gln Leu
                245                 250                 255

Val Asn Ser Thr Gly Ala Ala Val Leu Thr Gly Lys Ser Thr Val Lys
            260                 265                 270

Gly Ala Asp Arg Ala Ser Gly Asp Asn Val His Ile Ile Asp Phe Ser
        275                 280                 285

Ser Tyr Thr Thr Pro Gly Thr Asp Tyr Lys Ile Val Thr Asp Val Ser
        290                 295                 300

Val Thr Lys Ala Gly Asp Asn Glu Ser Met Lys Phe Asn Ile Gly Asp
305                 310                 315                 320

Asp Leu Phe Thr Gln Met Lys Tyr Asp Ser Met Lys Tyr Phe Tyr His
                325                 330                 335

Asn Arg Ser Ala Ile Pro Ile Gln Met Pro Tyr Cys Asp Gln Ser Gln
            340                 345                 350

Trp Ala Arg Pro Ala Gly His Thr Thr Asp Ile Leu Ala Pro Asp Pro
        355                 360                 365

Thr Lys Asp Tyr Lys Ala Asn Tyr Thr Leu Asp Val Thr Gly Gly Trp
    370                 375                 380

Tyr Asp Ala Gly Asp His Gly Lys Tyr Val Val Asn Gly Gly Ile Ala
385                 390                 395                 400

Thr Trp Thr Val Met Asn Ala Tyr Glu Arg Ala Leu His Met Gly Gly
                405                 410                 415

Asp Thr Ser Val Ala Pro Phe Lys Asp Gly Ser Leu Asn Ile Pro Glu
            420                 425                 430

Ser Gly Asn Gly Tyr Pro Asp Ile Leu Asp Glu Ala Arg Tyr Asn Met
        435                 440                 445

Lys Thr Leu Leu Asn Met Gln Val Pro Ala Gly Asn Glu Leu Ala Gly
    450                 455                 460

Met Ala His His Lys Ala His Asp Glu Arg Trp Thr Ala Leu Ala Val
465                 470                 475                 480

Arg Pro Asp Gln Asp Thr Met Lys Arg Trp Leu Gln Pro Pro Ser Thr
```

-continued

```
                485                 490                 495
Ala Ala Thr Leu Asn Leu Ala Ala Ile Ala Ala Gln Ser Ser Arg Leu
                500                 505                 510

Trp Lys Gln Phe Asp Ser Ala Phe Ala Thr Lys Cys Leu Thr Ala Ala
                515                 520                 525

Glu Thr Ala Trp Asp Ala Ala Val Ala His Pro Glu Ile Tyr Ala Thr
                530                 535             540

Met Glu Gln Gly Ala Gly Gly Ala Tyr Gly Asp Asn Tyr Val Leu
545                 550                 555                 560

Asp Asp Phe Tyr Trp Ala Ala Cys Glu Leu Tyr Ala Thr Thr Gly Ser
                565                 570                 575

Asp Lys Tyr Leu Asn Tyr Ile Lys Ser Ser Lys His Tyr Leu Glu Met
                580                 585                 590

Pro Thr Glu Leu Thr Gly Gly Glu Asn Thr Gly Ile Thr Gly Ala Phe
                595                 600             605

Asp Trp Gly Cys Thr Ala Gly Met Gly Thr Ile Thr Leu Ala Leu Val
                610                 615             620

Pro Thr Lys Leu Pro Ala Ala Asp Val Ala Thr Ala Lys Ala Asn Ile
625                 630                 635                 640

Gln Ala Ala Ala Asp Lys Phe Ile Ser Ile Ser Lys Ala Gln Gly Tyr
                        645                 650                 655

Gly Val Pro Leu Glu Glu Lys Val Ile Ser Ser Pro Phe Asp Ala Ser
                660                 665                 670

Val Val Lys Gly Phe Gln Trp Gly Ser Asn Ser Phe Val Ile Asn Glu
                675                 680                 685

Ala Ile Val Met Ser Tyr Ala Tyr Glu Phe Ser Asp Val Asn Gly Thr
690                 695                 700

Lys Asn Asn Lys Tyr Ile Asn Gly Ala Leu Thr Ala Met Asp Tyr Leu
705                 710                 715                 720

Leu Gly Arg Asn Pro Asn Ile Gln Ser Tyr Ile Thr Gly Tyr Gly Asp
                        725                 730                 735

Asn Pro Leu Glu Asn Pro His His Arg Phe Trp Ala Tyr Gln Ala Asp
                740                 745                 750

Asn Thr Phe Pro Lys Pro Pro Gly Cys Leu Ser Gly Gly Pro Asn
                755                 760             765

Ser Gly Leu Gln Asp Pro Trp Val Lys Gly Ser Gly Trp Gln Pro Gly
                770                 775                 780

Glu Arg Pro Ala Glu Lys Cys Phe Met Asp Asn Ile Glu Ser Trp Ser
785                 790                 795                 800

Thr Asn Glu Ile Thr Ile Asn Trp Asn Ala Pro Leu Val Trp Ile Ser
                        805                 810                 815

Ala Tyr Leu Asp Glu Lys Gly Pro Glu Ile Gly Gly Ser Val Thr Pro
                820                 825                 830

Pro Thr Asn Leu Gly Asp Val Asn Gly Asp Gly Asn Lys Asp Ala Leu
                835                 840                 845

Asp Phe Ala Ala Leu Lys Lys Ala Leu Leu Ser Gln Asp Thr Ser Thr
                850                 855             860

Ile Asn Val Ala Asn Ala Asp Ile Asn Lys Asp Gly Ser Ile Asp Ala
865                 870                 875                 880

Val Asp Phe Ala Leu Leu Lys Ser Phe Leu Leu Gly Lys Ile Thr Leu
                        885                 890                 895

Gly Gly Gly Ser Gly Gly Gly Ser His His His His His His
                900                 905             910
```

<210> SEQ ID NO 11
<211> LENGTH: 2362
<212> TYPE: DNA
<213> ORGANISM: Clostridium cellulolyticum

<400> SEQUENCE: 11

```
gcggccgcgc tattttttcat aaaaaaccaa gcaactgctt atcaacacac ttaattaaaa      60
acaaaatggt ttcttttcact tctttgttgg ccggtgttgc tgctatctct ggtgttttgg     120
ctgctccagc tgctgaagtt gaaccagttg ccgtcgaaaa gcgtgaagct gaagctgaag     180
ctgcttcttc cccagctaac aaggtttacc aagacagatt cgaatctatg tactctaaaa     240
tcaaggaccc agccaacggt tacttctccg aacaaggtat tccataccat tctatcgaaa     300
ccttgatggt tgaagctcca gactacggtc acgtcactac ttctgaagct atgtcctact     360
acatgtggtt ggaagctatg cacggtagat tttctggtga cttcactggt ttcgacaagt     420
cttggtccgt caccgaacaa tatttgattc caaccgaaaa agatcaacca aacacctcta     480
tgtctagata cgacgctaac aagccagcca cctacgcccc agaatttcaa gacccatcta     540
agtatccatc cccacttgac acttctcaac cagtcggtag agatccaatt aactcccaat     600
tgacttctgc ttacggtacc tctatgttgt acggtatgca ctggatcttg gatgttgata     660
actggtacgg tttcggtgct agagctgatg gtacttccaa gccatcctac atcaacacct     720
tccaaagagg tgaacaagaa agcacctggg aaactattcc acaaccatgt tgggatgaac     780
acaagttcgg tggtcaatac ggtttcttgg acttgttcac caaggatacc ggtactccag     840
ctaagcaatt caagtacact aacgctccag acgctgatgc tcgtgctgtt caagctacct     900
actgggctga tcaatgggct aaggaacaag gtaagtccgt ctccacttct gttggtaagg     960
ctactaagat gggtgactac ttgagatact cttttttttcga caagtacttc agaaagatcg    1020
gtcaaccatc tcaagctggt accggttacg acgccgctca ctacttgttg tcttggtact    1080
atgcctgggg tggtggtatt gattccactt ggtcctggat tattggttct tcgcacaacc    1140
acttcggtta ccaaaaccca ttcgctgcct gggtcttgtc cactgatgcc aacttcaagc    1200
caaagtcttc caacggtgct tccgactggg ctaagtcttt ggatagacaa ttagaatttt    1260
accaatggtt gcaatctgcc gaaggtgcta ttgctggtgg tgccaccaac tcctggaacg    1320
gtagatacga agctgtccca tctggtactt ccaccttcta cggtatgggt tacgttgaaa    1380
acccagtcta cgctgaccca ggatctaaca cctggttcgg tatgcaagtc tggtccatgc    1440
aacgtgtcgc cgaattgtac tacaaaaccg gtgacgctcg tgctaagaag ttgttggaca    1500
agtgggctaa gtggatcaac ggtgaaatta aatttaacgc tgatggtacc ttccaaattc    1560
catctaccat cgactgggaa ggtcaaccag atacttggaa cccaaccaaa ggttataccg    1620
gtaacgccaa cttgcacgtt aaggtcgtta actacggtac tgacttgggt tgtgcttctt    1680
ctttggctaa caccttgacc tactacgctg ccaagtctgg tgacgaaact tctagacaaa    1740
acgctcaaaa gttgttggac gctatgtgga acaactactc tgattccaag ggtatttcca    1800
ctgttgaaca aagaggtgac taccacagat tcttggatca agaagttttc gttccagccg    1860
gttggaccgg taagatgcca aacggtgacg tcattaagtc tggtgtcaag ttcatcgaca    1920
tcagatctaa gtacaaacaa gacccagaat ggcaaaccat ggttgccgct tgcaagccg    1980 gtcaagttcc aacccaaaga ttgcatagat tctgggctca atctgaattt gccgttgcca    2040
acggtgtcta cgctatcttg ttcccagacc aaggtccaga aaaattgttg ggtgacgtca    2100
```

```
atggtgacga aactgttgat gctatcgact tagctatctt gaagaagtac ttgttgaact   2160
cttccactac tatcaacacc gccaacgccg acatgaactc tgataacgcc atcgacgcca   2220
ttgattacgc cttgttgaag aaggccttgt tgtctatcca aggtggtggt tccggtggtg   2280
gttcccacca tcaccaccac cactaaggcg cgccgctttt gattaagcct tctagtccaa   2340
aaaacacgtt ttttgcggcc gc                                            2362
```

<210> SEQ ID NO 12
<211> LENGTH: 746
<212> TYPE: PRT
<213> ORGANISM: Clostridium cellulolyticum

<400> SEQUENCE: 12

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Ala Ser Ser Pro Ala Asn Lys Val Tyr
        35                  40                  45

Gln Asp Arg Phe Glu Ser Met Tyr Ser Lys Ile Lys Asp Pro Ala Asn
    50                  55                  60

Gly Tyr Phe Ser Glu Gln Gly Ile Pro Tyr His Ser Ile Glu Thr Leu
65                  70                  75                  80

Met Val Glu Ala Pro Asp Tyr Gly His Val Thr Thr Ser Glu Ala Met
                85                  90                  95

Ser Tyr Tyr Met Trp Leu Glu Ala Met His Gly Arg Phe Ser Gly Asp
            100                 105                 110

Phe Thr Gly Phe Asp Lys Ser Trp Ser Val Thr Glu Gln Tyr Leu Ile
        115                 120                 125

Pro Thr Glu Lys Asp Gln Pro Asn Thr Ser Met Ser Arg Tyr Asp Ala
    130                 135                 140

Asn Lys Pro Ala Thr Tyr Ala Pro Glu Phe Gln Asp Pro Ser Lys Tyr
145                 150                 155                 160

Pro Ser Pro Leu Asp Thr Ser Gln Pro Val Gly Arg Asp Pro Ile Asn
                165                 170                 175

Ser Gln Leu Thr Ser Ala Tyr Gly Thr Ser Met Leu Tyr Gly Met His
            180                 185                 190

Trp Ile Leu Asp Val Asp Asn Trp Tyr Gly Phe Gly Ala Arg Ala Asp
        195                 200                 205

Gly Thr Ser Lys Pro Ser Tyr Ile Asn Thr Phe Gln Arg Gly Glu Gln
    210                 215                 220

Glu Ser Thr Trp Glu Thr Ile Pro Gln Pro Cys Trp Asp Glu His Lys
225                 230                 235                 240

Phe Gly Gly Gln Tyr Gly Phe Leu Asp Leu Phe Thr Lys Asp Thr Gly
                245                 250                 255

Thr Pro Ala Lys Gln Phe Lys Tyr Thr Asn Ala Pro Asp Ala Asp Ala
            260                 265                 270

Arg Ala Val Gln Ala Thr Tyr Trp Ala Asp Gln Trp Ala Lys Glu Gln
        275                 280                 285

Gly Lys Ser Val Ser Thr Ser Val Gly Lys Ala Thr Lys Met Gly Asp
    290                 295                 300

Tyr Leu Arg Tyr Ser Phe Phe Asp Lys Tyr Phe Arg Lys Ile Gly Gln
305                 310                 315                 320

Pro Ser Gln Ala Gly Thr Gly Tyr Asp Ala Ala His Tyr Leu Leu Ser

```
                    325                 330                 335
Trp Tyr Tyr Ala Trp Gly Gly Ile Asp Ser Thr Trp Ser Trp Ile
                340                 345                 350
Ile Gly Ser Ser His Asn His Phe Gly Tyr Gln Asn Pro Phe Ala Ala
                355                 360                 365
Trp Val Leu Ser Thr Asp Ala Asn Phe Lys Pro Lys Ser Ser Asn Gly
                370                 375                 380
Ala Ser Asp Trp Ala Lys Ser Leu Asp Arg Gln Leu Glu Phe Tyr Gln
385                 390                 395                 400
Trp Leu Gln Ser Ala Glu Gly Ala Ile Ala Gly Gly Ala Thr Asn Ser
                405                 410                 415
Trp Asn Gly Arg Tyr Glu Ala Val Pro Ser Gly Thr Ser Thr Phe Tyr
                420                 425                 430
Gly Met Gly Tyr Val Glu Asn Pro Val Tyr Ala Asp Pro Gly Ser Asn
                435                 440                 445
Thr Trp Phe Gly Met Gln Val Trp Ser Met Gln Arg Val Ala Glu Leu
                450                 455                 460
Tyr Tyr Lys Thr Gly Asp Ala Arg Ala Lys Lys Leu Leu Asp Lys Trp
465                 470                 475                 480
Ala Lys Trp Ile Asn Gly Glu Ile Lys Phe Asn Ala Asp Gly Thr Phe
                485                 490                 495
Gln Ile Pro Ser Thr Ile Asp Trp Glu Gly Gln Pro Asp Thr Trp Asn
                500                 505                 510
Pro Thr Gln Gly Tyr Thr Gly Asn Ala Asn Leu His Val Lys Val Val
                515                 520                 525
Asn Tyr Gly Thr Asp Leu Gly Cys Ala Ser Ser Leu Ala Asn Thr Leu
                530                 535                 540
Thr Tyr Tyr Ala Ala Lys Ser Gly Asp Glu Thr Ser Arg Gln Asn Ala
545                 550                 555                 560
Gln Lys Leu Leu Asp Ala Met Trp Asn Asn Tyr Ser Asp Ser Lys Gly
                565                 570                 575
Ile Ser Thr Val Glu Gln Arg Gly Asp Tyr His Arg Phe Leu Asp Gln
                580                 585                 590
Glu Val Phe Val Pro Ala Gly Trp Thr Gly Lys Met Pro Asn Gly Asp
                595                 600                 605
Val Ile Lys Ser Gly Val Lys Phe Ile Asp Ile Arg Ser Lys Tyr Lys
                610                 615                 620
Gln Asp Pro Glu Trp Gln Thr Met Val Ala Ala Leu Gln Ala Gly Gln
625                 630                 635                 640
Val Pro Thr Gln Arg Leu His Arg Phe Trp Ala Gln Ser Glu Phe Ala
                645                 650                 655
Val Ala Asn Gly Val Tyr Ala Ile Leu Phe Pro Asp Gln Gly Pro Glu
                660                 665                 670
Lys Leu Leu Gly Asp Val Asn Gly Asp Glu Thr Val Asp Ala Ile Asp
                675                 680                 685
Leu Ala Ile Leu Lys Lys Tyr Leu Leu Asn Ser Ser Thr Thr Ile Asn
                690                 695                 700
Thr Ala Asn Ala Asp Met Asn Ser Asp Asn Ala Ile Asp Ala Ile Asp
705                 710                 715                 720
Tyr Ala Leu Leu Lys Lys Ala Leu Leu Ser Ile Gln Gly Gly Gly Ser
                725                 730                 735
Gly Gly Gly Ser His His His His His
                740                 745
```

<210> SEQ ID NO 13
<211> LENGTH: 1630
<212> TYPE: DNA
<213> ORGANISM: Clostridium cellulolyticum

<400> SEQUENCE: 13

```
gcggccgcgc tattttttcat aaaaaaccaa gcaactgctt atcaacacac ttaattaaaa      60
acaaaatggt ttcctttact tctttgttgg ctggtgttgc tgctatctcc ggtgttttgg     120
ctgccccagc tgctgaagtt gaaccagtcg ctgttgaaaa gagagaagct gaagctgaag     180
cttacgacgc ttccttgatc ccaaacttac aaatcccaca aaagaacatc ccaaacaatg     240
atggtatgaa cttcgttaag ggtctaagat tgggttggaa cttgggtaac acctttgacg     300
ccttcaacgg tactaacatt accaatgaat tggattacga aacttcctgg tccggtatca     360
aaaccactaa gcaaatgatt gacgctatta agcaaaaggg tttcaacact gttagaatcc     420
cagtatcctg gcaccacaca gtttccggtt ctgactacaa gatctctgac gtctggatga     480
acagagttca agaagttgtt aactactgta ttgacaacaa gatgtacgtt atcttgaaca     540
cccaccatga cgtcgacaag gtcaagggtt acttcccttc ttcccaatac atggcctctt     600
ctaagaagta cattacctct gtctgggctc aaatcgccgc ccgtttcgct aactacgacg     660
aacatttgat attcgaaggt atgaacgaac caagattggt cggtcacgcc aatgaatggt     720
ggccagaatt gaccaactct gatgtcgtcg actctattaa ctgcattaac caattgaacc     780
aagacttcgt taacaccgtc agagctaccg gtggtaagaa cgcttctaga tatttgatgt     840
gtccaggtta cgttgcttct ccagatggtg ctaccaacga ctacttcaga atgccaaacg     900
acatttccgg taacaacaac aagatcatcg tttctgttca tgcttactgt ccatggaact     960
cgccggtttt agccatggct gacggtggta ccaacgcttg gaacattaac gattctaagg    1020
atcaatccga gtcacctgg ttcatggata acatttacaa caagtacacc tctagaggta    1080
ttccagtcat tattggtgaa tgtggtgctg ttgacaagaa taacttgaag accagagttg    1140
aatacatgtc ctactacgtt gctcaagcta aggctagagg tatcttgtgt attttgtggg    1200
ataacaacaa cttctctggt accggtgaat tgttcggttt cttcgacaga gatcctgtc    1260
aattcaagtt cccagaaatc atcgacggta tggttaagta cgccttcgaa gctaagaccg    1320
atccagaccc agttatcgtt tatggtgact acaacaacga tggtaacgtt gacgccttgg    1380
acttcgctgg tttgaagaag tacattatgg ctgctgacca cgcttacgtc aagaacttgg    1440
acgttaattt ggacaacgaa gttaacgctt tcgatttggc catcttgaag aagtacttat    1500
tgggtatggt ttctaagcta ccatccaacg gtggtggttc cggtggtggt tctcaccacc    1560
accaccacca ctaaggcgcg ccgctttttga ttaagccttc tagtccaaaa aacacgtttt    1620
ttgcggccgc                                                           1630
```

<210> SEQ ID NO 14
<211> LENGTH: 502
<212> TYPE: PRT
<213> ORGANISM: Clostridium cellulolyticum

<400> SEQUENCE: 14

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

```
Arg Glu Ala Glu Ala Glu Ala Tyr Asp Ala Ser Leu Ile Pro Asn Leu
            35                  40                  45

Gln Ile Pro Gln Lys Asn Ile Pro Asn Asn Asp Gly Met Asn Phe Val
    50                  55                  60

Lys Gly Leu Arg Leu Gly Trp Asn Leu Gly Asn Thr Phe Asp Ala Phe
65                  70                  75                  80

Asn Gly Thr Asn Ile Thr Asn Glu Leu Asp Tyr Glu Thr Ser Trp Ser
                85                  90                  95

Gly Ile Lys Thr Thr Lys Gln Met Ile Asp Ala Ile Lys Gln Lys Gly
                100                 105                 110

Phe Asn Thr Val Arg Ile Pro Val Ser Trp His Pro His Val Ser Gly
            115                 120                 125

Ser Asp Tyr Lys Ile Ser Asp Val Trp Met Asn Arg Val Gln Glu Val
    130                 135                 140

Val Asn Tyr Cys Ile Asp Asn Lys Met Tyr Val Ile Leu Asn Thr His
145                 150                 155                 160

His Asp Val Asp Lys Val Lys Gly Tyr Phe Pro Ser Ser Gln Tyr Met
                165                 170                 175

Ala Ser Lys Lys Tyr Ile Thr Ser Val Trp Ala Gln Ile Ala Ala
            180                 185                 190

Arg Phe Ala Asn Tyr Asp Glu His Leu Ile Phe Glu Gly Met Asn Glu
    195                 200                 205

Pro Arg Leu Val Gly His Ala Asn Glu Trp Trp Pro Glu Leu Thr Asn
    210                 215                 220

Ser Asp Val Val Asp Ser Ile Asn Cys Ile Asn Gln Leu Asn Gln Asp
225                 230                 235                 240

Phe Val Asn Thr Val Arg Ala Thr Gly Gly Lys Asn Ala Ser Arg Tyr
                245                 250                 255

Leu Met Cys Pro Gly Tyr Val Ala Ser Pro Asp Gly Ala Thr Asn Asp
            260                 265                 270

Tyr Phe Arg Met Pro Asn Asp Ile Ser Gly Asn Asn Lys Ile Ile
    275                 280                 285

Val Ser Val His Ala Tyr Cys Pro Trp Asn Phe Ala Gly Leu Ala Met
    290                 295                 300

Ala Asp Gly Gly Thr Asn Ala Trp Asn Ile Asn Asp Ser Lys Asp Gln
305                 310                 315                 320

Ser Glu Val Thr Trp Phe Met Asp Asn Ile Tyr Asn Lys Tyr Thr Ser
                325                 330                 335

Arg Gly Ile Pro Val Ile Gly Glu Cys Gly Ala Val Asp Lys Asn
            340                 345                 350

Asn Leu Lys Thr Arg Val Glu Tyr Met Ser Tyr Tyr Val Ala Gln Ala
    355                 360                 365

Lys Ala Arg Gly Ile Leu Cys Ile Leu Trp Asp Asn Asn Phe Ser
370                 375                 380

Gly Thr Gly Glu Leu Phe Gly Phe Phe Asp Arg Arg Ser Cys Gln Phe
385                 390                 395                 400

Lys Phe Pro Glu Ile Ile Asp Gly Met Val Lys Tyr Ala Phe Glu Ala
                405                 410                 415

Lys Thr Asp Pro Asp Pro Val Ile Val Tyr Gly Asp Tyr Asn Asn Asp
            420                 425                 430

Gly Asn Val Asp Ala Leu Asp Phe Ala Gly Leu Lys Lys Tyr Ile Met
        435                 440                 445

Ala Ala Asp His Ala Tyr Val Lys Asn Leu Asp Val Asn Leu Asp Asn
```

```
            450                 455                 460
Glu Val Asn Ala Phe Asp Leu Ala Ile Leu Lys Lys Tyr Leu Leu Gly
465                 470                 475                 480

Met Val Ser Lys Leu Pro Ser Asn Gly Gly Ser Gly Gly Ser
                485                 490                 495

His His His His His His
            500

<210> SEQ ID NO 15
<211> LENGTH: 4840
<212> TYPE: DNA
<213> ORGANISM: Clostridium cellulolyticum

<400> SEQUENCE: 15
gcggccgcgc tattttttcat aaaaaaccaa gcaactgctt atcaacacac ttaattaaaa      60
acaaaatggt ctctttcacc tccttgctag ctggagttgc tgccatttcc ggggttttgg     120
ccgccccagc tgccgaagtt gaaccagttg ctgtcgaaaa gagagaagct gaagctgaag     180
ctgccggtac tggtgtcgtc tctgttcaat caacaacgg ttcctctcca gcttcctcca      240
actctatcta cgccagattt aaggttacta cacctctgg ttctccaatc aacttggccg      300
acttgaagtt aagatactac tacacccaag atgccgacaa gccattgact ttctggtgtg     360
accacgccgg ttacatgtct ggttctaact cattgatgc tacctccaag gttactggtt      420
ccttcaaggc cgtttctcca gctgttacta acgctgatca ttacttagaa gttgctttga     480
actctgatgc cggttccttg ccagccggtg gtagcatcga aattcaaact agattcgcta     540
gaaacgattg gtctaatttc gatcaatcca acgactggtc ttacaccgct gctggttcct     600
acatggactg gcaaaagatc tctgctttcg tcggtggtac tttggcttac ggttctactc     660
cagacggtgg taacccacca ccacaagatc caaccattaa cccaacctct atttctgcta     720
aggctggttc tttcgccgac accaagatca ctttgactcc aaacggtaac actttcaacg     780
gtatctctga attgcaatct tctcaataca ctaaaggtac caacgaagtc actttgttgg     840
cttcttactt gaacaccttg ccagaaaaca ctaccaagac tttgaccttt gactttggtg     900
ttggtactaa gaacccaaag ttgactatca ctgtcttgcc aaaggatatc ccaggtgact     960
ccttgaaggt tactgttggt accgctaatg gtaagccagg tgacaccgtt actgtccctg    1020
tcactttcgc tgatgtcgct aagatgaaga acgtcggtac ttgtaacttc tatttgggtt    1080
acgacgcttc cttgttagaa gttgtttccg ttgacgctgg tccaatcgtc aagaacgctg    1140
ccgtcaactt ttctagttct gcttccaacg gtactatatc tttcctgttc ctagataaca    1200
ccattaccga cgagttgatc accgctgacg gtgtcttcgc caacattaag ttcaagctga    1260
aatccgtcac cgccaagacc actactccag tcacattcaa ggacggtggt gcttttggtg    1320
atggtaccat gtctaagatc gcttccgtca ccaagaccaa cggttctgtt accatagacc    1380
caggtactca accaactaag gaactaaagg ttgctgttgg tactgctaac ggtaagccag    1440
gtgataccgt cactgtccca gtcacctttg ctgacgttgt caacgttggt aacgttggta    1500
cttgcaattt ctacttggcc tacgatgcct ctttgctaga agttgtttcc gtcgatgctg    1560
gtccaatcgt taagaacgct gcagtgaact tctcctcttc agcttccaac ggtactatct    1620
ccttcttgtt tctagacaat actattaccg acgaattgat cacctctgac ggtgtctttg    1680
caaacatcaa gtttaagttg aagtccgttg ctactaagac caccaccca gttactttca    1740 aggatggtgg agccttcggt gatggtacta tggcaaagat tgctactgtt accaaaacca    1800
```

```
acggttccgt taccattgac ccaggtaccc aaccaactaa agaattgaag gtggctgtcg   1860
gtaccgctaa cggaaaacca ggtgatactg tcactgttcc cgttaccttc gccgacgtcg   1920
cttctgcagg taacgttggc acctgtaact tttacttggc atacgatgct tccttgttgg   1980
aagttgtttc tgttgacgct ggtccaattg tcaagaacgc tgctgttaac ttctcttctt   2040
ctgcctctaa tggttccatt tccttcctgt tcttggataa tactatcact gacgagttga   2100
ttaccgctga cggtgttttc gccaacatca agttcaaatt gaagtctgtc gctgccaaga   2160
ccactacccc agtcaccttc aaggacggtg gcgccttcgg ggacggtacc atgactaaga   2220
ttgctaccgt cactaagacc aacggttccg tcacaatcga cccagggact caaccaacaa   2280
aggaattaaa ggttgccgtc ggcactgccg aaggtaacgt aggtgacact gtcaccgtcc   2340
cagtcacctt cgctgacgtt gcttctgccg gtaacgtcgg tacatgtaac ttctacttgg   2400
cctacgacgc ttctttgttg gacgtcgttt ctgtcgcagc cggtcccatc gttaagaatg   2460
ccgctgtcaa cttctcctcg tctgcttcca acgttccat ttctttcttg ttcctggata   2520
acaccatcac tgacgaattg attactgccg acggtgtttt cgctaacatt accttttaagt  2580
taaagtccgt taccgctaag actaccaccc cagtcacttt caaggatggc ggtgcttttg   2640
gtgatggcac aatggctaag attgctactg tcactaagac gaacggttct gttactatcg   2700
tcccaggaat ccaaccaacc aaagaattga aggttgctgt tggtaccgct gaaggtaacg   2760
tcggtgcacac cgttactgtt ccagttacct tcgctgatgt tgcctctgct ggtaacgttg   2820
gaacttgtaa cttctatttg gcttacgatg cttccttgtt agatgttgtt tctgtcgctg   2880
ccggtccaat tgtcaagaac gccgccgtca acttctcttc ctctgcctct aacggttcca   2940
tctccttctt gtttctggat aacacgatca ctgatgaatt gattactgct gacggtgtct   3000
tcgctaacat ctccttcaag ttgaaatccg tcacttctaa gaccactacc cctgtcacct   3060
ttaaggacgg tggtgcattc ggtgacggta caatggctaa gatcgctacc gttattaaga   3120
ctaacggatc agttaccatt gttccaggta tccaacctac taaggaattg aaggtcgccg   3180
ttggtaccgc cgaaggtaac gtcggtgata ctgttaccgt tccagtcact ttcgctgacg   3240
tcgcctccgg tgggaacgtt ggtacttgta acttctactt ggcttacgac gcttctctat   3300
tggatgttgt ttcccatgcc gctggtccaa ttgttaagaa cagagccgtc aacttctcct   3360
cttctgcttc taacggttct atctccttct tgttcttaga caacacgatt accgatgaac   3420
tgattactgc cgatggtgtt tttgccaaca tcaccttcaa gttgaagtca gtcgctgcta   3480
agactaccac tccagttacc ttcaaagacg gcggtgcttt cggtgatggc actatggcta   3540
agattgctac cgttactaag acgaatggca gcgtgaccat cgttccaggt atccaaccaa   3600
ccaaggaatt gaaggtcgct gtcggtactg cctccggtaa agccggtgac accgtcactg   3660
ttcctgttac tttcgctgac gtcgccactg ttggtaacgt tggaacctgt aacttctacg   3720
ttacctacga caccaacttg ttggaagttg cttccgttac cccaggttct atcgttacta   3780
acgctgccgt taacttctct tcctccacct ctaacggtac catttccttc ttgttcttgg   3840
ataacactat taccgaccaa ctaattaaga ccgacggtac cttcgctgaa atcaagttca   3900
agttgaagtc cgtcaccgct aagactacta cccctgttgc cttcaaggac ggtggtgcct   3960
tcggtgatgg cacaatggcc aagattgcca ctgtcactaa gactaacggc tccgtcacta   4020
ttgacgttgg tgacgttacc ccagtcaacc caaccatcac tccatctacc gcctcttttcg   4080
acaagtacgt cccagctaac gtcaacgtca ccttgactcc caacggtaac actttcaagg   4140
gtattaccgg tttaaccagt ggtactgatt tcactgtctc taacaacgtt gttaccatct   4200
```

-continued

```
ctaagtctta cttgtctacc ttggctgtcg gttccaagac cttgaccttc gacttcggtg   4260
ttaccaacaa cccagttttg accttgacca tcaccgactc tactccagtc gtcactggtt   4320
tgggtgtcaa gatcgcttct gtcactggta agaccggtga caccattact gttccagtta   4380
ctttgtctaa cgttgtcaag tctggtaacg ttggtacctg taacttctac atcacctacg   4440
atgcatccat gttgcaagct gtttctgcta ccgctggtga tatcgtcttg aacgctccag   4500
ttaacttctc ctcttccatc aacgctacca ccggtaccat ctctatcttg ttcttggaca   4560
acaccattgg tgatcaattg atcacctccg acggtgttgt tgctaactta actttcaagg   4620
ttgttggtac ctcttctact actactccta ttgctttcaa ggccggtggt gcttttggga   4680
acggtaacat gtccaagatc tccgacatta ctttcaccaa cggttctgct aagttgaacg   4740
gaggcggttc aggaggcggc tcccaccacc atcatcatca ttaaggcgcg ccgcttttga   4800
ttaagccttc tagtccaaaa aacacgtttt ttgcggccgc                        4840
```

<210> SEQ ID NO 16
<211> LENGTH: 1572
<212> TYPE: PRT
<213> ORGANISM: Clostridium cellulolyticum

<400> SEQUENCE: 16

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Ala Gly Thr Gly Val Val Ser Val Gln
        35                  40                  45

Phe Asn Asn Gly Ser Ser Pro Ala Ser Ser Asn Ser Ile Tyr Ala Arg
    50                  55                  60

Phe Lys Val Thr Asn Thr Ser Gly Ser Pro Ile Asn Leu Ala Asp Leu
65                  70                  75                  80

Lys Leu Arg Tyr Tyr Tyr Thr Gln Asp Ala Asp Lys Pro Leu Thr Phe
                85                  90                  95

Trp Cys Asp His Ala Gly Tyr Met Ser Gly Ser Asn Tyr Ile Asp Ala
            100                 105                 110

Thr Ser Lys Val Thr Gly Ser Phe Lys Ala Val Ser Pro Ala Val Thr
        115                 120                 125

Asn Ala Asp His Tyr Leu Glu Val Ala Leu Asn Ser Asp Ala Gly Ser
    130                 135                 140

Leu Pro Ala Gly Gly Ser Ile Glu Ile Gln Thr Arg Phe Ala Arg Asn
145                 150                 155                 160

Asp Trp Ser Asn Phe Asp Gln Ser Asn Asp Trp Ser Tyr Thr Ala Ala
                165                 170                 175

Gly Ser Tyr Met Asp Trp Gln Lys Ile Ser Ala Phe Val Gly Gly Thr
            180                 185                 190

Leu Ala Tyr Gly Ser Thr Pro Asp Gly Gly Asn Pro Pro Gln Asp
        195                 200                 205

Pro Thr Ile Asn Pro Thr Ser Ile Ser Ala Lys Ala Gly Ser Phe Ala
    210                 215                 220

Asp Thr Lys Ile Thr Leu Thr Pro Asn Gly Asn Thr Phe Asn Gly Ile
225                 230                 235                 240

Ser Glu Leu Gln Ser Ser Gln Tyr Thr Lys Gly Thr Asn Glu Val Thr
                245                 250                 255

```
Leu Leu Ala Ser Tyr Leu Asn Thr Leu Pro Glu Asn Thr Thr Lys Thr
            260                 265                 270

Leu Thr Phe Asp Phe Gly Val Gly Thr Lys Asn Pro Lys Leu Thr Ile
        275                 280                 285

Thr Val Leu Pro Lys Asp Ile Pro Gly Asp Ser Leu Lys Val Thr Val
    290                 295                 300

Gly Thr Ala Asn Gly Lys Pro Gly Asp Thr Val Thr Val Pro Val Thr
305                 310                 315                 320

Phe Ala Asp Val Ala Lys Met Lys Asn Val Gly Thr Cys Asn Phe Tyr
                325                 330                 335

Leu Gly Tyr Asp Ala Ser Leu Leu Glu Val Val Ser Val Asp Ala Gly
            340                 345                 350

Pro Ile Val Lys Asn Ala Ala Val Asn Phe Ser Ser Ser Ala Ser Asn
        355                 360                 365

Gly Thr Ile Ser Phe Leu Phe Leu Asp Asn Thr Ile Thr Asp Glu Leu
    370                 375                 380

Ile Thr Ala Asp Gly Val Phe Ala Asn Ile Lys Phe Lys Leu Lys Ser
385                 390                 395                 400

Val Thr Ala Lys Thr Thr Thr Pro Val Thr Phe Lys Asp Gly Gly Ala
                405                 410                 415

Phe Gly Asp Gly Thr Met Ser Lys Ile Ala Ser Val Thr Lys Thr Asn
            420                 425                 430

Gly Ser Val Thr Ile Asp Pro Gly Thr Gln Pro Thr Lys Glu Leu Lys
        435                 440                 445

Val Ala Val Gly Thr Ala Asn Gly Lys Pro Gly Asp Thr Val Thr Val
    450                 455                 460

Pro Val Thr Phe Ala Asp Val Val Asn Val Gly Asn Val Gly Thr Cys
465                 470                 475                 480

Asn Phe Tyr Leu Ala Tyr Asp Ala Ser Leu Leu Glu Val Val Ser Val
                485                 490                 495

Asp Ala Gly Pro Ile Val Lys Asn Ala Ala Val Asn Phe Ser Ser Ser
            500                 505                 510

Ala Ser Asn Gly Thr Ile Ser Phe Leu Phe Leu Asp Asn Thr Ile Thr
        515                 520                 525

Asp Glu Leu Ile Thr Ser Asp Gly Val Phe Ala Asn Ile Lys Phe Lys
    530                 535                 540

Leu Lys Ser Val Ala Thr Lys Thr Thr Thr Pro Val Thr Phe Lys Asp
545                 550                 555                 560

Gly Gly Ala Phe Gly Asp Gly Thr Met Ala Lys Ile Ala Thr Val Thr
                565                 570                 575

Lys Thr Asn Gly Ser Val Thr Ile Asp Pro Gly Thr Gln Pro Thr Lys
            580                 585                 590

Glu Leu Lys Val Ala Val Gly Thr Ala Asn Gly Lys Pro Gly Asp Thr
        595                 600                 605

Val Thr Val Pro Val Thr Phe Ala Asp Val Ala Ser Ala Gly Asn Val
    610                 615                 620

Gly Thr Cys Asn Phe Tyr Leu Ala Tyr Asp Ala Ser Leu Leu Glu Val
625                 630                 635                 640

Val Ser Val Asp Ala Gly Pro Ile Val Lys Asn Ala Ala Val Asn Phe
                645                 650                 655

Ser Ser Ser Ala Ser Asn Gly Ser Ile Ser Phe Leu Phe Leu Asp Asn
            660                 665                 670

Thr Ile Thr Asp Glu Leu Ile Thr Ala Asp Gly Val Phe Ala Asn Ile
```

-continued

```
                675                 680                 685
Lys Phe Lys Leu Lys Ser Val Ala Ala Lys Thr Thr Thr Pro Val Thr
690                 695                 700
Phe Lys Asp Gly Gly Ala Phe Gly Asp Gly Thr Met Thr Lys Ile Ala
705                 710                 715                 720
Thr Val Thr Lys Thr Asn Gly Ser Val Thr Ile Asp Pro Gly Thr Gln
                725                 730                 735
Pro Thr Lys Glu Leu Lys Val Ala Val Gly Thr Ala Glu Gly Asn Val
            740                 745                 750
Gly Asp Thr Val Thr Val Pro Val Thr Phe Ala Asp Val Ala Ser Ala
                755                 760                 765
Gly Asn Val Gly Thr Cys Asn Phe Tyr Leu Ala Tyr Asp Ala Ser Leu
770                 775                 780
Leu Asp Val Val Ser Val Ala Ala Gly Pro Ile Val Lys Asn Ala Ala
785                 790                 795                 800
Val Asn Phe Ser Ser Ser Ala Ser Asn Gly Ser Ile Ser Phe Leu Phe
                805                 810                 815
Leu Asp Asn Thr Ile Thr Asp Glu Leu Ile Thr Ala Asp Gly Val Phe
            820                 825                 830
Ala Asn Ile Thr Phe Lys Leu Lys Ser Val Thr Ala Lys Thr Thr Thr
            835                 840                 845
Pro Val Thr Phe Lys Asp Gly Gly Ala Phe Gly Asp Gly Thr Met Ala
850                 855                 860
Lys Ile Ala Thr Val Thr Lys Thr Asn Gly Ser Val Thr Ile Val Pro
865                 870                 875                 880
Gly Ile Gln Pro Thr Lys Glu Leu Lys Val Ala Val Gly Thr Ala Glu
                885                 890                 895
Gly Asn Val Gly Asp Thr Val Thr Val Pro Val Thr Phe Ala Asp Val
            900                 905                 910
Ala Ser Ala Gly Asn Val Gly Thr Cys Asn Phe Tyr Leu Ala Tyr Asp
            915                 920                 925
Ala Ser Leu Leu Asp Val Val Ser Val Ala Ala Gly Pro Ile Val Lys
        930                 935                 940
Asn Ala Ala Val Asn Phe Ser Ser Ser Ala Ser Asn Gly Ser Ile Ser
945                 950                 955                 960
Phe Leu Phe Leu Asp Asn Thr Ile Thr Asp Glu Leu Ile Thr Ala Asp
                965                 970                 975
Gly Val Phe Ala Asn Ile Ser Phe Lys Leu Lys Ser Val Thr Ser Lys
            980                 985                 990
Thr Thr Thr Pro Val Thr Phe Lys Asp Gly Gly Ala Phe Gly Asp Gly
        995                 1000                1005
Thr Met Ala Lys Ile Ala Thr Val Ile Lys Thr Asn  Gly Ser Val
    1010                1015                1020
Thr Ile Val Pro Gly Ile Gln Pro Thr Lys Glu Leu  Lys Val Ala
    1025                1030                1035
Val Gly Thr Ala Glu Gly Asn Val Gly Asp Thr Val  Thr Val Pro
    1040                1045                1050
Val Thr Phe Ala Asp Val Ala Ser Ala Gly Asn Val  Gly Thr Cys
    1055                1060                1065
Asn Phe Tyr Leu Ala Tyr Asp Ala Ser Leu Leu Asp  Val Val Ser
    1070                1075                1080
His Ala Ala Gly Pro Ile Val Lys Asn Arg Ala Val  Asn Phe Ser
    1085                1090                1095
```

```
Ser  Ser  Ala  Ser  Asn  Gly  Ser  Ile  Ser  Phe  Leu  Phe  Leu  Asp  Asn
     1100                1105                1110

Thr  Ile  Thr  Asp  Glu  Leu  Ile  Thr  Ala  Asp  Gly  Val  Phe  Ala  Asn
     1115                1120                1125

Ile  Thr  Phe  Lys  Leu  Lys  Ser  Val  Ala  Ala  Lys  Thr  Thr  Thr  Pro
     1130                1135                1140

Val  Thr  Phe  Lys  Asp  Gly  Gly  Ala  Phe  Gly  Asp  Gly  Thr  Met  Ala
     1145                1150                1155

Lys  Ile  Ala  Thr  Val  Thr  Lys  Thr  Asn  Gly  Ser  Val  Thr  Ile  Val
     1160                1165                1170

Pro  Gly  Ile  Gln  Pro  Thr  Lys  Glu  Leu  Lys  Val  Ala  Val  Gly  Thr
     1175                1180                1185

Ala  Ser  Gly  Lys  Ala  Gly  Asp  Thr  Val  Thr  Val  Pro  Val  Thr  Phe
     1190                1195                1200

Ala  Asp  Val  Ala  Thr  Val  Gly  Asn  Val  Gly  Thr  Cys  Asn  Phe  Tyr
     1205                1210                1215

Val  Thr  Tyr  Asp  Thr  Asn  Leu  Leu  Glu  Val  Ala  Ser  Val  Thr  Pro
     1220                1225                1230

Gly  Ser  Ile  Val  Thr  Asn  Ala  Ala  Val  Asn  Phe  Ser  Ser  Ser  Thr
     1235                1240                1245

Ser  Asn  Gly  Thr  Ile  Ser  Phe  Leu  Phe  Leu  Asp  Asn  Thr  Ile  Thr
     1250                1255                1260

Asp  Gln  Leu  Ile  Lys  Thr  Asp  Gly  Thr  Phe  Ala  Glu  Ile  Lys  Phe
     1265                1270                1275

Lys  Leu  Lys  Ser  Val  Thr  Ala  Lys  Thr  Thr  Thr  Pro  Val  Ala  Phe
     1280                1285                1290

Lys  Asp  Gly  Gly  Ala  Phe  Gly  Asp  Gly  Thr  Met  Ala  Lys  Ile  Ala
     1295                1300                1305

Thr  Val  Thr  Lys  Thr  Asn  Gly  Ser  Val  Thr  Ile  Asp  Val  Gly  Asp
     1310                1315                1320

Val  Thr  Pro  Val  Asn  Pro  Thr  Ile  Thr  Pro  Ser  Thr  Ala  Ser  Phe
     1325                1330                1335

Asp  Lys  Tyr  Val  Pro  Ala  Asn  Val  Asn  Val  Thr  Leu  Thr  Pro  Asn
     1340                1345                1350

Gly  Asn  Thr  Phe  Lys  Gly  Ile  Thr  Gly  Leu  Thr  Ser  Gly  Thr  Asp
     1355                1360                1365

Phe  Thr  Val  Ser  Asn  Asn  Val  Val  Thr  Ile  Ser  Lys  Ser  Tyr  Leu
     1370                1375                1380

Ser  Thr  Leu  Ala  Val  Gly  Ser  Lys  Thr  Leu  Thr  Phe  Asp  Phe  Gly
     1385                1390                1395

Val  Thr  Asn  Asn  Pro  Val  Leu  Thr  Leu  Thr  Ile  Thr  Asp  Ser  Thr
     1400                1405                1410

Pro  Val  Val  Thr  Gly  Leu  Gly  Val  Lys  Ile  Ala  Ser  Val  Thr  Gly
     1415                1420                1425

Lys  Thr  Gly  Asp  Thr  Ile  Thr  Val  Pro  Val  Thr  Leu  Ser  Asn  Val
     1430                1435                1440

Val  Lys  Ser  Gly  Asn  Val  Gly  Thr  Cys  Asn  Phe  Tyr  Ile  Thr  Tyr
     1445                1450                1455

Asp  Ala  Ser  Met  Leu  Gln  Ala  Val  Ser  Ala  Thr  Ala  Gly  Asp  Ile
     1460                1465                1470

Val  Leu  Asn  Ala  Pro  Val  Asn  Phe  Ser  Ser  Ser  Ile  Asn  Ala  Thr
     1475                1480                1485
```

```
Thr Gly Thr Ile Ser Ile Leu Phe Leu Asp Asn Thr Ile Gly Asp
    1490            1495                1500

Gln Leu Ile Thr Ser Asp Gly Val Val Ala Asn Leu Thr Phe Lys
    1505            1510                1515

Val Val Gly Thr Ser Ser Thr Thr Thr Pro Ile Ala Phe Lys Ala
    1520            1525                1530

Gly Gly Ala Phe Gly Asn Gly Asn Met Ser Lys Ile Ser Asp Ile
    1535            1540                1545

Thr Phe Thr Asn Gly Ser Ala Lys Leu Asn Gly Gly Gly Ser Gly
    1550            1555                1560

Gly Gly Ser His His His His His His
    1565            1570
```

<210> SEQ ID NO 17
<211> LENGTH: 1567
<212> TYPE: DNA
<213> ORGANISM: Clostridium cellulolyticum

<400> SEQUENCE: 17

```
gcggccgcgc tattttcat aaaaaaccaa gcaactgctt atcaacacac ttaattaaaa      60
acaaatggt ctccttcact tccttgttgg ctggtgtcgc tgccatttct ggtgttttgg     120
ccgctccagc tgccgaagtc gaaccagttg ctgttgaaaa gagagaagct gaagctaaag   180
ctgctgatca aatcccattc ccatacgacg ctaagtaccc aaacggtgcc tactcctgtt   240
tggctgattc tcaatctatc ggtaacaact tggtcagatc tgaatgggaa caatggaagt   300
ctgctcacat tacttccaac ggtgctgagg ttacaagag agttcaaaga gacgctacca   360
ccaactacga caccgtttct gaaggttgg gttacggttt gttgttgtct gtctacttcg     420
gtgaacaaca attgttcgac gatttgtaca gatacgttaa ggttttcttg aactctaacg   480
gtttaatgtc ttggagaatc gactcttctg gcaacattat gggtaaggac tctattggtg   540
ccgctaccga cgctgatgaa gacatcgctg ttttccttgg tttcgctcac aagaagtggg   600
gcacttctgg tggtttcaac taccaaaccg aagctaagaa ctacattaac aacatttaca   660
acaagatggt tgaaccaggt acttatgtca tcaaggctgg tgacacttgg ggtggttcca   720
acgttactaa cccatcttac ttcgctccag cttggtacag aatcttcgct gacttcaccg   780
gtaactccgg ttggatcaac gtcgctaaca agtgttacga aatcgctgat aaagcccgta   840
attctaacac cggtttggtc ccagactggt gtactgccaa cggtaccca gcctctggtc   900
aaggtttcga cttctactac gacgccatta gataccaatg gagagctgcc atcgactact   960
cttggtacgg tactgctaag gctaagaccc actgtgacgc tatctctaac ttcttcaaga  1020
acatcggtta cgctaacatc aaggatggtt acaccatctc cggttctcaa atctcctcca  1080
accacactgc cactttcgtc tcttgtgccg ctgctgctgc tatgactggt actgacacca  1140
cctatgctaa gaacatctac aacgaatgtg ttaaggttaa ggattctggt aactacactt  1200
acttcggtaa caccttgaga tgatggtgt tgttatacac taccggtaac ttcccaaatt  1260
tgtacaccta caactcccaa ccaaagccag acttgaaggg tgacgtcaat aacgatggtg  1320
ctatcgacgc cttagatatt gctgcccaa agaaggccat cttgacccaa ccacttcca   1380
acatttcttt gactaacgca gatatgaaca acgacggtaa cattgatgct attgactttg  1440
ctcaattgaa ggttaagtta ttgaacggtg gtggttctgg tggtggttct caccaccacc  1500
accaccacta aggcgcgccg cttttgatta agccttctag tccaaaaaac acgttttttg  1560
cggccgc                                                            1567
```

<210> SEQ ID NO 18
<211> LENGTH: 481
<212> TYPE: PRT
<213> ORGANISM: Clostridium cellulolyticum

<400> SEQUENCE: 18

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
                20                  25                  30

Arg Glu Ala Glu Ala Glu Ala Asp Gln Ile Pro Phe Pro Tyr Asp
            35                  40                  45

Ala Lys Tyr Pro Asn Gly Ala Tyr Ser Cys Leu Ala Asp Ser Gln Ser
    50                  55                  60

Ile Gly Asn Asn Leu Val Arg Ser Glu Trp Glu Gln Trp Lys Ser Ala
65                  70                  75                  80

His Ile Thr Ser Asn Gly Ala Arg Gly Tyr Lys Arg Val Gln Arg Asp
                85                  90                  95

Ala Thr Thr Asn Tyr Asp Thr Val Ser Glu Gly Leu Gly Tyr Gly Leu
            100                 105                 110

Leu Leu Ser Val Tyr Phe Gly Glu Gln Gln Leu Phe Asp Asp Leu Tyr
        115                 120                 125

Arg Tyr Val Lys Val Phe Leu Asn Ser Asn Gly Leu Met Ser Trp Arg
130                 135                 140

Ile Asp Ser Ser Gly Asn Ile Met Gly Lys Asp Ser Ile Gly Ala Ala
145                 150                 155                 160

Thr Asp Ala Asp Glu Asp Ile Ala Val Ser Leu Val Phe Ala His Lys
                165                 170                 175

Lys Trp Gly Thr Ser Gly Gly Phe Asn Tyr Gln Thr Glu Ala Lys Asn
            180                 185                 190

Tyr Ile Asn Asn Ile Tyr Asn Lys Met Val Glu Pro Gly Thr Tyr Val
        195                 200                 205

Ile Lys Ala Gly Asp Thr Trp Gly Gly Ser Asn Val Thr Asn Pro Ser
210                 215                 220

Tyr Phe Ala Pro Ala Trp Tyr Arg Ile Phe Ala Asp Phe Thr Gly Asn
225                 230                 235                 240

Ser Gly Trp Ile Asn Val Ala Asn Lys Cys Tyr Glu Ile Ala Asp Lys
                245                 250                 255

Ala Arg Asn Ser Asn Thr Gly Leu Val Pro Asp Trp Cys Thr Ala Asn
            260                 265                 270

Gly Thr Pro Ala Ser Gly Gln Gly Phe Asp Phe Tyr Tyr Asp Ala Ile
        275                 280                 285

Arg Tyr Gln Trp Arg Ala Ala Ile Asp Tyr Ser Trp Tyr Gly Thr Ala
290                 295                 300

Lys Ala Lys Thr His Cys Asp Ala Ile Ser Asn Phe Lys Asn Ile
305                 310                 315                 320

Gly Tyr Ala Asn Ile Lys Asp Gly Tyr Thr Ile Ser Gly Ser Gln Ile
                325                 330                 335

Ser Ser Asn His Thr Ala Thr Phe Val Ser Cys Ala Ala Ala Ala
            340                 345                 350

Met Thr Gly Thr Asp Thr Thr Tyr Ala Lys Asn Ile Tyr Asn Glu Cys
        355                 360                 365

Val Lys Val Lys Asp Ser Gly Asn Tyr Thr Tyr Phe Gly Asn Thr Leu
```

```
                370             375             380
Arg Met Met Val Leu Leu Tyr Thr Thr Gly Asn Phe Pro Asn Leu Tyr
385                     390                     395                 400

Thr Tyr Asn Ser Gln Pro Lys Pro Asp Leu Lys Gly Asp Val Asn Asn
                405                     410                     415

Asp Gly Ala Ile Asp Ala Leu Asp Ile Ala Ala Leu Lys Lys Ala Ile
                420                     425                     430

Leu Thr Gln Thr Thr Ser Asn Ile Ser Leu Thr Asn Ala Asp Met Asn
            435                     440                     445

Asn Asp Gly Asn Ile Asp Ala Ile Asp Phe Ala Gln Leu Lys Val Lys
            450                     455                     460

Leu Leu Asn Gly Gly Gly Ser Gly Gly Gly Ser His His His His His
465                     470                     475                     480

His
```

<210> SEQ ID NO 19
<211> LENGTH: 3159
<212> TYPE: DNA
<213> ORGANISM: Artificial
<220> FEATURE:
<223> OTHER INFORMATION: Chimeric DNA

<400> SEQUENCE: 19

```
tcataaaaaa ccaagcaact gcttatcaac acacttaatt aaaatggtct ctttcacttc    60
tttgttggcg ggtgtcgctg ctatcagtgg tgtcttggct gccccagccg ctgaagtcga   120
accagttgcc gttgaaaaga gaggtgttgt ttctgtccaa ttcaacaacg ttctagccc    180
agcttcctcc aactccatct acgccagatt caaggttact aacacttctg gttctccaat   240
caatctagct gatttgaagt tgagatacta ctacactcaa gatgctgaca agccattgac   300
cttctggtgt gaccacgctg gttacatgtc tggttccaac tacatcgacg ccacctccaa   360
ggttactggt agcttcaagg ccgtttctcc agccgttact aacgctgatc actacttgga   420
agtcgctttg aactccgatg ccggttcttt gccagctggt ggttccatcg aaattcaaac   480
ccgtttcgct agaaacgatt ggtccaactt tgaccaatct aacgactggt cctacactgc   540
cgctggttct tacatggact ggcaaaagat ttctgctttc gttggtggta ccttagctta   600
cggttccacc ccagacggtg gtaacccacc accacaagat ccaactatta cccaacttc    660
catctctgct aaggctggtt ccttcgctga tactaagatt accttgactc aaacggtaa    720
cacccttcaac ggcatctctg aattgcaatc ttctcaatac accaagggta ctaacgaagt   780
taccttgttg gcttcttact tgaacacttt gccagaaaac accactaaga ctttgacctt   840
cgacttcggt gttggtacca agaatccaaa gttgactatt accgttctac caaaggacat   900
cccaggtgat tctttaaagg ttgctgttgg taccgctgaa ggcaacgtcg gcgacaccgt   960
taccgtccca gttaccttcg ctgacgtcgc ctctgctggt aacgtcggta cttgtaactt  1020
ctacttggct tacgatgcct ccttgttgga cgttgtctct gtcgctgctg gtccaatcgt  1080
taagaacgct gctgtcaatt tctcttcttc cgcctctaac ggctccatca gtttcttatt  1140
cttggataac actatcaccg acgaattgat tactgctgac ggtgtttttg ctaacattac  1200
cttcaagttg aagtctgtta ctgccaagac taccactcca gtcactttca aggacggtgg  1260
tgctttcggt gacggtacta tggccaaaat tgctaccgtt actaagacta acggttccgt  1320
tactattgtc ccaggtatcc aaccaactaa ggaagccgtc agaattaagg ttgacactgt  1380
taacgctaag ccaggtgaca ctgtcagaat tccagtcaga ttctctggta tcccatctaa  1440
```

```
gggtattgcc aactgtgact tcgtttactc ttacgatcca aacgttttag aaatcatcga   1500
aattgaacca ggtgatatca tcgttgatcc aaacccagac aagtccttcg acactgctgt   1560
ttacccagac agaaagatta tcgtcttctt gttcgctgaa gactctggta ccggtgctta   1620
cgctattacc aaggatggtg tctttgccac tatcgttgct aaggttaagt ctggtgcccc   1680
aaacggttta agcgttatca agttcgttga agtcggtggt ttcgctaaca acgacttggt   1740
tgaacaaaag acccaattct tcgatggtgg tgtcaacgtt ggtgtccacg tgaccccagt   1800
caccttgtct aacgttccag gtatcgctac cgctgaatta caagtcggtt tcgatgctac   1860
tttgttggaa gttgcttcca tcaccgtcgg tgacatcgtc ttgaacccat ctgtcaactt   1920
ctcctccgtt gttaacggtt ctactattaa gttgttgttc ttggacgaca ctttgggttc   1980
ccaattgatt tccaaggacg cgtcttggc taccatcaac ttcaaggcta agaccgttac   2040
ctctaaggtc actactccag ttgctgtttc tggtactcca gtcttcgctg atggtacctt   2100
ggctgaattg aagtatgaaa ccgttgctgg tagcgttacc attgaaccct tcaaccagt    2160 taagaccgtc acagctaccg tcggtaccgc taccggtaaa gttggtgaaa ctgttgctgt   2220
ttacgtaaag aaagatgatc caaacggctt tactgttaac gttgattctg ttaacggtaa   2280
cgttggtgaa caaattgtcg ttccagtctc cttcgccaac gttccatcca acggtgtttc   2340
cactgctgac atgactatca cctatgattc tctaagttg gaatacgttt ccggtgctgc    2400
tggttctatc gtcactaacc caaccgtcaa cttcggtatc aataaggaag ctgatggtaa   2460
attgaaggtt ctattttgg actacactat gtccaccggt tacattcta ctaacggtgt     2520 cttcgctaac gttactttca aggtcttaaa ctctgctcca accaccgttg gtatcactgg   2580
tgctactttt ggtgataaga acttgggtaa catctccgct accattaacg ctggttccat   2640
taacggtggt tactacgtaa tcaacccaga tttcgttact acttccacca ccgctccaat   2700
tgtcaaggct ggtttcactg tcgaaatcgt tggtactacc aagtccgctg ttaccgactc   2760
caacggttac tttgaaatca aggatgttgc tgctggtact acactgtta agatcactaa    2820 agctaactac cttaccagag aaattgctaa cgtctccgtt accgctgaca aggaattgtc   2880
cacttctgct tccccaattt tgatgtgggc tatttctcaa attactgatg gtcaaattca   2940
agctaccact accgctacca ctgaagctac tactactgct gccccatctt ccactgttga   3000
aaccgtctcc ccatcttcta ccgaaactat ctctcaacaa accgaaaacg gtgctgccaa   3060
ggccgctgtc ggtatgggtg ctggtgcctt agctgccgct gctatgttgt tataaggcgc   3120
gccgcttttg attaagcctt ctagtccaaa aaacacgtt                          3159

<210> SEQ ID NO 20
<211> LENGTH: 1023
<212> TYPE: PRT
<213> ORGANISM: Artificial
<220> FEATURE:
<223> OTHER INFORMATION: Chimeric amino acid

<400> SEQUENCE: 20

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Gly Val Val Ser Val Gln Phe Asn Asn Gly Ser Ser Pro Ala Ser
        35                  40                  45

Ser Asn Ser Ile Tyr Ala Arg Phe Lys Val Thr Asn Thr Ser Gly Ser
```

-continued

```
            50                  55                  60
Pro Ile Asn Leu Ala Asp Leu Lys Leu Arg Tyr Tyr Thr Gln Asp
65                  70                  75                  80

Ala Asp Lys Pro Leu Thr Phe Trp Cys Asp His Ala Gly Tyr Met Ser
                85                  90                  95

Gly Ser Asn Tyr Ile Asp Ala Thr Ser Lys Val Thr Gly Ser Phe Lys
                100                 105                 110

Ala Val Ser Pro Ala Val Thr Asn Ala Asp His Tyr Leu Glu Val Ala
                115                 120                 125

Leu Asn Ser Asp Ala Gly Ser Leu Pro Ala Gly Ser Ile Glu Ile
130                 135                 140

Gln Thr Arg Phe Ala Arg Asn Asp Trp Ser Asn Phe Asp Gln Ser Asn
145                 150                 155                 160

Asp Trp Ser Tyr Thr Ala Ala Gly Ser Tyr Met Asp Trp Gln Lys Ile
                165                 170                 175

Ser Ala Phe Val Gly Gly Thr Leu Ala Tyr Gly Ser Thr Pro Asp Gly
                180                 185                 190

Gly Asn Pro Pro Gln Asp Pro Thr Ile Asn Pro Thr Ser Ile Ser
    195                 200                 205

Ala Lys Ala Gly Ser Phe Ala Asp Thr Lys Ile Thr Leu Thr Pro Asn
210                 215                 220

Gly Asn Thr Phe Asn Gly Ile Ser Glu Leu Gln Ser Ser Gln Tyr Thr
225                 230                 235                 240

Lys Gly Thr Asn Glu Val Thr Leu Leu Ala Ser Tyr Leu Asn Thr Leu
                245                 250                 255

Pro Glu Asn Thr Thr Lys Thr Leu Thr Phe Asp Phe Gly Val Gly Thr
                260                 265                 270

Lys Asn Pro Lys Leu Thr Ile Thr Val Leu Pro Lys Asp Ile Pro Gly
                275                 280                 285

Asp Ser Leu Lys Val Ala Val Gly Thr Ala Glu Gly Asn Val Gly Asp
290                 295                 300

Thr Val Thr Val Pro Val Thr Phe Ala Asp Val Ala Ser Ala Gly Asn
305                 310                 315                 320

Val Gly Thr Cys Asn Phe Tyr Leu Ala Tyr Asp Ala Ser Leu Leu Asp
                325                 330                 335

Val Val Ser Val Ala Ala Gly Pro Ile Val Lys Asn Ala Ala Val Asn
                340                 345                 350

Phe Ser Ser Ser Ala Ser Asn Gly Ser Ile Ser Phe Leu Phe Leu Asp
                355                 360                 365

Asn Thr Ile Thr Asp Glu Leu Ile Thr Ala Asp Gly Val Phe Ala Asn
370                 375                 380

Ile Thr Phe Lys Leu Lys Ser Val Thr Ala Lys Thr Thr Thr Pro Val
385                 390                 395                 400

Thr Phe Lys Asp Gly Gly Ala Phe Gly Asp Gly Thr Met Ala Lys Ile
                405                 410                 415

Ala Thr Val Thr Lys Thr Asn Gly Ser Val Thr Ile Val Pro Gly Ile
                420                 425                 430

Gln Pro Thr Lys Glu Ala Val Arg Ile Lys Val Asp Thr Val Asn Ala
                435                 440                 445

Lys Pro Gly Asp Thr Val Arg Ile Pro Val Arg Phe Ser Gly Ile Pro
                450                 455                 460

Ser Lys Gly Ile Ala Asn Cys Asp Phe Val Tyr Ser Tyr Asp Pro Asn
465                 470                 475                 480
```

-continued

```
Val Leu Glu Ile Ile Glu Ile Glu Pro Gly Asp Ile Ile Val Asp Pro
            485                 490                 495
Asn Pro Asp Lys Ser Phe Asp Thr Ala Val Tyr Pro Asp Arg Lys Ile
        500                 505                 510
Ile Val Phe Leu Phe Ala Glu Asp Ser Gly Thr Gly Ala Tyr Ala Ile
            515                 520                 525
Thr Lys Asp Gly Val Phe Ala Thr Ile Val Ala Lys Val Lys Ser Gly
    530                 535                 540
Ala Pro Asn Gly Leu Ser Val Ile Lys Phe Val Glu Val Gly Gly Phe
545                 550                 555                 560
Ala Asn Asn Asp Leu Val Glu Gln Lys Thr Gln Phe Phe Asp Gly Gly
                565                 570                 575
Val Asn Val Gly Val His Val Thr Pro Val Thr Leu Ser Asn Val Pro
            580                 585                 590
Gly Ile Ala Thr Ala Glu Leu Gln Val Gly Phe Asp Ala Thr Leu Leu
            595                 600                 605
Glu Val Ala Ser Ile Thr Val Gly Asp Ile Val Leu Asn Pro Ser Val
    610                 615                 620
Asn Phe Ser Ser Val Val Asn Gly Ser Thr Ile Lys Leu Leu Phe Leu
625                 630                 635                 640
Asp Asp Thr Leu Gly Ser Gln Leu Ile Ser Lys Asp Gly Val Leu Ala
                645                 650                 655
Thr Ile Asn Phe Lys Ala Lys Thr Val Thr Ser Lys Val Thr Thr Pro
            660                 665                 670
Val Ala Val Ser Gly Thr Pro Val Phe Ala Asp Gly Thr Leu Ala Glu
            675                 680                 685
Leu Lys Tyr Glu Thr Val Ala Gly Ser Val Thr Ile Glu Pro Ser Gln
    690                 695                 700
Pro Val Lys Thr Val Thr Ala Thr Val Gly Thr Ala Thr Gly Lys Val
705                 710                 715                 720
Gly Glu Thr Val Ala Val Tyr Val Lys Lys Asp Asp Pro Asn Gly Phe
                725                 730                 735
Thr Val Asn Val Asp Ser Val Asn Gly Asn Val Gly Glu Gln Ile Val
            740                 745                 750
Val Pro Val Ser Phe Ala Asn Val Pro Ser Asn Gly Val Ser Thr Ala
            755                 760                 765
Asp Met Thr Ile Thr Tyr Asp Ser Ser Lys Leu Glu Tyr Val Ser Gly
    770                 775                 780
Ala Ala Gly Ser Ile Val Thr Asn Pro Thr Val Asn Phe Gly Ile Asn
785                 790                 795                 800
Lys Glu Ala Asp Gly Lys Leu Lys Val Leu Phe Leu Asp Tyr Thr Met
                805                 810                 815
Ser Thr Gly Tyr Ile Ser Thr Asn Gly Val Phe Ala Asn Val Thr Phe
            820                 825                 830
Lys Val Leu Asn Ser Ala Pro Thr Thr Val Gly Ile Thr Gly Ala Thr
    835                 840                 845
Phe Gly Asp Lys Asn Leu Gly Asn Ile Ser Ala Thr Ile Asn Ala Gly
    850                 855                 860
Ser Ile Asn Gly Gly Tyr Tyr Val Ile Asn Pro Asp Phe Val Thr Thr
865                 870                 875                 880
Ser Thr Thr Ala Pro Ile Val Lys Ala Gly Phe Thr Val Glu Ile Val
                885                 890                 895
```

```
Gly Thr Thr Lys Ser Ala Val Thr Asp Ser Asn Gly Tyr Phe Glu Ile
            900                 905                 910

Lys Asp Val Ala Ala Gly Thr Tyr Thr Val Lys Ile Thr Lys Ala Asn
        915                 920                 925

Tyr Leu Thr Arg Glu Ile Ala Asn Val Ser Val Thr Ala Asp Lys Glu
    930                 935                 940

Leu Ser Thr Ser Ala Ser Pro Ile Leu Met Trp Ala Ile Ser Gln Ile
945                 950                 955                 960

Thr Asp Gly Gln Ile Gln Ala Thr Thr Thr Ala Thr Thr Glu Ala Thr
                965                 970                 975

Thr Thr Ala Ala Pro Ser Ser Thr Val Glu Thr Val Ser Pro Ser Ser
            980                 985                 990

Thr Glu Thr Ile Ser Gln Gln Thr  Glu Asn Gly Ala Ala  Lys Ala Ala
        995                 1000                1005

Val Gly Met Gly Ala Gly Ala  Leu Ala Ala Ala Ala  Met Leu Leu
    1010                1015                1020
```

<210> SEQ ID NO 21
<211> LENGTH: 2667
<212> TYPE: DNA
<213> ORGANISM: Artificial
<220> FEATURE:
<223> OTHER INFORMATION: Chimeric DNA

<400> SEQUENCE: 21

```
atggtctctt tcacttcttt gttggcgggt gtcgctgcta tcagtggtgt cttggctgcc      60
ccagccgctg aagtcgaacc agttgccgtt gaaaagagag tgttgtttc tgtccaattc     120
aacaacggtt ctagcccagc ttcctccaac tccatctacg ccagattcaa ggttactaac     180
acttctggtt ctccaatcaa tctagctgat ttgaagttga gatactacta cactcaagat     240
gctgacaagc cattgacctt ctggtgtgac cacgctggtt acatgtctgg ttccaactac     300
atcgacgcca cctccaaggt tactggtagc ttcaaggccg tttctccagc cgttactaac     360
gctgatcact acttggaagt cgctttgaac tccgatgccg gttctttgcc agctggtggt     420
tccatcgaaa ttcaaacccg tttcgctaga acgattggt ccaactttga ccaatctaac     480
gactggtcct acactgccgc tggttcttac atggactggc aaaagatttc tgctttcgtt     540
ggtggtacct tagcttacgg ttccacccca gacggtggta acccaccacc acaagatcca     600
actattaacc aacttccat ctctgctaag ctggttcct tcgctgatac taagattacc     660
ttgactccaa acggtaacac cttcaacggc atctctgaat tgcaatcttc tcaatacacc     720
aagggtacta cgaagttac cttgttggct tcttacttga cactttgcc agaaaacacc     780
actaagactt tgaccttcga cttcggtgtt ggtaccaaga atccaaagtt gactattacc     840
gttctaccaa aggacatccc aggtgattct ttaaaggttg ctgttggtac cgctgaaggc     900
aacgtcggcg acaccgttac cgtcccagtt accttgctg acgtcgcctc tgctggtaac     960
gtcggtactt gtaacttcta cttggcttac gatgcctcct gttggacgt tgtctctgtc    1020
gctgctggtc aatcgttaa gaacgctgct gtcaatttct cttcttccgc tctaacggc    1080
tccatcagtt tcttattctt ggataacact atcaccgacg aattgattac tgctgacggt    1140
gttttgcta acattacctt caagttgaag tctgttactg ccaagactac cactccagtc    1200
actttcaagg acgtggtgc tttcggtgac gtactatgg ccaaaattgc taccgttact    1260
aagactaacg gttccgttac tattgtccca ggtatccaac caactaagga agccgtcaga    1320
attaaggttg acactgttaa cgctaagcca ggtgacactg tcagaattcc agtcagattc    1380
```

```
tctggtatcc catctaaggg tattgccaac tgtgacttcg tttactctta cgatccaaac    1440
gttttagaaa tcatcgaaat tgaaccaggt gatatcatcg ttgatccaaa cccagacaag    1500
tccttcgaca ctgctgttta cccagacaga aagattatcg tcttcttgtt cgctgaagac    1560
tctggtaccg tgcttacgc tattaccaag gatggtgtct tgccactat cgttgctaag     1620
gttaagtctg gtgccccaaa cggtttaagc gttatcaagt tcgttgaagt cggtggtttc    1680
gctaacaacg acttggttga acaaaagacc caattcttcg atggtggtgt caacgttggt    1740
gtccacgtga ccgccgaagt tgaaccagtc gctgttgaaa agagaccagt cactttgtcc    1800
aacgttccag gtattgctac tgctgaattg caagttggtt tcgacgccac cttgttggaa    1860
gttgcctcta tcactgtcgg tgacatcgtt ttgaacccat ccgttaactt ctcttctgtc    1920
gtcaacggtt ctaccattaa gttgttgttc ttggacgaca ctttgggtag tcaattgatc    1980
tctaaggacg gtgttttggc tactatcaac ttcaaggcta agacggttac ctccaaggtt    2040
accactccag tcgctgtttc tggtactcca gtcttcgctg atggtacttt ggctgaatta    2100
aaatacgaaa ccgttgctgg ttccgttacc atcgaaccat cccaaccagt taagactgtt    2160
actgctactg tcggtaccgc taccggtaag gtcggtgaaa ctgtcgctgt cattctcgag    2220
actgcggccg cattggttcc tagaggatca ccaattgtca aggctggttt cactgtcgaa    2280
atcgttggta ctaccaagtc cgctgttacc gactccaacg ttactttga aatcaaggat    2340
gttgctgctg gtacttacac tgttaagatc actaaagcta actaccttac cagagaaatt    2400
gctaacgtct ccgttaccgc tgacaaggaa ttgtccactt ctgcttcccc aattttgatg    2460
tgggctattt ctcaaattac tgatggtcaa attcaagcta ccactaccgc taccactgaa    2520
gctactacta ctgctgcccc atcttccact gttgaaaccg tctccccatc ttctaccgaa    2580
actatctctc aacaaaccga aaacggtgct gccaaggccg ctgtcggtat gggtgctggt    2640
gccttagctg ccgctgctat gttgtta                                        2667
```

<210> SEQ ID NO 22
<211> LENGTH: 889
<212> TYPE: PRT
<213> ORGANISM: Artificial
<220> FEATURE:
<223> OTHER INFORMATION: Chimeric amino acid

<400> SEQUENCE: 22

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
                20                  25                  30

Arg Gly Val Val Ser Val Gln Phe Asn Asn Gly Ser Ser Pro Ala Ser
            35                  40                  45

Ser Asn Ser Ile Tyr Ala Arg Phe Lys Val Thr Asn Thr Ser Gly Ser
        50                  55                  60

Pro Ile Asn Leu Ala Asp Leu Lys Leu Arg Tyr Tyr Tyr Thr Gln Asp
65                  70                  75                  80

Ala Asp Lys Pro Leu Thr Phe Trp Cys Asp His Ala Gly Tyr Met Ser
                85                  90                  95

Gly Ser Asn Tyr Ile Asp Ala Thr Ser Lys Val Thr Gly Ser Phe Lys
            100                 105                 110

Ala Val Ser Pro Ala Val Thr Asn Ala Asp His Tyr Leu Glu Val Ala
        115                 120                 125

```
Leu Asn Ser Asp Ala Gly Ser Leu Pro Ala Gly Gly Ser Ile Glu Ile
130                 135                 140

Gln Thr Arg Phe Ala Arg Asn Asp Trp Ser Asn Phe Asp Gln Ser Asn
145                 150                 155                 160

Asp Trp Ser Tyr Thr Ala Ala Gly Ser Tyr Met Asp Trp Gln Lys Ile
                165                 170                 175

Ser Ala Phe Val Gly Gly Thr Leu Ala Tyr Gly Ser Thr Pro Asp Gly
            180                 185                 190

Gly Asn Pro Pro Pro Gln Asp Pro Thr Ile Asn Pro Thr Ser Ile Ser
                195                 200                 205

Ala Lys Ala Gly Ser Phe Ala Asp Thr Lys Ile Thr Leu Thr Pro Asn
210                 215                 220

Gly Asn Thr Phe Asn Gly Ile Ser Glu Leu Gln Ser Ser Gln Tyr Thr
225                 230                 235                 240

Lys Gly Thr Asn Glu Val Thr Leu Leu Ala Ser Tyr Leu Asn Thr Leu
                245                 250                 255

Pro Glu Asn Thr Thr Lys Thr Leu Thr Phe Asp Phe Gly Val Gly Thr
                260                 265                 270

Lys Asn Pro Lys Leu Thr Ile Thr Val Leu Pro Lys Asp Ile Pro Gly
            275                 280                 285

Asp Ser Leu Lys Val Ala Val Gly Thr Ala Glu Gly Asn Val Gly Asp
290                 295                 300

Thr Val Thr Val Pro Val Thr Phe Ala Asp Val Ala Ser Ala Gly Asn
305                 310                 315                 320

Val Gly Thr Cys Asn Phe Tyr Leu Ala Tyr Asp Ala Ser Leu Leu Asp
                325                 330                 335

Val Val Ser Val Ala Ala Gly Pro Ile Val Lys Asn Ala Ala Val Asn
            340                 345                 350

Phe Ser Ser Ser Ala Ser Asn Gly Ser Ile Ser Phe Leu Phe Leu Asp
        355                 360                 365

Asn Thr Ile Thr Asp Glu Leu Ile Thr Ala Asp Gly Val Phe Ala Asn
        370                 375                 380

Ile Thr Phe Lys Leu Lys Ser Val Thr Ala Lys Thr Thr Thr Pro Val
385                 390                 395                 400

Thr Phe Lys Asp Gly Gly Ala Phe Gly Asp Gly Thr Met Ala Lys Ile
                405                 410                 415

Ala Thr Val Thr Lys Thr Asn Gly Ser Val Thr Ile Val Pro Gly Ile
                420                 425                 430

Gln Pro Thr Lys Glu Ala Val Arg Ile Lys Val Asp Thr Val Asn Ala
            435                 440                 445

Lys Pro Gly Asp Thr Val Arg Ile Pro Val Arg Phe Ser Gly Ile Pro
450                 455                 460

Ser Lys Gly Ile Ala Asn Cys Asp Phe Val Tyr Ser Tyr Asp Pro Asn
465                 470                 475                 480

Val Leu Glu Ile Ile Glu Ile Glu Pro Gly Asp Ile Ile Val Asp Pro
                485                 490                 495

Asn Pro Asp Lys Ser Phe Asp Thr Ala Val Tyr Pro Asp Arg Lys Ile
            500                 505                 510

Ile Val Phe Leu Phe Ala Glu Asp Ser Gly Thr Gly Ala Tyr Ala Ile
        515                 520                 525

Thr Lys Asp Gly Val Phe Ala Thr Ile Val Ala Lys Val Lys Ser Gly
        530                 535                 540

Ala Pro Asn Gly Leu Ser Val Ile Lys Phe Val Glu Val Gly Gly Phe
```

```
            545                 550                 555                 560
Ala Asn Asn Asp Leu Val Glu Gln Lys Thr Gln Phe Phe Asp Gly Gly
                565                 570                 575

Val Asn Val Gly Val His Val Thr Ala Glu Val Glu Pro Val Ala Val
                580                 585                 590

Glu Lys Arg Pro Val Thr Leu Ser Asn Val Pro Gly Ile Ala Thr Ala
                595                 600                 605

Glu Leu Gln Val Gly Phe Asp Ala Thr Leu Leu Glu Val Ala Ser Ile
                610                 615                 620

Thr Val Gly Asp Ile Val Leu Asn Pro Ser Val Asn Phe Ser Ser Val
625                 630                 635                 640

Val Asn Gly Ser Thr Ile Lys Leu Leu Phe Leu Asp Asp Thr Leu Gly
                645                 650                 655

Ser Gln Leu Ile Ser Lys Asp Gly Val Leu Ala Thr Ile Asn Phe Lys
                660                 665                 670

Ala Lys Thr Val Thr Ser Lys Val Thr Thr Pro Val Ala Val Ser Gly
                675                 680                 685

Thr Pro Val Phe Ala Asp Gly Thr Leu Ala Glu Leu Lys Tyr Glu Thr
                690                 695                 700

Val Ala Gly Ser Val Thr Ile Glu Pro Ser Gln Pro Val Lys Thr Val
705                 710                 715                 720

Thr Ala Thr Val Gly Thr Ala Thr Gly Lys Val Gly Glu Thr Val Ala
                725                 730                 735

Val Ile Leu Glu Thr Ala Ala Leu Val Pro Arg Gly Ser Pro Ile
                740                 745                 750

Val Lys Ala Gly Phe Thr Val Glu Ile Val Gly Thr Thr Lys Ser Ala
                755                 760                 765

Val Thr Asp Ser Asn Gly Tyr Phe Glu Ile Lys Asp Val Ala Ala Gly
                770                 775                 780

Thr Tyr Thr Val Lys Ile Thr Lys Ala Asn Tyr Leu Thr Arg Glu Ile
785                 790                 795                 800

Ala Asn Val Ser Val Thr Ala Asp Lys Glu Leu Ser Thr Ser Ala Ser
                805                 810                 815

Pro Ile Leu Met Trp Ala Ile Ser Gln Ile Thr Asp Gly Gln Ile Gln
                820                 825                 830

Ala Thr Thr Thr Ala Thr Thr Glu Ala Thr Thr Ala Ala Pro Ser
                835                 840                 845

Ser Thr Val Glu Thr Val Ser Pro Ser Ser Thr Glu Thr Ile Ser Gln
                850                 855                 860

Gln Thr Glu Asn Gly Ala Ala Lys Ala Val Gly Met Gly Ala Gly
865                 870                 875                 880

Ala Leu Ala Ala Ala Ala Met Leu Leu
                885

<210> SEQ ID NO 23
<211> LENGTH: 3138
<212> TYPE: DNA
<213> ORGANISM: Artificial Sequence
<220> FEATURE:
<223> OTHER INFORMATION: Chimeric DNA

<400> SEQUENCE: 23
atggtctctt tcacttcttt gttggcgggt gtcgctgcta tcagtggtgt cttggctgcc        60
ccagccgctg aagtcgaacc agttgccgtt gaaaagagag gtgttgtttc tgtccaattc       120
```

-continued

```
aacaacggtt ctagcccagc ttcctccaac tccatctacg ccagattcaa ggttactaac      180
acttctggtt ctccaatcaa tctagctgat tgaagttga gatactacta cactcaagat       240
gctgacaagc cattgacctt ctggtgtgac cacgctggtt acatgtctgg ttccaactac      300
atcgacgcca cctccaaggt tactggtagc ttcaaggccg tttctccagc cgttactaac      360
gctgatcact acttggaagt cgctttgaac tccgatgccg gttctttgcc agctggtggt      420
tccatcgaaa ttcaaacccg tttcgctaga aacgattggt ccaactttga ccaatctaac      480
gactggtcct acactgccgc tggttcttac atggactggc aaaagatttc tgctttcgtt      540
ggtggtacct tagcttacgg ttccaccccca gacggtggta acccaccacc acaagatcca     600
actattaacc caacttccat ctctgctaag gctggttcct cgctgatac taagattacc       660 ttgactccaa acggtaacac cttcaacggc atctctgaat tgcaatcttc tcaatacacc      720
aagggtacta acgaagttac cttgttggct tcttacttga acactttgcc agaaaacacc      780
actaagactt tgaccttcga cttcggtgtt ggtaccaaga atccaaagtt gactattacc      840
gttctaccaa aggacatccc aggtgattct ttaaaggttg ctgttggtac cgctgaaggc      900
aacgtcggcg acaccgttac cgtcccagtt accttcgctg acgtcgcctc tgctggtaac      960
gtcggtactt gtaacttcta cttggcttac gatgcctcct tgttggacgt tgtctctgtc     1020
gctgctggtc caatcgttaa gaacgctgct gtcaatttct cttcttccgc ctctaacggc     1080
tccatcagtt tcttattctt ggataacact atcaccgacg aattgattac tgctgacggt     1140
gtttttgcta acattacctt caagttgaag tctgttactg ccaagactac cactccagtc     1200
actttcaagg acggtggtgc tttcggtgac ggtactatgg ccaaaattgc taccgttact     1260
aagactaacg gttccgttac tattgtccca ggtatccaac caactaagga agccgtcaga     1320
attaaggttg acactgttaa cgctaagcca ggtgacactg tcagaattcc agtcagattc     1380
tctggtatcc catctaaggg tattgccaac tgtgacttcg tttactctta cgatccaaac     1440
gttttagaaa tcatcgaaat tgaaccaggt gatatcatcg ttgatccaaa cccagacaag     1500
tccttcgaca ctgctgtttta cccagacaga aagattatcg tcttcttgtt cgctgaagac     1560
tctggtaccg gtgcttacgc tattaccaag gatggtgtct tgccactat cgttgctaag      1620 gttaagtctg gtgccccaaa cggtttaagc gttatcaagt tcgttgaagt cggtggtttc     1680
gctaacaacg acttggttga acaaaagacc caattcttcg atggtggtgt caacgttggt     1740
gtccacgtga ccgccgaagt tgaaccagtc gctgttgaaa agagaccagt cactttgtcc     1800
aacgttccag gtattgctac tgctgaattg caagttggtt tcgacgccac cttgttggaa     1860
gttgcctcta tcactgtcgg tgacatcgtt ttgaacccat ccgttaactt ctcttctgtc     1920
gtcaacggtt ctaccattaa gttgttgttc ttggacgaca ctttgggtag tcaattgatc     1980
tctaaggacg gtgttttggc tactatcaac ttcaaggcta agacggttac ctccaaggtt     2040
accactccag tcgctgtttc tggtactcca gtcttcgctg atggtacttt ggctgaatta     2100
aaatacgaaa ccgttgctgg ttccgttacc atcgaaccat cccaaccagt taagactgtt     2160
actgctactg tcggtaccgc taccggtaag gtcggtgaaa ctgtcgctgt cattctcgag     2220
actaataaac ctgtaataga aggatataaa actgaagact tgaacgttgc tgtcggtacc     2280
gccgaaggta acgtcggtga aactgtcact gtcccagtta ccttcgccaa cgtcgccaag     2340
gtcaataacg ttggtacctg taacttctac ttggcttacg acgcttcctt gttggatgtt     2400
gtctccgtcg atgctggtcc aattgttaag aacgccgccg ttaacttctc ttcttctgcc     2460
tctaacggta ctatctcctt cttgttcttg gacaacacta ttactgacga attgatcacc     2520
```

```
tccgacggtg tcttcgctaa cattaccttc aagttgaaga acgtttctac taagactacc   2580
accccaatct ccttcaagga cggtggtgct ttcggtgatg gtaacatggc taagattgct   2640
accgttgtca aaaccaacgg ttctgtcact atcatcccag gtgacccaga accagcggcc   2700
gcattggttc ctagaggatc accaattgtc aaggctggtt tcactgtcga aatcgttggt   2760
actaccaagt ccgctgttac cgactccaac ggttactttg aaatcaagga tgttgctgct   2820
ggtacttaca ctgttaagat cactaaagct aactaccta ccagagaaat tgctaacgtc   2880
tccgttaccg ctgacaagga attgtccact tctgcttccc caattttgat gtgggctatt   2940
tctcaaatta ctgatggtca aattcaagct accactaccg ctaccactga agctactact   3000
actgctgccc catcttccac tgttgaaacc gtctccccat cttctaccga aactatctct   3060
caacaaaccg aaaacggtgc tgccaaggcc gctgtcggta tgggtgctgg tgccttagct   3120
gccgctgcta tgttgtta                                                 3138
```

<210> SEQ ID NO 24
<211> LENGTH: 1046
<212> TYPE: PRT
<213> ORGANISM: Artificial
<220> FEATURE:
<223> OTHER INFORMATION: Chimeric amino acid

<400> SEQUENCE: 24

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Gly Val Val Ser Val Gln Phe Asn Asn Gly Ser Ser Pro Ala Ser
        35                  40                  45

Ser Asn Ser Ile Tyr Ala Arg Phe Lys Val Thr Asn Thr Ser Gly Ser
    50                  55                  60

Pro Ile Asn Leu Ala Asp Leu Lys Leu Arg Tyr Tyr Tyr Thr Gln Asp
65                  70                  75                  80

Ala Asp Lys Pro Leu Thr Phe Trp Cys Asp His Ala Gly Tyr Met Ser
                85                  90                  95

Gly Ser Asn Tyr Ile Asp Ala Thr Ser Lys Val Thr Gly Ser Phe Lys
            100                 105                 110

Ala Val Ser Pro Ala Val Thr Asn Ala Asp His Tyr Leu Glu Val Ala
        115                 120                 125

Leu Asn Ser Asp Ala Gly Ser Leu Pro Ala Gly Gly Ser Ile Glu Ile
    130                 135                 140

Gln Thr Arg Phe Ala Arg Asn Asp Trp Ser Asn Phe Asp Gln Ser Asn
145                 150                 155                 160

Asp Trp Ser Tyr Thr Ala Ala Gly Ser Tyr Met Asp Trp Gln Lys Ile
                165                 170                 175

Ser Ala Phe Val Gly Gly Thr Leu Ala Tyr Gly Ser Thr Pro Asp Gly
            180                 185                 190

Gly Asn Pro Pro Gln Asp Pro Thr Ile Asn Pro Thr Ser Ile Ser
        195                 200                 205

Ala Lys Ala Gly Ser Phe Ala Asp Thr Lys Ile Thr Leu Thr Pro Asn
    210                 215                 220

Gly Asn Thr Phe Asn Gly Ile Ser Glu Leu Gln Ser Ser Gln Tyr Thr
225                 230                 235                 240

Lys Gly Thr Asn Glu Val Thr Leu Leu Ala Ser Tyr Leu Asn Thr Leu
```

-continued

```
                245                 250                 255
Pro Glu Asn Thr Thr Lys Thr Leu Thr Phe Asp Phe Gly Val Gly Thr
                260                 265                 270
Lys Asn Pro Lys Leu Thr Ile Thr Val Leu Pro Lys Asp Ile Pro Gly
                275                 280                 285
Asp Ser Leu Lys Val Ala Val Gly Thr Ala Glu Gly Asn Val Gly Asp
            290                 295                 300
Thr Val Thr Val Pro Val Thr Phe Ala Asp Val Ala Ser Ala Gly Asn
305                 310                 315                 320
Val Gly Thr Cys Asn Phe Tyr Leu Ala Tyr Asp Ala Ser Leu Leu Asp
                325                 330                 335
Val Val Ser Val Ala Ala Gly Pro Ile Val Lys Asn Ala Ala Val Asn
                340                 345                 350
Phe Ser Ser Ser Ala Ser Asn Gly Ser Ile Ser Phe Leu Phe Leu Asp
                355                 360                 365
Asn Thr Ile Thr Asp Glu Leu Ile Thr Ala Asp Gly Val Phe Ala Asn
            370                 375                 380
Ile Thr Phe Lys Leu Lys Ser Val Thr Ala Lys Thr Thr Pro Val
385                 390                 395                 400
Thr Phe Lys Asp Gly Gly Ala Phe Gly Asp Gly Thr Met Ala Lys Ile
                405                 410                 415
Ala Thr Val Thr Lys Thr Asn Gly Ser Val Thr Ile Val Pro Gly Ile
                420                 425                 430
Gln Pro Thr Lys Glu Ala Val Arg Ile Lys Val Asp Thr Val Asn Ala
            435                 440                 445
Lys Pro Gly Asp Thr Val Arg Ile Pro Val Arg Phe Ser Gly Ile Pro
        450                 455                 460
Ser Lys Gly Ile Ala Asn Cys Asp Phe Val Tyr Ser Tyr Asp Pro Asn
465                 470                 475                 480
Val Leu Glu Ile Ile Glu Ile Glu Pro Gly Asp Ile Ile Val Asp Pro
                485                 490                 495
Asn Pro Asp Lys Ser Phe Asp Thr Ala Val Tyr Pro Asp Arg Lys Ile
            500                 505                 510
Ile Val Phe Leu Phe Ala Glu Asp Ser Gly Thr Gly Ala Tyr Ala Ile
        515                 520                 525
Thr Lys Asp Gly Val Phe Ala Thr Ile Val Ala Lys Val Lys Ser Gly
        530                 535                 540
Ala Pro Asn Gly Leu Ser Val Ile Lys Phe Val Glu Val Gly Gly Phe
545                 550                 555                 560
Ala Asn Asn Asp Leu Val Glu Gln Lys Thr Gln Phe Phe Asp Gly Gly
            565                 570                 575
Val Asn Val Gly Val His Val Thr Ala Glu Val Glu Pro Val Ala Val
            580                 585                 590
Glu Lys Arg Pro Val Thr Leu Ser Asn Val Pro Gly Ile Ala Thr Ala
            595                 600                 605
Glu Leu Gln Val Gly Phe Asp Ala Thr Leu Leu Glu Val Ala Ser Ile
        610                 615                 620
Thr Val Gly Asp Ile Val Leu Asn Pro Ser Val Asn Phe Ser Ser Val
625                 630                 635                 640
Val Asn Gly Ser Thr Ile Lys Leu Leu Phe Leu Asp Asp Thr Leu Gly
            645                 650                 655
Ser Gln Leu Ile Ser Lys Asp Gly Val Leu Ala Thr Ile Asn Phe Lys
            660                 665                 670
```

```
Ala Lys Thr Val Thr Ser Lys Val Thr Thr Pro Val Ala Val Ser Gly
        675                 680                 685

Thr Pro Val Phe Ala Asp Gly Thr Leu Ala Glu Leu Lys Tyr Glu Thr
    690                 695                 700

Val Ala Gly Ser Val Thr Ile Glu Pro Ser Gln Pro Val Lys Thr Val
705                 710                 715                 720

Thr Ala Thr Val Gly Thr Ala Thr Gly Lys Val Gly Glu Thr Val Ala
                725                 730                 735

Val Ile Leu Glu Thr Asn Lys Pro Val Ile Glu Gly Tyr Lys Thr Glu
            740                 745                 750

Asp Leu Asn Val Ala Val Gly Thr Ala Glu Gly Asn Val Gly Glu Thr
            755                 760                 765

Val Thr Val Pro Val Thr Phe Ala Asn Val Ala Lys Val Asn Asn Val
        770                 775                 780

Gly Thr Cys Asn Phe Tyr Leu Ala Tyr Asp Ala Ser Leu Leu Asp Val
785                 790                 795                 800

Val Ser Val Asp Ala Gly Pro Ile Val Lys Asn Ala Ala Val Asn Phe
                805                 810                 815

Ser Ser Ser Ala Ser Asn Gly Thr Ile Ser Phe Leu Phe Leu Asp Asn
            820                 825                 830

Thr Ile Thr Asp Glu Leu Ile Thr Ser Asp Gly Val Phe Ala Asn Ile
        835                 840                 845

Thr Phe Lys Leu Lys Asn Val Ser Thr Lys Thr Thr Pro Ile Ser
850                 855                 860

Phe Lys Asp Gly Gly Ala Phe Gly Asp Gly Asn Met Ala Lys Ile Ala
865                 870                 875                 880

Thr Val Val Lys Thr Asn Gly Ser Val Thr Ile Ile Pro Gly Asp Pro
                885                 890                 895

Glu Pro Ala Ala Ala Leu Val Pro Arg Gly Ser Pro Ile Val Lys Ala
            900                 905                 910

Gly Phe Thr Val Glu Ile Val Gly Thr Thr Lys Ser Ala Val Thr Asp
        915                 920                 925

Ser Asn Gly Tyr Phe Glu Ile Lys Asp Val Ala Ala Gly Thr Tyr Thr
    930                 935                 940

Val Lys Ile Thr Lys Ala Asn Tyr Leu Thr Arg Glu Ile Ala Asn Val
945                 950                 955                 960

Ser Val Thr Ala Asp Lys Glu Leu Ser Thr Ser Ala Ser Pro Ile Leu
                965                 970                 975

Met Trp Ala Ile Ser Gln Ile Thr Asp Gly Gln Ile Gln Ala Thr Thr
            980                 985                 990

Thr Ala Thr Thr Glu Ala Thr Thr  Thr Ala Ala Pro Ser  Ser Thr Val
        995                 1000                 1005

Glu Thr  Val Ser Pro Ser Ser  Thr Glu Thr Ile Ser  Gln Gln Thr
    1010                 1015                 1020

Glu Asn  Gly Ala Ala Lys Ala  Ala Val Gly Met Gly  Ala Gly Ala
    1025                 1030                 1035

Leu Ala  Ala Ala Ala Met Leu  Leu
    1040                 1045

<210> SEQ ID NO 25
<211> LENGTH: 2794
<212> TYPE: DNA
<213> ORGANISM: Saccharomycopsis fibuligera
```

```
<400> SEQUENCE: 25
gcggccgctc aaggaagtaa ttatctactt tttacaacaa atattaatta aaatggtgtc      60
cttcacctct tgttggctg gtgtcgctgc tattagcggt gttttggccg ctccagctgc      120
tgaagtcgaa tctgttgccg ttgaaaagag atcccgtgtc ccaatccaaa actacaccca     180
atccccatct caaagagatg aatcttccca atgggtctct ccacactact accctacccc    240
acaaggtggt cgtttacaag acgtctggca agaagcctac gctagagcca aggctattgt    300
cggtcaaatg actattgttg aaaaggtcaa tttgactacc ggcaccggtt ggcaattgga    360
cccatgtgtc ggtaacactg gttctgttcc aagattcggt attccaaact tgtgtttaca    420
agatggtcct ttgggtgtca gattcgctga ttttgtcacc ggttacccat ctggtttggc    480
taccggtgct accttcaaca aggatttgtt cttacaaaga ggtcaagctt tgggtcacga    540
atttaactct aagggtgtcc acatcgcttt aggtccagct gtcggtccat gggtgttaa     600 ggccagaggt ggtagaaact ttgaagcttt cggttccgat ccatacttgc aaggtaccgc    660
tgctgctgcc actatcaagg gtttgcaaga aaacaacgtc atggcttgtg ttaagcactt    720
catcggtaac gaacaagaaa agtacagaca acctgacgat atcaacccag ctactaacca    780
aaccactaag gaagctatct ccgccaacat tccagacaga gctatgcacg ctttgtactt    840
gtggccattc gctgactccg tccgtgccgg tgttggttct gtcatgtgct cttacaacag    900
agtcaacaac acttacgctt gtgaaaactc ttacatgatg aaccatttgt tgaaagaaga    960
attgggtttc caaggtttcg tcgtctctga ctggggtgct caattgtccg gtgtttactc   1020
tgctatttcc ggtttggata tgtccatgcc aggtgaagtt tacggtggtt ggaacactgg   1080
tacctctttc tggggtcaaa acttgactaa ggctatctac aacgaaactg ttccaattga   1140
aagattggac gatatggcca ccagaatctt ggctgctttg tacgctacta actcttttcc   1200
aaccgaagac cacttgccaa acttcagttc ttggactacc aaggaatacg gtaacaagta   1260
ctacgctgac aacaccaccg aaattgtcaa agtcaactac aacgttgacc catctaatga   1320
tttcaccgaa gacaccgctt tgaaggttgc cgaagaatct attgtcttgt taaagaacga   1380
aaacaacact ttgccaattt ccccagaaaa ggccaaaaga ttattgttgt ctggtatcgc   1440
tgctggtcca gatccaatcg gttaccaatg tgaggaccaa tcttgtacta acggtgcttt   1500
gttccaaggc tggggttccg gttctgtcgg ttctccaaag taccaagtta ctccattcga   1560
agaaatttct tacttggcca gaaagaacaa gatgcaattc gactacatca gagaatctta   1620
cgacctagct caagttacta aggtcgcttc tgatgctcat ttgtctatcg tcgttgtctc   1680
cgctgcttct ggtgaaggtt acattactgt tgacggtaac caaggtgata gaaagaactt   1740
gaccttgtgg aacaacggtg ataagttgat cgaaaccgtc gctgaaaact gtgctaacac   1800
tgttgttgtt gtcacttcca ctggtcaaat caacttcgaa ggtttcgctg atcacccaaa   1860
cgttaccgct attgtctggg ctggtccatt aggtgataga tccggtactg ctatcgctaa   1920
catcctattc ggtaaggcta atccatctgg tcacttacca ttcactattg ctaagaccga   1980
cgatgactac atcccaattg aaacctactc tccatcttcc ggtgaaccag aagacaacca   2040
tttggttgaa aacgacttgt tagtcgacta tagatacttt gaagaaaaga acatcgaacc   2100
tagatacgcc ttcggttacg gtttgtctta caacgaatac gaagtttcca cgctaaggt    2160 ttctgctgct aagaaggtcg atgaagaatt gcccgaacca gctacttact tgtctgaatt   2220
ttcttaccaa aacgccaagg actctaagaa cccatccgat gctttcgccc cagccgattt   2280
gaatagagtt aacgaatact tgtacccata cttggactct aacgtcaccct tgaaggacgg   2340
```

```
taattacgaa tacccagatg gttactccac tgaacaaaga actaccccaa accaaccagg    2400
tggtggtttg ggtggtaacg acgctttatg ggaagttgct tacaactcca ccgacaaatt    2460
tgtcccacaa ggtaactcta ctgataagtt cgttccacaa ttgtatttga agcaccctga    2520
agatggtaag ttcgaaactc caatccaatt gagaggtttc gaaaaggttg aattgtctcc    2580
tggtgaaaag aagactgtcg atttgagatt gttgcgtaga gacttgtctg tctgggatac    2640
tactcgtcaa tcttggatcg ttgaatctgg tacttacgaa gccttgattg gtgtcgcagt    2700
caacgacatc aagacatctg tcctgtttac tatttgaggc gcgccggatc tgcgatagat    2760 caatttttt cttttctctt gagctcgcgg ccgc                                 2794
```

<210> SEQ ID NO 26
<211> LENGTH: 894
<212> TYPE: PRT
<213> ORGANISM: Saccharomycopsis fibuligera

<400> SEQUENCE: 26

```
Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Ser Arg Val Pro Ile Gln Asn Tyr Thr Gln Ser Pro Ser Gln Arg
        35                  40                  45

Asp Glu Ser Ser Gln Trp Val Ser Pro His Tyr Tyr Pro Thr Pro Gln
    50                  55                  60

Gly Gly Arg Leu Gln Asp Val Trp Gln Glu Ala Tyr Ala Arg Ala Lys
65                  70                  75                  80

Ala Ile Val Gly Gln Met Thr Ile Val Glu Lys Val Asn Leu Thr Thr
                85                  90                  95

Gly Thr Gly Trp Gln Leu Asp Pro Cys Val Gly Asn Thr Gly Ser Val
            100                 105                 110

Pro Arg Phe Gly Ile Pro Asn Leu Cys Leu Gln Asp Gly Pro Leu Gly
        115                 120                 125

Val Arg Phe Ala Asp Phe Val Thr Gly Tyr Pro Ser Gly Leu Ala Thr
    130                 135                 140

Gly Ala Thr Phe Asn Lys Asp Leu Phe Leu Gln Arg Gly Gln Ala Leu
145                 150                 155                 160

Gly His Glu Phe Asn Ser Lys Gly Val His Ile Ala Leu Gly Pro Ala
                165                 170                 175

Val Gly Pro Leu Gly Val Lys Ala Arg Gly Gly Arg Asn Phe Glu Ala
            180                 185                 190

Phe Gly Ser Asp Pro Tyr Leu Gln Gly Thr Ala Ala Ala Thr Ile
        195                 200                 205

Lys Gly Leu Gln Glu Asn Asn Val Met Ala Cys Val Lys His Phe Ile
    210                 215                 220

Gly Asn Glu Gln Glu Lys Tyr Arg Gln Pro Asp Ile Asn Pro Ala
225                 230                 235                 240

Thr Asn Gln Thr Thr Lys Glu Ala Ile Ser Ala Asn Ile Pro Asp Arg
                245                 250                 255

Ala Met His Ala Leu Tyr Leu Trp Pro Phe Ala Asp Ser Val Arg Ala
            260                 265                 270

Gly Val Gly Ser Val Met Cys Ser Tyr Asn Arg Val Asn Asn Thr Tyr
        275                 280                 285
```

```
Ala Cys Glu Asn Ser Tyr Met Met Asn His Leu Leu Lys Glu Glu Leu
290                 295                 300
Gly Phe Gln Gly Phe Val Val Ser Asp Trp Gly Ala Gln Leu Ser Gly
305                 310                 315                 320
Val Tyr Ser Ala Ile Ser Gly Leu Asp Met Ser Met Pro Gly Glu Val
            325                 330                 335
Tyr Gly Gly Trp Asn Thr Gly Thr Ser Phe Trp Gly Gln Asn Leu Thr
            340                 345                 350
Lys Ala Ile Tyr Asn Glu Thr Val Pro Ile Glu Arg Leu Asp Asp Met
            355                 360                 365
Ala Thr Arg Ile Leu Ala Ala Leu Tyr Ala Thr Asn Ser Phe Pro Thr
370                 375                 380
Glu Asp His Leu Pro Asn Phe Ser Ser Trp Thr Thr Lys Glu Tyr Gly
385                 390                 395                 400
Asn Lys Tyr Tyr Ala Asp Asn Thr Thr Glu Ile Val Lys Val Asn Tyr
            405                 410                 415
Asn Val Asp Pro Ser Asn Asp Phe Thr Glu Asp Thr Ala Leu Lys Val
            420                 425                 430
Ala Glu Glu Ser Ile Val Leu Leu Lys Asn Glu Asn Asn Thr Leu Pro
            435                 440                 445
Ile Ser Pro Glu Lys Ala Lys Arg Leu Leu Leu Ser Gly Ile Ala Ala
450                 455                 460
Gly Pro Asp Pro Ile Gly Tyr Gln Cys Glu Asp Gln Ser Cys Thr Asn
465                 470                 475                 480
Gly Ala Leu Phe Gln Gly Trp Gly Ser Gly Ser Val Gly Ser Pro Lys
            485                 490                 495
Tyr Gln Val Thr Pro Phe Glu Glu Ile Ser Tyr Leu Ala Arg Lys Asn
            500                 505                 510
Lys Met Gln Phe Asp Tyr Ile Arg Glu Ser Tyr Asp Leu Ala Gln Val
            515                 520                 525
Thr Lys Val Ala Ser Asp Ala His Leu Ser Ile Val Val Ser Ala
            530                 535                 540
Ala Ser Gly Glu Gly Tyr Ile Thr Val Asp Gly Asn Gln Gly Asp Arg
545                 550                 555                 560
Lys Asn Leu Thr Leu Trp Asn Asn Gly Asp Lys Leu Ile Glu Thr Val
            565                 570                 575
Ala Glu Asn Cys Ala Asn Thr Val Val Val Thr Ser Thr Gly Gln
            580                 585                 590
Ile Asn Phe Glu Gly Phe Ala Asp His Pro Asn Val Thr Ala Ile Val
            595                 600                 605
Trp Ala Gly Pro Leu Gly Asp Arg Ser Gly Thr Ala Ile Ala Asn Ile
610                 615                 620
Leu Phe Gly Lys Ala Asn Pro Ser Gly His Leu Pro Phe Thr Ile Ala
625                 630                 635                 640
Lys Thr Asp Asp Asp Tyr Ile Pro Ile Glu Thr Tyr Ser Pro Ser Ser
            645                 650                 655
Gly Glu Pro Glu Asp Asn His Leu Val Glu Asn Asp Leu Leu Val Asp
            660                 665                 670
Tyr Arg Tyr Phe Glu Glu Lys Asn Ile Glu Pro Arg Tyr Ala Phe Gly
            675                 680                 685
Tyr Gly Leu Ser Tyr Asn Glu Tyr Glu Val Ser Asn Ala Lys Val Ser
            690                 695                 700
Ala Ala Lys Lys Val Asp Glu Glu Leu Pro Glu Pro Ala Thr Tyr Leu
```

```
                705                 710                 715                 720
Ser Glu Phe Ser Tyr Gln Asn Ala Lys Asp Ser Lys Asn Pro Ser Asp
                        725                 730                 735

Ala Phe Ala Pro Ala Asp Leu Asn Arg Val Asn Glu Tyr Leu Tyr Pro
                740                 745                 750

Tyr Leu Asp Ser Asn Val Thr Leu Lys Asp Gly Asn Tyr Glu Tyr Pro
                755                 760                 765

Asp Gly Tyr Ser Thr Glu Gln Arg Thr Thr Pro Asn Gln Pro Gly Gly
        770                 775                 780

Gly Leu Gly Gly Asn Asp Ala Leu Trp Glu Val Ala Tyr Asn Ser Thr
785                 790                 795                 800

Asp Lys Phe Val Pro Gln Gly Asn Ser Thr Asp Lys Phe Val Pro Gln
                805                 810                 815

Leu Tyr Leu Lys His Pro Glu Asp Gly Lys Phe Glu Thr Pro Ile Gln
                820                 825                 830

Leu Arg Gly Phe Glu Lys Val Glu Leu Ser Pro Gly Glu Lys Lys Thr
                835                 840                 845

Val Asp Leu Arg Leu Leu Arg Arg Asp Leu Ser Val Trp Asp Thr Thr
850                 855                 860

Arg Gln Ser Trp Ile Val Glu Ser Gly Thr Tyr Glu Ala Leu Ile Gly
865                 870                 875                 880

Val Ala Val Asn Asp Ile Lys Thr Ser Val Leu Phe Thr Ile
                        885                 890

<210> SEQ ID NO 27
<211> LENGTH: 316
<212> TYPE: DNA
<213> ORGANISM: Acetivibrio cellulolyticus

<400> SEQUENCE: 27
tcaacgacat caagacatct gtcctgttta ctattgtcac cactcccact ccaactcctg      60
cccaatacgt ttacggtgat gtcaacggtg atggttcctt gaactctatc gatttcggtg     120
tcatgagaaa gtacttattg gtatgatca aggaattctc ctacgaaaac ggtttgaagg      180
ccggtgacgt tgacggtaac ggtatgttca actctttgga cttcgcttac atgagacaat     240
acatgttggg tatcatctcc aaattcccag ttcaaaagta aggcgcgccg gatctgcgat     300
agatcaattt ttttct                                                     316

<210> SEQ ID NO 28
<211> LENGTH: 92
<212> TYPE: PRT
<213> ORGANISM: Acetivibrio cellulolyticus

<400> SEQUENCE: 28

Asn Asp Ile Lys Thr Ser Val Leu Phe Thr Ile Val Thr Thr Pro Thr
1               5                   10                  15

Pro Thr Pro Ala Gln Tyr Val Tyr Gly Asp Val Asn Gly Asp Gly Ser
                20                  25                  30

Leu Asn Ser Ile Asp Phe Gly Val Met Arg Lys Tyr Leu Leu Gly Met
            35                  40                  45

Ile Lys Glu Phe Ser Tyr Glu Asn Gly Leu Lys Ala Gly Asp Val Asp
                50                  55                  60

Gly Asn Gly Met Phe Asn Ser Leu Asp Phe Ala Tyr Met Arg Gln Tyr
65                  70                  75                  80

Met Leu Gly Ile Ile Ser Lys Phe Pro Val Gln Lys
```

<210> SEQ ID NO 29
<211> LENGTH: 292
<212> TYPE: DNA
<213> ORGANISM: Clostridium cellulolyticum

<400> SEQUENCE: 29

```
tcaacgacat caagacatct gtcctgttta ctattgtcac taccccaacc ccaactccag      60
ctcaatacgt ttacccagtt attgtctacg gtgacgttaa cggtgatggt aacgtcaact     120
ccactgactt gactatgttg aaaagatact tgttgaagtc cgttactaac atcaatagag     180
aagctgctga cgtcaacaga gatggtgcta tcaactcctc cgatatgacc attttgaaga     240
gatacttgat caagtaaggc gcgccggatc tgcgatagat caattttttt ct            292
```

<210> SEQ ID NO 30
<211> LENGTH: 84
<212> TYPE: PRT
<213> ORGANISM: Clostridium cellulolyticum

<400> SEQUENCE: 30

Asn Asp Ile Lys Thr Ser Val Leu Phe Thr Ile Val Thr Pro Thr
1               5                   10                  15

Pro Thr Pro Ala Gln Tyr Val Tyr Pro Val Ile Val Tyr Gly Asp Val
            20                  25                  30

Asn Gly Asp Gly Asn Val Asn Ser Thr Asp Leu Thr Met Leu Lys Arg
        35                  40                  45

Tyr Leu Leu Lys Ser Val Thr Asn Ile Asn Arg Glu Ala Ala Asp Val
    50                  55                  60

Asn Arg Asp Gly Ala Ile Asn Ser Ser Asp Met Thr Ile Leu Lys Arg
65                  70                  75                  80

Tyr Leu Ile Lys

<210> SEQ ID NO 31
<211> LENGTH: 286
<212> TYPE: DNA
<213> ORGANISM: Clostridium cellulovorans

<400> SEQUENCE: 31

```
tcaacgacat caagacatct gtcctgttta ctattgttac cacccccaacc ccaactccag     60
ctcaatacgt ttactacagc ttgggtgacg tcaacaaaga cggtaaagtc aacgctattg    120
attacgccgt tttgaagtcc atcttgttgg gtaccaacac caacgttgac ttgtctgtct    180
ccgacatgaa caaggacggt aaggttaacg ctttggattt ggctgttttg aagaaaatgt    240
tgttgtctta aggcgcgccg gatctgcgat agatcaattt ttttct                    286
```

<210> SEQ ID NO 32
<211> LENGTH: 82
<212> TYPE: PRT
<213> ORGANISM: Clostridium cellulovorans

<400> SEQUENCE: 32

Asn Asp Ile Lys Thr Ser Val Leu Phe Thr Ile Val Thr Pro Thr
1               5                   10                  15

Pro Thr Pro Ala Gln Tyr Val Tyr Tyr Ser Leu Gly Asp Val Asn Lys
            20                  25                  30

Asp Gly Lys Val Asn Ala Ile Asp Tyr Ala Val Leu Lys Ser Ile Leu
        35                  40                  45

```
Leu Gly Thr Asn Thr Asn Val Asp Leu Ser Val Ser Asp Met Asn Lys
        50                  55                  60

Asp Gly Lys Val Asn Ala Leu Asp Leu Ala Val Leu Lys Lys Met Leu
 65                  70                  75                  80

Leu Ser

<210> SEQ ID NO 33
<211> LENGTH: 289
<212> TYPE: DNA
<213> ORGANISM: Clostridium josui

<400> SEQUENCE: 33
tcaacgacat caagacatct gtcctgttta ctattgtcac taccccaact ccaactccag      60
ctcaatacgt ttacggtttg aagggtgatg ttaacaacga tggtgctatc gacgctttgg     120
acatcgctgc tttgaagaag gccatttga ctcaatctac ctccaacatc aacttaacta      180
acgctgacat gaacaacgac ggtaacattg acgctatcga cttcgctcaa ttgaaggtta     240
agttgttgaa ctaaggcgcg ccggatctgc gatagatcaa ttttttttct                289

<210> SEQ ID NO 34
<211> LENGTH: 83
<212> TYPE: PRT
<213> ORGANISM: Clostridium josui

<400> SEQUENCE: 34

Asn Asp Ile Lys Thr Ser Val Leu Phe Thr Ile Val Thr Thr Pro Thr
 1               5                   10                  15

Pro Thr Pro Ala Gln Tyr Val Tyr Gly Leu Lys Gly Asp Val Asn Asn
             20                  25                  30

Asp Gly Ala Ile Asp Ala Leu Asp Ile Ala Ala Leu Lys Lys Ala Ile
         35                  40                  45

Leu Thr Gln Ser Thr Ser Asn Ile Asn Leu Thr Asn Ala Asp Met Asn
    50                   55                  60

Asn Asp Gly Asn Ile Asp Ala Ile Asp Phe Ala Gln Leu Lys Val Lys
 65                  70                  75                  80

Leu Leu Asn

<210> SEQ ID NO 35
<211> LENGTH: 274
<212> TYPE: DNA
<213> ORGANISM: Clostridium thermocellum

<400> SEQUENCE: 35
tcaacgacat caagacatct gtcctgttta ctattgtcac caccccaacc ccaactccag      60
ctcaatacgt ttacggtgac gttaacgacg acggtaaggt taactccact gacgccgttg     120
ctttgaagag atacgttttg agatccggta tctctatcaa caccgacaac gctgatttga     180
acgaagacgg tagagtcaac tccaccgact gggtatctt gaaaagatac attttgtaag      240
gcgcgccgga tctgcgatag atcaatttttt ttct                                274

<210> SEQ ID NO 36
<211> LENGTH: 78
<212> TYPE: PRT
<213> ORGANISM: Clostridium thermocellum

<400> SEQUENCE: 36

Asn Asp Ile Lys Thr Ser Val Leu Phe Thr Ile Val Thr Thr Pro Thr
```

```
1               5                   10                  15
Pro Thr Pro Ala Gln Tyr Val Tyr Gly Asp Val Asn Asp Gly Lys
                    20                  25                  30

Val Asn Ser Thr Asp Ala Val Ala Leu Lys Arg Tyr Val Leu Arg Ser
            35                  40                  45

Gly Ile Ser Ile Asn Thr Asp Asn Ala Asp Leu Asn Glu Asp Gly Arg
    50                  55                  60

Val Asn Ser Thr Asp Leu Gly Ile Leu Lys Arg Tyr Ile Leu
65                  70                  75
```

<210> SEQ ID NO 37
<211> LENGTH: 280
<212> TYPE: DNA
<213> ORGANISM: Bacteroides cellulosolvens

<400> SEQUENCE: 37

```
tcaacgacat caagacatct gtcctgttta ctattgttaa gttgaagggt gatttgaacg    60
gtgacggcgt tatcaacatg gctgacgtca tgatcttagc tcaatccttc ggtaaagcta   120
ttggtaaccc aggtgttaac gaaaaggctg atttgaacaa cgacggtgtt attaacatgg   180
ccgacgctat catcttggct caatacttcg gtaagactaa gtccgccgaa gtggttatgt   240
tctaaggcgc gccggatctg cgatagatca attttttct                          280
```

<210> SEQ ID NO 38
<211> LENGTH: 80
<212> TYPE: PRT
<213> ORGANISM: Bacteroides cellulosolvens

<400> SEQUENCE: 38

```
Asn Asp Ile Lys Thr Ser Val Leu Phe Thr Ile Val Lys Leu Lys Gly
1               5                   10                  15

Asp Leu Asn Gly Asp Gly Val Ile Asn Met Ala Asp Val Met Ile Leu
                20                  25                  30

Ala Gln Ser Phe Gly Lys Ala Ile Gly Asn Pro Gly Val Asn Glu Lys
            35                  40                  45

Ala Asp Leu Asn Asn Asp Gly Val Ile Asn Met Ala Asp Ala Ile Ile
    50                  55                  60

Leu Ala Gln Tyr Phe Gly Lys Thr Lys Ser Ala Glu Val Val Met Phe
65                  70                  75                  80
```

<210> SEQ ID NO 39
<211> LENGTH: 1039
<212> TYPE: DNA
<213> ORGANISM: Artificial
<220> FEATURE:
<223> OTHER INFORMATION: Chimeric DNA

<400> SEQUENCE: 39

```
aaccaagcaa ctgcttatca acacacttaa ttaaaatggt ttctttcacc tctttgttag    60
ctggtgttgc cgccatctct ggtgtcttgg ctgctccagc tgccgaagtt gaaccagtcg   120
ctgttgaaaa gagaggtttc accgtcaacg ttgattccgt caatggtaac gttggtgaac   180
aaatcgttgt cccagttagt ttcgccaatg tcccatctaa cggtgtttcc accgctgata   240
tgaccattac ttacgacagt tctaagttgg aatacgtttc tggtgctgcc ggttccatcg   300
tcactaaccc aactgttaac ttcggtatca acaaggaagc tgacggtaag ttgaaggttt   360
tgttcttaga ctacactatg tccaccggtt acatctctac caacggtgtc ttcgccaacg   420
```

```
tcactttcaa ggttttgaac tccgctccaa ccactgttgg tatcaccggt gctaccttcg    480
gtgacaagaa cttaggtaac atctccgcca ccattaacgc tggttctatc aacggtggtg    540
tcgactacat caacccagac ttcgttacta cctccaccac cgccccaatc gtcaaggctg    600
gtttcactgt tgaaattgtc ggtaccacta gtccgccgt caccgactct aacggttact    660
tcgaaattaa ggacgttgct gctggtacct acactgttaa gattactaag gctaactact    720
tgactagaga aatcgctaac gtctccgtta ctgctgacaa agaattgtcc acttctgctt    780
ccccaatttt gatgtgggct atttctcaaa ttactgatgg tcaaattcaa gctaccacca    840
ctgccaccac cgaagctact accaccgccg ctccttcttc caccgtcgaa accgtttctc    900
catcttctac tgaaactatc tctcaacaaa ctgaaaacgg tgctgctaag gctgccgtcg    960
gtatgggtgc tggtgctttg gctgctgctg ctatgctatt gtaaggcgcg ccgcttttga   1020
ttaagccttc tagtccaaa                                                1039

<210> SEQ ID NO 40
<211> LENGTH: 320
<212> TYPE: PRT
<213> ORGANISM: Artificial
<220> FEATURE:
<223> OTHER INFORMATION: Chimeric amino acid

<400> SEQUENCE: 40

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Gly Phe Thr Val Asn Val Asp Ser Val Asn Gly Asn Val Gly Glu
        35                  40                  45

Gln Ile Val Val Pro Val Ser Phe Ala Asn Val Pro Ser Asn Gly Val
    50                  55                  60

Ser Thr Ala Asp Met Thr Ile Thr Tyr Asp Ser Ser Lys Leu Glu Tyr
65                  70                  75                  80

Val Ser Gly Ala Ala Gly Ser Ile Val Thr Asn Pro Thr Val Asn Phe
                85                  90                  95

Gly Ile Asn Lys Glu Ala Asp Gly Lys Leu Lys Val Leu Phe Leu Asp
            100                 105                 110

Tyr Thr Met Ser Thr Gly Tyr Ile Ser Thr Asn Gly Val Phe Ala Asn
        115                 120                 125

Val Thr Phe Lys Val Leu Asn Ser Ala Pro Thr Thr Val Gly Ile Thr
    130                 135                 140

Gly Ala Thr Phe Gly Asp Lys Asn Leu Gly Asn Ile Ser Ala Thr Ile
145                 150                 155                 160

Asn Ala Gly Ser Ile Asn Gly Gly Tyr Ile Asn Pro Asp Phe Val Thr
                165                 170                 175

Thr Ser Thr Thr Ala Pro Ile Val Lys Ala Gly Phe Thr Val Glu Ile
            180                 185                 190

Val Gly Thr Thr Lys Ser Ala Val Thr Asp Ser Asn Gly Tyr Phe Glu
        195                 200                 205

Ile Lys Asp Val Ala Ala Gly Thr Tyr Thr Val Lys Ile Thr Lys Ala
    210                 215                 220

Asn Tyr Leu Thr Arg Glu Ile Ala Asn Val Ser Val Thr Ala Asp Lys
225                 230                 235                 240

Glu Leu Ser Thr Ser Ala Ser Pro Ile Leu Met Trp Ala Ile Ser Gln
                245                 250                 255
```

```
Ile Thr Asp Gly Gln Ile Gln Ala Thr Thr Thr Ala Thr Thr Glu Ala
            260                 265                 270

Thr Thr Thr Ala Ala Pro Ser Ser Thr Val Glu Thr Val Ser Pro Ser
        275                 280                 285

Ser Thr Glu Thr Ile Ser Gln Gln Thr Glu Asn Gly Ala Ala Lys Ala
    290                 295                 300

Ala Val Gly Met Gly Ala Gly Ala Leu Ala Ala Ala Ala Met Leu Leu
305                 310                 315                 320

<210> SEQ ID NO 41
<211> LENGTH: 497
<212> TYPE: DNA
<213> ORGANISM: Clostridium cellulolyticum

<400> SEQUENCE: 41
gcggccgcct gccgaagttg aaccagtcgc tgttgaaaag agattgaagg ttgctgtcgg      60
tactgctgaa ggtaacgtcg gtgacaccgt taccgttcca gtcactttcg ctgatgttgc     120
ctcagctggt aacgttggta cctgtaactt ctacctagct tacgacgcct ccttgttgga     180
cgtcgtctct gttgctgctg gtccaatcgt caagaacgct gctgttaact tctcttcttc     240
tgcttctaac ggttctattt ccttcttgtt cttggataac actattaccg acgaattaat     300
taccgctgac ggtgttttcg ccaacatcac tttcaagttg aagtccgtta ccgctaagac     360
cactacccca gttaccttca aggacggtgg tgccttcggt gatggtacta tggctaagat     420
cgctactgtt accaagacta acggttccgt tacctacatc aacccagact tcgttactac     480
ctccaccacg cggccgc                                                    497

<210> SEQ ID NO 42
<211> LENGTH: 159
<212> TYPE: PRT
<213> ORGANISM: Clostridium cellulolyticum

<400> SEQUENCE: 42

Ala Glu Val Glu Pro Val Ala Val Glu Lys Arg Leu Lys Val Ala Val
1               5                   10                  15

Gly Thr Ala Glu Gly Asn Val Gly Asp Thr Val Thr Val Pro Val Thr
            20                  25                  30

Phe Ala Asp Val Ala Ser Ala Gly Asn Val Gly Thr Cys Asn Phe Tyr
        35                  40                  45

Leu Ala Tyr Asp Ala Ser Leu Leu Asp Val Val Ser Val Ala Ala Gly
    50                  55                  60

Pro Ile Val Lys Asn Ala Ala Val Asn Phe Ser Ser Ser Ala Ser Asn
65                  70                  75                  80

Gly Ser Ile Ser Phe Leu Phe Leu Asp Asn Thr Ile Thr Asp Glu Leu
                85                  90                  95

Ile Thr Ala Asp Gly Val Phe Ala Asn Ile Thr Phe Lys Leu Lys Ser
            100                 105                 110

Val Thr Ala Lys Thr Thr Thr Pro Val Thr Phe Lys Asp Gly Gly Ala
        115                 120                 125

Phe Gly Asp Gly Thr Met Ala Lys Ile Ala Thr Val Thr Lys Thr Asn
    130                 135                 140

Gly Ser Val Thr Tyr Ile Asn Pro Asp Phe Val Thr Thr Ser Thr
145                 150                 155

<210> SEQ ID NO 43
```

<211> LENGTH: 512
<212> TYPE: DNA
<213> ORGANISM: Clostridium cellulovorans

<400> SEQUENCE: 43

```
gcggccgcct gccgaagttg aaccagtcgc tgttgaaaag agaccagtca ctttgtccaa      60
cgttccaggt attgctactg ctgaattgca agttggtttc gacgccacct tgttggaagt     120
tgcctctatc actgtcggtg acatcgtttt gaacccatcc gttaacttct cttctgtcgt     180
caacggttct accattaagt tgttgttctt ggacgacact ttgggtagtc aattgatctc     240
taaggacggt gttttggcta ctatcaactt caaggctaag acggttacct ccaaggttac     300
cactccagtc gctgtttctg gtactccagt cttcgctgat ggtactttgg ctgaattaaa     360
atacgaaacc gttgctggtt ccgttaccat cgaaccatcc caaccagtta agactgttac     420
tgctactgtc ggtaccgcta ccggtaaggt cggtgaaact gtcgctgtct acatcaaccc     480
agacttcgtt actacctcca ccacgcggcc gc                                   512
```

<210> SEQ ID NO 44
<211> LENGTH: 164
<212> TYPE: PRT
<213> ORGANISM: Clostridium cellulovorans

<400> SEQUENCE: 44

Ala Glu Val Glu Pro Val Ala Val Glu Lys Arg Pro Val Thr Leu Ser
1               5                   10                  15

Asn Val Pro Gly Ile Ala Thr Ala Glu Leu Gln Val Gly Phe Asp Ala
            20                  25                  30

Thr Leu Leu Glu Val Ala Ser Ile Thr Val Gly Asp Ile Val Leu Asn
        35                  40                  45

Pro Ser Val Asn Phe Ser Ser Val Val Asn Gly Ser Thr Ile Lys Leu
    50                  55                  60

Leu Phe Leu Asp Asp Thr Leu Gly Ser Gln Leu Ile Ser Lys Asp Gly
65                  70                  75                  80

Val Leu Ala Thr Ile Asn Phe Lys Ala Lys Thr Val Thr Ser Lys Val
                85                  90                  95

Thr Thr Pro Val Ala Val Ser Gly Thr Pro Val Phe Ala Asp Gly Thr
            100                 105                 110

Leu Ala Glu Leu Lys Tyr Glu Thr Val Ala Gly Ser Val Thr Ile Glu
        115                 120                 125

Pro Ser Gln Pro Val Lys Thr Val Thr Ala Thr Val Gly Thr Ala Thr
    130                 135                 140

Gly Lys Val Gly Glu Thr Val Ala Val Tyr Ile Asn Pro Asp Phe Val
145                 150                 155                 160

Thr Thr Ser Thr

<210> SEQ ID NO 45
<211> LENGTH: 530
<212> TYPE: DNA
<213> ORGANISM: Clostridium josui

<400> SEQUENCE: 45

```
gcggccgcct gccgaagttg aaccagtcgc tgttgaaaag agaactgaag acttgaacgt      60
tgctgtcggt accgccgaag gtaacgtcgg tgaaactgtc actgtcccag ttaccttcgc     120
caacgtcgcc aaggtcaata acgttggtac ctgtaacttc tacttggctt acgacgcttc     180
cttgttggat gttgtctccg tcgatgctgg tccaattgtt aagaacgccg ccgttaactt     240
```

```
ctcttcttct gcctctaacg gtactatctc cttcttgttc ttggacaaca ctattactga    300
cgaattgatc acctccgacg gtgtcttcgc taacattacc ttcaagttga agaacgtttc    360
tactaagact accaccccaa tctccttcaa ggacggtggt gctttcggtg atggtaacat    420
ggctaagatt gctaccgttg tcaaaaccaa cggttctgtc actatcatcc caggtgaccc    480
agaaccatac atcaacccag acttcgttac tacctccacc acgcggccgc               530
```

<210> SEQ ID NO 46
<211> LENGTH: 170
<212> TYPE: PRT
<213> ORGANISM: Clostridium josui

<400> SEQUENCE: 46

```
Ala Glu Val Glu Pro Val Ala Val Glu Lys Arg Thr Glu Asp Leu Asn
1               5                   10                  15

Val Ala Val Gly Thr Ala Glu Gly Asn Val Gly Glu Thr Val Thr Val
            20                  25                  30

Pro Val Thr Phe Ala Asn Val Ala Lys Val Asn Asn Val Gly Thr Cys
        35                  40                  45

Asn Phe Tyr Leu Ala Tyr Asp Ala Ser Leu Leu Asp Val Val Ser Val
    50                  55                  60

Asp Ala Gly Pro Ile Val Lys Asn Ala Ala Val Asn Phe Ser Ser Ser
65                  70                  75                  80

Ala Ser Asn Gly Thr Ile Ser Phe Leu Phe Leu Asp Asn Thr Ile Thr
                85                  90                  95

Asp Glu Leu Ile Thr Ser Asp Gly Val Phe Ala Asn Ile Thr Phe Lys
            100                 105                 110

Leu Lys Asn Val Ser Thr Lys Thr Thr Thr Pro Ile Ser Phe Lys Asp
        115                 120                 125

Gly Gly Ala Phe Gly Asp Gly Asn Met Ala Lys Ile Ala Thr Val Val
    130                 135                 140

Lys Thr Asn Gly Ser Val Thr Ile Ile Pro Gly Asp Pro Glu Pro Tyr
145                 150                 155                 160

Ile Asn Pro Asp Phe Val Thr Thr Ser Thr
                165                 170
```

<210> SEQ ID NO 47
<211> LENGTH: 515
<212> TYPE: DNA
<213> ORGANISM: Clostridium thermocellum

<400> SEQUENCE: 47

```
gcggccgcct gccgaagttg aaccagtcgc tgttgaaaag agagctgttc gtattaaggt    60
cgacaccgtc aacgctaagc caggtgatac tgtcagaatc ccagtcagat tctctggtat    120
tccatccaag ggtatcgcta actgtgattt cgtttactcc tacgatccaa acgttttgga    180
aattatcgaa atcgaaccag gtgacatcat cgtcgatcca aacccagata agtccttcga    240
cactgctgtt tacccagaca gaaagattat cgtcttcttg ttcgctgaag actccggtac    300
tggtgcttac gctattacca aggacggtgt cttcgctact attgttgcca agtgaagtc    360 tggtgcccca aacggtttgt ctgttatcaa gttcgttgaa gttggtggtt cgctaacaa    420 cgatttagtc gaacaaaaga cccaattctt cgacggtggt gttaacgtcg gttacatcaa    480
cccagacttc gttactacct ccaccacgcg gccgc                              515
```

<210> SEQ ID NO 48
<211> LENGTH: 165
<212> TYPE: PRT
<213> ORGANISM: Clostridium thermocellum

<400> SEQUENCE: 48

```
Ala Glu Val Glu Pro Val Ala Val Glu Lys Arg Ala Val Arg Ile Lys
1               5                   10                  15

Val Asp Thr Val Asn Ala Lys Pro Gly Asp Thr Val Arg Ile Pro Val
            20                  25                  30

Arg Phe Ser Gly Ile Pro Ser Lys Gly Ile Ala Asn Cys Asp Phe Val
        35                  40                  45

Tyr Ser Tyr Asp Pro Asn Val Leu Glu Ile Ile Glu Ile Glu Pro Gly
    50                  55                  60

Asp Ile Ile Val Asp Pro Asn Pro Asp Lys Ser Phe Asp Thr Ala Val
65                  70                  75                  80

Tyr Pro Asp Arg Lys Ile Ile Val Phe Leu Phe Ala Glu Asp Ser Gly
                85                  90                  95

Thr Gly Ala Tyr Ala Ile Thr Lys Asp Gly Val Phe Ala Thr Ile Val
            100                 105                 110

Ala Lys Val Lys Ser Gly Ala Pro Asn Gly Leu Ser Val Ile Lys Phe
        115                 120                 125

Val Glu Val Gly Gly Phe Ala Asn Asn Asp Leu Val Glu Gln Lys Thr
    130                 135                 140

Gln Phe Phe Asp Gly Val Asn Val Gly Tyr Ile Asn Pro Asp Phe
145                 150                 155                 160

Val Thr Thr Ser Thr
                165
```

<210> SEQ ID NO 49
<211> LENGTH: 554
<212> TYPE: DNA
<213> ORGANISM: Bacteroides cellulosovens

<400> SEQUENCE: 49

```
gcggccgcct gccgaagttg aaccagtcgc tgttgaaaag agagttactg ctactgtcga    60
caagactacc gcctccgttg gtgacattat cacctacact attaacgtta aggacgttgc   120
tggtttcgcc ggttatcaag ccaacgtcaa gtacgaccca tctgttttgc aaccagttta   180
cgacgacaga tctgcttacg actctgctgc tgtcccagaa tacggtacct tgttgcaaaa   240
gagatactcc ccaaccgaca tggcttctaa cgacttgtct aagggtacct tgacttttgg   300
tagaacttac atgaacttgg attcttacaa agcttctggt tctgccgaaa ccaccggttc   360
tatcgctgtt attagattca aggtcttgaa gaacactgct accaccatta agttgcaaaa   420
tgccgcttcc ttgaccaacg ctgtcgacgg taccatgttg ttcgactggt ctggtgccca   480
attagctggt tacaaggttg ctcaagctcc ttacatcaac ccagacttcg ttactacctc   540
caccacgcgg ccgc                                                    554
```

<210> SEQ ID NO 50
<211> LENGTH: 178
<212> TYPE: PRT
<213> ORGANISM: Bacteroides cellulosovens

<400> SEQUENCE: 50

```
Ala Glu Val Glu Pro Val Ala Val Glu Lys Arg Val Thr Ala Thr Val
1               5                   10                  15
```

Asp Lys Thr Thr Ala Ser Val Gly Asp Ile Ile Thr Tyr Thr Ile Asn
                20                  25                  30

Val Lys Asp Val Ala Gly Phe Ala Gly Tyr Gln Ala Asn Val Lys Tyr
             35                  40                  45

Asp Pro Ser Val Leu Gln Pro Val Tyr Asp Asp Arg Ser Ala Tyr Asp
         50                  55                  60

Ser Ala Ala Val Pro Glu Tyr Gly Thr Leu Leu Gln Lys Arg Tyr Ser
65                  70                  75                  80

Pro Thr Asp Met Ala Ser Asn Asp Leu Ser Lys Gly Thr Leu Thr Phe
                 85                  90                  95

Gly Arg Tyr Met Asn Leu Asp Ser Tyr Lys Ala Ser Gly Ser Ala
                100                 105                 110

Glu Thr Thr Gly Ser Ile Ala Val Ile Arg Phe Lys Val Leu Lys Asn
            115                 120                 125

Thr Ala Thr Thr Ile Lys Leu Gln Asn Ala Ala Ser Leu Thr Asn Ala
130                 135                 140

Val Asp Gly Thr Met Leu Phe Asp Trp Ser Gly Ala Gln Leu Ala Gly
145                 150                 155                 160

Tyr Lys Val Ala Gln Ala Pro Tyr Ile Asn Pro Asp Phe Val Thr Thr
                165                 170                 175

Ser Thr

<210> SEQ ID NO 51
<211> LENGTH: 1368
<212> TYPE: DNA
<213> ORGANISM: Talaromyces emersonii

<400> SEQUENCE: 51

| | | | | |
|---|---|---|---|---|
| atgctaagaa gagcttttact attgagctct tctgctatct tggccgttaa ggctcaacaa | 60 |
| gccggtaccg ctactgctga aaaccaccct ccattgacct ggcaagaatg taccgctcca | 120 |
| ggttcttgta ccacccaaaa cggtgctgtc gtcttggacg ctaactggag atgggtccac | 180 |
| gacgtcaacg gttacactaa ctgttacacc ggtaacacct gggacccaac ttactgtcca | 240 |
| gacgacgaaa cttgcgctca aaactgtgcc ttggacggtg ctgactacga aggtacttac | 300 |
| ggtgttaccc ctctggttc ttccttgaag ttgaacttcg tcactggttc taacgtcggt | 360 |
| tccagattgt atttgttgca agatgactcc acttaccaaa tcttcaagtt gttgaacaga | 420 |
| gaatttctt tcgacgtcga tgtgtccaac ttgccttgtg gtttgaacgg tgctctatac | 480 |
| ttcgttgcta tggacgctga tggtggtgtt tccaagtacc aaacaacaa ggctggtgcc | 540 |
| aaatacggta ctggttactg tgactctcaa tgtccacgtg acttgaagtt tattgatggt | 600 |
| gaagctaatg tcgaaggttg gcaaccatct tctaacaacg ctaacactgg catcggtgac | 660 |
| cacggttctt gctgtgccga atggacgtt tgggaagcca actccattcc caacgccgtc | 720 |
| actccacacc catgtgacac tccaggtcaa actatgtgtt ccggcgatga ctgtggtggt | 780 |
| acttactcta cgatagata cgctggtacc tgtgatccag acggttgcga cttcaatcca | 840 |
| tacagaatgg gtaacacttc cttttacggt ccaggcaaga tcatcgacac tactaagcca | 900 |
| ttcactgttg tcacccaatt cttgaccgac gatggtactg ataccggtac tttgtccgaa | 960 |
| atcaagagat tctacatcca aaactctaac gtcatccac aaccaaattc cgacatctct | 1020 |
| ggtgtcactg gtaactccat taccaccgaa ttttgtaccg cccaaaagca agctttcggt | 1080 |
| gacaccgacg acttctctca acacggtggt ttggctaaga tgggtgctgc tatgcaacaa | 1140 |
| ggtatggttt tggtcatgtc tttgtgggac gactacgctg ctcaaatgtt gtggttggac | 1200 |

-continued

```
tccgattacc caaccgatgc cgacccaacc acccctggta tcgctagagg tacctgtcca    1260
actgactctg gtgttccatc tgacgtcgaa tcccaatctc caaactccta cgtcacttac    1320
tccaacatta aattcggtcc aatcaactcc actttcactg cttcttaa                 1368
```

<210> SEQ ID NO 52
<211> LENGTH: 455
<212> TYPE: PRT
<213> ORGANISM: Talaromyces emersonii

<400> SEQUENCE: 52

```
Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
```

```
                340               345               350
Thr Ala Gln Lys Gln Ala Phe Gly Asp Thr Asp Phe Ser Gln His
            355               360               365
Gly Gly Leu Ala Lys Met Gly Ala Ala Met Gln Gln Gly Met Val Leu
        370               375               380
Val Met Ser Leu Trp Asp Asp Tyr Ala Ala Gln Met Leu Trp Leu Asp
385               390               395               400
Ser Asp Tyr Pro Thr Asp Ala Asp Pro Thr Thr Pro Gly Ile Ala Arg
            405               410               415
Gly Thr Cys Pro Thr Asp Ser Gly Val Pro Ser Asp Val Glu Ser Gln
        420               425               430
Ser Pro Asn Ser Tyr Val Thr Tyr Ser Asn Ile Lys Phe Gly Pro Ile
        435               440               445
Asn Ser Thr Phe Thr Ala Ser
        450               455
```

<210> SEQ ID NO 53
<211> LENGTH: 1449
<212> TYPE: DNA
<213> ORGANISM: Chrysosporium lucknowense

<400> SEQUENCE: 53

```
atggccaaga agttgttcat taccgctgcc ttagctgccg cagtgcttgc tgcaccagtg    60
atcgaagaga gacaaaattg cggagccgtc tggacacagt gcggaggcaa cggctggcaa   120
ggcccaacat gttgtgcttc tggctcaacg tgcgtggcac agaacgagtg gtattcccag   180
tgccttccaa actcccaggt gacttcttca caaccccca gctcaacgtc tacttcacag   240
agatccacaa gtacctcttc tagcacaacc agaagtggct catcctcatc tagcagtacg   300
accctccac ccgtatcaag tcctgtcacg agtatccctg gcggagcaac ctcaacagcc   360
agttattccg gcaatccttt ctctggagtg agattatttg caaacgacta ttatagatca   420
gaggttcaca accttgcaat tccttctatg acgggaaccc tagccgcaaa ggcttccgcc   480
gtagcagaag tccctagttt ccaatggctt gacagaaacg ttacaataga tacacttatg   540
gtacagactt tatctcaggt tagagctttg aataaggccg gtgccaaccc accttatgct   600
gcccaattag tagtctatga cttgccagat agagactgtg ctgccgcagc ttctaatggt   660
gaattttcca tcgcaaatgg cggagctgca aactatagat catacattga tgcaataaga   720
aaacacatca ttgagtattc tgatattaga ataatccttg tgattgaacc agactccatg   780
gctaatatgg ttaccaacat gaatgtagcc aagtgttcta acgcagcttc acataccat    840
gagctaaccg tatatgcatt aaaacaactg aatctaccta acgttgctat gtacttagat   900
gccggtcatg ccgatggtt gggctggcct gcaaatatcc aacccgcagc tgaattgttc   960
gctggaatct acaacgacgc cggaaagccc gctgccgtta gaggcttagc cacaaatgtt  1020
gcaaattaca acgcttggtc aattgctagt gcccttcttt ataccccacc aaatcctaac  1080
tacgatgaga acattacat agaagcattt tcccccattgt taaactccgc tggattccct  1140
gccagattca tcgtggatac cggtagaaac ggcaaacaac caactggaca caacaatgg   1200
ggagattggt gtaacgtcaa gggaaccggc ttcggcgtca ggcctacggc aaacaccgga  1260
cacgagctag tcgacgcttt tgtatgggtt aagccaggtg gcgaaagtga cggaacaagt  1320
gacacgagtg ctgcaagata cgattaccac tgtggtctgt ccgacgcttt acagcccgcc  1380
cccgaggctg gacaatggtt ccaggcttat tttgaacaat tgttaacgaa cgcaaatcca  1440
```

```
ccattctaa                                                           1449
```

<210> SEQ ID NO 54
<211> LENGTH: 482
<212> TYPE: PRT
<213> ORGANISM: Chrysosporium lucknowense

<400> SEQUENCE: 54

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

```
Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
                420                 425                 430

Gly Gly Glu Ser Asp Gly Thr Ser Asp Thr Ser Ala Ala Arg Tyr Asp
            435                 440                 445

Tyr His Cys Gly Leu Ser Asp Ala Leu Gln Pro Ala Pro Glu Ala Gly
        450                 455                 460

Gln Trp Phe Gln Ala Tyr Phe Glu Gln Leu Leu Thr Asn Ala Asn Pro
465                 470                 475                 480

Pro Phe
```

<210> SEQ ID NO 55
<211> LENGTH: 1356
<212> TYPE: DNA
<213> ORGANISM: Coptotermes formosanus

<400> SEQUENCE: 55

```
atgagattcc cttccatttt cactgctgtt tgttcgcag cctcaagtgc tttagcagcc      60
tatgactaca agacagtatt gaagaactcc ttgttgttct acgaagctca agaagtgga    120
aaattgcctg cagaccagaa ggtgacctgg agaaaagatt ccgcattaaa cgacaaggga    180
cagaagggag aggacttaac tggaggttat tacgacgccg gagactttgt gaagttcggt    240
tttccaatgg catacacagt taccgtgttg gcctggggtt tagtcgatta tgaatctgct    300
tacagtactg cgggtgcctt ggatgatggt agaaaggcct tgaaatgggg tacagattat    360
ttcttgaaag cacataccgc tgccaatgag ttttacggac aggtgggtca gggagatgtg    420
gatcatgctt actggggacg tcctgaggac atgactatgt ctagaccagc ttacaagatc    480
gatacatcaa aacctggtag tgacttagct gcagaaacag cagccgcttt agcagcaacc    540
gcaatagctt acaagtcagc cgattctacc tacagtaaca acttaattac tcatgcaaag    600
cagttgttcg attttgcaaa caattataga ggaaagtact ctgatagtat taccgatgcc    660
aagaatttct atgcatccgg tgattataag gacgaattag tatgggctgc agcctggttg    720
tatagagcta caaatgataa cacttactta accaaagccg aatcattgta taatgaattt    780
ggtttaggat cttggaacgg tgcattcaat tgggataaca agatatccgg agttcaggtc    840
ttattagcca aattgacatc caaacaagca tacaaagata agttcaggg ttatgttgat    900
tacttagtct cctctcaaaa gaaaactcca aagggattgg tctatattga ccaatgggga    960
accttaagac acgcagctaa tagtgccttg atcgctttac aggccgctga tttgggtata   1020
aacgctgcta gttatagaca atacgcaaag aagcaaattg attatgcctt aggtgacgga   1080
ggtcgttctt acgtggtcgg attcggaact aaccctccag taagacctca tcatagatcc   1140
agttcctgtc ctgacgcacc agccgcttgc gactggaata cttacaactc tgccggacca   1200
aatgcccacg tcttgaccgg agccttagta ggtggaccag attccaacga tagttacaca   1260
gattcacgtt ctgattatat cagtaacgaa gtcgctactg attacaatgc cggtttccaa   1320
tctgcagttg ctggtttgtt gaaagccgga gtataa                              1356
```

<210> SEQ ID NO 56

<211> LENGTH: 451
<212> TYPE: PRT
<213> ORGANISM: Coptotermes formosanus

<400> SEQUENCE: 56

```
Met Arg Phe Pro Ser Ile Phe Thr Ala Val Leu Phe Ala Ala Ser Ser
1               5                   10                  15

Ala Leu Ala Ala Tyr Asp Tyr Lys Thr Val Leu Lys Asn Ser Leu Leu
            20                  25                  30

Phe Tyr Glu Ala Gln Arg Ser Gly Lys Leu Pro Ala Asp Gln Lys Val
        35                  40                  45

Thr Trp Arg Lys Asp Ser Ala Leu Asn Asp Lys Gly Gln Lys Gly Glu
50                  55                  60

Asp Leu Thr Gly Gly Tyr Tyr Asp Ala Gly Asp Phe Val Lys Phe Gly
65                  70                  75                  80

Phe Pro Met Ala Tyr Thr Val Thr Val Leu Ala Trp Gly Leu Val Asp
                85                  90                  95

Tyr Glu Ser Ala Tyr Ser Thr Gly Ala Leu Asp Asp Gly Arg Lys
            100                 105                 110

Ala Leu Lys Trp Gly Thr Asp Tyr Phe Leu Lys Ala His Thr Ala Ala
        115                 120                 125

Asn Glu Phe Tyr Gly Gln Val Gly Gln Gly Asp Val Asp His Ala Tyr
    130                 135                 140

Trp Gly Arg Pro Glu Asp Met Thr Met Ser Arg Pro Ala Tyr Lys Ile
145                 150                 155                 160

Asp Thr Ser Lys Pro Gly Ser Asp Leu Ala Ala Glu Thr Ala Ala Ala
                165                 170                 175

Leu Ala Ala Thr Ala Ile Ala Tyr Lys Ser Ala Asp Ser Thr Tyr Ser
            180                 185                 190

Asn Asn Leu Ile Thr His Ala Lys Gln Leu Phe Asp Phe Ala Asn Asn
        195                 200                 205

Tyr Arg Gly Lys Tyr Ser Asp Ser Ile Thr Asp Ala Lys Asn Phe Tyr
    210                 215                 220

Ala Ser Gly Asp Tyr Lys Asp Glu Leu Val Trp Ala Ala Ala Trp Leu
225                 230                 235                 240

Tyr Arg Ala Thr Asn Asp Asn Thr Tyr Leu Thr Lys Ala Glu Ser Leu
                245                 250                 255

Tyr Asn Glu Phe Gly Leu Gly Ser Trp Asn Gly Ala Phe Asn Trp Asp
            260                 265                 270

Asn Lys Ile Ser Gly Val Gln Val Leu Leu Ala Lys Leu Thr Ser Lys
        275                 280                 285

Gln Ala Tyr Lys Asp Lys Val Gln Gly Tyr Val Asp Tyr Leu Val Ser
    290                 295                 300

Ser Gln Lys Lys Thr Pro Lys Gly Leu Val Tyr Ile Asp Gln Trp Gly
305                 310                 315                 320

Thr Leu Arg His Ala Ala Asn Ser Ala Leu Ile Ala Leu Gln Ala Ala
                325                 330                 335

Asp Leu Gly Ile Asn Ala Ala Ser Tyr Arg Gln Tyr Ala Lys Lys Gln
            340                 345                 350

Ile Asp Tyr Ala Leu Gly Asp Gly Arg Ser Tyr Val Val Gly Phe
        355                 360                 365

Gly Thr Asn Pro Pro Val Arg Pro His His Arg Ser Ser Ser Cys Pro
    370                 375                 380

Asp Ala Pro Ala Ala Cys Asp Trp Asn Thr Tyr Asn Ser Ala Gly Pro
```

Asn Ala His Val Leu Thr Gly Ala Leu Val Gly Gly Pro Asp Ser Asn
            405                 410                 415

Asp Ser Tyr Thr Asp Ser Arg Ser Asp Tyr Ile Ser Asn Glu Val Ala
            420                 425                 430

Thr Asp Tyr Asn Ala Gly Phe Gln Ser Ala Val Ala Gly Leu Leu Lys
            435                 440                 445

Ala Gly Val
    450

<210> SEQ ID NO 57
<211> LENGTH: 1425
<212> TYPE: DNA
<213> ORGANISM: Trichoderma reesei

<400> SEQUENCE: 57

```
atggtctcct tcacctccct gctggccggc gttgccgcta tctctggtgt cctagcagcc      60
cctgccgcag aagttgaacc tgtcgcagtt gagaaacgtg aggccgaagc agaagctcaa     120
caaccaggaa catcaacacc agaagtccat ccaaagttaa caacctataa atgtactaag     180
agtggagggt gtgtagcgca ggacacaagt gtggtcttag actggaatta tcgttggatg     240
catgatgcca attataattc ctgtactgtt aacggcggtg ttaacactac gttatgcccc     300
gatgaagcga cttgtggtaa gaattgtttt attgaagggg ttgactacgc cgctagtggt     360
gttacgacga gtgggtcatc cttgacgatg aatcaataca tgccttcttc tagtggtggg     420
tattcctctg tgtctccaag gctgtattta ttggattccg atggggaata tgttatgtta     480
aaattaaatg ggcaagaact gagttttgat gtggatctat ctgcattacc ttgtggagaa     540
aatggtagtc tttatttatc acaaatggac gaaaacggcg gagccaatca gtacaataca     600
gctggtgcta attatggttc aggctattgt gatgctcaat gtccagtgca gacttggagg     660
aatggcacct aaacacatc acatcaagga ttttgctgta acgaaatgga catattagaa     720
ggtaattcaa gagctaatgc actaactccg cactcttgta ctgcgaccgc atgtgattct     780
gccggttgtg gtttcaaccc ttatggttct ggttataaga gttactacgg tccgggagac     840
accgtggata cgtcaaagac cttcactata atcactcagt ttaacacaga taacggatct     900
ccgagtggta atttggtgag tattactagg aaatatcagc agaacggtgt tgatattccg     960
tccgcgcagc aggcggtga cactatatct agctgtcctt ccgccagtgc ctatggcgga    1020
cttgctacaa tgggtaaggc attgtcctca ggtatggtcc tagtattttc tatttggaat    1080
gataattcac aatacatgaa ttggctggat tctggtaatg caggcccttg ctcctctaca    1140
gaaggtaacc caagcaatat actagctaat aacccaaata ctcatgttgt ctttagtaat    1200
attagatggg gcgatatagg tagcactacg aacagtaccg cacctcctcc tccacctgct    1260
agctccacga cattttccac tactagaagg tccagcacta ccagctcatc accatcttgt    1320
actcaaaccc attggggaca gtgtggtggt ataggttaca gcggttgcaa aacttgcaca    1380
tctggtacta catgccaata cagtaatgac tattactcac aatgt                    1425
```

<210> SEQ ID NO 58
<211> LENGTH: 475
<212> TYPE: PRT
<213> ORGANISM: Trichoderma reesei

<400> SEQUENCE: 58

Met Val Ser Phe Thr Ser Leu Leu Ala Gly Val Ala Ala Ile Ser Gly

-continued

```
1               5                   10                  15
Val Leu Ala Ala Pro Ala Glu Val Glu Pro Val Ala Val Glu Lys
            20                  25                  30
Arg Glu Ala Glu Ala Glu Gln Gln Pro Gly Thr Ser Thr Pro Glu
            35                  40                  45
Val His Pro Lys Leu Thr Thr Tyr Lys Cys Thr Lys Ser Gly Gly Cys
    50                  55                      60
Val Ala Gln Asp Thr Ser Val Val Leu Asp Trp Asn Tyr Arg Trp Met
65                  70                  75                  80
His Asp Ala Asn Tyr Asn Ser Cys Thr Val Asn Gly Gly Val Asn Thr
                85                  90                  95
Thr Leu Cys Pro Asp Glu Ala Thr Cys Gly Lys Asn Cys Phe Ile Glu
                100                 105                 110
Gly Val Asp Tyr Ala Ala Ser Gly Val Thr Thr Ser Gly Ser Ser Leu
                115                 120                 125
Thr Met Asn Gln Tyr Met Pro Ser Ser Gly Gly Tyr Ser Ser Val
                130                 135                 140
Ser Pro Arg Leu Tyr Leu Leu Asp Ser Asp Gly Glu Tyr Val Met Leu
145                 150                 155                 160
Lys Leu Asn Gly Gln Glu Leu Ser Phe Asp Val Asp Leu Ser Ala Leu
                165                 170                 175
Pro Cys Gly Glu Asn Gly Ser Leu Tyr Leu Ser Gln Met Asp Glu Asn
                180                 185                 190
Gly Gly Ala Asn Gln Tyr Asn Thr Ala Gly Ala Asn Tyr Gly Ser Gly
                195                 200                 205
Tyr Cys Asp Ala Gln Cys Pro Val Gln Thr Trp Arg Asn Gly Thr Leu
210                 215                 220
Asn Thr Ser His Gln Gly Phe Cys Cys Asn Glu Met Asp Ile Leu Glu
225                 230                 235                 240
Gly Asn Ser Arg Ala Asn Ala Leu Thr Pro His Ser Cys Thr Ala Thr
                245                 250                 255
Ala Cys Asp Ser Ala Gly Cys Gly Phe Asn Pro Tyr Gly Ser Gly Tyr
                260                 265                 270
Lys Ser Tyr Tyr Gly Pro Gly Asp Thr Val Asp Thr Ser Lys Thr Phe
                275                 280                 285
Thr Ile Ile Thr Gln Phe Asn Thr Asp Asn Gly Ser Pro Ser Gly Asn
                290                 295                 300
Leu Val Ser Ile Thr Arg Lys Tyr Gln Gln Asn Gly Val Asp Ile Pro
305                 310                 315                 320
Ser Ala Gln Pro Gly Gly Asp Thr Ile Ser Ser Cys Pro Ser Ala Ser
                325                 330                 335
Ala Tyr Gly Gly Leu Ala Thr Met Gly Lys Ala Leu Ser Ser Gly Met
                340                 345                 350
Val Leu Val Phe Ser Ile Trp Asn Asp Asn Ser Gln Tyr Met Asn Trp
                355                 360                 365
Leu Asp Ser Gly Asn Ala Gly Pro Cys Ser Ser Thr Glu Gly Asn Pro
                370                 375                 380
Ser Asn Ile Leu Ala Asn Asn Pro Asn Thr His Val Val Phe Ser Asn
385                 390                 395                 400
Ile Arg Trp Gly Asp Ile Gly Ser Thr Thr Asn Ser Thr Ala Pro Pro
                405                 410                 415
Pro Pro Pro Ala Ser Ser Thr Thr Phe Ser Thr Thr Arg Arg Ser Ser
                420                 425                 430
```

Thr Thr Ser Ser Ser Pro Ser Cys Thr Gln Thr His Trp Gly Gln Cys
            435                 440                 445

Gly Gly Ile Gly Tyr Ser Gly Cys Lys Thr Cys Thr Ser Gly Thr Thr
    450                 455                 460

Cys Gln Tyr Ser Asn Asp Tyr Tyr Ser Gln Cys
465                 470                 475

<210> SEQ ID NO 59
<211> LENGTH: 1479
<212> TYPE: DNA
<213> ORGANISM: Trichoderma reesei

<400> SEQUENCE: 59

| | | | | | |
|---|---|---|---|---|---|
| atggtctcct | tcacctccct | gctggccggc | gttgccgcta | tctctggtgt | cctagcagcc | 60 |
| cctgccgcag | aagttgaacc | tgtcgcagtt | gagaaacgtg | aggccgaagc | agaagctgtc | 120 |
| ccattagaag | aaagacaagc | ctgctcctct | gtttggggtc | aatgtggtgg | tcaaaactgg | 180 |
| tctggtccaa | cttgttgtgc | ttccggttct | acctgtgttt | actccaacga | ctactattcc | 240 |
| caatgtttgc | caggtgctgc | ttcctcttcc | tcttcaacta | gagctgcttc | tacaacttct | 300 |
| agggtctccc | caaccacttc | cagatcctct | tctgctactc | caccaccagg | ttctactacc | 360 |
| actagagttc | caccagtcgg | ttccggtact | gctacttact | ctggtaaccc | tttcgtcggt | 420 |
| gttactccat | gggctaacgc | ttactacgct | tctgaagttc | cttctttggc | tatcccatct | 480 |
| ttgactggtg | ctatggctac | cgctgctgct | gctgtcgcca | agttccatc | cttcatgtgg | 540 |
| ttggacacct | tggacaaaac | tccattaatg | aacaaacct | ggcagacat | aaggactgct | 600 |
| aacaagaacg | gcggtaacta | cgctggtcaa | tttgttgtgt | acgacttgcc | agacagagac | 660 |
| tgtgctgctt | tggcttccaa | cggtgaatac | tccatcgctg | acggtggtgt | cgccaagtac | 720 |
| aagaactaca | ttgataccat | tagacaaatc | gttgtcgaat | actctgacat | cagaaccttg | 780 |
| ttagtcatcg | aaccagattc | tttagccaat | ttagtcacca | acttgggtac | tccaaagtgt | 840 |
| gctaacgctc | aatctgccta | cttagaatgt | atcaattatg | cagttaccca | attgaacttg | 900 |
| ccaaacgttg | ctatgtactt | ggacgctggt | cacgccggtt | ggttggggttg | gccagctaac | 960 |
| caagacccag | ccgctcaatt | attcgccaac | gtttacaaga | atgcctcttc | tcctagagcc | 1020 |
| ttgcgtggtt | tggctactaa | cgtcgctaac | tacaacggtt | ggaacatcac | ttctccacca | 1080 |
| tcttacaccc | aaggtaacgc | tgtttacaac | gaaaagttgt | acattcacgc | tatcggtcca | 1140 |
| ttattggcta | accatggttg | gtctaacgcc | ttcttcatca | ccgaccaagg | tagatccggt | 1200 |
| aaacaaccaa | ctggtcaaca | caatggggt | gattggtgta | acgtcatcgg | tactggtttc | 1260 |
| ggtatcagac | catccgctaa | cactggtgat | tccttgttgg | attccttcgt | ctgggttaag | 1320 |
| ccaggtggtg | aatgtgatgg | cacctctgat | tcctctgctc | aagattcga | ttcccactgc | 1380 |
| gccttgccag | acgctttgca | accagcccca | aagctggtg | catggttcca | agcttacttt | 1440 |
| gtccaattgt | tgaccaacgc | taacccatct | ttcttgtaa | | | 1479 |

<210> SEQ ID NO 60
<211> LENGTH: 492
<212> TYPE: PRT
<213> ORGANISM: Trichoderma reesei

<400> SEQUENCE: 60

Met Val Ser Phe Thr Ser Leu Leu Ala Gly Val Ala Ala Ile Ser Gly
1               5                   10                  15

```
Val Leu Ala Ala Pro Ala Ala Glu Val Glu Pro Val Ala Val Glu Lys
         20                  25                  30

Arg Glu Ala Glu Ala Glu Ala Val Pro Leu Glu Arg Gln Ala Cys
         35                  40                  45

Ser Ser Val Trp Gly Gln Cys Gly Gly Gln Asn Trp Ser Gly Pro Thr
50                   55                  60

Cys Cys Ala Ser Gly Ser Thr Cys Val Tyr Ser Asn Asp Tyr Tyr Ser
65                   70                  75                  80

Gln Cys Leu Pro Gly Ala Ala Ser Ser Ser Ser Thr Arg Ala Ala
                 85                  90                  95

Ser Thr Thr Ser Arg Val Ser Pro Thr Thr Ser Arg Ser Ser Ser Ala
             100                 105                 110

Thr Pro Pro Pro Gly Ser Thr Thr Arg Val Pro Pro Val Gly Ser
             115                 120                 125

Gly Thr Ala Thr Tyr Ser Gly Asn Pro Phe Val Gly Val Thr Pro Trp
    130                 135                 140

Ala Asn Ala Tyr Tyr Ala Ser Glu Val Ser Ser Leu Ala Ile Pro Ser
145                 150                 155                 160

Leu Thr Gly Ala Met Ala Thr Ala Ala Ala Val Ala Lys Val Pro
                 165                 170                 175

Ser Phe Met Trp Leu Asp Thr Leu Asp Lys Thr Pro Leu Met Glu Gln
             180                 185                 190

Thr Leu Ala Asp Ile Arg Thr Ala Asn Lys Asn Gly Gly Asn Tyr Ala
         195                 200                 205

Gly Gln Phe Val Val Tyr Asp Leu Pro Asp Arg Asp Cys Ala Ala Leu
    210                 215                 220

Ala Ser Asn Gly Glu Tyr Ser Ile Ala Asp Gly Gly Val Ala Lys Tyr
225                 230                 235                 240

Lys Asn Tyr Ile Asp Thr Ile Arg Gln Ile Val Val Glu Tyr Ser Asp
                 245                 250                 255

Ile Arg Thr Leu Leu Val Ile Glu Pro Asp Ser Leu Ala Asn Leu Val
             260                 265                 270

Thr Asn Leu Gly Thr Pro Lys Cys Ala Asn Ala Gln Ser Ala Tyr Leu
         275                 280                 285

Glu Cys Ile Asn Tyr Ala Val Thr Gln Leu Asn Leu Pro Asn Val Ala
    290                 295                 300

Met Tyr Leu Asp Ala Gly His Ala Gly Trp Leu Gly Trp Pro Ala Asn
305                 310                 315                 320

Gln Asp Pro Ala Ala Gln Leu Phe Ala Asn Val Tyr Lys Asn Ala Ser
                 325                 330                 335

Ser Pro Arg Ala Leu Arg Gly Leu Ala Thr Asn Val Ala Asn Tyr Asn
             340                 345                 350

Gly Trp Asn Ile Thr Ser Pro Pro Ser Tyr Thr Gln Gly Asn Ala Val
         355                 360                 365

Tyr Asn Glu Lys Leu Tyr Ile His Ala Ile Gly Pro Leu Leu Ala Asn
    370                 375                 380

His Gly Trp Ser Asn Ala Phe Phe Ile Thr Asp Gln Gly Arg Ser Gly
385                 390                 395                 400

Lys Gln Pro Thr Gly Gln Gln Trp Gly Asp Trp Cys Asn Val Ile
                 405                 410                 415

Gly Thr Gly Phe Gly Ile Arg Pro Ser Ala Asn Thr Gly Asp Ser Leu
             420                 425                 430

Leu Asp Ser Phe Val Trp Val Lys Pro Gly Gly Glu Cys Asp Gly Thr
```

```
                435                 440                 445
Ser Asp Ser Ser Ala Pro Arg Phe Asp Ser His Cys Ala Leu Pro Asp
            450                 455                 460
Ala Leu Gln Pro Ala Pro Gln Ala Gly Ala Trp Phe Gln Ala Tyr Phe
465                 470                 475                 480
Val Gln Leu Leu Thr Asn Ala Asn Pro Ser Phe Leu
            485                 490

<210> SEQ ID NO 61
<211> LENGTH: 491
<212> TYPE: PRT
<213> ORGANISM: Piromyces equi

<400> SEQUENCE: 61

Met Lys Ala Ser Ile Ala Leu Thr Ala Ile Ala Leu Ala Ala Asn
1               5                   10                  15

Ala Ser Ala Ala Cys Phe Ser Glu Arg Leu Gly Tyr Pro Cys Cys Arg
            20                  25                  30

Gly Asn Glu Val Phe Tyr Thr Asp Asn Asp Gly Asp Trp Gly Val Glu
        35                  40                  45

Asn Gly Asn Trp Cys Gly Ile Gly Gly Ala Ser Ala Thr Thr Cys Trp
    50                  55                  60

Ser Gln Ala Leu Gly Tyr Pro Cys Cys Thr Ser Thr Ser Asp Val Ala
65                  70                  75                  80

Tyr Val Asp Gly Asp Gly Asn Trp Gly Val Glu Asn Gly Asn Trp Cys
                85                  90                  95

Gly Ile Ile Ala Gly Gly Asn Ser Ser Asn Asn Ser Gly Ser Thr
            100                 105                 110

Ile Asn Val Gly Asp Val Thr Ile Gly Asn Gln Tyr Thr His Thr Gly
        115                 120                 125

Asn Pro Phe Ala Gly His Lys Phe Phe Ile Asn Pro Tyr Tyr Thr Ala
    130                 135                 140

Glu Val Asp Gly Ala Ile Ala Gln Ile Ser Asn Ala Ser Leu Arg Ala
145                 150                 155                 160

Lys Ala Glu Lys Met Lys Glu Phe Ser Asn Ala Ile Trp Leu Asp Thr
                165                 170                 175

Ile Lys Asn Met Asn Glu Trp Leu Glu Lys Asn Leu Lys Tyr Ala Leu
            180                 185                 190

Ala Glu Gln Asn Glu Thr Gly Lys Thr Val Leu Thr Val Phe Val Val
        195                 200                 205

Tyr Asp Leu Pro Gly Arg Asp Cys His Ala Leu Ala Ser Asn Gly Glu
    210                 215                 220

Leu Leu Ala Asn Asp Ser Asp Trp Ala Arg Tyr Gln Ser Glu Tyr Ile
225                 230                 235                 240

Asp Val Ile Glu Glu Lys Leu Lys Thr Tyr Lys Ser Gln Pro Val Val
                245                 250                 255

Leu Val Val Glu Pro Asp Ser Leu Ala Asn Met Val Thr Asn Leu Asp
            260                 265                 270

Ser Thr Pro Ala Cys Arg Asp Ser Glu Lys Tyr Tyr Met Asp Gly His
        275                 280                 285

Ala Tyr Leu Ile Lys Lys Leu Gly Val Leu Pro His Val Ala Met Tyr
    290                 295                 300

Leu Asp Ile Gly His Ala Phe Trp Leu Gly Trp Asp Asp Asn Arg Leu
305                 310                 315                 320
```

```
Lys Ala Gly Lys Val Tyr Ser Lys Val Ile Gln Ser Gly Ala Pro Gly
                325                 330                 335

Asn Val Arg Gly Phe Ala Ser Asn Val Ala Asn Tyr Thr Pro Trp Glu
            340                 345                 350

Asp Pro Thr Leu Ser Arg Gly Pro Asp Thr Glu Trp Asn Pro Cys Pro
        355                 360                 365

Asp Glu Lys Arg Tyr Ile Glu Ala Met Tyr Lys Asp Phe Lys Ser Ala
370                 375                 380

Gly Ile Lys Ser Val Tyr Phe Ile Asp Asp Thr Ser Arg Asn Gly His
385                 390                 395                 400

Lys Thr Asp Arg Thr His Pro Gly Glu Trp Cys Asn Gln Thr Gly Val
                405                 410                 415

Gly Ile Gly Ala Arg Pro Gln Ala Asn Pro Ile Ser Gly Met Asp Tyr
            420                 425                 430

Leu Asp Ala Phe Tyr Trp Val Lys Pro Leu Gly Glu Ser Asp Gly Tyr
        435                 440                 445

Ser Asp Thr Thr Ala Val Arg Tyr Asp Gly Tyr Cys Gly His Ala Thr
450                 455                 460

Ala Met Lys Pro Ala Pro Glu Ala Gly Gln Trp Phe Gln Lys His Phe
465                 470                 475                 480

Glu Gln Gly Leu Glu Asn Ala Asn Pro Pro Leu
                485                 490

<210> SEQ ID NO 62
<211> LENGTH: 478
<212> TYPE: PRT
<213> ORGANISM: Piromyces equi

<400> SEQUENCE: 62

Met Phe Lys Gln Ile Gly Ile Thr Ala Leu Leu Val Ala Ser Ala Ser
1               5                   10                  15

Ala Ala Cys Trp Ser Glu Ser Gln Gly Phe Lys Cys Cys Ser Ser Lys
            20                  25                  30

Asn Thr Pro Val Val Tyr Thr Asp Ala Ser Gly Asp Trp Gly Val Glu
        35                  40                  45

Asn Asn Asp Trp Cys Gly Ile Pro Lys Glu Glu Ala Val Thr Cys Phe
    50                  55                  60

Ser Gln Lys Leu Cys Tyr Gly Cys Cys Pro Lys Arg Thr Ala Val Ser
65                  70                  75                  80

Tyr Thr Asp Ala Asp Gly Asp Trp Gly Tyr Ala Asn Gly Asp Trp Cys
                85                  90                  95

Gly Ile Val Ala Glu Glu Lys Pro Thr Cys Trp Ser Glu Ala Leu Gly
            100                 105                 110

Tyr Lys Cys Cys Gln Thr Thr Ser Lys Ile Glu Phe Thr Asp Asn Asp
        115                 120                 125

Gly Asn Trp Gly Phe Glu Asn Gly Asp Trp Cys Gly Leu Gln Lys Val
    130                 135                 140

Ser Gly Arg Thr Thr Thr Thr Arg Arg Thr Thr Thr Thr Arg Arg Thr
145                 150                 155                 160

Thr Thr Thr Thr Arg Arg Thr Thr Thr Thr Arg Lys Val Ser Ala
                165                 170                 175

Thr Tyr Ser Val Val Tyr Glu Thr Gly Lys Lys Leu Asn Ser Gly Phe
            180                 185                 190

Asp Asn Trp Gly Trp Asp Ser Lys Met Ser Phe Lys Asp Asn Ser Leu
        195                 200                 205
```

Val Leu Thr Ala Asp Pro Asp Glu Tyr Gly Ala Ile Ser Leu Lys Asn
    210                 215                 220

Leu Asn Ser Asn Tyr Tyr Gly Lys Gly Gly Cys Ile Tyr Leu Gln Val
225                 230                 235                 240

Lys Thr Glu Thr Glu Gly Leu Val Lys Val Gln Gly Val Arg Gly Tyr
                245                 250                 255

Asp Glu Thr Glu Ala Phe Asn Val Gly Ser Phe Arg Ser Ser Ser Asp
                260                 265                 270

Phe Thr Glu Tyr Lys Phe Glu Val Asp Asp Glu Tyr Gln Phe Asp Arg
            275                 280                 285

Ile Ile Val Gln Asp Gly Pro Ala Ser Asn Ile Pro Ile Tyr Met Arg
        290                 295                 300

Tyr Ile Ile Tyr Ser Thr Gly Ser Cys Asp Asp Phe Asn Pro Pro Val
305                 310                 315                 320

Asp Thr Thr Lys Val Pro Val Thr Thr Thr Lys Lys Ser Asn Val
                325                 330                 335

Arg Ala Thr Tyr Thr Val Ile Phe Lys Asn Ala Ser Gly Leu Pro Asn
                340                 345                 350

Gly Tyr Asp Asn Trp Gly Trp Gly Cys Thr Leu Ser Tyr Gly Gly
            355                 360                 365

Ala Met Ile Ile Asn Pro Gln Glu Gly Lys Tyr Gly Ala Val Ser Leu
        370                 375                 380

Lys Arg Asn Ser Gly Ser Phe Arg Gly Gly Ser Leu Arg Phe Asp Met
385                 390                 395                 400

Lys Asn Glu Gly Lys Val Lys Ile Leu Val Glu Asn Ser Glu Ala Asp
                405                 410                 415

Glu Lys Phe Glu Val Glu Thr Ile Ser Pro Ser Asp Gly Tyr Val Thr
            420                 425                 430

Tyr Ile Leu Asp Val Asp Phe Asp Leu Pro Phe Asp Arg Ile Asp Phe
        435                 440                 445

Gln Asp Ala Pro Gly Asn Gly Asp Arg Ile Trp Ile Lys Asn Leu Val
    450                 455                 460

His Ser Thr Gly Ser Ala Asp Asp Phe Val Asp Pro Ile Asn
465                 470                 475

<210> SEQ ID NO 63
<211> LENGTH: 867
<212> TYPE: PRT
<213> ORGANISM: Piromyces equi

<400> SEQUENCE: 63

Met Lys Ile Gln Asn Ile Leu Val Ala Leu Thr Cys Gly Leu Val Ser
1               5                   10                  15

Gln Val Phe Ala Thr Ser Trp Ser Glu Ala Asp Glu Lys Ala Lys Ser
            20                  25                  30

Phe Met Ser Asp Leu Ser Glu Ser Glu Lys Ile Asp Ile Val Thr Gly
        35                  40                  45

Tyr Met Asn Met Gln Gly Thr Cys Val Gly Asn Ile Lys Pro Leu Asp
    50                  55                  60

Arg Lys Asn Phe Lys Gly Leu Cys Leu Gln Asp Gly Pro Ala Gly Val
65                  70                  75                  80

Arg Phe Asn Gly Gly Thr Ser Thr Thr Trp Gln Ala Gly Ile Asn Asn
                85                  90                  95

Ala Ala Thr Phe Asn Lys Asp Leu Leu Tyr Lys Ile Gly Lys Asp Gln

-continued

```
                100                 105                 110
Gly Ala Glu Phe Tyr Ala Lys Gly Ile Asn Ile Ala Leu Ala Pro Ser
            115                 120                 125
Met Asn Ile Leu Arg Ala Pro Ala Ser Gly Arg Val Trp Glu Asn Phe
        130                 135                 140
Gly Glu Asp Pro Tyr Leu Ser Gly Val Cys Gly Ala Gln Ile Thr Lys
145                 150                 155                 160
Gly Tyr Gln Asp Ser Gly Val Ile Val Ala Ala Lys His Tyr Val Ala
                165                 170                 175
Asn Asp Ile Glu His Asn Arg Glu Ala Ser Ser Asn Met Asp Asp
            180                 185                 190
Gln Thr Leu Met Glu Ile His Val Glu Pro Phe Tyr Arg Thr Ile Lys
        195                 200                 205
Asp Gly Asp Ala Gly Ser Val Met Ala Ser Tyr Asn Ala Val Asn Asn
    210                 215                 220
Ile Tyr Val Val Gln Asn Lys Lys Val Leu Thr Glu Ile Leu Lys Glu
225                 230                 235                 240
Gly Ile Gly Phe Gln Gly Phe Val Met Ser Asp Trp Ala Ile His
                245                 250                 255
Asp Leu Glu Gly Ser Phe Asn Ala Gly Met Asp Met Asn Met Pro Gly
            260                 265                 270
Gly Lys Ala Trp Gly Pro Asp Tyr Val Asn Asn Ser Phe Trp Gly Ser
        275                 280                 285
Asn Ile Ser Asn Ala Ile Arg Ser Gly Gln Val Ser Ser Ser Arg Leu
    290                 295                 300
Asp Asp Ala Val Arg Arg Ile Ile Arg Thr Leu Tyr Arg Phe Asp Gln
305                 310                 315                 320
Met Ser Gly Tyr Pro Asn Val Asn Leu Lys Ala Pro Ser Met His Ala
                325                 330                 335
Asp Thr Asn Arg Gln Ala Ala Ile Glu Ser Ser Val Leu Leu Lys Asn
            340                 345                 350
Ala Asp Asp Ile Leu Pro Leu Thr Lys Lys Tyr Arg Lys Ile Ala Ile
        355                 360                 365
Ile Gly Lys Asp Ala Asp Lys Ala Gln Ser Cys Thr Asp Thr Ala Cys
    370                 375                 380
Ser Gly Asn Ile Ile Gln Gly Trp Gly Ser Gly Thr Thr Asp Phe
385                 390                 395                 400
Thr Gly Ile Ser Asp Pro Ile Thr Ala Ile Lys Asn Arg Ala Ser Lys
                405                 410                 415
Glu Gly Ile Ser Ile Val Ser Ser Ile Ser Asp Ser Ala Asn Glu Gly
            420                 425                 430
Ala Asn Val Ala Lys Asp Ala Asp Val Ala Val Phe Val Arg Ala
        435                 440                 445
Thr Ser Gly Glu Glu Tyr Ile Val Val Asp Asn Asn Lys Gly Asp Arg
    450                 455                 460
Asn Asn Leu Asp Leu Trp His Gly Gly Asn Asp Leu Val Lys Ser Val
465                 470                 475                 480
Ala Ala Val Asn Lys Asn Thr Val Val Ile His Ala Pro Ala Thr
                485                 490                 495
Val Asn Leu Pro Phe Leu Asn Asn Val Lys Ala Ile Ile His Ala Gly
            500                 505                 510
Met Pro Gly Ala Glu Ser Gly Asn Ala Ile Ala Ser Ile Leu Phe Gly
        515                 520                 525
```

Asp Ser Asn Pro Ser Gly His Leu Pro Phe Thr Trp Ala Ala Arg Glu
            530                 535                 540

Asp Tyr Cys Cys Asp Val Ser Tyr Pro Ala Glu Leu Pro His Gly Gly
545                 550                 555                 560

Asn Ser Lys Thr Ala Tyr Asp Tyr Lys Glu Gly Leu Phe Val Gly Tyr
            565                 570                 575

Arg Trp Phe Asp Lys Lys Asn Lys Thr Pro Ile Phe Pro Phe Gly His
            580                 585                 590

Gly Leu Ser Tyr Thr Thr Phe Asp Tyr Ser Asn Leu Ser Val Ser Leu
            595                 600                 605

Lys Lys Ser Gly Thr Gln Val Thr Gly Leu Glu Ala Thr Val Thr Val
            610                 615                 620

Ala Asn Thr Gly Ser Tyr Glu Gly Ala Thr Val Pro Met Leu Phe Leu
625                 630                 635                 640

Gly Phe Pro Ala Val Ser Glu Leu Gly Asp Tyr Pro Val Arg Asn Leu
            645                 650                 655

Lys Ala Phe Glu Lys Val Asn Leu Lys Ala Gly Glu Lys Lys Thr Val
            660                 665                 670

Thr Leu Thr Val Asp Gln His Gly Leu Ser Tyr Tyr Asn Thr Ser Lys
            675                 680                 685

Lys Ser Phe Val Val Pro Thr Gly Gly Glu Phe Thr Val Tyr Val Gly
            690                 695                 700

Lys Ser Ala Gly Asp Leu Pro Leu Lys Lys Ala Ile Lys Asn Thr Gln
705                 710                 715                 720

Gly Thr Asn Glu Ser Ser Ser Val Gly Asp Glu Asn Asn Asn
            725                 730                 735

Pro Asn Asn Asn Ala Asp Cys Ser Val Asn Gly Tyr Lys Cys Cys Ser
            740                 745                 750

Asn Ser Asn Ala Glu Val Val Tyr Thr Asp Gly Asp Gly Asn Trp Gly
            755                 760                 765

Val Glu Asn Gly Gln Trp Cys Ile Ile Lys Glu Gln Gln Gln Gln Gln
            770                 775                 780

Thr Cys Phe Ser Ile Lys Leu Gly Tyr Pro Cys Cys Lys Gly Asn Glu
785                 790                 795                 800

Val Ala Tyr Thr Asp Asn Asp Gly Gln Trp Gly Phe Glu Asn Gly Gln
            805                 810                 815

Trp Cys Gly Ile Ala Thr Ala Thr Ser Gly Ala Gly Gly Cys Pro Tyr
            820                 825                 830

Thr Ser Lys Asn Gly Tyr Pro Val Cys Gln Thr Thr Lys Val Glu
            835                 840                 845

Tyr Val Asp Ser Asp Lys Trp Gly Val Glu Asn Gly Asn Trp Cys Ile
850                 855                 860

Met Cys Asn
865

<210> SEQ ID NO 64
<211> LENGTH: 1714
<212> TYPE: PRT
<213> ORGANISM: Piromyces equi

<400> SEQUENCE: 64

Met Lys Phe Leu Asn Val Leu Ser Ile Thr Gly Leu Ile Ile Val Gly
1               5                   10                  15

Ser Asn Ala Ala Ser Ser Cys Trp Ser Glu Lys Leu Gly Tyr Lys Cys

-continued

```
               20                  25                  30
Cys Glu Gly Asp Lys Val Val Tyr Thr Asp Asn Asp Gly Lys Trp Gly
                35                  40                  45
Val Glu Asn Gln Lys Trp Cys Gly Ile Ile Glu Asn Glu Pro Thr Thr
 50                  55                  60
Ile Val Glu Pro Val Glu Pro Thr Thr Ile Val Glu Pro Val Glu Pro
 65                  70                  75                  80
Ser Thr Thr Val Glu Glu Pro Val Glu Pro Thr Ser Thr Ile Val Glu
                 85                  90                  95
Pro Glu Glu Thr Val Glu Leu Glu Pro Ile Arg Asp Ile Ser Ser Lys
                100                 105                 110
Glu Leu Ile Lys Glu Met Asn Phe Gly Trp Asn Leu Gly Asn Thr Leu
                115                 120                 125
Asp Ala Glu Cys Thr Ser Trp Met Asn Tyr Lys Asp Pro Ile Gly
                130                 135                 140
Ser Glu Thr Cys Trp Gly Asn Pro Lys Thr Thr Glu Asp Met Tyr Lys
145                 150                 155                 160
Ile Leu Met Asp Asn Gln Phe Asn Val Phe Arg Ile Pro Thr Thr Trp
                165                 170                 175
Thr Gly His Ile Gly Glu Ala Pro Asp Tyr Lys Ile Asn Glu Lys Trp
                180                 185                 190
Met Lys Arg Val His Glu Ile Val Asp Tyr Pro Tyr Lys Asn Gly Ala
                195                 200                 205
Phe Val Ile Leu Asn Ile His His Glu Ser Trp Asn His Ala Phe Glu
                210                 215                 220
Glu Thr Val Glu Glu Ala Lys Val Glu Leu Ala Lys Val Trp Ala Gln
225                 230                 235                 240
Ile Ala Glu Glu Phe Lys Asp Tyr Asp Glu His Leu Ile Phe Glu Gly
                245                 250                 255
Gln Asn Glu Pro Arg Lys Asn Asp Thr Pro Val Glu Trp Asn Gly Gly
                260                 265                 270
Asp Gln Glu Gly Trp Asp Val Val Asn Ala Met Asn Ala Val Phe Met
                275                 280                 285
Lys Thr Val Arg Ser Ser Gly Gly Asn Asn Ala Lys Arg His Leu Met
                290                 295                 300
Ile Pro Pro Tyr Ala Ala Ala Cys Asn Lys Asn Ser Phe Asp Asn Phe
305                 310                 315                 320
Asp Phe Pro Glu Asp Asp Lys Val Ile Ala Ser Val His Ala Tyr
                325                 330                 335
Ser Pro Tyr Asn Phe Ala Leu Asn Asn Gly Glu Gly Ala Val Asp Lys
                340                 345                 350
Phe Asp Ala Thr Gly Lys Asn Glu Leu Asp Tyr Asn Leu Gly Leu Ile
                355                 360                 365
Lys Lys Arg Phe Val Ser Lys Gly Ile Pro Val Ile Met Gly Glu Tyr
                370                 375                 380
Gly Ala Met Asn Arg Asp Asn Glu Glu Val Arg Ala Thr Trp Ala Glu
385                 390                 395                 400
Tyr Tyr Met Lys Glu Ile Thr Ala Leu Gly Val Pro Gln Val Trp Trp
                405                 410                 415
Asp Asn Gly Ile Phe Glu Gly Glu Gly Glu Arg Phe Gly Leu Ile Asp
                420                 425                 430
Arg Lys Asn Leu Lys Val Val Tyr Pro Ser Ile Val Ala Ala Leu Gln
                435                 440                 445
```

```
Lys Gly Arg Gly Leu Glu Val Asn Val Leu His Ala Ile Glu Pro Lys
450                 455                 460

Pro Glu Pro Glu Pro Thr Thr Thr Val Val Glu Pro Glu Glu Thr Thr
465                 470                 475                 480

Ala Val Asp Glu Pro Thr Ser Thr Val Glu Pro Thr Gly Asn Ile Arg
                485                 490                 495

Asp Ile Ser Ser Lys Glu Leu Ile Lys Glu Met Asn Phe Gly Trp Asn
                500                 505                 510

Leu Gly Asn Thr Leu Asp Ala Glu Cys Thr Ser Trp Met Asn Tyr Glu
                515                 520                 525

Lys Asp Pro Ile Gly Ser Glu Thr Cys Trp Gly Asn Pro Lys Thr Thr
530                 535                 540

Glu Asp Met Tyr Lys Ile Leu Met Asp Asn Gln Phe Asn Val Phe Arg
545                 550                 555                 560

Ile Pro Thr Thr Trp Thr Gly His Ile Gly Glu Ala Pro Asp Tyr Lys
                565                 570                 575

Ile Asn Glu Lys Trp Met Lys Arg Val His Glu Ile Val Asp Tyr Pro
                580                 585                 590

Tyr Lys Asn Gly Ala Phe Val Ile Leu Asn Ile His His Glu Ser Trp
            595                 600                 605

Asn His Ala Phe Glu Glu Thr Val Glu Glu Ala Lys Val Glu Leu Ala
        610                 615                 620

Lys Val Trp Ala Gln Ile Ala Glu Glu Phe Lys Asp Tyr Asp Glu His
625                 630                 635                 640

Leu Ile Phe Glu Gly Gln Asn Glu Pro Arg Lys Asn Asp Thr Pro Val
                645                 650                 655

Glu Trp Asn Gly Gly Asp Gln Glu Gly Trp Asp Val Val Asn Ala Met
                660                 665                 670

Asn Ala Val Phe Met Lys Thr Val Arg Ser Ser Gly Gly Asn Asn Ala
            675                 680                 685

Lys Arg His Leu Met Ile Pro Pro Tyr Ala Ala Ala Cys Asn Gln Asn
690                 695                 700

Ser Phe Asp His Phe Asp Phe Pro Glu Asp Asp Asp Lys Val Ile Ala
705                 710                 715                 720

Ser Val His Ala Tyr Ser Pro Tyr Asn Phe Ala Leu Asn Asn Gly Glu
                725                 730                 735

Gly Ala Val Asp Lys Phe Asp Ala Thr Gly Lys Asn Glu Leu Asp Tyr
                740                 745                 750

Asn Leu Gly Leu Ile Lys Lys Arg Phe Val Ser Lys Gly Ile Pro Val
            755                 760                 765

Ile Met Gly Glu Tyr Gly Ala Met Asn Arg Asp Asn Glu Glu Glu Arg
770                 775                 780

Ala Thr Trp Ala Glu Tyr Tyr Met Lys Glu Ile Thr Ala Leu Gly Ile
785                 790                 795                 800

Pro Gln Val Trp Trp Asp Asn Gly Ile Phe Glu Gly Glu Gly Glu Arg
                805                 810                 815

Phe Gly Leu Ile Asp Arg Lys Asn Leu Lys Val Val Tyr Pro Ser Ile
                820                 825                 830

Val Ala Ala Leu Gln Lys Gly Arg Gly Leu Glu Val Asn Val Leu His
            835                 840                 845

Ala Ile Glu Pro Glu Pro Thr Thr Val Val Glu Pro Glu Glu Thr
850                 855                 860
```

```
Thr Ala Val Asp Glu Pro Thr Ser Thr Val Glu Pro Thr Gly Asn Ile
865                 870                 875                 880

Arg Asp Ile Ser Ser Lys Lys Leu Ile Lys Glu Met Asn Phe Gly Trp
                885                 890                 895

Asn Leu Gly Asn Thr Leu Asp Ala Glu Cys Thr Ser Trp Met Asn Tyr
                900                 905                 910

Glu Lys Asp Pro Ile Gly Ser Glu Thr Cys Trp Gly Asn Pro Lys Thr
                915                 920                 925

Thr Glu Asp Met Tyr Lys Ile Leu Met Asp Asn Gln Phe Asn Val Phe
                930                 935                 940

Arg Ile Pro Thr Thr Trp Thr Gly His Ile Gly Glu Ala Pro Asp Tyr
945                 950                 955                 960

Lys Ile Asn Glu Lys Trp Met Lys Arg Val His Glu Ile Val Asp Tyr
                965                 970                 975

Pro Tyr Lys Asn Gly Ala Phe Val Ile Leu Asn Ile His His Glu Ser
                980                 985                 990

Trp Asn His Ala Phe Glu Glu Thr Val Glu Glu Ala Lys Val Glu Leu
                995                 1000                1005

Ala Lys Val Trp Ala Gln Ile Ala Glu Glu Phe Lys Asp Tyr Asp
        1010                1015                1020

Glu His Leu Ile Phe Glu Gly Gln Asn Glu Pro Arg Lys Asn Asp
        1025                1030                1035

Thr Pro Val Glu Trp Asn Gly Gly Asp Gln Glu Gly Trp Asp Val
        1040                1045                1050

Val Asn Ala Met Asn Ala Val Phe Met Lys Thr Val Arg Ser Ser
        1055                1060                1065

Gly Gly Asn Asn Ala Lys Arg His Leu Met Ile Pro Pro Tyr Ala
        1070                1075                1080

Ala Ala Cys Asn Lys Asn Ser Phe Asp Asn Phe Asp Phe Pro Glu
        1085                1090                1095

Asp Asp Asp Lys Val Ile Ala Ser Val His Ala Tyr Ser Pro Tyr
        1100                1105                1110

Asn Phe Ala Leu Asn Asn Gly Glu Gly Ala Val Asp Lys Phe Asp
        1115                1120                1125

Ala Thr Gly Lys Asn Glu Leu Asp Tyr Asn Leu Gly Leu Ile Lys
        1130                1135                1140

Lys Arg Phe Val Ser Lys Gly Ile Pro Val Ile Met Gly Glu Tyr
        1145                1150                1155

Gly Ala Met Asn Arg Asp Asn Glu Glu Glu Arg Ala Thr Trp Ala
        1160                1165                1170

Glu Tyr Tyr Met Lys Glu Ile Thr Ala Leu Gly Ile Pro Gln Val
        1175                1180                1185

Trp Trp Asp Asn Gly Ile Phe Glu Gly Glu Gly Glu Arg Phe Gly
        1190                1195                1200

Leu Ile Asp Arg Lys Asn Leu Lys Val Val Tyr Pro Ser Ile Val
        1205                1210                1215

Ala Ala Leu Gln Lys Gly Arg Gly Leu Glu Val Asn Val Leu His
        1220                1225                1230

Ala Ile Glu Pro Lys Pro Glu Pro Glu Pro Thr Thr Thr Val Val
        1235                1240                1245

Glu Pro Glu Glu Thr Thr Ala Val Asp Glu Pro Thr Ser Thr Val
        1250                1255                1260

Glu Pro Thr Gly Asn Ile Arg Asp Ile Ser Ser Lys Glu Leu Ile
```

-continued

```
              1265                1270                1275
Lys Glu Met Asn Phe Gly Trp Asn Leu Gly Asn Thr Leu Asp Ala
        1280                1285                1290
Glu Cys Thr Ser Trp Met Asn Tyr Glu Lys Asp Pro Ile Gly Ser
        1295                1300                1305
Glu Thr Cys Trp Gly Asn Pro Lys Thr Thr Glu Asp Met Tyr Lys
        1310                1315                1320
Ile Leu Met Asp Asn Gln Phe Asn Val Phe Arg Ile Pro Thr Thr
        1325                1330                1335
Trp Thr Gly His Ile Gly Glu Ala Pro Asp Tyr Lys Ile Asn Glu
        1340                1345                1350
Lys Trp Met Lys Arg Val His Glu Ile Val Asp Tyr Pro Tyr Lys
        1355                1360                1365
Asn Gly Ala Phe Val Ile Leu Asn Ile His His Glu Ser Trp Asn
        1370                1375                1380
His Ala Phe Glu Glu Thr Val Glu Glu Ala Lys Val Glu Leu Ala
        1385                1390                1395
Lys Val Trp Ala Gln Ile Ala Glu Glu Phe Lys Asp Tyr Asp Glu
        1400                1405                1410
His Leu Ile Phe Glu Gly Gln Asn Glu Pro Arg Lys Asn Asp Thr
        1415                1420                1425
Pro Val Glu Trp Asn Gly Gly Asp Gln Glu Gly Trp Asp Val Val
        1430                1435                1440
Asn Ala Met Asn Ala Val Phe Met Lys Thr Val Arg Ser Ser Gly
        1445                1450                1455
Gly Asn Asn Ala Lys Arg His Leu Met Ile Pro Pro Tyr Ala Ala
        1460                1465                1470
Ala Cys Asn Lys Asn Ser Phe Asp Asn Phe Asp Phe Pro Glu Asp
        1475                1480                1485
Asp Asp Lys Val Ile Ala Ser Val His Ala Tyr Ser Pro Tyr Asn
        1490                1495                1500
Phe Ala Leu Asn Asn Gly Glu Gly Ala Val Asp Lys Phe Asp Ala
        1505                1510                1515
Thr Gly Lys Asn Glu Leu Asp Tyr Asn Leu Gly Leu Ile Lys Lys
        1520                1525                1530
Arg Phe Val Ser Lys Gly Ile Pro Val Ile Met Gly Glu Tyr Gly
        1535                1540                1545
Ala Met Asn Arg Asp Asn Glu Glu Glu Arg Ala Thr Trp Ala Glu
        1550                1555                1560
Tyr Tyr Met Lys Glu Ile Thr Ala Leu Gly Ile Pro Gln Val Trp
        1565                1570                1575
Trp Asp Asn Gly Val Phe Glu Gly Glu Gly Glu Arg Phe Gly Leu
        1580                1585                1590
Ile Asp Arg Lys Asn Leu Lys Val Val Tyr Pro Ser Ile Val Ala
        1595                1600                1605
Ala Leu Gln Lys Gly Arg Gly Leu Glu Val Asn Val Leu His Ala
        1610                1615                1620
Ile Glu Glu Pro Ala Glu Cys Trp Ala Glu Lys Leu Gly Tyr
        1625                1630                1635
Gln Cys Cys Ser Pro Asn Asn Thr Arg Val Val Val Thr Asp Glu
        1640                1645                1650
Ser Gly Lys Trp Gly Val Glu Asn Ala Asp Trp Cys Gly Ile Ile
        1655                1660                1665
```

```
Glu Thr Lys Asp Lys Cys Trp Ser Ile Pro Tyr Gly Tyr Lys Cys
    1670            1675                1680

Cys Asp His Cys Arg Val Leu Thr Lys Asp Glu Thr Gly Lys Trp
    1685            1690                1695

Gly Glu Met Asn Gly Glu Trp Cys Gly Ile Asp Thr Asn Lys Cys
    1700            1705                1710

Lys

<210> SEQ ID NO 65
<211> LENGTH: 778
<212> TYPE: PRT
<213> ORGANISM: Piromyces equi

<400> SEQUENCE: 65

Met Lys Phe Gln Ser Ile Ile Ser Ala Val Ala Ala Leu Val Ala Pro
1               5                   10                  15

Met Ala Val Gly Ala Lys Ser Gln Asp Tyr Ala Arg His Ile Glu Leu
            20                  25                  30

Ser Leu Leu Phe Tyr Glu Ala Gln Arg Ser Gly Lys Leu Pro Glu Asn
        35                  40                  45

Asn Arg Ile Tyr Trp Arg His Asp Ser Met Leu Asp Ala Gly Ala Asp
50                  55                  60

Asn Lys Val Asp Leu Thr Gly Gly Tyr Tyr Asp Ala Gly Asp Asn Val
65                  70                  75                  80

Lys Phe Asn Phe Pro Gln Ala Ala Ala Leu Thr Leu Leu Ala Trp Ser
                85                  90                  95

Gly Trp Tyr Tyr Ala Asp Gly Tyr Lys Glu Ala Gly Gln Trp Glu Tyr
            100                 105                 110

Ile Leu Asp Ala Val Arg Trp Gly Ala Asp Tyr Phe Val Lys Cys His
        115                 120                 125

Thr Gly Lys Asn Glu Leu Tyr Val Gln Val Gly Lys Gly Ala Thr Asp
    130                 135                 140

His Gly Phe Trp Tyr Pro Pro Glu Tyr Ile Gln Tyr Asp His Pro Ser
145                 150                 155                 160

Tyr Lys Ile Thr Ala Ser Ala Pro Gly Ser Glu Val Ala Gly Asp Thr
                165                 170                 175

Ala Ser Phe Leu Ala Ala Ala Ser Ile Leu Phe Lys Glu Glu Asp Pro
            180                 185                 190

Ser Tyr Ser Ala Asn Leu Leu Lys His Ala Ile Glu Ile Tyr Asp Phe
        195                 200                 205

Ala Asp Ala Tyr Arg Gly Glu Tyr Ile Lys Ala Val Pro Asp Ala Gln
    210                 215                 220

Gly Phe Tyr Ser Asn Trp Ser Gly Tyr Asn Asp Glu Leu Ala Phe Gly
225                 230                 235                 240

Ala Leu Trp Leu Tyr Arg Ala Thr Gly Glu Ser Lys Tyr Met Asp Lys
                245                 250                 255

Phe Ser Lys Ile Ala Asp Ala Ser Tyr Gly Glu Gln Asp Thr Lys Ala
            260                 265                 270

Tyr Gly Thr Cys Thr Gly Pro Ile Ser Trp Asp Asp Lys Arg Pro Gly
        275                 280                 285

Ala Tyr Ile Leu Ala Ala Ile Val Thr Gly Asp Glu Lys Arg Lys Gln
    290                 295                 300

Gln Ala Tyr Trp Tyr Cys Asp Asn Val Leu Thr Gln Pro Arg Thr Pro
305                 310                 315                 320
```

-continued

```
Gly Gly Leu Trp Tyr Asp Ser Asn Leu Ser Lys Trp Ala Ser Asn Arg
            325                 330                 335

Tyr Ala Ser Asn Ala Ala Ala Met Leu Ala Met Phe Ala Asn Tyr Leu
            340                 345                 350

Pro Lys Thr Asp Ser Lys Arg Ser Lys Tyr Val Asp Phe Val Lys Lys
            355                 360                 365

Gln Thr Asp Tyr Ile Leu Gly Asp Asn Pro Met Lys Ile Asn Tyr Val
        370                 375                 380

Val Gly Ala Glu Ala Asn Ser Pro Lys Ala Val His His Arg Ala Ala
385                 390                 395                 400

Ser Gly Thr Tyr Asp Ser Gln Asp Thr Asn Ala Arg Pro Thr Asp Tyr
            405                 410                 415

Asn Ile Phe Thr Leu Trp Gly Ala Leu Ala Gly Gly Pro Gly Pro Lys
            420                 425                 430

Asp Glu Tyr Thr Asp Ser Arg Lys Asn Tyr Glu Met Asn Glu Val Ala
            435                 440                 445

Leu Asp Tyr Asn Ala Ala Phe Gln Thr Asn Leu Ala Phe Leu Val Lys
        450                 455                 460

Glu Gly Tyr Asn Lys Pro Asp Pro Asp Ser Val Lys Val His Asp Arg
465                 470                 475                 480

Ser Phe Pro Lys Lys Ala Asp Thr Pro Asp Ile Thr Val Glu Val Thr
            485                 490                 495

Asp Lys Thr Ile Glu Val Ser Thr Gly Ser Asn Met Met Cys Ser Ser
            500                 505                 510

Trp Cys Val Glu Phe Thr Thr Asp Tyr Lys Ile Glu Ala Val His Asp
            515                 520                 525

Cys Ile Met Tyr Gln Ser Gly Pro Asp Tyr Ile Ile Cys Asn Arg Arg
        530                 535                 540

Glu Ser Asn Phe Leu Asp Gly Lys Gly Thr Pro Gln Val Ile Lys Tyr
545                 550                 555                 560

Gln Gly Ser Asn Gly Gln Gly Pro Leu Thr Ile Asp Glu Ser Val Val
            565                 570                 575

Met Cys Asp Gly Trp His Ala Pro Gln Ser Ser His Lys Pro Met Tyr
            580                 585                 590

Lys Pro Glu Asn Gly Arg Lys Tyr Lys Val Val Gly Ser Gly Gly Val
            595                 600                 605

Gly Asn Thr Thr Pro Leu Phe Glu Gln Ser Glu Cys Trp Pro Ala Phe
            610                 615                 620

Leu Cys Gly Gly Ser Thr Ser Pro Lys Thr Thr Ile Lys Lys Thr
625                 630                 635                 640

Thr Thr Thr Thr Lys Lys Ser Asp Pro Thr Asn Ser Asn Ser Cys Phe
            645                 650                 655

Ser Val Ala Gln Gly Tyr Pro Cys Cys Gly Ala Gly Ile Pro Val Ser
            660                 665                 670

Tyr Glu Asp Asp Ser Gly Gln Trp Gly Ile Glu Asn Gly Asn Trp Cys
            675                 680                 685

Gly Ile Ala Pro Ile Lys Glu Ser Cys Gly Asp Tyr Pro Cys Cys Thr
            690                 695                 700

Gly Cys Asp Val Gln Tyr Thr Asp Asp Lys Lys Trp Gly Val Glu Asn
705                 710                 715                 720

Asn Asn Trp Cys Leu Ile Lys Glu Asp Lys Cys Gln Gly Ser Ser Gly
            725                 730                 735
```

```
Thr Val Thr Cys Thr Gly Gln Asn Leu Gly Tyr Pro Cys Cys Asp Thr
            740                 745                 750

Cys Glu Ala Ile Tyr Thr Asp Glu Ser Gly Lys Trp Gly Ile Lys Asn
        755                 760                 765

Gly Asp Trp Cys Gly Leu Lys Ser Ser Cys
    770                 775

<210> SEQ ID NO 66
<211> LENGTH: 410
<212> TYPE: PRT
<213> ORGANISM: Piromyces equi

<400> SEQUENCE: 66

Met Arg Leu Ala Leu Thr Ser Cys Ile Ala Leu Ala Ala Ser Ile Ala
1               5                   10                  15

Lys Val Ser Ala Ala Cys Trp Ala Gln Ser Gln Gly Tyr Asn Cys Cys
            20                  25                  30

Asn Asn Pro Ser Ser Thr Lys Val Glu Tyr Thr Asp Ala Ser Gly Gln
        35                  40                  45

Trp Gly Val Gln Asn Gly Gln Trp Cys Gly Ile Asp Tyr Ser Tyr Gly
    50                  55                  60

Gln Asn Gln Gly Asn Glu Ser Cys Thr Gly Asn Gly Ser Tyr Pro Cys
65                  70                  75                  80

Cys Asn Thr Cys Gln Ala Thr Tyr Thr Asp Gly Asp Gly Asp Trp Ala
                85                  90                  95

Phe Glu Asn Gly Asn Trp Cys Gly Ile Lys Asn Ser Cys Lys Gln Gln
            100                 105                 110

Pro Gln Asn Asn Asn Gln Cys Thr Gly Asn Gly Ala Tyr Arg Cys Cys
        115                 120                 125

Asn Thr Cys Gln Ala Thr Tyr Thr Asp Asn Glu Gly Lys Trp Ala Phe
    130                 135                 140

Glu Asn Gly Asp Trp Cys Gly Ile Lys Tyr Ser Cys Pro Ser Gln Gln
145                 150                 155                 160

Val Thr Thr Thr Thr Thr Arg Arg Thr Thr Thr Thr Gln Gln Gln
                165                 170                 175

Gln Pro Thr Gly Ser Gly Gly Asn Ser Asn Val Pro Leu Asn Pro Pro
        180                 185                 190

Asp Phe Ser Gly Gln Thr Gly Lys Thr Thr Arg Tyr Trp Asp Cys Cys
    195                 200                 205

Leu Ala Ser Cys Ser Trp Gln Glu Asn Cys Lys Asn Asp Gly Ala Gln
210                 215                 220

Gly Val Val Arg Ser Cys Asn Val Asp Gly Ile Thr Pro Phe Thr Asp
225                 230                 235                 240

Leu Ser Asn Leu Trp Arg Val Lys Ser Gly Cys Asn Gly Gly Ser Val
                245                 250                 255

Tyr Met Cys Asn Asp Gln Gln Pro Trp Ala Ile Asn Asp Asn Val Ala
            260                 265                 270

Tyr Gly Phe Val Ala Ser His Glu Lys Cys Cys Thr Cys Gln Arg Leu
        275                 280                 285

Lys Phe Thr Ser Gly Pro Ile Ala Gly Lys Gln Met Ile Val Gln Thr
    290                 295                 300

Thr Asn Thr Gly Gly Asp Leu Ser Ser Asn His Phe Asp Ile Gln Met
305                 310                 315                 320

Pro Gly Gly Gly Phe Gly Ile Phe Asp Gly Cys Thr Ser Gln Phe Gly
                325                 330                 335
```

```
Gly Ser Tyr Gln Trp Gly Glu Arg Tyr Gly Ile Ser Ser Ala Ser
            340                 345                 350

Gln Cys Ala Asn Leu Pro Pro Gln Leu Lys Ala Gly Cys Glu Trp Arg
        355                 360                 365

Phe Asn Trp Phe Lys Asn Ala Asp Asn Pro Ala Val Val Phe Glu Arg
    370                 375                 380

Val Gln Cys Pro Lys Glu Leu Thr Glu Ile Thr Gly Cys Val Pro Gly
385                 390                 395                 400

Asp Asp Ala Ser Ala Lys Lys Leu Pro Trp
                405                 410

<210> SEQ ID NO 67
<211> LENGTH: 760
<212> TYPE: PRT
<213> ORGANISM: Piromyces equi

<400> SEQUENCE: 67

Met Pro Ser Ile Arg Ser Ser Leu Ala Leu Leu Gly Ala Thr Ala Ala
1               5                   10                  15

Phe Ala Ala Pro Ala Met Arg Lys Arg Tyr Asn Asp Glu Tyr Ala Gln
            20                  25                  30

Arg Val Thr Asp Leu Tyr Asp Thr Met Thr Gly Asn Gly Ser Tyr Ser
        35                  40                  45

Ser Glu Tyr Phe Ser Pro Glu Lys Val Pro Tyr His Ser Val Glu Thr
    50                  55                  60

Leu Met Val Glu Ala Pro Asp Gln Gly His Glu Ser Val Ser Glu Thr
65                  70                  75                  80

Tyr Ser Phe Trp Ile Trp Leu Glu Ala Val Asn Gly Lys Ile Thr Gly
                85                  90                  95

Asn Tyr Asp Gly Val Glu Ala Trp Ser Tyr Leu Glu Lys His Ile
            100                 105                 110

Ile Pro Asp Ser Lys Asn Gln Pro Gly Asn Ser Arg Tyr Asn Pro Ser
        115                 120                 125

Ser Pro Ala Thr Tyr Ala Ala Glu His Asp Glu Ile Tyr Asp Tyr Pro
130                 135                 140

Ser Lys Leu Ile Phe Gln Asp Gly Leu Val Gly Glu Asp Pro Ile Ala
145                 150                 155                 160

Lys Glu Leu Gln Gln Ala Tyr Gly Asn Trp Asp Ile Tyr Ile Met His
            165                 170                 175

Trp Ile Ile Asp Gly Asp Asn Trp Tyr Gly Tyr Gly Gln Gln Gly Asp
        180                 185                 190

Gly Thr Ser Lys Pro Ser Phe Ile Asn Thr Phe Gln Arg Gly Pro Ser
    195                 200                 205

Glu Ser Thr Trp Lys Thr Val Pro His Pro Cys Trp Glu Ala Met Lys
210                 215                 220

Trp Gly Gly Arg Asn Gly Phe Leu Asp Leu Phe Thr Val Asp Asn Ser
225                 230                 235                 240

Tyr Ala Lys Gln Trp Arg Tyr Thr Ala Ala Pro Asp Ala Asp Ala Arg
            245                 250                 255

Ala Ile Gln Ala Ala Tyr Phe Ala Tyr Met Trp Ala Glu Glu Asp Gly
        260                 265                 270

Val Asn Leu Ser Ser Val Ala Ser Lys Ala Ala Lys Leu Gly Asp Tyr
    275                 280                 285

Leu Arg Tyr Ala Gln Tyr Asp Lys Tyr Phe Lys Lys Ile Gly Asn Cys
```

-continued

```
                290                 295                 300
Val Gly Tyr Asp Lys Cys Ser Ala Gly Arg Gly Lys Asn Ser Ala His
305                 310                 315                 320

Tyr Leu Ile Ser Trp Tyr Phe Ala Trp Gly Gly Leu Gln Gly Asp
                325                 330                 335

Trp Ala Trp Arg Ile Gly Ser Ser His Thr His Thr Gly Tyr Gln Asn
                340                 345                 350

Pro Leu Ala Ala Trp Ile Leu Ser Thr Gln Ser Ala Phe Lys Pro Lys
                355                 360                 365

Ser Ser Thr Gly Ala Lys Asp Trp Ala Thr Ser Leu Asp Arg Gln Leu
370                 375                 380

Glu Leu Phe Arg Trp Leu Gln Ser Ala Glu Gly Cys Ile Ala Gly Gly
385                 390                 395                 400

Ala Thr Asn Ser Trp Gln Gly Ala Tyr Glu Gln Pro Ser Ser Asp Ile
                405                 410                 415

Thr Thr Phe Tyr Gly Met Trp Tyr Asp Trp Gln Pro Val Tyr His Asp
                420                 425                 430

Pro Pro Ser Asn Asn Trp Thr Gly Met Gln Gly Trp Gly Met Glu Arg
                435                 440                 445

Val Cys Ser Leu Tyr Tyr Leu Ser Gly Asn Glu Lys Ala Gly Lys Val
                450                 455                 460

Cys Gln Glu Trp Ala Lys Trp Val Lys Asn Thr Thr Arg Val Thr Gly
465                 470                 475                 480

Glu Glu Ile Val His Ala Thr Thr Leu Asp Trp Gly Asn Pro Asp
                485                 490                 495

Glu Trp Asn Ala Ser Asn Phe Asn Lys Ser Asn Leu Asn Arg Ser Leu
                500                 505                 510

His Gly Thr Val Ser Ser Glu Gly Val Asp Leu Gly Thr Ile Ala Ser
                515                 520                 525

Ile Met Lys Gly Leu Met Trp Val Ser Met Lys Asp Asn Asp Gln Glu
                530                 535                 540

Gly Ile Asn Leu Ala Val Gln Val Met Asp Ala Ile Glu Gly Tyr Arg
545                 550                 555                 560

Asp Asn Leu Gly Tyr Ser Ser Leu Glu Ala Arg Gly Asp Tyr Glu Lys
                565                 570                 575

Phe Gly Gly Glu Val Tyr Ile Pro Ser Gly Trp Thr Gly Lys Asn Ala
                580                 585                 590

Gln Gly Ala Asn Leu Lys Asn Gly Val Thr Phe Ile Asp Ile Arg Pro
                595                 600                 605

Lys Tyr Lys Gln Asp Pro Asp Trp Pro Gln Val Glu Glu Phe Leu Asn
610                 615                 620

Gly Gly Asn Pro Pro Glu Phe Asn Tyr His Arg Phe Trp Ala Gln Thr
625                 630                 635                 640

Glu Ile Ala Val Ala Asn Gly Leu Ile Ser Ile Tyr Gly Leu Lys Ser
                645                 650                 655

Thr Gly Gly Ser Ser Pro Ile Tyr Gly Gly Asp Glu Val Thr Glu Cys
                660                 665                 670

Pro Ala Ser Ile Thr Arg Gln Gly Tyr Ser Cys Cys Lys Val Gly Cys
                675                 680                 685

Gln Val Val Tyr Gln Asp Ala Asp Gly Asp Trp Gly Val Glu Asn Asn
                690                 695                 700
```

-continued

```
Asp Trp Cys Gly Cys Gly Lys Ala Pro Ala Pro Lys Pro Lys Cys Pro
705                 710                 715                 720

Thr Ser Ile Thr Asn Gln Gly Tyr Ser Cys Cys Ser Ser Cys Gly Pro
                725                 730                 735

Val Tyr Tyr Gln Asp Ala Asp Gly Asp Trp Gly Val Glu Asn Gly Asp
            740                 745                 750

Trp Cys Gly Met Pro Thr Ser Cys
        755                 760

<210> SEQ ID NO 68
<211> LENGTH: 42
<212> TYPE: PRT
<213> ORGANISM: Artificial
<220> FEATURE:
<223> OTHER INFORMATION: Optimized linker 1

<400> SEQUENCE: 68

Gly Gly Gly Gly Ser Gly Gly Gly Ser Ala Trp His Pro Gln Phe
1               5                   10                  15

Gly Gly Glu Asn Leu Tyr Phe Gln Gly Asp Tyr Lys Asp Asp Asp Lys
            20                  25                  30

Gly Gly Gly Gly Ser Gly Gly Gly Gly Ser
        35                  40

<210> SEQ ID NO 69
<211> LENGTH: 143
<212> TYPE: DNA
<213> ORGANISM: Artificial
<220> FEATURE:
<223> OTHER INFORMATION: Optimized linker 1

<400> SEQUENCE: 69
ggaggaggtg gttcaggagg tggtgggtct gcttggcatc acaatttgga ggaggcggtg       60
gtgaaaatct gtatttccag ggaggcggag gtgattacaa ggatgacgac aaaggaggtg      120
gtggatcagg aggtggtggc tcc                                              143

<210> SEQ ID NO 70
<211> LENGTH: 117
<212> TYPE: DNA
<213> ORGANISM: Artificial
<220> FEATURE:
<223> OTHER INFORMATION: Optimized linker 2

<400> SEQUENCE: 70
ggtggcggtg gatctggagg aggcggttct tggtctcacc cacaatttga aaagggtgga       60
gaaaacttgt actttcaagg cggtggtgga ggttctggcg gaggtggctc cggctca         117
```

YEAST CELLS EXPRESSING AN EXOGENOUS CELLULOSOME AND METHODS OF USING THE SAME

CROSS-REFERENCE TO RELATED APPLICATIONS

The present application is a '371 of International Application No. PCT/US2010/024592, filed Feb. 18, 2010, which claims the benefit of U.S. Provisional Application No. 61/202,352, filed Feb. 20, 2009, the disclosures of which are incorporated herein by reference in their entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful products. Lignocellulosic biomass contains carbohydrate fractions (e.g., cellulose and hemicellulose) that can be converted into ethanol and other products. In order to convert these fractions, the cellulose and hemicellulose must ultimately be converted or hydrolyzed into monosaccharides; this hydrolysis has historically proven to be problematic.

Biologically mediated processes are promising avenues for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two basic strategies: engineering naturally occurring cellulolytic microorganisms to improve product-related properties, such as yield and titer, and engineering non-cellulolytic organisms that exhibit high product yields and titers to express a heterologous cellulase and hemicellulase system enabling cellulose and hemicellulose utilization.

Three major types of enzymatic activities are required for native cellulose degradation: The first type are endoglucanases (1,4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-O-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

Bakers' yeast (*Saccharomyces cerevisiae*) remains the preferred micro-organism for the production of ethanol (Hahn-Hägerdal, B., et al., *Adv. Biochem. Eng. Biotechnol.* 73, 53-84 (2001)). Favorable attributes of this microbe include (i) high productivity at close to theoretical yields (0.51 g ethanol produced/g glucose used), (ii) high osmo- and ethanol tolerance, (iii) natural robustness in industrial processes, (iv) being generally regarded as safe (GRAS) due to its long association with wine and bread making, and beer brewing. Furthermore, *S. cerevisiae* exhibits tolerance to inhibitors commonly found in hydrolyzates resulting from biomass pretreatment.

One major shortcoming of *S. cerevisiae* is its inability to utilize complex polysaccharides such as cellulose, or its break-down products, such as cellobiose and cellodextrins. In attempt to address this problem, several heterologous cellulases from bacterial and fungal sources have been transferred to *S. cerevisiae*, enabling the degradation of cellulosic derivatives (Van Rensburg, P., et al., *Yeast* 14:67-76 (1998)), or growth on cellobiose (Van Rooyen, R., et al., *J. Biotech.* 120:284-295 (2005); McBride, J. E., et al., *Enzyme Microb. Techol.* 37:93-101 (2005)). However current levels of expression and specific activity of cellulases heterologously expressed in yeast are still not sufficient to enable efficient growth and ethanol production by yeast on cellulosic substrates without externally added enzymes. There remains a significant need for improvement in the amount of cellulase activity in order to attain the goal of achieving a consolidated bioprocessing (CBP) system capable of efficiently and cost-effectively converting cellulosic substrates to ethanol or other useful products.

Heterologous cellulase enzymes are usually produced by recombinant organisms in such low concentrations that the amount of saccharified substrate available is unable to sustain growth of the organisms. Cellulase enzymes can be expressed as secreted enzymes that are not purposely attached to the yeast cell wall, resulting in a physical separation of the cellulase enzyme and the cell that made it, or they can be expressed tethered to the cell surface. This covalent linkage to the cell surface may provide benefits due to the ability to select enhanced cellulase secreting organisms in liquid culture, and/or because of the concentration increase of cellulase close to a particular cell. However, tethered cellulase expression suffers from a limited surface area on the cell surface to bind to, and it is not clear whether secreting or tethering cellulase enzymes will ultimately provide better results.

Various cellulase genes have been expressed in *Saccharomyces cerevisiae* and other yeasts with the aim of direct ethanol production from cellulose, including components of both non-complexed and complexed cellulase systems (see comprehensive review in (Gal L., et al., *J. Bacteriol.* 179(21): 6595-601 (1997); van Zyl W. H., et al., *Adv. Biochem. Eng. Biotechnol.* 108:205-35 (2007)). In one such attempt, a rudimentary non-complexed cellulase system consisting of a single endoglucanase and an single beta-glucosidase allowed the yeast to convert phosphoric acid swollen cellulose (PASC) directly to ethanol (Den Haan R., *Metab. Eng.* 9(1): 87-94 (2007)).

Complexed cellulases, or cellulosomes (first described by (Lamed R., et al., *J. Bacteriol.* 156(2):828-36 (1983)), on the other hand, are multi-protein complexes comprised of catalytic component linked via binding domains called "dockerins" to a structural component called a "scaffoldin." This structural protein, which may or may not contain a catalytic domain, often contains a cellulose binding module, in addition to domains called "cohesins," which serve to bind to the dockerins found on the catalytic components. The catalytic components can include cellulases with similar activities to those found in non-complexed cellulase systems, and can also include a wide range of hydrolyzing activities, such as hemicellulase and pectinase activities.

The activity of non-complexed and complexed cellulase systems has rarely been directly compared on a consistent basis. However, specific activity data collected broadly from across the literature indicate that cellulosomes are substantially (~5 to 10 times) more active on a mass basis than non-complexed systems (Lynd L., et al., *Microbiol. Mol. Biol. Rev.* 66:506 (2002)). Additionally, it is well-established that organisms with cellulosomes, like *C. thermocellum*, can grow at relatively high rates on crystalline cellulose, including pretreated lignocellulose (Lynd L., et al., *Microbiol. Mol. Biol. Rev.* 66:506 (2002)). Cellulosomes have been found mainly in anaerobic environments, and largely in bacterial species. However, species of anaerobic fungi that live in the rumen have also been shown to have cellulosomes, with very high cellulase specific activity (Wilson C. A. and Wood T. M., *Appl. Microbiol. Biotechnol.* 37(1):125-9 (1992)).

However, organisms that contain cellulosomes lack the ability to form useful products, such as ethanol, in appreciable quantities. Therefore, there is a need in the art to generate organisms which benefit from the increased cellulolytic capacity of cellulosomes while also having the ability to convert the liberated sugars to useful products, such as ethanol.

Knowledge of complexed cellulase expression in yeast is rudimentary. Production of a scaffoldin in yeast has been accomplished, but simultaneous expression of other necessary components of a cellulosome has not been demonstrated. Additionally, no cellulosome reconstruction has been shown to allow the direct conversion of cellulose to ethanol or other useful products. Constructing cellulosomes in yeast for CBP has a great deal of potential because of the high specific activity of cellulosomes might lead to more efficient production of useful products.

Because heterologous cellulase enzymes are often poorly expressed and secreted by yeast and, because they are the rate limiting factor for cellulose hydrolysis, they need to be expressed as highly as possible. Relative to non-complexed cellulases, as little as a fifth to a tenth of the expression level might be required to achieve similar cellulose hydrolysis rates.

The present invention provides for the heterologous expression of cellulosomes in various microbes as well as methods for their use.

BRIEF DESCRIPTION OF THE INVENTION

The present invention is directed to cellulytic host cells that express an exogenous scaffoldin polypeptide and at least one exogenous polypeptide comprising a dockerin domain. In some embodiments, the host cells of the invention express cellulosome components and are able to produce useful products from biomass.

In particular, in some embodiments, the invention provides a transformed yeast host cell comprising at least one heterologous polynucleotide comprising a nucleic acid encoding a biomass degrading enzyme, and at least one heterologous polynucleotide comprising a nucleic acid encoding a scaffoldin wherein the yeast host cell is capable of producing ethanol when grown using cellulose as a carbon source.

In another embodiment, the invention provides a transformed host cell comprising: (a) at least one heterologous polynucleotide comprising a nucleic acid which encodes an endoglucanase; (b) at least one heterologous polynucleotide comprising a nucleic acid which encodes a β-glucosidase; (c) at least one heterologous polynucleotides comprising a nucleic acid which encodes a first cellobiohydrolase; and (d) at least one heterologous polynucleotides comprising a nucleic acid which encodes a second cellobiohydrolase.

In other embodiments, the invention provides for combinations of two or more biomass degrading activities. In some embodiments, the biomass degrading activities are non-covalently linked to a proximate location via a central scaffoldin protein tethered to the cell surface. One or more of the biomass degrading activities may be linked to the extracellular scaffoldin protein via the interaction of a dockerin domain with a cohesin domain. Scaffoldin proteins of the present invention may have multiple cohesin domains and may therefore link multiple (and different) biomass degrading activities to a proximate location on the extracellular surface. In some embodiments, the scaffoldin can have one, two, three, four, five, six, seven, or eight cohesin domains. In some embodiments, the scaffoldin can have more than eight cohesion domains.

In some embodiments, the invention relates to a cellulosome produced by a cell of the invention. The cellulosomes of the invention contain biomass-degrading activity. In some embodiments, at least one endoglucanase, cellobiohydrolase, or β-glucosidase is fused to a dockerin domain. A dockerin domain can interact and bind with a cohesin domain to form a noncovalent linkage.

In another embodiment, the invention provides a transformed yeast host cell comprising: (a) at least one heterologous polynucleotides comprising a nucleic acid which encodes a cellulase which is an endoglucanase; (b) at least one heterologous polynucleotides comprising a nucleic acid which encodes a cellulase which is a β-glucosidase; (c) at least one heterologous polynucleotides comprising a nucleic acid which encodes a cellulase which is a first cellobiohydrolase; and (d) at least one heterologous polynucleotides comprising a nucleic acid which encodes a cellulase which is a second cellobiohydrolase, wherein at least two of the cellulases are secreted by the cell.

In still another embodiment, the invention provides a co-culture comprising at least two host cells wherein at least one of the host cells comprises a first heterologous polynucleotide comprising a nucleic acid which encodes at least one cellulase containing a dockerin domain and at least one host cell which comprises a heterologous polynucleotide which encodes a cohesin domain.

In some particular embodiments of the invention, the cellulose carbon source is insoluble cellulose, crystalline cellulose, cellulose derived from lignocellulose, hardwood, phosphoric acid swollen cellulose or microcrystalline cellulose.

In some embodiments, the host cells of the invention comprise a heterologous polynucleotide comprising a nucleic acid encoding a first cellobiohydrolase, a polynucleotide comprising a nucleic acid encoding an endoglucanase, a polynucleotide comprising a nucleic acid encoding a β-glucosidase and/or a polynucleotide comprising a nucleic acid encoding a second cellobiohydrolase. The various biomass degrading enzymes can be expressed as fusion proteins containing dockerin domains of the present invention.

DETAILED DESCRIPTION OF THE INVENTION

Figure 1:
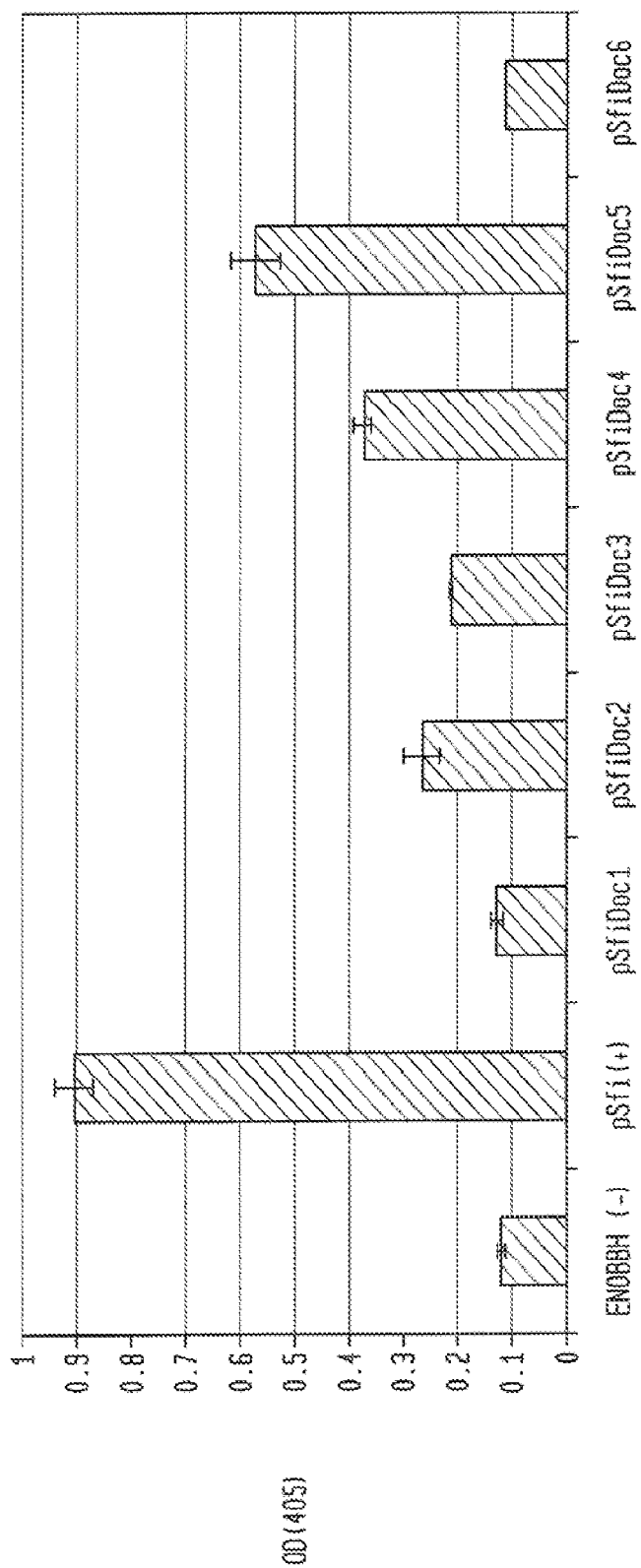
FIG. 1 depicts β-glucosidase activity of all the dockerin containing constructs measured on PNPG. ENOBBH represents a S. cerevisiae Y294 strain containing a plasmid with no expression cassette and represents the negative control strain. pSfi contains the native S.f.bgl1. All strains were cultured in 2×SC-ura buffered at pH 6 for 48 hours.
Figure 2:
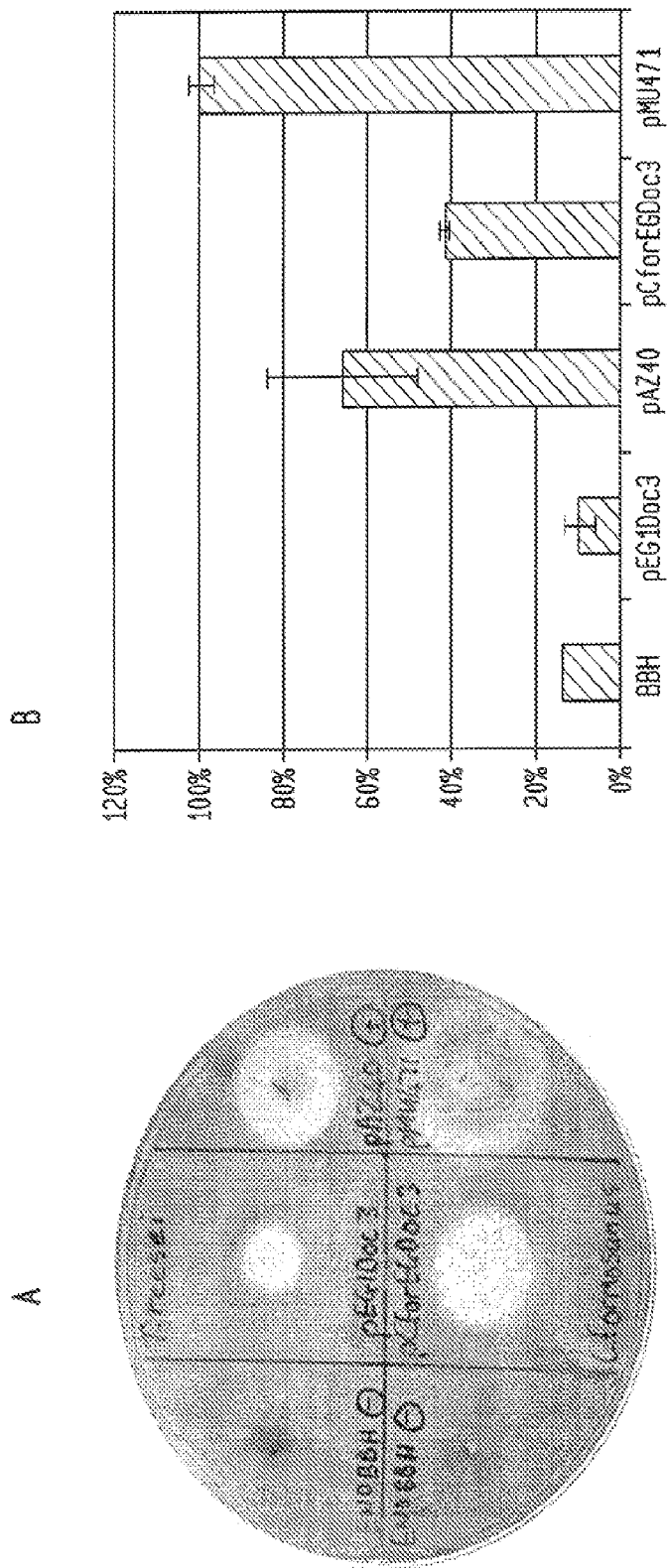
FIG. 2 depicts activity of endoglucanase fusions with dockerin domains on CMC. Panel A shows a plate assay, and panel B gives quantitative results from a liquid assay. pEG1doc3 is the EG1 from T. reesei fused with the dockerin of C. cellulovorans EngB gene. pAZ40 is the native T. reesei EG1 without dockerin. pCforEGDoc3 is the EG from C. formosanus with same dockerin described above, and pMU471 is the C. formosanus EG with no dockerin attached.
Figure 3:
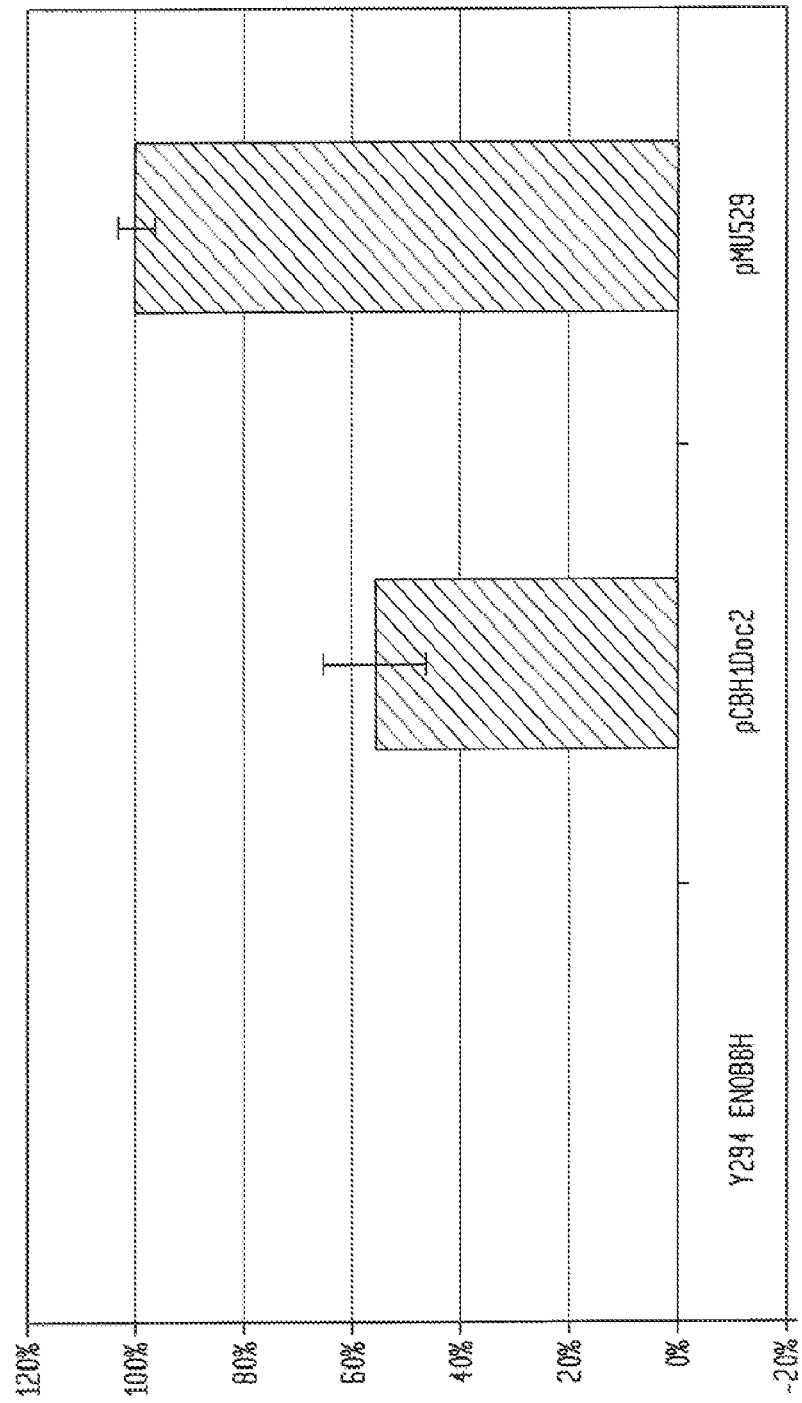
FIG. 3 depicts activity of a T. emersonii fusion with the dockerin from C. cellulolyticum CelA (pCBH1Doc2) on MU-lactoside. Y294 ENOBBH is a non-expressing control strain. pMI529 is a construct with T. emersonii CBH1 with attached C-terminal CBD from T. reesei.
Figure 4:
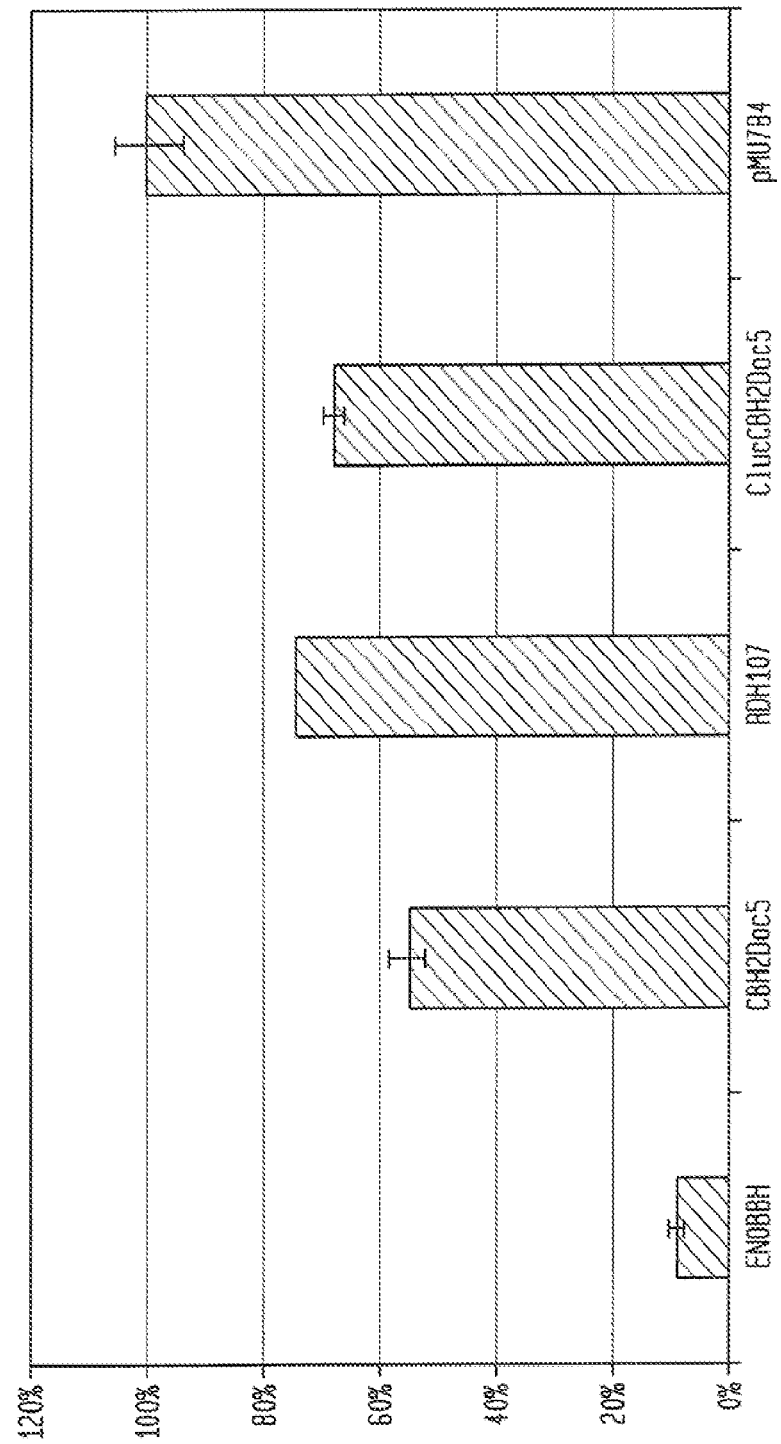
FIG. 4 depicts activity of CBH2 constructs fused with the dockerin from C. thermocellum CelS on avicel. "CBH2Doc5" is the CBH2 from T. reesei fused with the dockerin, while "RDH107" is the CBH2 sequence without a dockerin. "ClucCBH2Doc5" is the CBH2 from C. lucknowense fused to the dockerin, while "pMU784" is the C. lucknowense CBH2 without a dockerin.

The disclosed methods and materials are useful generally in the field of engineered cells for creating useful products from cellulosic materials.

Definitions

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook J., et al., 1989, *Molecular Cloning: A Laboratory Manual,* 2d ed., Cold Spring Harbor Laboratory Press (New York), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and may have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

The polypeptides of the present invention further include variants of the polypeptides. A "variant" of the polypeptide can be a conservative variant, or an allelic variant. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

"Allelic variant" is intended to indicate alternate forms of a gene occupying a given locus on a chromosome of an organism. Genes II, Lewin, B., ed., John Wiley & Sons, New York (1985). Non-naturally occurring variants may be produced using known mutagenesis techniques. Allelic variants, though possessing a slightly different amino acid sequence than those recited above, will still have the same or similar biological functions associated with the H. grisea, T. aurantiacus, T. emersonii, T. reesei, C. lacteus, C. formosanus, N. takasagoensis, C. acinaciformis, M. darwinensis, N. walkeri, S. fibuligera, C. luckowense or R. speratus cellobiohydrolase, endoglucanase or beta-glucosidase protein.

The allelic variants, the conservative substitution variants, and members of the endoglucanase, cellobiohydrolase or β-glucosidase protein families, can have an amino acid sequence having at least 75%, at least 80%, at least 90%, or at least 95% or more amino acid sequence identity with a H. grisea, T. aurantiacus, T. emersonii, T. reesei, C. lacteus, C. formosanus, N. takasagoensis, C. acinaciformis, M. darwinensis, N. walkeri, S. fibuligera, C. luckowense or R. speratus cellobiohydrolase, endoglucanase or beta-glucosidase amino acid sequence. The allelic variants, the conservative substitution variants, and members of the endoglucanase, cellobiohydrolase or β-glucosidase protein families, can have an amino acid sequence having at least 75%, at least 80%, at least 90%, or at least 95% or more amino acid sequence identity with a amino acid sequence set forth in any one of SEQ ID NOs: 6, 8, 10, 12, 14, 16, 18, 26, 28, 30, 32, 34, 36, 38, 54, 56, 58, or 60-67. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the nucleic acids, proteins and peptides of the present invention include molecules comprising the amino acid sequence of SEQ ID NOs: 5-67 or fragments thereof having a consecutive sequence of at least about 3, 4, 5, 6, 10, 15, 20, 25, 30, 35 or more amino acid residues of the H. grisea, T. aurantiacus, T. emersonii, T. reesei, C. lacteus, C. formosanus, N. takasagoensis, C. acinaciformis, M. darwinensis, N walkeri, S. fibuligera, C. luckowense or R. speratus cellobiohydrolase, endoglucanase or beta-glucosidase polypeptide sequences; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to bacterial, fungal, insect, rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the biomass degrading or scaffoldin polypeptides. For instance, one or more amino acids can be deleted from the N-terminus or C-terminus of the secreted protein without substantial loss of biological function.

Thus, the invention further includes *H. grisea, T. aurantiacus, T. emersonii, T reesei, C. lacteus, C. formosanus, N. takasagoensis, C. acinaciformis, M. darwinensis, N walkeri, S. fibuligera, C. luckowense* or *R. speratus* cellobiohydrolase, endoglucanase or beta-glucosidase polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used (Cunningham and Wells, Science 244: 1081-1085 (1989)). The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense* or *R. speratus* cellobiohydrolase, endoglucanase or beta-glucosidase polypeptide, but retaining essential properties thereof. Generally, derivatives and analogs are overall closely similar, and, in many regions, identical to the *H. grisea, T. aurantiacus, T emersonii, T. reesei, C. lacteus, C. formosanus, N. takasagoensis, C. acinaciformis, M darwinensis, N. walkeri, S. fibuligera, C. luckowense* or *R. speratus* cellobiohydrolase, endoglucanase or β-glucosidase polypeptides. The terms "derivative" and "analog" when referring to *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense* or *R. speratus* cellobiohydrolase, endoglucanase or beta-glucosidase polypeptides include any polypeptides which retain at least some of the activity of the corresponding native polypeptide, e.g., the exoglucanase activity, or the activity of the its catalytic domain.

Derivatives of *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense* or *R. speratus* cellobiohydrolase, endoglucanase or beta-glucosidase polypeptides, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins discussed in more detail below.

An analog is another form of a *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense* or *R. speratus* cellobiohydrolase, endoglucanase or beta-glucosidase polypeptide of the present invention. An "analog" also retains substantially the same biological function or activity as the polypeptide of interest, e.g., functions as a cellobiohydrolase. An analog includes a proprotein which can be activated by cleavage of the proprotein portion to produce an active mature polypeptide.

The polypeptide of the present invention may be a recombinant polypeptide, a natural polypeptide or a synthetic polypeptide. In some particular embodiments, the polypeptide is a recombinant polypeptide.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 5-67, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

Host Cells Expressing Heterologous Biomass Degrading Enzymes

In order to address the limitations of the previous systems, the present invention provides host cells expressing heterologous biomass degrading enzymes that can be effectively and efficiently utilized to produce ethanol and other products from cellulosic materials. In some embodiments, the host cells can be a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K lactis, K. marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. The selection of an appropriate host is deemed to be within the scope of those skilled in the art from the teachings herein.

In some embodiments of the present invention, the host cell is an oleaginous cell. According to the present invention, the oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments of the present invention, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells of the invention can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells.

In some particular embodiments of the present invention, the host cell is a *Kluyveromyces* host cell. For example, the *Kluyveromyces* host cell can be a *K. lactis, K. marxianus, K blattae, K phaffii, K. yarrowii K. aestuarii, K. dobzhanskii, K wickerhamii K. thermotolerans*, or *K. waltii* host cell. In one embodiment, the host cell is a *K. lactis*, or *K. marxianus* host cell. In another embodiment, the host cell is a *K. marxianus* host cell.

Host cells are genetically engineered (transduced or transformed or transfected) with the polynucleotides encoding biomass degrading enzymes of this invention which are described in more detail below. The polynucleotides encoding biomass degrading enzymes can be introduced to the host cell on a vector of the invention, which may be, for example, a cloning vector or an expression vector comprising a sequence encoding a heterologous cellulase. The host cells can comprise polynucleotides of the invention as genomically integrated copies or plasmid copies.

In certain aspects, the present invention relates to host cells containing the polynucleotide constructs described below. The host cells of the present invention can express one or more heterologous cellulase polypeptides. In some embodiments, the host cell comprises a combination of polynucleotides that encode heterologous cellulases or fragments, variants or derivatives thereof. The host cell can, for example, comprise multiple copies of the same nucleic acid sequence, for example, to increase expression levels, or the host cell can comprise a combination of unique polynucleotides. In other embodiments, the host cell comprises a single polynucleotide that encodes a heterologous cellulase or a fragment, variant or derivative thereof. In particular, such host cells expressing a single heterologous biomass degrading enzymes can be used in co-culture with other host cells of the invention comprising a polynucleotide that encodes at least one other heterologous biomass degrading enzymes or fragment, variant or derivative thereof.

Introduction of a polynucleotide encoding a heterologous cellulase into a host cell can be performed by methods known in the art. Introduction of polynucleotides encoding heterologous cellulases into, for example yeast host cells, can be effected by lithium acetate transformation, spheroplast transformation, or transformation by electroporation, as described in Current Protocols in Molecular Biology, 13.7.1-13.7.10. Introduction of the construct in other host cells can be effected by calcium phosphate transfection, DEAE-Dextran mediated transfection, or electroporation. (Davis, L., et al., Basic Methods in Molecular Biology, (1986)).

The transformed host cells or cell cultures, as described above, can be examined for endoglucanase, cellobiohydrolase and/or β-glucosidase protein content. For the use of secreted heterologous cellulases, protein content can be determined by analyzing the host (e.g., yeast) cell supernatants. In certain embodiments, high molecular weight material can be recovered from the yeast cell supernatant either by acetone precipitation or by buffering the samples with disposable de-salting cartridges. Proteins, including tethered heterologous scaffoldins or cellulases, can also be recovered and purified from recombinant yeast cell cultures by methods including spheroplast preparation and lysis, cell disruption using glass beads, and cell disruption using liquid nitrogen for example. Additional protein purification methods include ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method or the protein assay method according to BioRad's manufacturer's protocol. Using such methods, the protein content of saccharolytic enzymes can be estimated. Additionally, to accurately measure protein concentration a heterologous cellulase can be expressed with a tag, for example a His-tag or HA-tag and purified by standard methods using, for example, antibodies against the tag, a standard nickel resin purification technique or similar approach.

The transformed host cells or cell cultures, as described above, can be further analyzed for hydrolysis of cellulose (e.g., by a sugar detection assay), for a particular type of cellulase activity (e.g., by measuring the individual endoglucanase, cellobiohydrolase or β glucosidase activity) or for total cellulase activity. Endoglucanase activity can be determined, for example, by measuring an increase of reducing ends in an endoglucanase specific CMC substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase and β-glucosidase, can hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose. Specific activity of cellulases can also be detected by methods known to one of ordinary skill in the art, such as by the Avicel assay (described supra) that would be normalized by protein (cellulase) concentration measured for the sample.

One aspect of the invention is thus related to the efficient production of cellulases to aid in the digestion of cellulose and generation of ethanol. A cellulase can be any enzyme involved in cellulase digestion, metabolism and/or hydrolysis, including an endoglucanase, exogluconase, or β-glucosidase. However, in some embodiments, other enzymatic activities may be useful for incorporation into cellulosomes of the present invention and include xylanase, β-xylosidase, arabinoxylan esterase, pectinase, laccase, amylase, serine protease inhibitor activities (serpins). Suitable enzymatic activities for incorporation into cellulosome of the invention can be found at the website of Carbohydrate-Active enZYmes Database.

In additional embodiments, the transformed host cells or cell cultures are assayed for ethanol production. Ethanol production can be measured by techniques known to one or ordinary skill in the art e.g. by a standard HPLC refractive index method.

Heterologous Scaffoldins

"Scaffoldin" proteins can serve as a backbone of a cellulosome. Many different cellulase and other enzymatic activities can be non-covalently attached to a scaffoldin protein by a cohesin-dockerin domain interaction. In some embodiments, a scaffoldin protein can be derived from a *C. cellulolyticum* scaffoldin. In some embodiments, the scaffoldin can be *C. cellulolyticum* CipC. However, suitable scaffoldin-like proteins can be used and engineered as scaffoldins according to the present invention. In some embodiments, the yeast protein FLO1 can be engineered as a scaffoldin.

According to the present invention and teachings known in the art, any suitable protein can be used as a scaffoldin provided it has an anchoring domain (to maintain the scaffoldin on the cell surface) and one or more protein-protein interaction domains which can create interaction with a biomass-degrading enzyme of the present invention. One or more cohesin domains are found within the scaffoldin protein.

Additionally, in some embodiments scaffoldin proteins can be chimeric proteins taken from two or more species and engineered as fusions to produce a useful scaffoldin backbone of the invention. In some embodiments, the engineered scaffoldin protein can be codon optimized for the host organism. In some embodiments the chimeric scaffoldin protein can comprise the amino acid sequence of SEQ ID NOs: 20, 22, or 24.

"Cohesin" domains are protein domains that have a high affinity for dockerin domains. The cohesion domains can be contained within the scaffoldin protein and the cohesion domains mediate the interaction with dockerin domains.

"Dockerin" domains are protein domains which can be found naturally in some biomass degrading enzymes of the present invention. In some embodiments, the dockerin domains are fused to biomass-degrading enzymes of the present invention and thereby facilitate the interaction of the biomass-degrading enzyme with the scaffoldin by virtue of the dockerin domain-cohesin domain interaction. Because the scaffoldin protein (comprising the cohesion domain(s)) is in turn anchored to the cell surface, the scaffoldin protein can organize the make-up of the cellulosome. It is possible to engineer scaffoldin proteins to contain many or few cohesin domains (or other protein-protein interaction domains) which are able to complex with binding-partner domains fused to proteins containing various enzymatic activities. In some embodiments the dockerin domains comprise the amino acid sequence found in SEQ ID NOs: 28, 30, 32, 34, 36, or 38.

In some embodiments, the cohesin domain and the dockerin domain are selected from known protein interacting domains which may then be fused to the scaffoldin and biomass-degrading enzyme respectively. Known protein interaction domains are available, for example, at the website of Saccharomyces Genome Database, and other databases of known protein-protein interactions. Suitable protein-protein interaction domains may be determined by co-precipitation experiments or yeast two hybrid assays which are standard in the art. In some embodiments the cohesin domains comprise the amino acid sequence found in SEQ ID NOs: 40, 42, 44, 46, 48, or 50.

Typically, the affinity of a particular cohesin domain for a particular dockerin domain is subject to co-evolution within the organism from which the domains are taken. For this reason, it is often advantageous to derive cohesin-dockerin interacting pairs from the same original organism. If a high degree of binding efficiency is desired between a cohesin domain and a dockerin domain of the present invention, it is usually desired that a particular cohesin and dockerin domain pair originate from the same species. However, according to the present invention, the strength of interaction between the binding partners can be modulated by altering the affinity of the two protein-protein interaction domains. For example, in certain embodiments, it may be useful for approximately 70% of a particular cellulase activity to be linked to a cellulosome, but to have approximately 30% of the cellulase activity secreted away from the cell.

Suitable species from which scaffoldin, cohesin, and dockerin domains may be obtained include *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis,*

*Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum* or any suitable cellulose utilizing organism that expresses a cellulosome or components of a cellulosome.

In some embodiments, the scaffoldin protein is derived from *C. cellulolyticum* CipC.

In alternate embodiments, the scaffoldin may have one, two, three, four, five, six, seven, eight, nine, ten, eleven, twelve, thirteen, fourteen, fifteen, or sixteen cohesin domains. Recombinant methods to generate various numbers of cohesins on the scaffoldin are well known in the art.

In some embodiments, the scaffoldin may be derived from endogenous extracellular proteins such as the *S. cerevisiae* FLO1 protein. One or more cohesin domains can be added to the amino acid sequence by methods well known in the art. Indeed any structurally suitable protein can be engineered to be a scaffoldin backbone according to the present invention. Usually a suitable scaffoldin protein will be anchored to the cell wall or cell membrane. In some embodiments, the scaffoldin protein may be fused to a carbohydrate binding module (CBM) or carbohydrate binding module. Suitable CBMs are discussed below.

In some embodiments, the scaffoldin protein can contain a cleavage site to allow the cleavage of the scaffoldin protein away from the cell surface. In this way, the cellulosome can be liberated into the media and separated from the cells. In some embodiments, the cleavage site is a Thrombin cleavage site. The cleavage site can be introduced anywhere along the length of the scaffoldin. In some embodiments, the cleavage site is introduced on the C-terminal side of the first cohesin domain of the scaffoldin.

Heterologous Biomass-degrading Enzymes

According to the present invention the expression of heterologous cellulases in a host cell can be used advantageously to produce products from cellulosic sources. Cellulases from a variety of sources can be heterologously expressed to successfully increase efficiency of product production. For example, the biomass degrading enzymes can be from fungi, bacteria, plant, protozoan or termite sources. In some embodiments, the biomass degrading enzyme is a *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus,* or *Arabidopsis thaliana* cellulase.

In some embodiments of the invention, multiple cellulases from a single organism are co-expressed in the same host cell. In some embodiments of the invention, multiple cellulases from different organisms are co-expressed in the same host cell. In particular, cellulases from two, three, four, five, six, seven, eight, nine or more organisms can be co-expressed in the same host cell. Similarly, the invention can encompass co-cultures of yeast strains, wherein the yeast strains express different cellulases. Co-cultures can include yeast strains expressing heterologous cellulases from the same organisms or from different organisms. Co-cultures can include yeast strains expressing cellulases from two, three, four, five, six, seven, eight, nine or more organisms.

The cellulases of the present invention can be, for example, endoglucanases, β-glucosidases or cellobiohydrolases. Additionally, heterologous xylanases, β-xylosidases, arabinoxylan esterases, pectinases, laccases, amylases, and/or serine protease inhibitors can be optionally expressed and are included within the scope of "biomass degrading enzyme" as used herein.

In some embodiments, the cellulase, endoglucanase, β-glucosidase or cellobiohydrolase is a *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense* or *R. speratus,* endoglucanase, β-glucosidase or cellobiohydrolase.

In some particular embodiments, the cellobiohydrolase is an *H. grisea* CBH1, a *T. aurantiacus* CBH1, a *T. emersonii* CBH1, a *T. reesei* CBH1, a *T. emersonii* CBH2, a *C. lucknowense* CBH2 or a *T. reesei* CBH2. In some embodiments, the heterologous polynucleotide comprising a nucleic acid which encodes a cellulase, encodes a fusion protein comprising a cellobiohydrolase and a carbohydrate binding module (CBM). In some particular embodiments, the CBM is a CBM from *T. reesei* Cbh2, the CBM of *T. reesei* Cbh1 or the CBM from *C. lucknowense* CBH2b. In some particular embodiments, the CBM is fused to the cellobiohydrolase via a linker sequence. In some particular embodiments, the host cell expresses a first and a second cellobiohydrolase, wherein the first cellobiohydrolase is a *T. emersonii* CBH1 and CBM fusion, and the second cellobiohydrolase is a *C. lucknowense* CBH2b.

In other particular embodiments, the β-glucosidase is a *S. fibuligera* β-glucosidase. In another particular embodiment, the endoglucanase is a *C. formosanus* endoglucanase.

In some embodiments of the invention, the nucleic acid encoding a biomass degrading enzymes is codon optimized.

In some embodiments, the host cell can be a thermotolerant host cell. In some embodiments, the host cell is a *Issatchenkia orientalis, Pichia mississippiensis, Pichia mexicana, Pichia farinosa, Clavispora opuntiae, Clavispora lusitaniae, Candida mexicana, Hansenula polymorpha* or *Kluveryomyces* host cell. For example, in some embodiments, the host cell is a *K. lactic* or *K. marxianus* host cell.

In some embodiments, the host cell can be an oleaginous yeast cell. In some particular embodiments, the oleaginous yeast cell is a *Blakeslea, Candida, Cryptococcus, Cunninghamella, Lipomyces, Mortierella, Mucor, Phycomces, Pythium, Rhodosporidium, Rhodotorula, Trichosporon* or *Yarrowia* cell.

In some embodiments, the host cell is a *Saccharomyces cerevisiae* cell.

In some particular embodiments, the host cell can produce ethanol from cellulose at temperatures above about 30° C., 37° C., 42° C., 45° C. or 50° C.

The present invention also provides methods of using the host cells and co-cultures of the invention. For example, the present invention is also directed to a method for hydrolyzing a cellulosic substrate, comprising contacting said cellulosic substrate with a host cell or co-culture of the invention. The invention is also directed to a method of fermenting cellulose comprising culturing a host cell or co-culture of the invention in medium that contains insoluble cellulose under suitable conditions for a period sufficient to allow saccharification and fermentation of the cellulose. In some particular embodiments, the methods further comprise contacting the cellulosic substrate with externally produced cellulase enzymes.

In some particular methods of the invention, the cellulosic substrate is a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

In some particular methods of the invention, the host cell or co-culture produces ethanol. The ethanol can be produced at a rate of at least about 10 mg per hour per liter, at least about 30 mg per hour per liter or at least about 1 g per hour per liter.

In other particular methods of the invention, the host cell or co-cultures contact a cellulosic substance at a temperature of at least about 37° C., least about 42° C., from about 42° C. to about 45° C., or from about 42° C. to about 50° C.

In certain embodiments of the invention, the endoglucanase(s) can be an endoglucanase I or an endoglucanase II isoform, paralogue or orthologue. In some embodiments, the endoglucanase expressed by the host cells of the present invention can be recombinant endo-1,4-β-glucanase. In particular embodiments, the endoglucanase is a *T. reesei, C. lacteus, C. formosanus, N. takasagoensis, C. acinaciformis, M. darwinensis, N. walkeri,* or *R. speratus* endoglucanase. In some embodiments, the endoglucanase comprises an amino acid sequence selected from SEQ ID NOs: 6, 8, 10, 12, 14, 16, 18, 56, 58, and 61-67, as shown below. In certain other embodiments, the endoglucanase comprises an amino acid sequence that is at least about 70, about 80, about 90, about 95, about 96, about 97, about 98, about 99, or 100% identical to an amino acid sequence selected from SEQ ID NOs: 6, 8, 10, 12, 14, 16, 18, 56, 58, and 61-67

As a practical matter, whether any polypeptide is at least 70%, 80%, 85%, 90%, 95%, 96%, 97%, 98%, 99% or 100% identical to a polypeptide of the present invention can be determined conventionally using known computer programs. Methods for determining percent identity, as discussed in more detail below in relation to polynucleotide identity, are also relevant for evaluating polypeptide sequence identity.

In one particular embodiment, the endoglucanase is an endoglucanase I ("eg1") from *Trichoderma reesei*. In certain embodiments, the endoglucanase comprises an amino acid sequence at least about 70, about 80, about 90, about 95, about 96, about 97, about 98, about 99, or 100% identical to SEQ ID NO: 58.

In another particular embodiment, the endoglucanase is an endoglucanase from *C. formosanus*. In certain embodiments, the endoglucanase comprises an amino acid sequence at least about 70, about 80, about 90, about 95, about 96, about 97, about 98, about 99, or 100% identical to SEQ ID NO: 56.

In certain embodiments, the β-glucosidase is a β-glucosidase I or a β-glucosidase II isoform, paralogue or orthologue. In certain embodiments of the present invention the β-glucosidase is derived from *Saccharomycopsis fibuligera*. In particular embodiments, the β-glucosidase comprises an amino acid sequence at least about 70, about 80, about 90, about 95, about 96, about 97, about 98, about 99, or 100% identical to SEQ ID NO:26.

In certain embodiments of the invention, the cellobiohydrolase(s) can be a cellobiohydrolase I and/or a cellobiohydrolase II isoform, paralogue or orthologue. In some particular embodiments, the cellobiohydrolase comprises an amino acid sequence selected from SEQ ID NOs: 6, 8, 10, 12, 14, 16, 18, 52, 54, and 60-67, as shown below. In particular embodiments of the present invention the cellobiohydrolase is a cellobiohydrolase I or II from *Trichoderma reesei*. In other particular embodiments of the present invention the cellobiohydrolase is a cellobiohydrolase I or II from *T. emersonii*. In another embodiment, the cellobiohydrolase comprises a sequence at least about 70, about 80, about 90, about 95, about 96, about 97, about 98, about 99, or 100% identical to SEQ ID NO: 52, 54, or 60.

In another embodiment, the cellobiohydrolase of the invention is a *C. lucknowense* cellobiohydrolase. In a particular embodiment, the cellobiohydrolase is *C. lucknowense* cellobiohydrolase Cbh2b. In one embodiment, the cellobiohydrolase comprises a sequence at least about 70, about 80, about 90, about 95, about 96, about 97, about 98, about 99, or 100% identical to SEQ ID NO: 54.

In some particular embodiments of the invention, the cellulase comprises a sequence selected from the sequences in Table 6 and Table 7 below. The cellulases of the invention also include cellulases that comprise a sequence at least about 70, about 80, about 90, about 95, about 96, about 97, about 98, about 99 or 100% identical to the sequences of Table 6 and Table 7.

Some embodiments of the invention encompass a polypeptide comprising at least 10, 20, 30, 40, 50, 60, 70, 80, 90, 100, 200, 300, 400, or 500 or more consecutive amino acids of any of SEQ ID NOs: 6, 8, 10, 12, 14, 16, 18, 20, 22, 24, 26, 28, 30, 32, 34, 36, 38, 40, 42, 44, 46, 48, 50, 52, 54, 56, 58, and 60-67 or domains, fragments, variants, or derivatives thereof.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, at least about 85%, at least about 90%, at least about 95%, at least about 96%, at least about 97%, at least about 98%, at least about 99% similar to the polypeptide of any of SEQ ID NOs: 6, 8, 10, 12, 14, 16, 18, 20, 22, 24, 26, 28, 30, 32, 34, 36, 38, 40, 42, 44, 46, 48, 50, 52, 54, 56, 58, and 60-67, and to portions of such polypeptide with such portion of the polypeptide generally containing at least 30 amino acids and more preferably at least 50 amino acids.

The present invention also encompasses biomass degrading enzymes which are fused to a dockerin domain. The dockerin domain can be from *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Thermobifida fusca, Orpinomyces* sp. PC-2, *Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum* or any organism that has a suitable dockerin domain. In some embodiments, the cellulases of the invention may be fused to other protein domains which have binding partner domains incorporated into the scaffoldin of the invention. Such pairs of binding partner proteins and protein domains are available from the website of Saccharomyces Genome Database and other resources known to those skilled in the art.

The present invention also encompasses scaffoldin enzymes comprising cohesin domains. The cohesin domain, or any cellulosome component, can be from *Orpinomyces joynii, Neocallimastix frontalis, Anaeromyces mucronatus, Anaeromyces elegans, Trichoderma reesei, Chrysosporium*

*lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Thermobifida fusca, Orpinomyces* sp. PC-2, *Clostridium acetobutylicum, Piromyces equii, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum.* or any organism that has a suitable cohesin domain. In some embodiments, the scaffoldins of the invention may be fused to other protein domains such as carbohydrate binding modules (CBM). The CBM can be derived from any suitable organism and can be at the terminus of the scaffoldin, or anywhere along its length.

In some embodiments, the scaffoldin is CipC from *C. cellulolyticum*.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 6, 8, 10, 12, 14, 16, 18, 20, 22, 24, 26, 28, 30, 32, 34, 36, 38, 40, 42, 44, 46, 48, 50, 52, 54, 56, 58, and 60-67.

Fragments or portions of the polypeptides of the present invention may be employed for producing the corresponding full-length polypeptide by peptide synthesis. Therefore, the fragments may be employed as intermediates for producing the full-length polypeptides.

Fragments of cellobiohydrolase, endoglucanase or beta-glucosidase polypeptides encompass domains, proteolytic fragments, deletion fragments and in particular, fragments of *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense* or *R. speratus* cellobiohydrolase, endoglucanase or beta-glucosidase polypeptides which retain any specific biological activity of the cellobiohydrolase, endoglucanase or beta-glucosidase proteins. Polypeptide fragments further include any portion of the polypeptide which retains a catalytic activity of cellobiohydrolase, endoglucanase or beta-glucosidase proteins.

The variant, derivative or analog of the polypeptide of any of SEQ ID NOs: 6, 8, 10, 12, 14, 16, 18, 20, 22, 24, 26, 28, 30, 32, 34, 36, 38, 40, 42, 44, 46, 48, 50, 52, 54, 56, 58, and 60-67, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

It will be apparent to a person of ordinary skill in the art that if the addition of a particular dockerin domain to a cellulase inhibits the expression, secretion, and/or activity of the biomass-degrading enzyme, the dockerin domain may be substituted for a different dockerin domain and/or a linker sequence may be added to spatially separate the dockerin domain from the biomass degrading enzyme.

Combinations of Biomass-Degrading Enzymes

In many embodiments of the present invention the host cells express a combination of heterologous biomass-degrading enzymes. For example, the host cell can contain at least two heterologous cellulases, at least three heterologous cellulases, at least four heterologous cellulases, at least five heterologous cellulases, at least six heterologous cellulases, at least seven heterologous cellulases, at least eight heterologous cellulases, at least nine heterologous cellulases, at least ten heterologous cellulases, at least eleven heterologous cellulases, at least twelve heterologous cellulases, at least thirteen heterologous cellulases, at least fourteen heterologous cellulases or at least fifteen heterologous cellulases. The heterologous cellulases in the host cell can be from the same or from different species. Additionally, in any of the aforementioned embodiments, the host cells may contain other non-cellulase biomass degrading enzymes such as a xylanase, an acetyl-xylan esterase, a β-xylosidase, an arabinoxylan esterase, a pectinase, a laccase, an amylases, or a serine protease inhibitor.

In some embodiments of the present invention, the host cells express a combination of heterologous cellulases which includes at least one endoglucanase, at least one β-glucosidase and at least one cellobiohydrolase. In another embodiment of the invention, the host cells express a combination of heterologous cellulases which includes at least one endoglucanase, at least one β-glucosidase and at least two cellobiohydrolases. The at least two cellobiohydrolases can be both be cellobiohydrolase I, can both be cellobiohydrolase II, or can be one cellobiohydrolase I and one cellobiohydrolase II.

In one particular embodiment of the invention, the host cells express a combination of cellulases that includes a *C. formosanus* endoglucanase I and an *S. fibuligera* β-glucosidase I. In another embodiment of the invention, the host cells express a combination of cellulases that includes a *T. emersonii* cellobiohydrolase I, and a *T. reesei* cellobiohydrolase II.

In yet another embodiment the host cells express a combination of cellulases that includes a *C. formosanus* endoglucanase I, an *S. fibuligera* β-glucosidase I, a *T. emersonii* cellobiohydrolase I, and a *C. lucknowense* cellobiohydrolase IIb. In still another embodiment, the host cells express a combination of cellulases that includes a *C. formosanus* endoglucanase I, an *S. fibuligera* β-glucosidase I, a *T. emersonii* cellobiohydrolase I, and a *T. reesei* cellobiohydrolase II.

In some embodiments, the cellulases of the invention include cellulases that are derived from *C. cellulolyticum*. In some embodiments, the cellulases of the invention are encoded by *C. cellulolyticum* Cel48, Cel5A, Cel9E, Cel5D, Cel9G, Cel8C, Cel8C, Cel9H, Cel9J, Cel9M, Cel5N, Cel9P, or Cel9Q.

Scaffoldin Anchors

In some embodiments, the tethering of the scaffoldin can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein can be tethered at its amino terminal end or optionally at its carboxy terminal end.

In some embodiments, scaffoldins can be chimeric proteins comprised of suitable cohesin domains arranged on a scaffoldin backbone. In some embodiments, the scaffoldins of the invention comprise the amino acid sequence of SEQ ID NOs: 20, 22, or 24.

Additionally, in some embodiments, scaffoldin anchoring can be accomplished via a dockerin/cohesin interaction which is different in specificity from the other dockerin/cohesins present in the scaffoldin. In this system, a protein separate from the primary scaffoldin is attached to the cell wall of the organism, and contains cohesins, which are bound by a dockerin on the primary scaffoldin.

As used herein, "secreted" means released into the extracellular milieu, for example into the media. Although tethered proteins may have secretion signals as part of their immature amino acid sequence, they are maintained as attached to the cell surface, and do not fall within the scope of secreted proteins as used herein.

As used herein, "flexible linker sequence" refers to an amino acid sequence which links two amino acid sequences, for example, a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and may also facilitate proper folding of the amino acid sequence that contains the desired enzymatic activity.

In some embodiments of the present invention, the tethered cellulase enzymes are tethered by a flexible linker sequence linked to an anchoring domain. In some embodiments, the anchoring domain is of CWP2 (for carboxy terminal anchoring) or FLO1 (for amino terminal anchoring) from *S. cerevisiae*.

In some embodiments, heterologous secretion signals may be added to the expression vectors of the present invention to facilitate the extra-cellular expression of cellulase proteins. In some embodiments, the heterologous secretion signal is the secretion signal from *T. reesei* Xyn2. Scaffoldin proteins can be derived from any suitable source. In some embodiments the scaffoldin protein is derived from *C. cellulolyticum* CipC or *S. cerevisiae* FLO1.

Fusion Proteins Comprising Cellulases

The present invention also encompasses fusion proteins. In general, the fusion proteins can be a fusion of a heterologous biomass degrading enzymes and a dockerin domain. The heterologous biomass degrading enzymes and the second peptide can be fused directly or indirectly, for example, through a linker sequence. The fusion protein can comprise for example, a second peptide that is N-terminal to the heterologous biomass degrading enzyme and/or a second peptide that is C-terminal to the heterologous biomass degrading enzyme. Thus, in certain embodiments, the polypeptide of the present invention comprises a first polypeptide and a second polypeptide, wherein the first polypeptide comprises a heterologous biomass degrading enzyme and the second peptide comprises a dockerin domain.

According to the present invention, the fusion protein can comprise a first and second polypeptide wherein the first polypeptide comprises a heterologous cellulase and the second polypeptide comprises a dockerin domain. According to another embodiment, the fusion protein can comprise a first and second polypeptide, wherein the first polypeptide comprises a heterologous cellulase and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, a MYC-tag, or a fluorescent protein.

According to yet another embodiment, the fusion protein can comprise a scaffoldin and a second polypeptide, wherein the second polypeptide comprises an anchoring peptide. In some embodiments, the anchoring domain is of CWP2 (for carboxy terminal anchoring) or FLO1 (for amino terminal anchoring) from *S. cerevisiae*.

According to yet another embodiment, the fusion protein can comprise a cellulose binding module (CBM). In some embodiments, the CBM is from, for example, *T. reesei* Cbh1 or Cbh2 or from *C. lucknowense* Cbh2b. In some particular embodiments, the CBM is fused to a cellobiohydrolase. In one particular embodiment, the fusion protein comprises a first and second polypeptide, wherein the first polypeptide comprises a heterologous cellobiohydrolase and the second polypeptide comprises a CBM. In yet another particular embodiment, the cellobiohydrolase is *T. emersonii* cellobiohydrolase I and the CBM is a *T. reesei* cellobiohydrolase CBM.

In certain embodiments, the polypeptide of the present invention encompasses a fusion protein comprising a first polypeptide and a second polypeptide, wherein the first polypeptide is a cellobiohydrolase, and the second polypeptide is a domain or fragment of a cellobiohydrolase. In certain embodiments, the polypeptide of the present invention encompasses a fusion protein comprising a first polypeptide, where the first polypeptide is a *T. emersonii* Cbh1, *H. grisea* Cbh1, *T. aurantiacusi* Cbh1, *T. emersonii* Cbh2, *T. reesei* Cbh1 *T. reesei* Cbh2, *C. lucknowense* Cbh2b, *S. fibuligera* Bgl, *C. formosanus* EG, a *C. cellulolyticum* Cel48, Cel5A, Cel9E, Cel5D, Cel9G, Cel8C, Cel8C, Cel9H, Cel9J, Cel9M, Cel5N, Cel9P, or Cel9Q or domain, fragment, variant, or derivative thereof, and a second polypeptide, where the second polypeptide is a *T. emersonii* Cbh1, *H. grisea* Cbh1, or *T. aurantiacusi* Cbh1, *T. emersonii* Cbh2, *T. reesei* Cbh1 or *T. reesei* Cbh2, *C. lucknowense* Cbh2b, *S. fibuligera* Bgl, *C. formosanus* EG, a *C. cellulolyticum* Cel48, Cel5A, Cel9E, Cel5D, Cel9G, Cel8C, Cel8C, Cel9H, Cel9J, Cel9M, Cel5N, Cel9P, or Cel9Q or domain, fragment, variant, or derivative thereof. In particular embodiments the first polypeptide is *T. emersonii* Cbh1 and the second polynucleotide is a CBM from *T. reesei* Cbh1 or Cbh2 or from *C. lucknowense* Cbh2b. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae* or *Kluveromyces*. In particular embodiments, the first polynucleotide is a codon-optimized *T. emersonii* Cbh1 and the second polynucleotide encodes for a codon-optimized CBM from *T. reesei* Cbh1 or Cbh2 fused to a dockerin domain to create a fusion of three polypeptides when the fusion is expressed.

In some embodiments, the polypeptides are fused via a linker sequence. The linker sequence can, in some embodiments, be encoded by a codon-optimized polynucleotide. (Codon-optimized polynucleotides are described in more detail below.) An amino acid sequence corresponding to a codon-optimized linker 1 according to the invention is a flexible linker-strep tag-TEV site-FLAG-flexible linker fusion and corresponds to GGGGSGGGGS AWHPQFGG ENLYFQG DYKDDDK GGGGSGGGGS. (SEQ ID NO: 68)

The DNA sequence is as follows:
ggaggaggtggttcaggaggtg-
gtgggtctgcttggcatcacaatttggaggaggcggtggtgaaaatctgtatttcc
agggaggcggaggtgattacaaggat-
gacgacaaaggaggtggtggatcaggaggtggtggctcc (SEQ ID NO: 69)

An amino acid sequence corresponding to optimized linker 2 is a flexible linker-strep tag-linker-TEV site-flexible linker and corresponds to GGGGSGGGGS WSHPQFEK GG ENLYFQG GGGGSGGGGS. The DNA sequence is as follows: ggtggcggtggatctggaggaggcggt-tcttggtctcacccacaatttgaaaagggtggagaaaacttgtactttcaaggcggtg gtggaggttctggcggaggtggctccggctca (SEQ ID NO: 70)

Co-Cultures

The present invention is also directed to co-cultures comprising at least two yeast host cells wherein at least one yeast host cell comprises an isolated polynucleotide encoding a heterologous biomass degrading enzyme and at least one host cell comprises a polynucleotide encoding a scaffoldin.

As used herein, "co-culture" refers to growing two different strains or species of host cells together in the same vessel. In some embodiments of the invention, at least one host cell of the co-culture comprises a heterologous polynucleotide comprising a nucleic acid which encodes an endoglucanase, and/or a heterologous polynucleotide comprising a nucleic acid which encodes a β-glucosidase, and/or a heterologous polynucleotide comprising a nucleic acid which encodes a cellobiohydrolase, while another host cell of the intention comprises a heterologous polynucleotide comprising a nucleic acid encoding a scaffoldin. In a further embodiment, the co-culture further comprises a host cell comprising a heterologous polynucleotide comprising a nucleic acid which encodes a second cellobiohydrolase.

The co-culture can comprise two or more strains of yeast host cells and the heterologous biomass degrading enzymes can be expressed in any combination in the two or more strains of host cells. For example, according to the present invention, the co-culture can comprise three strains: one strain of host cells that expresses an endoglucanase and a second strain of host cells that expresses a β-glucosidase, a cellobiohydrolase and a second cellobiohydrolase, and a third strain that expresses a scaffoldin. According to the present invention, the co-culture can also comprise five strains: one strain of host cells which expresses an endoglucanase, one strain of host cells that expresses a β-glucosidase, one strain of host cells which expresses a first cellobiohydrolase, one strain of host cells which expresses a second cellobiohydrolase, and a fifth strain which expresses a scaffoldin. Similarly, the co-culture can comprise one strain of host cells that expresses two cellulases, for example an endoglucanase and a beta-glucosidase and a second strain of host cells that expresses one or more cellulases, for example one or more cellobiohydrolases. The co-culture can, in addition to the at least two host cells comprising heterologous cellulases, also include other host cells which do not comprise heterologous cellulases.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells may be present in equal or unequal numbers.

The co-cultures of the present invention can include tethered cellulases, secreted cellulases or both tethered and secreted cellulases. For example, in some embodiments of the invention, the co-culture comprises at least one yeast host cell comprising a polynucleotide encoding a secreted heterologous cellulase fused to a dockerin domain. In another embodiment, the co-culture comprises at least one yeast host cell comprising a polynucleotide encoding a tethered heterologous cellulase. In addition, other cellulases, such as externally added cellulases may be present in the culture.

Polynucleotides Encoding Heterologous Biomass-Degrading Activities

The present invention also includes isolated polynucleotides encoding biomass-degrading activities of the present invention. Thus, the polynucleotides of the invention can encode endoglucanases or exoglucanases, β-glucosidases or cellobiohydrolases, xylanase, β-xylosidases, arabinoxylan esterases, pectinases, laccases, amylases, or serine protease inhibitors. The polynucleotides of the invention also include polynucleotides encoding scaffoldin and cohesin domains.

The present invention also encompasses an isolated polynucleotide comprising a nucleic acid that is at least about 70%, 75%, or 80% identical, at least about 90% to about 95% identical, or at least about 96%, 97%, 98%, 99% or 100% identical to a nucleic acid encoding a *T. emersonii*, *H. grisea*, *T. aurantiacus*, *C. lucknowense* or *T. reesei* Cbh1 or Cbh2 domain, as described above.

The present invention also encompasses variants of the cellulase genes, as described above. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *H. grisea*, *T. aurantiacus*, *T. emersonii*, *T. reesei*, *C. lacteus*, *C. formosanus*, *N. takasagoensis*, *C. acinaciformis*, *M. darwinensis*, *N. walkeri*, *S. fibuligera*, *C. luckowense* and *R. speratus* cellulase polynucleotide variants can be produced for a variety of reasons, e.g., to optimize codon expression for a particular host. Codon-optimized polynucleotides of the present invention are discussed further below.

The present invention also encompasses an isolated polynucleotide encoding a fusion protein. In certain embodiments, the nucleic acid encoding a fusion protein comprises a first polynucleotide encoding for a *T. emersonii* cbh1, *H. grisea* cbh1, *T. aurantiacusi* cbh1 or *T. emersonii* cbh1 and a second polynucleotide encoding for the CBM domain of *T. reesei* cbh1 or *T. reesei* cbh2 or *C. lucknowense* cbh2b. In particular embodiments of the nucleic acid encoding a fusion protein, the first polynucleotide encodes *T. emersonii* cbh1 and the second polynucleotide encodes for a CBM from *T. reesei* Cbh1 or Cbh2.

In further embodiments, the first and second polynucleotides are in the same orientation, or the second polynucleotide is in the reverse orientation of the first polynucleotide. In additional embodiments, the first polynucleotide encodes a polypeptide that is either N-terminal or C-terminal to the polypeptide encoded by the second polynucleotide. In certain other embodiments, the first polynucleotide and/or the second polynucleotide are encoded by codon-optimized polynucleotides, for example, polynucleotides codon-optimized for *S. cerevisiae*, *Kluyveromyces* or for both *S. cerevisiae* and *Kluyveromyces*. In particular embodiments of the nucleic acid encoding a fusion protein, the first polynucleotide is a codon-optimized *T. emersonii* cbh1 and the second polynucleotide encodes for a codon-optimized CBM from *T. reesei* Cbh1 or Cbh2.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 5-67, using information from the sequences disclosed herein. For example, allelic variants and/or species homologs may be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of any of SEQ ID NOs: 5-67, or any fragment, domain, or corresponding amino acid sequence specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, and 59, or domains, fragments, variants, or derivatives thereof.

The polynucleotide of the present invention may be in the form of RNA or in the foam of DNA, which DNA includes cDNA, genomic DNA, and synthetic DNA. The DNA may be double stranded or single-stranded, and if single stranded can be the coding strand or non-coding (anti-sense) strand. The coding sequence which encodes the mature polypeptide can be identical to the coding sequence encoding SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, or 59, or may be a different coding sequence which coding sequence, as a result of the redundancy or degeneracy of the genetic code, encodes the same mature polypeptide as the DNA of any one of SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, and 59.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 6, 8, 10, 12, 14, 16, 18, 20, 22, 24, 26, 28, 30, 32, 34, 36, 38, 54, 56, 58, or 60-67.

The polynucleotide encoding for the mature polypeptide of SEQ ID NOs: 6, 8, 10, 12, 14, 16, 18, 20, 22, 24, 26, 28, 30, 32, 34, 36, 38, 54, 56, 58, or 60-67 may include: only the coding sequence for the mature polypeptide; the coding sequence of any domain of the mature polypeptide; and the coding sequence for the mature polypeptide (or domain-encoding sequence) together with non coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least about 90%, 95%, 96%, 97%, 98% or 99% identical to the nucleic acid sequences disclosed herein, encode a polypeptide having cellobiohydrolase ("Cbh"), endoglucanase ("Eg") or beta-gluconase ("Bgl") functional activity. By "a polypeptide having Cbh, Eg or Bgl functional activity" is intended polypeptides exhibiting activity similar, but not necessarily identical, to a functional activity of the Cbh, Eg or Bgl polypeptides of the present invention, as measured, for example, in a particular biological assay. For example, a Cbh, Eg or Bgl functional activity can routinely be measured by determining the ability of a Cbh, Eg or Bgl polypeptide to hydrolyze cellulose, or by measuring the level of Cbh, Eg or Bgl activity. Standard methods of measuring cellulase activity are well known in the art. For example, dinitrosalicylic acid assays may be employed to quantify the release of reducing ends of sugars liberated by the cellulases of the invention and thereby measure the efficacy of the particular enzyme being examined.

Of course, due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs: 5, 7, 9, 11, 13, 15, 17, 19, 21, 23, 25, 55, 57, or 59 or fragments thereof, will encode polypeptides having Cbh, Eg or Bgl functional activity. In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Cbh, Eg or Bgl functional activity.

The polynucleotides of the present invention also comprise nucleic acids encoding a H. grisea, T. aurantiacus, T. emersonii, T. reesei, C. lacteus, C. formosanus, N takasagoensis, C. acinaciformis, M. darwinensis, N. walkeri, S. fibuligera, C. luckowense or R. speratus cellulase, or domain, fragment, variant, or derivative thereof, fused to a polynucleotide encoding a marker sequence which allows for detection of the polynucleotide of the present invention. In one embodiment of the invention, expression of the marker is independent from expression of the cellulase. The marker sequence may be a yeast selectable marker selected from the group consisting of URA3, HIS3, LEU2, TRP1, LYS2 or ADE2 (Casey, G. P. et al., *J. Inst. Brew.* 94:93-97 (1988)).

Codon Optimized Polynucleotides

According to one embodiment of the invention, the polynucleotides encoding heterologous cellulases can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F)<br>TTC Phe (F)<br>TTA Leu (L)<br>TTG Leu (L) | TCT Ser (S)<br>TCC Ser (S)<br>TCA Ser (S)<br>TCG Ser (S) | TAT Tyr (Y)<br>TAC Tyr (Y)<br>TAA Ter<br>TAG Ter | TGT Cys (C)<br>TGC Cys (C)<br>TGA Ter<br>TGG Trp (W) |
| C | CTT Leu (L)<br>CTC Leu (L)<br>CTA Leu (L)<br>CTG Leu (L) | CCT Pro (P)<br>CCC Pro (P)<br>CCA Pro (P)<br>CCG Pro (P) | CAT His (H)<br>CAC His (H)<br>CAA Gln (Q)<br>CAG Gln (Q) | CGT Arg (R)<br>CGC Arg (R)<br>CGA Arg (R)<br>CGG Arg (R) |
| A | ATT Ile (I)<br>ATC Ile (I)<br>ATA Ile (I)<br>ATG Met (M) | ACT Thr (T)<br>ACC Thr (T)<br>ACA Thr (T)<br>ACG Thr (T) | AAT Asn (N)<br>AAC Asn (N)<br>AAA Lys (K)<br>AAG Lys (K) | AGT Ser (S)<br>AGC Ser (S)<br>AGA Arg (R)<br>AGG Arg (R) |
| G | GTT Val (V)<br>GTC Val (V)<br>GTA Val (V)<br>GTG Val (V) | GCT Ala (A)<br>GCC Ala (A)<br>GCA Ala (A)<br>GCG Ala (A) | GAT Asp (D)<br>GAC Asp (D)<br>GAA Glu (E)<br>GAG Glu (E) | GGT Gly (G)<br>GGC Gly (G)<br>GGA Gly (G)<br>GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the web site of the University of Maryland, Baltimore County (visited May 7, 2008) or at the website of the Kazusa DNA Research Institute (visited Mar. 20, 2008), and these tables can be adapted in a number of ways. See Nakamura, Y., et al., *Nucl. Acids Res.* 28:292 (2000). Codon usage tables for yeast, calculated from GenBank Release 128.0[15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Total | | | |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |
| Total | | | |
| Met | AUG | 136805 | 20.9 |
| Total | | | |
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |

TABLE 2-continued

Codon Usage Table for *Saccharomyces cerevisiae* Genes

| Amino Acid | Codon | Number | Frequency per hundred |
|---|---|---|---|
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, WI, the backtranslation function in the VectorNT1 Suite, available from InforMax, Inc., Bethesda, MD, and the "backtranslate" function in the GCG- Wisconsin Package, available from Accelrys, Inc., San Diego, CA. In addition, various resources are publicly available to codon-optimize coding region sequences, e.g., the "backtranslation" function at the website of Entelechon (visited Apr. 15, 2008) and the "backtranseq" function available at the website of bioinformatics at PBI of the National Research Council Canada (visited My 9, 2002). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae* or *Kluveromyces*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be, for example, versions encoding a cellobiohydrolase, endoglucanase, beta-glucosidase, scaffoldin, or cohesin from *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reti-* culitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens, and Fervidobacterium islandicum or domains, fragments, variants, chimeras, or derivatives thereof.

Codon optimization is carried out for a particular species by methods described herein, for example, *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum*. In certain embodiments, codon-optimized coding regions encoding polypeptides of cellulases, scaffoldins, or cohesins, or domains, fragments, variants, chimeras or derivatives thereof are optimized according to yeast codon usage, e.g., *Saccharomyces cerevisiae, Kluyveromyces lactis* and/or *Kluyveromyces marxianus*. Also provided are polynucleotides, vectors, and other expression constructs comprising codon-optimized coding regions encoding polypeptides of *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum* cellulases or domains, fragments, variants, chimeras or derivatives thereof, and various methods of using such polynucleotides, vectors and other expression constructs.

In certain embodiments described herein, a codon-optimized coding region encoding any of SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, or 59 or domain, fragment, variant, or derivative thereof, is optimized according to codon usage in yeast (*Saccharomyces cerevisiae, Kluyveromyces lactis* or *Kluyveromyces marxianus*). In some embodiments, the sequences are codon-optimized specifically for expression in *Saccharomyces cerevisiae*. In some embodiments, the sequences are codon-optimized for expression in *Kluyveromyces*. In some embodiments, a sequence is simultaneously codon-optimized for optimal expression in both *Saccharomyces cerevisiae* and in *Kluyveromyces*. Alternatively, a codon-optimized coding region encoding any of SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, or 59 can be optimized according to codon usage in any plant, animal, or microbial species.

Vectors and Methods of Using Vectors in Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a linear polynucleotide fragment, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

| Gene | Organism | Systematic name | Reason for use/benefits |
| --- | --- | --- | --- |
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

Additionally, promoter sequences from stress and starvation response genes are useful in the present invention. In some embodiments, promoter regions from the *S. cerevisiae* genes GAC1, GET3, GLC7, GSHJ, GSH2, HSF1, HSP12, LCB5, LRE1, LSP1, NBP2, PIL1, PIM1, SGT2, SLG1, WHI2, WSC2, WSC3, WSC4, YAP1, YDC1, HSP104, HSP26, ENA1, MSN2, MSN4, SIP2, SIP4, SIP5, DPL1, IRS4, KOG1, PEP4, HAP4, PRB1, TAX4, ZPR1, ATG1, ATG2, ATG10. ATG11, ATG12, ATG13, ATG14, ATG15, ATG16, ATG17, ATG18, and ATG19 can be used. Any suitable promoter to drive gene expression in the host cells of the invention can be used. Additionally the *E. coli*, lac or trp, and other promoters known to control expression of genes in prokaryotic or lower eukaryotic cells can be used.

In addition, the expression vectors can contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in *E. coli*.

The expression vector can also contain a ribosome binding site for translation initiation and/or a transcription terminator. The vector may also include appropriate sequences for amplifying expression, or may include additional regulatory regions.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a host cell as described elsewhere in the application. The host cell can be, for example, a lower eukaryotic cell, such as a yeast cell, e.g., *Saccharomyces cerevisiae* or *Kluyveromyces*, or the host cell can be a prokaryotic cell, such as a bacterial cell.

Representative examples of appropriate hosts include: bacterial cells, such as *E. coli, Streptomyces, Salmonella typhimurium*; thermophilic or mesophlic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is selected from the group consisting of *Saccharomyces cerevisiae, Kluyveromyces lactis, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schwanniomyces occidentalis, Issatchenkia orientalis, Kluyveromyces marxianus, Blakeslea, Candida, Cryptococcus, Cunninghamella, Lipomyces, Mortierella, Mucor, Phycomces, Pythium, Rhodosporidium, Rhodotorula, Trichosporon* and *Yarrowia*.

Methods of Using Host Cells to Produce Useful Products

The present invention is also directed to use of host cells and co-cultures to produce useful products from cellulosic substrates. Such methods can be accomplished, for example, by contacting a cellulosic substrate with a host cell or a co-culture of the present invention. Useful products of the present invention include ethanol, lactic acid, acetic acid, triglycerides and other metabolic products of microbes of the invention.

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a host cell of the invention. In some embodiments, the invention is directed to a method for hydrolyzing a cellulosic substrate, for example a cellulosic substrate as described above, by contacting the cellulosic substrate with a co-culture comprising yeast cells expressing heterologous cellulases.

In some embodiments, the invention is directed to a method for fermenting cellulose. Such methods can be accomplished, for example, by culturing a host cell or co-culture in a medium that contains insoluble cellulose to allow saccharification and fermentation of the cellulose.

The production of ethanol can, according to the present invention, be performed at temperatures of at least about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a cellulosic substrate with a host cell or co-culture of the invention and additionally contacting the cellulosic substrate with externally produced cellulase enzymes. Exemplary externally produced cellulase enzymes are commercially available and are known to those of skill in the art.

Therefore, the invention is also directed to methods of reducing the amount of externally produced cellulase enzymes required to produce a given amount of ethanol from cellulose comprising contacting the cellulose with externally produced cellulases and with a host cell or co-culture of the invention. In some embodiments, the same amount of ethanol production can be achieved using at least about 5%, 10%, 15%, 20%, 25%, 30%, or 50% less externally produced cellulases. In some embodiments, no externally produced enzymes are required for a host cell of the invention to achieve a substantially similar rate of ethanol production as compared to a non-cellulosome-producing host cell using externally produced cellulases.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter more than a control strain (lacking heterologous biomass degrading enzymes) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

The following embodiments of the invention will now be described in more detail by way of these non-limiting examples.

EXAMPLES

Example 1

Media and Strain Cultivation

TOP10 *Escherichia coli* cells (Invitrogen) were used for plasmid transformation and propagation. Cells were grown in LB medium (5 g/L yeast extract, 5 g/L NaCl, 10 g/L tryptone) supplemented with ampicillin (100 mg/L) or kanamycin (50 mg/L). 15 g/L agar was added when solid media was desired.

Yeast strains, were routinely grown in YPD (10 g/L yeast extract, 20 g/L peptone, 20 g/L glucose), or YNB+glucose (6.7 g/L Yeast Nitrogen Base without amino acids, and supplemented with appropriate amino acids for strain, 20 g/L glucose) media, using G418 (250 mg/L unless specified) or zeocin (20 mg/L unless specified), or Nourseothricin sulfate (100 mg/L unless specified) for selection. 15 g/L agar was added for solid media.

Molecular Methods

Standard protocols were followed for DNA manipulations (Sambrook J., et al., 1989, *Molecular cloning: A Laboratory Manual*, 2d ed., Cold Spring Harbor Laboratory Press (New York)). PCR was performed using Phusion polymerase (New England Biolabs) for cloning, and Taq polymerase (New England Biolabs) for screening transformants. Manufacturers guidelines were followed as supplied. Restriction enzymes were purchased from New England Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA. Sequencing was performed by the Molecular Biology Core Facility at Dartmouth College. Yeast mediated ligation (YML) was used to create some constructs (Ma H., et al., *Gene,* 58(2-3):201-16 (1987)). This was done by creating DNA fragments to be cloned with 20-40 bp of homology with the other pieces to be combined and/or the backbone vector. A backbone vector, pMU451, able to replicate in yeast using the 2-micron origin of replication, having the Ura3 gene for selection, and with the ENO1 promoter and terminator for constitutive expression of recombinant genes, was then transformed into yeast by standard methods with the target sequences for cloning. Transformed yeast recombine these fragments to form a whole construct and the result plasmid allows selection on media without uracil. In some cases, an additional construct for disrupting the fur1 locus of *S. cerevisiae* with selection using the Clonat marker was co-transformed with the fragments to be cloned, or with intact plasmids. This allowed selection on YPD media with Nourseothricin sulfate (100 mg/L) for direct selection of strains with intact 2-micron plasmids carrying the Ura3 gene and fur1 disruptants carrying the Clonat gene.

Construction of Plasmids for Expression of Cellulosome Components and Non-Cellulosomal Components in Yeast Table 3 contains the plasmids built for this study. 2-micron plasmids for expression of *C. cellulolyticum* cellulosome components were created from synthetic DNA fragments synthesized by Genscript. For larger genes, fragments of ~1 to ~1.5 Kb were ordered, flanked by overlapping regions for assembly by YML. Smaller genes (Cel5A and Cel8C) were ordered as single constructs. NotI sites were inserted outside every flanking region used for YML. Constructs from Genscript were digested with NotI, and pMU451 was digested with PacI/AscI, pMU782 was digested with EcoRI, HindIII, and ApaLI. The fragments from these digests were mixed together and transformed into M0013 to perform YML. Selection was carried out on YPD with nourseothricin sulfate, and plasmids were verified by restriction digest of plasmids purified from single colonies of M0013 and subsequently transformed into *E. coli*. Additionally, the newly created yeast strains were verified for fur1 deletions via PCR. To identify insertions of the selective marker in the FUR gene 3 PCR tests were used. First, primers X03905 (SEQ ID NO: 4) and X030902 (SEQ ID NO: 3) were used, yielding a 2.9 kB band when an insertion was present, and a 2.4 kB band when no insertion was present. Primer pairs X03900/X03902 (SEQ ID NOs: 1 and 3) and X03901/X03905 (SEQ ID NOs: 2 and 4) each have one member that binds inside the Clonat marker used to disrupt the fur1 gene, and one primer that binds outside the region of the integration cassette, and therefore yield a band when the insertion is present and no band when no insertion is present. Primer sequences used can be found in Table 5.

Production and Purification of His-Tagged Components

Yeast strains from Table 4 were grown in YPD media with nourseothricin sulfate in 250 mL shake flasks at 30° C. After 3 days the cells were centrifuged at 4000 rpm for 5 minutes and the supernatant removed and stored at 4° C. The His-tagged proteins in the supernatant sample were purified by affinity columns (Pierce, HisPur columns), using an FPLC system. The supernatants were either diluted in appropriate buffer (50 mM Sodium Phosphate, 300 mM NaCl, 10 mM imidizol, pH 7.4), or were partially purified, concentrated, and diafiltered (against 50 mM Tris, 300 mM NaCl, 10 mM $CaCl_2$, pH 7.4) by ultrafiltration using Millipore Biomax filters with a 30, 50, or 100 kDa molecular weight cutoff as appropriate. Proteins bound to the HisPur column were eluted with a gradient of the buffers above also containing 100 mM imidizol.

Western blots were performed using anti-his tag antibodies to verify the presence of the cellulosome components and to determine if the purification strategy was working.

For supernatant samples where production of the recombinant protein is verified by western blot, the protein concentration is measured. From these measurements, the molar concentration of the cellulase components is determined for the cellulase assays described below.

Cellulase Activity Assays for Components and Reconstituted Cellulosomes

Qualitative CMC assays were carried out by placing 20 uL of culture supernatant onto a solid media plate containing SD-URA media with 0.1% CMC. The plates were incubated at 37° C. for 5 hours and stained with congo red (Beguin P., Anal. Biochem. 131(2):333-6 (1983)). Briefly, the plates were washed with 1M Tris-HCL buffer pH 7.5. The plates were then stained for 10 minutes with a 0.1% Congo red solution, and extra dye was subsequently washed off with 1M NaCl.

Avicel activity was measured using a 96-well plate method. Strains to be tested were grown in YPD in deep-well 96 well plates at 35° C. with shaking at 900 RPM, or if desired, shake flask growth conditions were used. After growing, plates were centrifuged at 4000 rpm for 10 min. 300 µL substrate (2% avicel, 50 mM sodium acetate buffer, 0.02% sodium azide, β-glucosidase-1 µL per mL) was added to a new 96-well deep well plate, without allowing the avicel to settle. For assays where higher pH was desired to test activity, the buffer used was changed to 50 mM Tris-HCL pH 7.0 and substituted for the sodium acetate buffer, and 10 mM $CaCl_2$ and 10 mM DTT were also added. 300 µL of yeast supernatant was added to this substrate, and 100 µL was taken for an initial sample. The assay plate is incubated at 35° C., with shaking at 800 rpm, and samples were taken at 24 and 48 hours. Samples were placed in 96-well PCR plates, and spun at 2000 rpm for 2 minutes. 50 µL of supernatant was then added to 100 µL of DNS reagent previously placed in a separate 96 well PCR plate, mixed, and heated to 99° C. for 5 minutes in a PCR machine, followed by cooling to 4° C. 50 µL was transferred to a microtiter plate and the absorbance was measured at 565 nm. The conversion of avicel was calculated as follows:

$$Y = \frac{(OD(T=24 \text{ or } 48) - OD(T=0)) \times 100\%}{S \times A} = \frac{\Delta OD \times 100}{0.1 \times 10} = \Delta OD \times 100$$

Y—% of Avicel converted at 24 or 48 hrs
S—DNS/glucose calibration slope that is 0.1 for DNS from May 8, 2007 at 565 nm
A—Avicel concentration at T=0 that is 10 g/L for 1% Avicel Cellulosomes are reconstituted from purified components by mixing the components in a variety of molar ratios in reaction buffer. These enzyme mixes will then be tested for activity at the same mass concentrations as purified non-cellulosomal cellulases.

Activity of Yeast Expressed Cellulosomal Components

Figure 5:
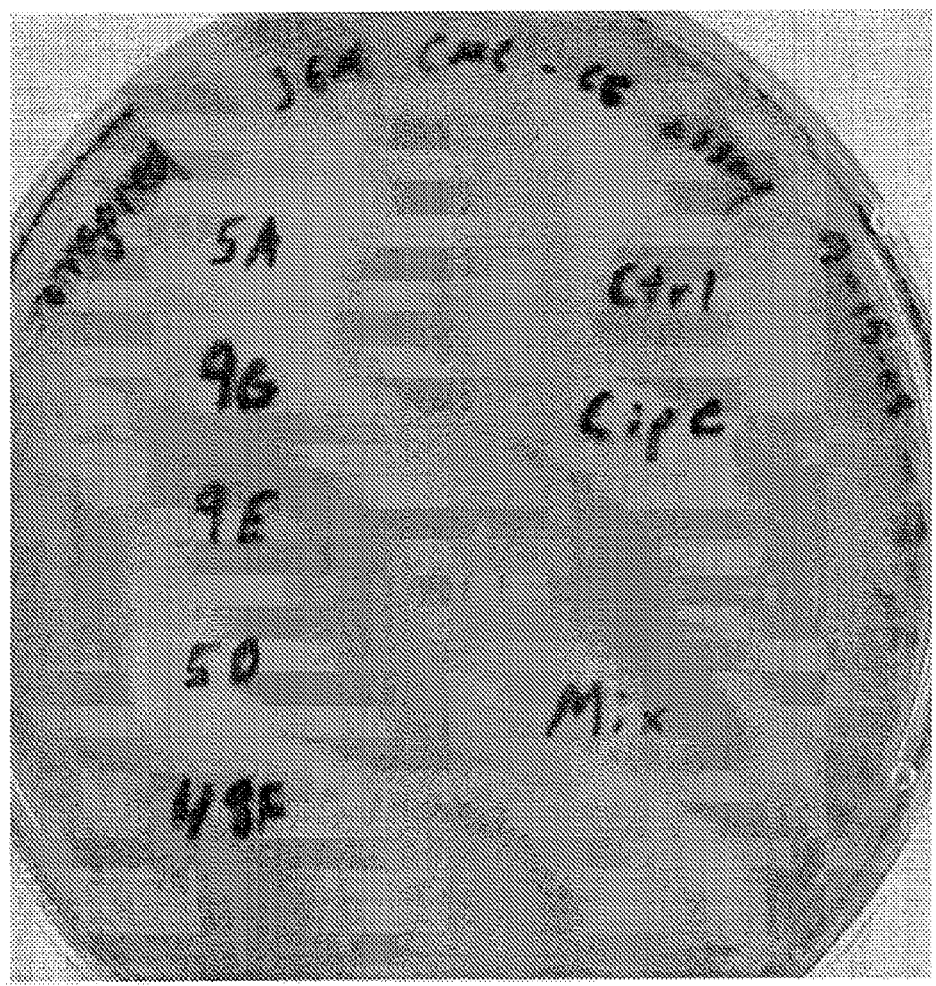
FIG. 5 depicts a CMC assay plate for cellulosome components expressed in S. cerevisiae.

Cellulosome components were tested for activity on CMC from the shake flask cultures used for purification. FIG. 5 shows the CMC activity of several of the components. Cel5A and Cel5D both show significant clearing of the CMC relative to the control. By eye (not visible on the picture) the Cel9G also showed a slight amount of CMC clearing.

Figure 6:
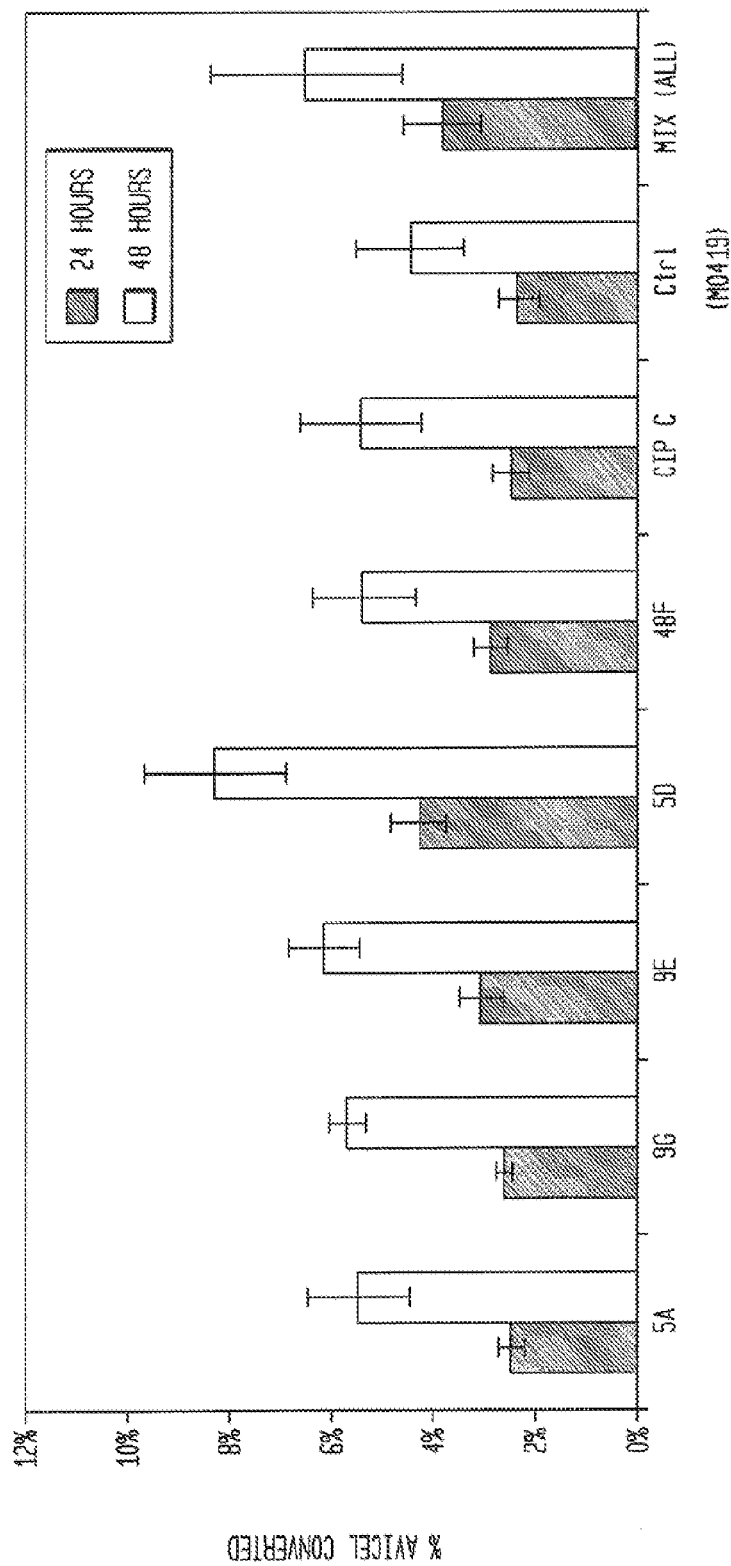
FIG. 6 depicts avicel assay results for cellulosome components expressed in S. cerevisiae.

Components were also tested for their ability to hydrolyze avicel. FIG. 6 shows the avicel assay results for individual cellulases as well as a mixture of all the components using the avicel assay with sodium acetate buffer, pH 5.0. Cel9E and Cel5D both showed activity above the level of the control strain, indicating that these cellulases are functionally expressed in yeast. Cel5D showed the highest activity on avicel.

Figure 7:
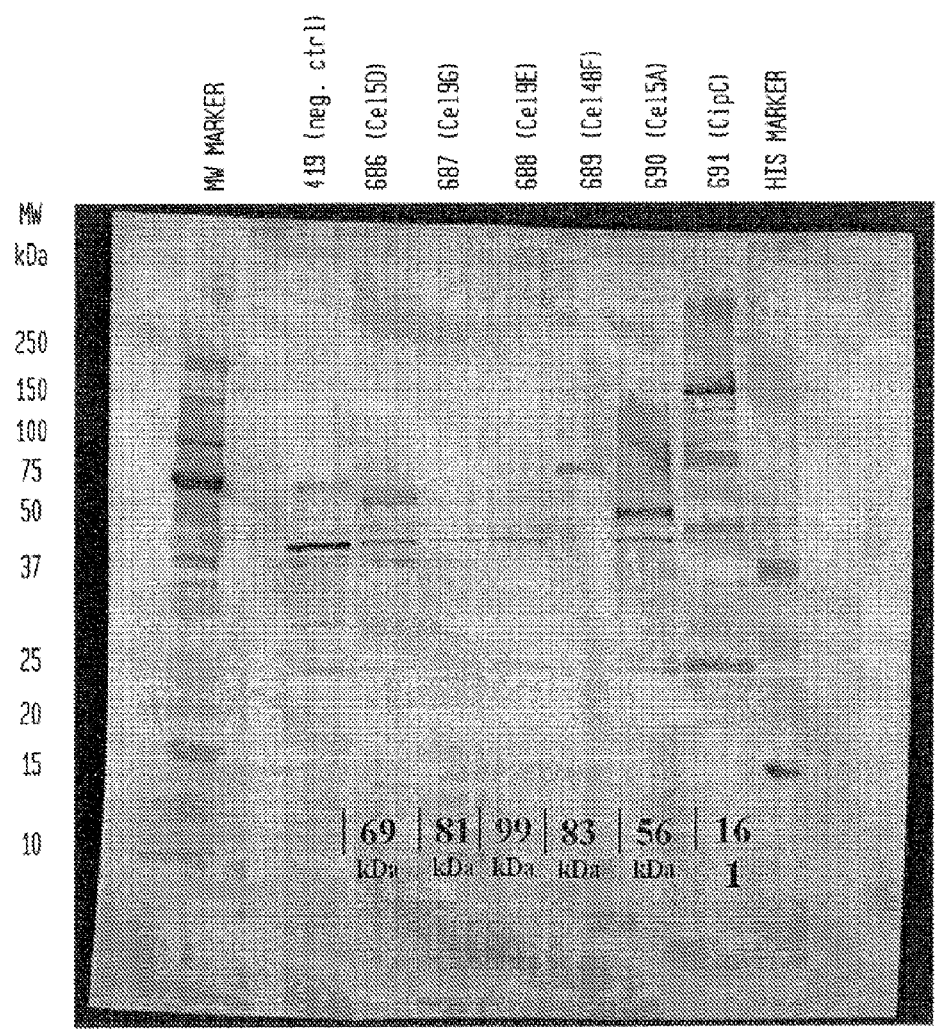
FIG. 7 depicts an anti-His tag western blot for several cellulosome components expressed in yeast, and partially purified on a Pierce HisPur cobalt column. Labels above the lanes indicate the cellulase tested. Labels below are the calculated molecular weights based on the amino acid sequence. The positive control was a commercially available HIS tagged protein; the negative control is yeast supernatant from a non-expressing strain.

Several samples were tested in western blot to confirm the presence of the cellulosome component in yeast supernatant. Those results can be found in FIG. 7. The western confirms the expression of C. cellulolyticum CipC, which is the ~160 kDa structural protein that serves as the scaffoldin in the C. cellulolyticum system. The western blot also confirmed the presence of HIS tagged Cel5D, Cel5A, Cel9E, and Cel48F. The western also shows a number of contaminating bands from the yeast supernatant, methods to remedy this are apparent to one of ordinary skill in the art.

This demonstrates the expression of C. cellulolyticum cellulases in yeast. The successful expression of these catalytic components and the scaffoldin means that a version of the C. cellulolyticum cellulosome can be expressed in yeast.

TABLE 3

Plasmid constructs used in this study.

| Plasmid | Genotype | Source/Reference |
| --- | --- | --- |
| pMU451 | bla URA3 $ENO1_P$ – $ENO1_T$ | Mascoma omnibus provisional patent application |
| pMU782 (pDF1) | bla fur1::LEU2 | La Grange et al. (1996) |
| pMU891 | bla URA3 $ENO1_P$-C.c.Cel5D–$ENO1_T$ | This study |
| pMU892 | bla URA3 $ENO1_P$-C.c.Cel9G–$ENO1_T$ | This study |
| pMU913 | bla URA3 $ENO1_P$-C.c.Cel9E–$ENO1_T$ | This study |
| pMU914 | bla URA3 $ENO1_P$-C.c.Cel48F–$ENO1_T$ | This study |
| pMU967 | bla URA3 $ENO1_P$-C.c.Cel5A–$ENO1_T$ | This study |
| pMU968 | bla URA3 $ENO1_P$-C.c.CipC–$ENO1_T$ | This study |
| pMU969 | bla URA3 $ENO1_P$-C.c.Cel8C–$ENO1_T$ | This study |
| pMU464 | bla URA3 $ENO1_P$-S.f. BGLI–$ENO1_T$ | U.S. 61/116,981 |
| pMU471 | bla URA3 $ENO1_P$-C.f. EG–$ENO1_T$ | U.S. 61/116,981 |
| pMU624 | bla URA3 $ENO1_P$-T.e. CBH1+CBD–$ENO1_T$ | U.S. 61/116,981 |
| pMU784 | bla URA3 $ENO1_P$-C.l. CBH2–$ENO1_T$ | U.S. 61/116,981 |
| pMU464-CHIS | bla URA3 $ENO1_P$-S.f. BGLI–6XHIS–$ENO1_T$ | This study |
| pMU464-NHIS | bla URA3 $ENO1_P$-6XHIS–S.f. BGLI–$ENO1_T$ | This study |
| pMU471-CHIS | bla URA3 $ENO1_P$-C.f. EG–6XHIS–$ENO1_T$ | This study |
| pMU471-NHIS | bla URA3 $ENO1_P$-6XHIS–C.f. EG–$ENO1_T$ | This study |
| pMU624-CHIS | bla URA3 $ENO1_P$-T.e. CBH1+CBD–6XHIS–$ENO1_T$ | This study |

TABLE 3-continued

Plasmid constructs used in this study.

| Plasmid | Genotype | Source/Reference |
|---|---|---|
| pMU624-NHIS | bla URA3 ENO1$_P$-6XHIS-T.e. CBH1+CBD-ENO1$_T$ | This study |
| pMU784-CHIS | bla URA3 ENO1$_P$-C.l. CBH2–6XHIS-ENO1$_T$ | This study |
| pMU784-NHIS | bla URA3 ENO1$_P$-6XHIS-C.l. CBH2-ENO1$_T$ | This study |

Abbreviations: C.c. = *C. cellulolyticum*; bla = β-lactamase gene for selection

TABLE 4

Yeast strains used in this study

| Name | Background strain *Saccharomyces cerevisiae* | Genes expressed and/or knocked out Genotype: α, leu2-3, 112 ura3-52 his3 trp1-289 | Constructs from this (these) plasmid(s) |
|---|---|---|---|
| M0013 | Y294 (ATCC 201160) | | None |
| M0686 | M0013 | C.c. Cel5D; fur1Δ | pMU891 |
| M0687 | M0013 | C.c. Cel9G; fur1Δ | pMU892 |
| M0688 | M0013 | C.c. Cel9E; fur1Δ | pMU913 |
| M0689 | M0013 | C.c. Cel48F; fur1Δ | pMU914 |
| M0690 | M0013 | C.c. Cel5A; fur1Δ | pMU967 |
| M0691 | M0013 | C.c. CipC; fur1Δ | pMU968 |
| M0692 | M0013 | C.c. Cel8C; fur1Δ | pMU969 |

TABLE 5

DNA oligonucleotides used in this study

| Name | Sequence |
|---|---|
| X03900 | GTACCACTCTTGACGACACGGCTTA (SEQ ID NO: 1) |
| X03901 | ATGCTCATGTAGAGCGCCTGCTC (SEQ ID NO: 2) |
| X03902 | TAATAGACAGAGTGGTTCCCATGGAC (SEQ ID NO: 3) |
| X03905 | AGGTGTATAGAGGTGGGGAATGATC (SEQ ID NO: 4) |

TABLE 6

DNA and amino acid sequences used in this study.

| Gene (size in kDa) | DNA sequence used (ORF flanked by consensus ATG context, YML cloning sites, and NotI sites) |
|---|---|
| *C. cellulolyticum* Cel5D (69 kDa) | gcggccgcgctattttcataaaaaaccaagcaactgcttatcaacacacttaattaaaaacaaaatggtttct ttcacctccttgttggctggtgttgctgcaatctccggtgtcttggctgctccagctgccgaagtcgaaccagt tgctgtcgaaaagagagaagccgaagctgaagccattaactctcaagatatggtcaagaagatgggtatc ggtatgaacttgggtaacaccttcgatgctccaactgaaggacttggtccaaggctgcccaagaatactac ttcgatgacttcaagcaagctggtttcaagcacgttaggattcccattcgttgggaccaacacaccttggcta actctccatacactgttgactctaacttcttgaaccgtattgaaactgttattgactggtcttttgtctcgtggtttc gtcactgtcatcaactctcaccacgacacctggttgatggacaactactctcaaaacatcggtagatttgaaa agatttgggaacaaatcgcccaaagattcaaaggtaagtctgaaaacttggtcttcgaaatcttgaacgaac cacacggtaacatcaccgactctcaaatcaacgatatgaataagagaattttgaacattattagaaagacca acccaactcgtaacgtcatcatcggtgctggttactggaactcttacaactcttttatctcaattggaaatccca aacgacccaaacttgattgctaccttccactactacgacccatactctttcacacaccaatggcaaggtacct ggggtaccaagaacgacatggacgccatcgctatggttttcaaccacgttaagaagtggtccgataagaat aacattccagtctatttgggtgaatacggtgtcatgggtcactctgacagaacctcagctgtcaaatggttcg acttcgtctccgatcaagccatctcccatggtttctcttgcggtgcttgggacaacggtgtcttcggttctgttg acaacgacatggccttctacaacagagataccagacaatttgacaaagaaattttgaatgccatcttgacta ctggtaccacctacgactggacccaccaaccgaaaaccaaccagaccaccaagaactccagccacc ccagcttacggtgaacaattgattgaagatttcgaaggtgccatgcaatgggctgcctactctggtgttgac gctaccgcttcctgtaagatctcttccggtaagtccaacaacggtttggaaattacctacgctggttcttctaa cggttactgggtgttgttgacaacgagcacagaaaccaagattgggaaaagtggcaaaagatctcttttg acattaagtcttcaaacactaacgaagttagattgttaatcgctgaacaatctaagatctgaaggtgaagacgg tgaacactggacctacgttatcaagccatctacttcctggactaccattgaaattccattctcttctttcactaag agaatggattaccaaccaccagctcaagacggttctgaaaccttcgacttgtacaaggtcggttcattgcac ttcatgtactctaactccaactccggtactttaaacattgacaacattaaattgatcggtttgccagaagaaca aatcggtggtaaaattggtgatgttaacgaagatggtaacatcgacgctattgactttgattattgaagaagt acttgttagactcctctatactatcaacaaggttaacgccgacattaatttggacggtgatatcaacgctatc gacttcgctaagttgaagatgatgttgttgggtgacggtggtggttctggtggtgctctcatcatcaccacc accactaaggcgcgccgcttttgattaagccttctagtccaaaaaacacgttttttgcggccgc (SEQ ID NO: 5) |
| *C. cellulolyticum* Cel9G (81 kDa) | gcggccgcgctattttcataaaaaaccaagcaactgcttatcaacacacttaattaaaaacaaaatggttc attcacttccttgttagctggtgtcgctgctatctccggtgttttagctgctccagctgctgaagttgaaccagt cgcagttgaaaagagagaagctgaagctgaagctgctggtacttacaattacggtgaagattgcaaaagt ctatcatgttctacgaatttcaaagatctggtgacttgccagccgacaagagagacaactggagagacgatt ccggtatgaaggatggttctgacgttggtgtcgatttgacttggtggttggtacgacgccggtgaccacgtca aattcaacttgccaatgtatacacctcagccatgctagctctggtctttgtatgaagacaaggacgcctacga caagtcaggtcaaaccaagtacattatggacggtatcaaatgggctaacgattacttcattaaaatgtaaccca actccaggtgtttactactaccaagtcggtgatggtggtaaggaccattcctggtggggtccagctgaagtc atgcaaatggaaagaccatccttcaaggtcgacgatctaagccaggttcagctgtttgcgcttcaaccgct gcctctttggctctgctgccgctcgttttcaagtatctgacccaacctacgccgaaaagtgtatctctcatgct |

TABLE 6-continued

DNA and amino acid sequences used in this study.

|  |  |
|---|---|
|  | aagaacttgttcgatatggctgacaaggctaagtctgatgctggttacactgccgcttctggttactactctag<br>ctcctcttctacgacgatttgtcttgggctgctgtttggttgtgtacttggctaccaacgattctacttacttggata<br>aggctgaatcttacgttccaaactggggtaaggaacaacaaaccgacatcatcgcttacaaatggggtcaa<br>tgttgggacgacgttcactacggtgccgaactattgttggctaagttgaccaacaagcaattgtacaaggac<br>tccatcgaaatgaacctagacttttggaccaccggtgtcaacggtactagagttcttacacccccaaagggtt<br>tggcttggttgtgtttcaatggggttctttgagacatgctaccaccccaagctttcttggctggtgtttacgctgaat<br>gggaaggttgtaccccatctaaggtctccgtttacaaggacttcttgaagtcccaaatcgactacgcttttggg<br>ttctaccggtagatcttttgtcgttggttacggtgttaaccaccacaacacccacaccatagaaccgctcac<br>ggttatggactgaccaaatgacttctccaacttaccacagacacaccatctacggtgccttggtcggtggtc<br>cagacaacgctgacggtacaccgacgaaatcaacaactacgttaacaacgagatcgcttgcgattacaa<br>cgctggttttactggtgctttggctaagatgtacaagcactccggtggtgatccaattccaaacttcaaggcc<br>atcgaaaagatcaccaacgatgaagtcattatcaaggctggttttgaactccactggtccaaactacaccga<br>aatcaaagccgttgtttacaaccaaaccggttggccagctagagtcaccgataagatctctttcaagtacttc<br>atggacttgtctgaaattgtcgctgccggtattgaccctttgtccttggttacttcctctaactactccgaaggta<br>agaacaccaaagtactggtgttttgccatgggacgtctccaacaacgtctactacgtcaacgttgacttgac<br>cggtgaaaacatttacccaggtggtcaatctgatgtagaagagaagttcaattccgtatcgctgctccacaa<br>ggtagaagatactggaaccccaaagaacgatttctcttacgatggtctaccaaccacctctactgttaataccg<br>ttaccaacattccagtttatgacaacggtgttaaggtcttggtaacgaaccagccggtggttctgaaaaccc<br>agatccagaaattttgtacggtgacgtcaactctgacaagaacgtcgacgcttttagattttcgccgccttgaa<br>gaagtacttgttgggtggcacttcctctattgatgnaaggctgctgatacttacaaggacggtaatatcgacg<br>ccattgacatggctaccttgaagaagtaccatttgggtaccatcactcaattgccacaaggtggtggcggtt<br>ctggtggcggttctcaccaccatcatcaccactaaggcgcgccgcttttgattaagccttctagtccaaaaa<br>acacgttttttgcggccgc (SEQ ID NO: 7) |
| C.<br>cellulolyticum<br>Cel9E<br>(99 kDa) | gcggccgcgctattatcataaaaaaccaagcaactgcttatcaacacacttaattaaaaacaaaatggtctc<br>tttcacttctttgttggctggtgttgctgctatctccggtgtgttggctgccccagccgccgaagtcgaaccag<br>tcgccgtcgaaaagagagaagctgaagctgaagctttggttggtgctggtgacttgattagaaatcatactt<br>cgacaacagagtcggtttaccttggcacgttgttgaatcctacccagctaaggcttccttcgaaatcacctcc<br>gacggtaagtacaagatcaccgctcaaaagattggtgaagctggtaagggtgaaagatgggacattcaat<br>tcagacacagaggtttggctctacaacaaggtcatacctacaccgtcaagttcactgttaccgcatctagag<br>cttgtaagatctacccaaagattggtgatcaaggtgatccatacgacgaatactggaacatgaaccaacat<br>ggaacttcttggaattgcaagctaacaccccaaagaccgttacccaaacttttcactcaaactaagggtgata<br>agaagaacgttgaatttgcttttcaccttgctccagataagactacctctgaagctcaaaacccagcctattc<br>caaccaattacttacactttttgacgaaatctacatccaagatccacagttcgccggttacaccgaagatccac<br>cagaaccaactaacgttgtcagattgaatcaagttggtttctacccaaacgctgacaagattgctaccgttgc<br>tacctcctctactaccccaattaactggcaacttgtcaactccaacggcgctgccgttttgaccggtaagtct<br>accgttaagggtgctgatagagcttccggtgacaacgttcacatcattgatttctcttcttacactactccaggt<br>accgattacaagatcgttaccgacgtctctgtcactaaggctggtgacaacgaatccatgaagttcaacatc<br>ggtgacgacttgttcacccaaatgaagtacgattccatgaagtacttctaccacaacagatctgctatcccaa<br>ttcaaatgccatactgtgaccaatcccaatgggctaagcagccggtcacaccaccgacattttgcctcca<br>gacccaaccaaggactacaaggccaactacaccttggacgttaccggtggttggtacgacgccggtgac<br>cacggtaagtatgttgtgaacggtggtatcgctacctggaccgtcatgaacgcttacaacgtgctttgcac<br>atgggtggtgacaccctccgtcgctccattcaaagatggttctttgaacattccagaatccggtaacggttacc<br>cagatatcttagatgaagctagatacaacatgaagacttttgttgaacatgcaagtcccagccggtaacgaat<br>tggctgtctatggctcaccacaaggctcacgacgagagatggaccgcttttggctgtccgtccagaccaaga<br>taccatgaagagatggttacaaccaccatctaccgctgctactagaaacttggccgctatcgccgcccagtc<br>ttctcgtttgtggaagcaattcgactctgccttcgctaccaagtgcttgactgccgctgaaactgcctgggac<br>gctgccgtcgcccacccagaaatttacgctaccatggaacaaggtgctggtggtggtgctttacggtgaca<br>actacgttttggatgatttctactgggctgcttgcgaattgtacgctactactggttccgacaagtacttgaact<br>atatcaagtcttctaagcactcacttggaaatgccaactgaattgactggtggtgaaaacaccggtattactgg<br>tgctttcgactgggtttgtactgccggtatgggtactatcactttggctttagttccaactaagctaccagccg<br>ctgacgttgctaccgccaaggctaacattcaagctgccgctgacaagttcatctctatttcaaaggcccaag<br>gttacggtgtcccattggaagaaaaggtcatttcttccccattcgatgcttccgttgtcaaggggttttcaatgg<br>ggttctaactccttcgtcattaacgaagctatcgtcatgtcttacgcttacgagttctccgatgtcaacggtact<br>aagaacaacaagtacatcaacggtgctttgactgctatggactacttgttgggtagaaacccaaacattcaa<br>tcctatatcaccggttacggtgataacccattggaaaacccacaccacagattctgggcttaccaagctgac<br>aatactttcccaaagccacctccaggttgtttgtccggttggtccaaactctggtttacaagatccttgggtcaa<br>gggtctggttggcaaccaggtgaaagaccagccgaaaagtgtttcatggacaacatcgaatcttggtcta<br>ctaacgaaattaccatcaactggaacgctccattggttttggatttcagcctacttggacgaaaagggtccag<br>aaatcggtggttctgtcactccaccaaccaacttgggtgacgttaacggtgacggtaacaaggacgctttg<br>gacttcgctgctttgaagaaggcttttgttgtctcaagacacttccaccatcaacgttgctaacgctgatatcaa<br>caaggacgttccatcgacgctgttgacttcgctctattgaagtctttcttgttaggtaagatcacttttgggtgg<br>tggttctggtggtggttccaccaccatcaccaccactaaggcgcgccgcttttgattaagccttctagtcca<br>aaaaacacgttttttgcggccgc (SEQ ID NO: 9) |
| C.<br>cellulolyticum<br>Cel48F<br>(83 kDa) | gcggccgcgctatttttcataaaaaaccaagcaactgcttatcaacacacttaattaaaaacaaaatggttct<br>ttcacttctttgttggccggtgttgctgctatctctggtgttttggctgctccagctgctgaagttgaaccagttg<br>ccgtcgaaaagcgtgaagctgaagctgaagctgcttcttccccagctaacaaggtttaccaagacagattc<br>gaatctatgtactctaaaatcaaggaccccagccaacggttacttctccgaacaagttattccatacattctat<br>cgaaacctctgatggttgaagctccagatactacggtcactcacttctgaagctatgtcctactacatgtgg<br>ttgaagctatgcacggtagattttctggtgacttcactggtttcgacaagtcttggtccgtcaccgaacaata<br>tttgattccaaccgaaaaagatcaaccaaaacacctctatgtctagatacgacgctaacaagccagccaccta<br>cgcccagaatttcaagaccccatctaagtatccatcccacctcacttgacacttctcaaccagtcggtagagatcc<br>aattaactcccaattgacttctgcttacgtgtacctctatgttgtacggtatgcactggatcttggatgttgataac<br>tggtacggtttcggtgctagagctgatggtacttccaagccatcctacatcaacacctttccaaagaggtgaa<br>caagaaagcacctgggaaactattccacaaccatgttgggatgaacacaagttcggtggtcaatacggttt<br>cttggacttgttcaccaaggataccggtactccagctaagcaattcaagtacactaacgctccagacgctga<br>tgctcgtgctgttcaagctacctactgggctgatcaatggggctaaggaacaaggtaagtccgtaccacttct |

TABLE 6-continued

DNA and amino acid sequences used in this study.

|   |   |
|---|---|
|   | gttggtaaggctactaagatgggtgactacttgagatactcttttttcgacaagtacttcagaaagatcggtca<br>accatctcaagctggtaccggttacgacgccgctcactacttgttgtcttggtactatgcctggggtggtggt<br>attgattccacttggtcctggattattggttcttcgcacaaccacttcggttaccaaaacccattcgctgcctgg<br>gtcttgtccactgatgccaacttcaagcaaagtcttccaacggtgcttccgactgggctaagtcttggata<br>gacaattagaattttaccaatggttgcaatctgccgaaggtgctattgctggtggtgccaccaactcctggaa<br>cggtagatacgaagctgtccctctggtacttccaccttctacggtatgggttacgttgaaaacccagtctac<br>gctgacccaggatctaacacctggttcggtatgcaagtctggtccatgcaacgtgtcgccgaattgtactac<br>aaaaccggtgacgctcgtgctaagaagttgttggacaagtgggctaagtggatcaacggtgaaattaaattt<br>aacgctgatggtaccttccaaattccatctaccatcgactgggaaggtcaaccagatacttggaacccaac<br>ccaaggttataccggtaacgccaacttgcacgttaaggtcgttaactacggtactgacttgggttgtgcttctt<br>ctttggctaacaccttgacctactacgctgccaagtctggtgacgaaacttctagacaaaacgctcaaaagtt<br>gttggacgctatgtggaacaactactctgattccaagggtatttccactgttgaacaaagaggtgactacca<br>cagattcttggatcaagaagttttcgttccagccggttggaccggtaagatgccaaacggtgacgtcattaa<br>gtctggtgtcaagttcatcgacatcagatctaagtacaaacaagacccagaatggcaaaccatggttgccg<br>ctttgcaagccggtcaagttccaacccaaagattgcatagattctgggctcaatctgaatttgccgttgccaa<br>cggtgtctacgctatcttgttcccagaccaaggtccagaaaaattgttgggtgacgtcaatggtgacgaaac<br>tgttgatgctatcgacttagctatcttgaagaagtacttgttgaactcttccactactatcaacaccgccaacgc<br>cgacatgaactctgataacgccatcgacgccattgattacgccttgttgaagaaggccttgttgtctatccaa<br>ggtggtggttccggtggtggttcccaccatcaccaccaccactaaggcgcgccgcttttgattaagccttct<br>agtccaaaaaacacgttttttgcggccgc (SEQ ID NO: 11) |
| C.<br>cellulolyticum<br>Cel5A<br>(56 kDa) | gcggccgcgctatttttcataaaaaaaccaagcaactgcttatcaacacacttaattaaaaacaaaatggtttc<br>ctttacttctttgttggctggtgttgctgctatctccggtgttttggctgccccagctgctgaagttgaaccagtc<br>gctgttgaaaagagagaagctgaagctgaagcttacgacgtcttcttgatcccaaacttacaaatcccaca<br>aaagaacatcccaaacaatgatggtatgaacttcgttaagggtctaagattgggttggaacttgggtaacac<br>ctttgacgccttcaacggtactaacattaccaatgaattggattacgaaacttcctggtccggtatcaaaacc<br>actaagcaaatgattgacgctattaagcaaaaggggtttcaacactgttagaatccagtatcctggcaccca<br>cacgtttccggttctgactacaagactctctgacgtctggatgaacagagttcaagaagttgttaactactgtat<br>tgacaacaagatgtacgttatcttgaacacccaccatgacgtcgacaaggtcaagggttacttccccttcttcc<br>caatacatggcctcttctaagaagtacattacctctgtctgggctcaaatcgccgcccgtttcgctaactacg<br>acgaacatttgatattcgaaggtatgaacgaaccaagattggtcggtcacgccaatgaatggtggccagaa<br>ttgaccaactctgatgtcgtcgactctattaactgctaaccaattgaaccaagacttcgttaacaccgtcag<br>agctaccggtggtaagaacgcttctagatatttgatgtgtccaggttacgttgcttctccagatggtgctacca<br>acgactacttcagaatgccaaacgacatttccggtaacaacaacaagatcatcgtttctgttcatgcttactgt<br>ccatggaacttcgccggtttagccatggctgacggtggtaccaacgcttggaacattaacgattctaaggat<br>caatccgaagtcaacctggttcatggataacatttacaacaagtacacctctagaggtattccagtcattattgg<br>tgaatgtggtgctgttgacaagaataacttgaagaccagagttgaatacatgtcctactacgttgctcaagct<br>aaggctagaggtatcttgtgtattttgtgggataacaacaacttctctggtaccggtgaattgttcggtttcttc<br>gacagaagatcctgtcaattcaagttcccagaaatcatcgacggtatggttaagtacgccttcgaagctaag<br>accgatccagacccagttatcgtttatggtgactacaacagtggtaacgttgacgccttggacttcgct<br>ggtttgaagaagtacattatggctgctgaccacgcttacgtcaagaacttggacgttaatttggacaacgaa<br>gttaacgctttcgatttggccatatgaagaagtacttattgggtatggtttctaagctaccatccaacggtggt<br>ggttccggtggtggttctcaccaccaccaccactaaggcgcgccgcttttgattaagccttctagtcca<br>aaaaacacgttttttgcggccgc (SEQ ID NO: 13) |
| C.<br>cellulolyticum<br>CipC<br>(161 kDa) | gcggccgcgctatttttcataaaaaaaccaagcaactgcttatcaacacacttaattaaaaacaaaatggtctc<br>tttcacctccttgctagctggagttgctgccatttccggggttttggccgccccagctgccgaagttgaacca<br>gttgctgtcgaaaagagagaagctgaagctgaagctgccgaagctggtgtcgtctcttgtcaattcaacaac<br>ggttcctctccagcttcctccaactctatctacgccagatttaaggttactaacacctctggttctccaatcaac<br>ttggccgacttgaagttaagatactactacacccaagatgccgacaagccattgactttctggtgtgaccac<br>gccggttacatgtctggttctaactacattgatgctacctccaaggttactggttccttcaaggccgttctcca<br>gctgttactaacgctgatcattacttagaagttgctttgaactctgatgccggttccttgccagccggtggtag<br>catcgaaattcaaactagattcgctagaaacgattggtctaatttcgatcaatccaacgactggtcttacacc<br>gctgctggttcctacatggactggcaaaagatctctgctttcgtcggtggtactttggcttacggttctactcc<br>agacggtggtaacccaccaccacaagatccaaccattaacccaacctctatttctgctaaggctggttcttttc<br>gccgacaccaagatcactttgactccaaacggtaacacttttcaacggtatctctgaattgcaatcttctcaata<br>cactaaaggtaccaacgaagtcacttttgttggcttcttacttgaacaccttgccagaaaaactaccaagact<br>tgacctttgactttggtgttggtactaagaacccaaagttgactatcactgtcttgccaaaggatatcccagg<br>tgactccttgaaggttactgttggtaccgctaatggtaagccaggtgacaccgttactgtccctgtcactttcg<br>ctgatgtcgctaagatgaagaacgtcggtacttgtaacttctatttgggttacgacgcttccttgttagaagttg<br>tttccgttgacgctggtccaatcgtcaagaactgtgccgtcaactttcctagttctgcttccaacggtactatat<br>cttccctgttcctagataacaccattaccgacgagttgatcaccgctgacggtgtcttcgccaacattaagttc<br>aagctgaaatccgtcaccgccaagaccactactccagtcaccttcaaggacggtggtgcttttggtgatggt<br>accatgtctaagatcgcttccgtcaccaagaccaacggttctgttaccatagacccaggtactcaaccaact<br>aaggaactaaaggttgctgttggtactgctaacggtaaggcaggtgataccgtcactgtcccagtcaccttt<br>gctgacgttgtcaacgttggtaacgttggtacttgcaatttctacttggcctacgatgcctcttcgctagaagtt<br>gtttccgtcgatgctggtccaatcgttaagaacgctgcagtgaacttctcctcttcagcttccaacggtactat<br>ctccttcttgtttctagacaatactattaccgacgaattgatcacctctgacggtgtctttgcaaacatcaagttt<br>aagttgaagtccgttgcttactaagaccaacccccagttcactttcaaggatggtggagccttcggtgatggt<br>actatggcaaagattgctactgttaccaaaaccaacggttccgttaccattgacccaggtacccaaccaact<br>aaagaattgaaggtggctgtcggtaccgctaacgaaaaccaggtgatactgtcactgttcccgttaccttc<br>gccgacgtcgcttctgcaggtaacgttggcacctgtaactttacttggcatacgatgcttccttgttggaagt<br>tgttctgttgacgctggtccaattgtcaagaacgctgctgttaacttctcttcttctgcctctaatggttccatttc<br>cttcctgttcttggataatactactcactgacgagttgattaccgctgacggtgttttcgccaacatcaagttcaa<br>attgaagtctgtcgctgccaagaccactaccccagtcaccttcaaggacggtggcgcttcggggacggt<br>accatgactaagattgctaccgtcactaagaccaacggttccgtcacaatcgacccagggactcaaccaa<br>caaaggaattaaaggttgccgtcggcactgccgaaggtaacgtaggtgacactgtcaccgtcccagtcac<br>cttcgctgacgttgcttctgccggtaacgtcggtacatgtaacttctacttggcctacgacgcttctttgttgga |

TABLE 6-continued

DNA and amino acid sequences used in this study.

```
cgtcgtttctgtcgcagccggtcccatcgttaagaatgccgctgtcaacttctcctcgtctgcttccaacggtt
ccatttctttctgttcctggataacaccatcactgacgaattgattactgccgacggtgttttcgctaacattac
ctttaagttaaagtccgttaccgctaagactaccaccccagtcactttcaaggatggcggtgcttttggtgatg
gcacaatggctaagattgctactgtcactaagacgaacggttctgttactatcgtcccaggaatccaaccaa
ccaaagaattgaaggttgctgttggtaccgctgaaggtaacgtcggtgacaccgttactgttccagttacctt
cgctgatgttgcctctgctggtaacgttgaacttgtaacttctatttggcttacgatgcttccttgttagatgttg
tttctgtcgctgccggtccaattgtcaagaacgccgccgtcaacttacttcctctgcctctaacggttccatct
ccttcttgtttctggataacacgatcactgatgaattgattactgctgacggtgtcttcgctaacatctccttcaa
gttgaaatccgtcacttctaagaccactacccctgtcacctttaaggacggtggtgcattcggtgacggtac
aatggctaagatcgctaccgttattaagactaacggatcagttaccattgttccaggtatccaacctactaag
gaattgaaggtcgccgttggtaccgccgaaggtaacgtcggtgatactgttaccgttccagtcactttcgct
gacgtcgcctccgctgggaacgttggtacttgtaacttctactctggcttacgacgcttctctattggatgttgtt
tcccatgccgctggtccaattgttaagaacagagccgtcaacttctcctcttctgcttctaacggttctatctcc
ttcttgttcttagacaacacgattaccgatgaactgattactgccgatggtgttttgccaacatcaccttcaagt
tgaagtcagtcgctgctaagactaccactccagttaccttcaaagacggcggtgctttcggtgatggcacta
tggctaagattgctaccgttactaagacgaatggcagcgtgaccatcgttccaggtatccaaccaaccaag
gaattgaaggtcgctgtcggtactgcctccggtaaagccggtgacaccgtcactgttcctgttacttcgctg
acgtcgccactgttggtaacgttggaacctgtaacttctacgttacctacgacaccaacttgttggaagttgct
tccgttaccccaggttctatcgttactaacgctgccgttaacttctcttcctccacctctaacggtaccatttcct
tcttgttcttggataacactattaccgaccaactaattaagaccgacggtaccttcgctgaaatcaagttcaag
ttgaagtccgtcaccgctaagactactacccctgttgccttcaaggacggtggtgccttcggtgatggcaca
atggccaagattgccactgtcactaagactaacggctccgtcactattgacgttggtgacgttacccccagtc
aacccaaccatcactccatctaccgcctcttcgacaagtacgtcccagctaacgtcaacgtcaccttgact
cccaacggtaacactttcaagggtattaccggtttaaccagtggtactgatttcactgtctctaacaacgttgtt
accatctctaagtcttacttgtctaccttggctgtcggttccaagaccttgaccttcgacttcggtgttaccaac
aacccagttttgaccttgaccatcaccgactctactccagtcgtcactggtttgggtgtcaagatcgcttctgt
cactggtaagaccggtgacaccattactgttccagttacttgtccagttactgtcaagtctggtaacgttggta
cctgtaacttctacatcacctacgatgcatccatgttgcaagctgtttctgctaccgctggtgatatcgtcttga
acgctccagttaacttctcctcttccatcaacgctaccaccggtaccatctctatcttgttcttggacaacacca
ttggtgatcaattgatcacctccgacggtgttgttgctaacttaactttcaaggttgttggtacctcttctactact
actcctattgctttcaaggccggtggtgcttttgggaacggtaacatgtccaagatctccgacattactttcac
caacggttctgctaagttgaacggaggcggttcaggaggcggctccaccaccatcatcatcattaaggc
gcgccgcttttgattaagccttctagtccaaaaaaacacgttttttgcggccgc (SEQ ID NO: 15)
```

| | |
|---|---|
| *C. cellulolyticum* Cel8C (49 kDa) | ```gcggccgcgctattttttcataaaaaaccaagcaactgcttatcaacacacttaattaaaaacaaaatggtctc
cttcacttccttgttggctggtgtcgctgccatttctggtgtttttggccgctccagctgccgaagtcgaaccag
ttgctgttgaaaagagagaagctgaagctgaagctgctgatcaaatcccatccgacgctaagtac
ccaaacggtgcctactcctgtttggctgattctcaatctatcggtaacaacttggtcagatctgaatgggaac
aatggaagtctgctcacattacttccaacggtgctagaggttacaagagagttcaaagagacgctaccacc
aactacgacaccgtttctgaaggtttgggttacgtttgttgttgtctgtctacttcggtgaacaacaattgttc
gacgatttgtacagatacgttaaggttttcttgaactctaacggtttaatgtcttggagaatcgactcttctggc
aacattatggctaaggactctattggtgccgctaccgacgctgatgaagacatcgctgtttccttggtttttcgc
tcacaagaagtgggcacttctggtggtttcaactaccaaaccgaagctaagaactacattaacaacattta
caacaagatggttgaaccaggtacttatgtcatcaaggctggtgacacttggggtggttccaacgttactaa
cccatcttacttcgctccagcttggtacagaatcttcgctgacttcaccggtaactccggttggatcaacgtc
gctaacaagtgttacgaaatcgctgataaagcccgtaattctaacaccggtttggtcccagactggtgtact
gccaaggtaccccagcctctggtcaaggtttcgacttctactacgacgccattagatacaataggagagc
tgccatcgactactcttggtacgtactgctaaggctaagacccactgtgacgctatctctaacttcttcaaga
acatcggttacgctaacatcaaggatggttacaccatctccggttctcaaatctcctccaaccacactgccac
tttcgtctcttgtgccgctgctgctgctatgactggtactgacaccacctatgctaagaacatctacaacgaat
gtgttaaggttaaggattctggtaactacacttacttcggtaacaccttgagaatgatggtgttgttatacacta
ccggtaacttcccaaatttgtacacctacaactcccaaccaaaagccagacttgaagggtgacgtcaataac
gatggtgctatcgacgcctagatattgctgccctaaagaaggccatcttgacccaaaccacttccaacattt
ctttgactaacgcagatatgaacaacgacggtaacattgatgctattgactttgctcaattgaaggttaagttat
tgaacggtggtggttctggtggtggttctcaccaccaccaccaccactaaggcgcgccgcttttgattaagc
cttctagtccaaaaaaacacgttttttgcggccgc (SEQ ID NO: 17)``` |

| Gene (size in kDa) | Accession number and amino acid sequence |
|---|---|
| *C. cellulolyticum* Cel5D (69 kDa) | P25472<br>Mvsftsllagvaaisgvlaapaaevepvavekreaeae<br>ainsqdmvkkmgigmnlgntfdaptegswskaaqe<br>yyfddfkqagfkhvripirwdqhtlanspytvdsnflnr<br>ietvidwslsrgfvtvinshhdtwlmdnysqnigrfeki<br>weqiaqrfkgksenlvfeilnephgnitdsqindmnkri<br>lniirktnptrnviigagywnsynslsqleipndpnliatf<br>hyydpysfthqwqgtwgtkndmdaiamvfnhvkk<br>wsdknnipvylgeygymghsdrtsavkwfdfvsdqa<br>ishgfscgawdngvfgsvdndmafynrdtrqfdkeiln<br>ailttgttydwtpptetnpdpprtpatpaygeqliedfega<br>mqwaaysgvdatasckissgksnngleityagssngy<br>wgvvdnehrnqdwekwqkisfdikssntnevrlliae |

TABLE 6-continued

DNA and amino acid sequences used in this study.

```
                qskiegedgehwtyvikpstswttieipfssftkrmdyq
                ppaqdgsetfdlykygslhfmysnsnsgtlnidnikligl
                peeqiggkigdvnedgnidaidfallkkyllddssisinkv
                nadinldgdinaidfaklkmmllgdgggsgggshhhh
                hh (SEQ ID NO: 6)

C.              P37700
cellulolyticum  Mvsftsllagvaaisgylaapaaevepvavekreaeae
Cel9G           aagtynygealqksimfyefqrsgdlpadkrdnwrdd
(81 kDa)        sgmkdgsdvgvdltggwydagdhvkfnlpmsytsa
                mlawslyedkdaydksgqtkyimdgikwandyfikc
                nptpgvyyyqvgdggkdhswwgpaevmqmerpsf
                kvdaskpgsavcastaaslasaavvfkssdptyaekcis
                haknlfdmadkaksdagytaasgyyssssfyddlswa
                avwlylatndstyldkaesyvpnwgkeqqtdiiaykw
                gqcwddvhygaelllakltnkqlykdsiemnldfwttg
                vngtrvsytpkglawlfqwgslrhattqaflagvyaew
                egctpskvsvykdflksqidyalgstgrsfvvgygvnp
                pqhphhrtahgswtdqmtsptyhrhtiygalvggpdn
                adgytdeinnyvnneiacdynagftgalakmykhsgg
                dpipnfkaiekitndeviikaglnstgpnyteikavvyn
                qtgwparvtdkisfkyfmdlseivaagidplslvtssny
                segkntkvsgylpwdvsnnvyyvnvdltgeniypgg
                qsacrrevqfriaapqgrrywnpkndfsydglpttstvn
                tytnipvydngvkvfgnepaggsenpdpeilygdvns
                dknvdaldfaallkkyllggtssidvkaadtykdgnidai
                dmatlkkyllgtitqlpqggggsgggshhhhhh
                (SEQ ID NO: 8)

C.              AAA73869
cellulolyticum  Mvsftsllagvaaisgvlaapaaevepvavekreaeae
Cel9E           alvgagdlirnhtfdnrvglpwhvvesypakasfeitsd
(99 kDa)        gkykitaqkigeagkgerwdiqfrhrglalqqghtytvk
                ftvtasrackiypkigdqgpdydeywnmnqqwnflel
                qantpktvtqtftqtkgdkknvefafhlapdkttseaqnp
                asfqpitytfdeiyiqdpqfagytedppeptnvvrlnqv
                gfypnadkiatvatssttpinwqlvnstgaavltgkstvk
                gadrasgdnvhiidfssyttpgtdykivtdvsvtkagdn
                esmkfnigddlftqmkydsmkyfyhnrsaipiqmpy
                cdqsqwarpaghttdilapdptkdykanytldvtggw
                ydagdhgkyvvnggiatwtvmnayeralhmggdts
                vapfkdgslnipesgngypdildearynmkttllnmqv
                pagnelagmahhkanderwtalavrpdqdtmkrwlq
                ppstaatlnlaaiaaqssrlwkqfdsafatkcltaaetawd
                aavahpeiyatmeqgagggaygdnyvlddfywaace
                lyattgsdkylnyiksskhylempteltggentgitgafd
                wgctagmgtitlalvptklpaadvatakaniqaaadkfi
                siskaqgygvpleekvisspfdasvvkgfqwgsnsfvi
                neaivmsyayefsdvngtknnkyingaltamdyllgr
                npniqsyitgygdnplenphhrfwayqadntfpkppp
                gclsgggpnsglqdpwvkgsgwqpgerpaekcfmdn
                ieswstneitinwnaplvwisayldekgpeiggsvtppt
                nlgdvngdgnkdaldfaallkkallsqdtstinvanadin
                kdgsidavdfallksfllgkitlgggsgggshhhhhh
                (SEQ ID NO: 10)

C.              P37698
cellulolyticum  Mvsftsllagvaaisgvlaapaaevepvavekreaeae
Cel48F          aasspankvyqdrfesmyskikdpangyfseqgipyh
(83 kDa)        sietlmveapdyghvttseamsyymwleamhgrfsg
                dftgfdkswsvteqyliptekdqpntsmsrydankpat
                yapefqdpskypspldtsqpvgrdpinsqltsaygtsml
                ygmhwildvdnwygfgaradgtskpsyintfqrgeqe
                stwetipqpcwdehkfggqygfldlftkdtgtpakqfk
                ytnapdadaravqatywadqwakeqgksystsvgkat
                kmgdylrysffdkyfrkigqpsqagtgydaahyllswy
                yawgggidstwswiigsshnhfgyqnpfaawvlstda
                nfkpkssngasdwaksldrqlefyqwlqsaegaiagga
                tnswngryeavpsgtstfygmgyvenpvyadpgsnt
                wfgmqvwsmqrvaelyyktgdarakklldkwakwi
                ngeikfnadgtfqipstidwegqpdtwnptqgytgnan
                lhvkvvnygtdlgcasslantltyyaaksgdetsrqnaq
                klldamwnnysdskgistveqrgdyhrfldqevfvpa
                gwtgkmpngdviksgvkfidirskykqdpewqtmv
                aalqagqvptqrlhrfwaqsefavangvyailfpdqgp
                ekllgdvngdetvdaidlailkkyllnsstttintanadmn
                sdnaidaidyallkkallsiqggggsgggshhhhhh
                (SEQ ID NO: 12)
```

TABLE 6-continued

DNA and amino acid sequences used in this study.

| | | |
|---|---|---|
| *C. cellulolyticum* Cel5A (56 kDa) | P17901 | Mvsftsllagvaaisgvlaapaaevepvavekreaeae aydaslipnlqipqknipnndgmnfvkglrlgwnlgnt fdafngtnitneldyetswsgikttkqmidaikqkgfnt vripvswhphvsgsdykisdvwmnrvqevvnycid nkmyvilnthhdvdkvkgyfpssqymasskkyitsv waqiaarfanydehlifegmneprlvghanewwpelt nsdvvdsincinqlnqdfvntvratggknasrylmcpg yvaspdgatndyfrmpndisgnnnkiivsvhaycpw nfaglamadggtnawnindskdqsevtwfmdniynk ytsrgipviigecgavdknnlktrveymsyyvaqakar gilcilwdnnnfsgtgelfgffdrrscqfkfpeiidgmvk yafeaktdpdpvivygdynndgnvdaldfaglkkyim aadhayvknldvnldnevnafdlailkkyllgmvsklp sngggsgggshhhhhh (SEQ ID NO: 14) |
| *C. cellulolyticum* CipC (161 kDa) | U40345 | mvsftsllagvaaisgvlaapaaevepvavekreaeaea agtgvvsvqfnngsspassnsiyarfkvtntsgspinlad lklryyytqdadkpltfwcdhagymsgsnyidatskvt gsfkavspavtnadhylevalnsdagslpaggsieiqtrf arndwsnfdqsndwsytaagsymdwqkisafvggtl aygstpdggnpppqdptinptsisakagsfadtkitltpn gntfngiselqssqytkgtnevtllasylntlpenttktltfd fgvgtknpkltitvlpkdipgdslkvtvgtangkpgdtvt vpvtfadvakmknvgtcnfylgydasllevvsvdagpi vknaavnfsssasngtisflfldntitdelitadgvfanikf klksvtakttpvtfkdggafgdgtmskiasvtktngsvt idpgtqptkelkvavgtangkpgdtvtvpvtfadvvnv gnvgtcnfylaydasllevvsvdagpivknaavnfsssa sngtisflfldntitdelitsdgvfanikfklksvatktttpvt fkdggafgdgtmakiatvtktngsvtidpgtqptkelkv avgtangkpgdtvtvpvtfadvasagnvgtcnfylayd asllevvsvdagpivknaavnfsssasngsisflfldntit delitadgvfanikfklksvaaktttpvtfkdggafgdgt mtkiatvtktngsvtidpgtqptkelkvavgtaegnvgd tvtvpvtfadvasagnvgtcnfylaydaslldvvsvaag pivknaavnfsssasngsisflfldntitdelitadgvfani tfklksvtaktttpvtfkdggafgdgtmakiatvtktngs vtivpgiqptkelkvavgtaegnvgdtvtvpvtfadvas agnvgtcnfylaydaslldvvsvaagpivknaavnfsss asngsisflfldntitdelitadgvfanisfklksvtsktttp vtfkdggafgdgtmakiatviktngsvtivpgiqptkel kvavgtaegnvgdtvtvpvtfadvasagnvgtcnfyla ydaslldvvshaagpivknravnfsssasngsisflfldn titdelitadgvfanitfklksvaaktttpvtfkdggafgdg tmakiatvtktngsvtivpgiqptkelkvavgtasgkag dtvtvpvtfadvatvgnvgtcnfyvtydtnllevasvtpg sivtnaavnfssstsngtisflfldntitdqliktdgtfaeikf klksvtaktttpvafkdggafgdgtmakiatvtktngsvt idvgdytpvnptitpstasfdkyvpanvnvtltpngntf kgitgltsgtdftvsnnvvtisksylstlavgsktltfdfgvt nnpvltltitdstpvvtglgvkiasvtgktgdtitvpvtlsn vvksgnvgtcnfyitydasmlqavsatagdivlnapvn fsssinattgtisilfldntigdqlitsdgvvanltfkvvgtss tttpiafkaggafgngnmskisditftngsaklngggsg ggshhhhhh (SEQ ID NO: 16) |
| *C. cellulolyticum* Cel8C (49 kDa) | P37699 | Mvsftsllagvaaisgvlaapaaevepvavekreaeae aadqipfpydakypngaysclaqsqsignnlyrsewe qwksahitsngargykrvqrdattnydtvseglgyglls vyfgeqqlfddlyryvkvflnsnglmswridssgnim gkdsigaatdadediavslvfahkkwgtsggfnyqtea knyinniynkmvepgtyvikagdtwggsnvtnpsyf apawyrifadftgnsgwinvankcyeiadkarnsntgl vpdwctangtpasgqgfdfyydairyqwraaidyswy gtakakthcdaisnffknigyanikdgytisgsqissnht atfvscaaaaamtgtdttyakniynecvkvkdsgnyty fgntlrmmvllyttgnfpnlytynsqpkpdlkgdvnnd gaidaldiaalkkailtqttsnisltnadmnndgnidaidf aglkvkllngggsgggshhhhhh (SEQ ID NO: 18) |

Example 2

Production of a Chimeric Cellulosome in Yeast

The pieces of a cellulosome system can also be created via chimeras of multiple proteins, from multiple sources. Creating recombinant cellulosomes in this way may have a number of advantages for incorporation into a yeast CBP organism. Such reconstructions have been carried out a number of times for expression in E. coli (e.g. (Caspi J., J. Biotechnol. 135(4): 351-7 (2008); Fierobe H. P., et al, J. Biol. Chem. 280(16): 16325-34 (2005)).

For example, a scaffoldin can be constructed with cohesin modules from a number of species of cellulosome producing organisms. These cohesin modules bind specifically to dockerin modules from the same species, which would be attached to the catalytic domains of interest. In this way, the exact order and concentration of components of a recombinant cellulosome could be controlled. This is particularly useful in the context of CBP yeast because the complex control mechanisms used by bacteria to control the make up of cellulosomes (which have not yet been described), cannot be easily replicated in a recombinant system.

An additional advantage of a chimeric cellulosome system is that components that are most easily expressed in yeast can be combined to yield greater overall production. For example, if a particular dockerin or cohesin domain is very well expressed in yeast, and functional, then this domain may be the best choice to combine with the catalytic component that requires the highest expression level.

Figure 8:
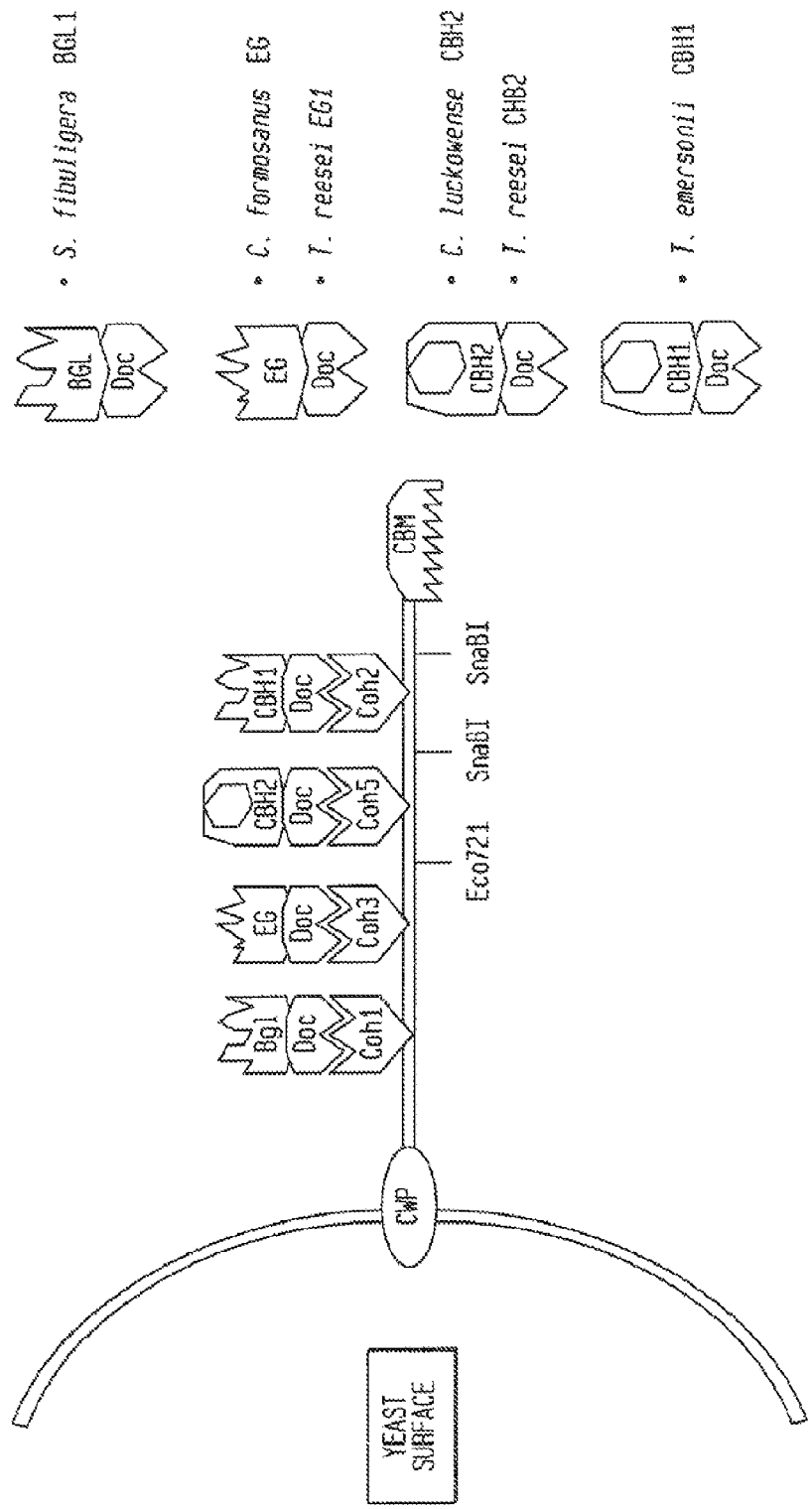
FIG. 8 depicts a schematic representation of a chimeric cellulosome designed for expression in yeast. The left side depicts the fully constructed version, with a scaffoldin (called "ScfA") attached to yeast cell surface via a fusion with CWP2. The right side shows the catalytic components that can be inserted into this structure.

A schematic of the approach to creating a chimeric cellulosome system taken here is shown below in FIG. 8. The interaction of 6 potential cohesin/dockerin pairs in yeast is evaluated. This will be accomplished by fusing BGLI from S. fibuligera to the dockerin candidates, and fusing the cohesin candidates to the cell wall anchoring protein from S. cerevisiae, CWP2. Enzyme assays of supernatant and cell pellet fractions allows detection of interaction between the domains. A scaffoldin (ScfA) with cohesins derived from four species (see Table 7 and Table 8 for details), and a carbohydrate binding domain (CBM) is attached to the yeast cell surface via a fusion with CWP2. Four separate catalytic domains are fused to dockerins from the same species the cohesins are taken from, and expressed in the same or separate yeast strains. Assembly occurs via the affinity of dockerin domains for ScfA.

Example 3

Synthetic Constructs for Cellulosome Expression

Table 7 gives the DNA sequences used in this study to express a chimeric cellulosome components. The left column denotes the species and gene from which sequences were obtained to create the chimeric scaffoldins in the case of ScfA, ScfB1, and ScfB2. Fusions of S. fibuligera BGLI with dockerins were completed by yeast mediated ligation, and the resulting constructs were tested for activity in yeast. Of the dockerins tested, those from Clostridium cellulolyticum, Clostridium thermocellum, Clostridium josui, and Clostridium cellulovorans allowed expression of active, secreted BGLI when fused. FIG. 1 shows the results of these activity assays. 4 of the 6 dockerins allowed S. fibuligera BGLI to be secreted to the supernatant.

Figure 9:
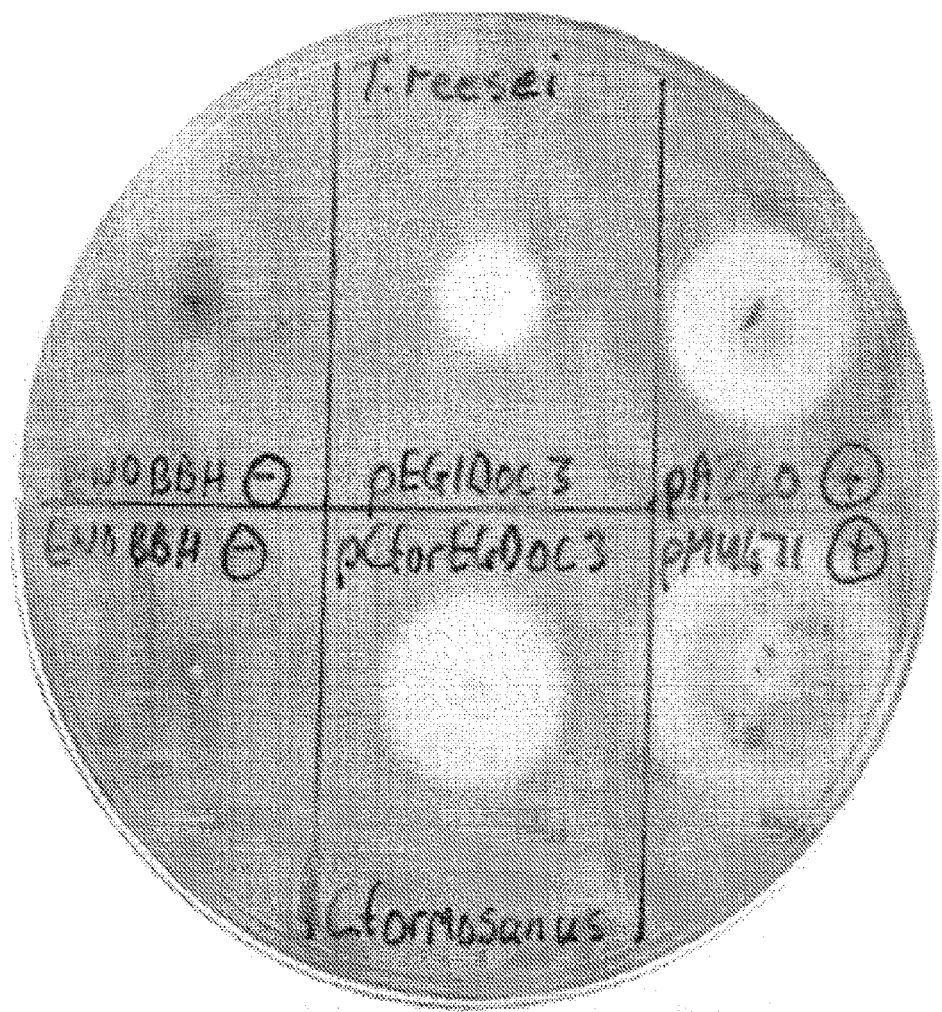
FIG. 9 depicts cellulase activity of the endoglucanase from T. reesei and C. formosanus on SC$_{-ura}$ plates containing 0.2% CMC. Plates were incubated at 30° C. for 48 hours before staining with Congo red. pA240 is a strain producing T. reesei EG1 without a dockerin, and pMU471 is a strain producing C.f. EG1 without a dockerin.

Fusions of dockerins with EGs were also created. EG1 from T. reesei and EG from C. formosanus were secreted when attached to the dockerin from C. cellulovorans. (FIG. 9).

The results provide a demonstration of a chimeric cellulosome expressed in yeast, and an engineered complete cellulosome assembly in a single strain. It also provides tools for further optimization of the chimeric cellulosome via the direct control of the orientation and concentration of catalytic domains in the recombinant cellulase system.

TABLE 7

DNA sequences used to express a chimeric cellulosome in yeast.

| Gene/Species and Genes derived from | DNA sequence used (ORF flanked by necessary restriction sites, and homologous regions for YML cloning) |
|---|---|
| ScfA CipA, Clostridium thermocellum CipC, Clostridium cellulolyticum CbpA, Clostridium cellulovorans ScaA, Acetivibrio cellulolyticus Saccharomyces cerevisiae CWP2 | tcataaaaaaccaagcaactgcttatcaacacacttaattaaaatggtctctttcacttctttgttggcgggtgtcgctgctatc<br>agtggtgtcttggctgcccagccgctgaagtcgaaccagttgccgttgaaaagagaggtgttgtttctgtccaattcaac<br>aacggttctagcccagcttcctccaactccatctacgccagattcaaggttactaacacttctggttctccaatcaatctagct<br>gatttgaagttgagatactactacactcaagatgctgacaagccattgaccttctggtgtgaccacgctggttacatgtctg<br>gttccaactacatcgacgccacctccaaggttactggtagcttcaaggccgtttctccagccgttactaacgctgatcacta<br>cttggaagtcgctttgaactccgatgccggttctttgccagctggtggttccatcgaaattcaaaccgtttcgctagaaac<br>gattggtccaactttgaccaatctaacgactggtcctacactgccgctggttcttacatggactggcaaaagatttctgctttc<br>gttggtggtaccttagcttacggttccaccccagacggtggtaacccaccaccacaagatccaactattaacccaacttcc<br>atactgctaaggctggttccttcgctgatactaagattaccttgactccaaacggtaacacctttcaacggcatctctgaatt<br>gcaatcttctcaatacaccaaggggtactaacgaagttaccttgttggcttatacttgaacactttgccagaaaacaccacta<br>agactttgaccttcgacttcggtgttggtaccaagaatccaaagttgactattaccgttctaccaaaggacatcccaggtga<br>ttctttaaaggttgctgttggtaccgctgaaggcaacgtcggcgacaccgttaccgtcccagttaccttcgctgacgtcgcc<br>tctgctggtaacgtcggtacttgtaacttctacttggcttacgatgcctccttgttggacgttgtctctgtcgctgaggtccaa<br>tcgttaagaacgctgctgtcaattctcttccgcctctaacggctccatcagtttcttattcttggataacactatcaccgac<br>gaattgattactgagacggtgtttttgctaacattaccttcaagttgaagtctgttactgccaagactaccactccagtcactt<br>tcaaggacggtggtgcttcggtgacggtactatggccaaaattgctaccgttactaagactaacggttccgttactattgtc<br>ccaggtatccaaccaactaaggaagccgtcagaattaaggttgacactgttaacgctaagccaggtgacactgtcagaat<br>tccagtcagattctctggtatcccatctaagggtattgccaactgtgacttcgtttacttctacgatccaaacgttttagaaatc<br>atcgaaattgaaccaggtgatatcatcgttgatccaaacccagacaagtccttcgacactgagtttacccagacagaaag<br>attatcgtcttcttgttcgctgaagactctggtaccggtgcttacgctattaccaaggatggtgtctttgccactatcgttgcta<br>aggttaagtctggtgcccaaacggtttaagcgttatcaagttcgttgaagtcggtggtttcgctaacaacgacttggttga<br>acaaaagaccaattcttcgatggtggtgtcaacgttggtgtccacgtgaccccagtcaccgtcaccttgtctaacgttcaggtatc<br>gctaccgctgaattacaagtcggtttcgatgctactttgttggaagttgcttccatcaccgtcggtgacatcgtcttgaaccc<br>atctgtcaacttctcctccgttgttaacggttctactattaagttgttgttcttggacgacactttgggttcccaattgatttccaa<br>ggacggcgtcttggctaccatcaacttcaaggctaagaccgttacctctaaggtcactactccagttgctgtttctggtactc<br>cagtcttcgctgatggtaccttggctgaattgaagtatgaaaccgttgctggtagcgttaccattgaaccttctcaaccagtt<br>aagaccgtcacagctaccgtcggtaccgctaccggtaaagttggtgaaactgttgctgtttacgtaaagaaagatgatcca |

TABLE 7-continued

DNA sequences used to express a chimeric cellulosome in yeast.

|  |  |
|---|---|
|  | aacggctttactgttaacgttgattctgttaacggtaacgttggtgaacaaattgtcgttccagtctcttcgccaacgttccat<br>ccaacggtgttccactgctgacatgactatcacctatgattcctctaagaggaatacgtttccggtgctgctggttctatcgt<br>cactaacccaaccgtcaacttcggtatcaataaggaagctgatggtaaattgaaggttctattttttggactacactatgtcca<br>ccggttacatttctactaacggtgtcttcgctaacgttactttcaaggtcttaaactctgctccaaccaccgttggtatcactgg<br>tgctacttttggtgataagaacttgggtaacataccgctaccattaacgctggttccattaacggtggttactacgtaatcaa<br>cccagatttcgttactacttccaccaccgctccaattgtcaaggctggtttcactgtcgaaatcgttggtactaccaagtccg<br>ctgttaccgactccaaccggttactttgaaatcaaggatgttgctgctggtacttacactgttaagatcactaaagctaactac<br>cttaccagagaaattgctaacgtctccgttaccgctgacaaggaattgtccacttctgcttccccaattttgatgtgggctatt<br>tctcaaattactgatggtcaaattcaagctaccactaccgctaccactgaagctactactactgctgcccatcttccactgtt<br>gaaaccgtctccccatcttctaccgaaactatctctcaacaaaccgaaaacggtgagccaaggccgctgtcggtatggg<br>tgctggtgccttagctgccgctgctatgttgttataaggcgcgccgcttttgattaagccttctagtccaaaaaacacgtt<br>(SEQ ID NO: 19) |
| ScfB 1<br>CipA,<br>*Clostridium*<br>*thermocellum*<br>CipC,<br>*Clostridium*<br>*cellulolyticum*<br>CbpA,<br>*Clostridium*<br>*cellulovorans*<br>*Saccharomyces*<br>*cerevisiae*<br>CWP2 | atggtctctttcacttctttgttggcgggtgtcgctgctatcagtggtgtcttggctgccccagccgctgaagtcgaaccagt<br>tgccgttgaaaagagaggtgttgtttctgtccaattcaacaacggttctagcccagcttcctccaactccatctacgccagat<br>tcaaggttactaacacttctggttaccaatcaatctagctgatttgaagttgagatactactacactcaagatgctgacaagc<br>cattgaccttctggtgtgaccacgctggttacatgtctggttccaactacatcgacgccacctccaaggttactggtagcttc<br>aaggccgtttaccagccgttactaacgctgatcactacttggaagtcgctttgaactccgatgccggttcttttgccagctg<br>gtggttccatcgaaattcaaacccgtttcgctagaaacgattggtccaacttttgaccaatctaacgactggtcctacactgc<br>cgctggttcttacatggactggcaaaagatttctgcttcgttggtggtaccttagcttacggttccacccccagacggtggta<br>acccaccaccacaagatccaactattaacccaacttccatctctgctaaggctggttccttcgctgatactaagattacctttg<br>actccaaacggtaacaccttcaacggcatctctgaattgcaatcttctcaatacaccaagggtactaacgaagttaccttgtt<br>ggcttcttacttgaacacttttgccagaaaacaccactaagacttttgaccttcgacttcggtgttggtaccaagaatccaaagt<br>tgactattaccgttctaccaaaggacatcccaggtgattcttttaaaggttgctgttggtaccgctgaaggcaacgtcggcga<br>caccgttaccgtcccagttaccttcgctgacgtcgcctctgctggtaacgtcggtacttgtaacttctacttggcttacgatg<br>cctccttgttggacgttgtctctgtcgctgctggtccaatcgttaagaacgctgctgtcaatttctcttcttccgcctctaacgg<br>ctccatcagttctcttattcttggataacactatcaccgacgaattgattactgctgacggtgtttttgctaacattaccttcaagtt<br>gaagtctgttactgccaagactaccactccagtcacttttcaaggacggtggtgctttcggtgacggtactatgccaaaatt<br>gctaccgttactaagactaacggttccgttactattgtcccaggtatccaaccaactaaggaagccgtcagaattaaggttg<br>acactgttaacgctaagccaggtgacactgtcagaattccagtcagattctctggtatcccatctaagggtattgccaactg<br>tgacttcgttttactcttacgatccaaacgttttagaaatcatcgaaattgaaccaggtgatatcatcgttgatccaaacccaga<br>caagtccttcgacactgctgttacccagacagaaagattatcgtcttcttgttcgctgaagactctggtaccggtgcttacg<br>ctattaccaaggatggtgtctttgccactatcgttgctaaggttaagtctggtgccccaaacggtttaagcgttatcaagttcg<br>ttgaagtcggtggtttcgctaacaacgacttggttgaacaaaagacccaattcttcgatggtggtgtcaacgttggtgtcca<br>cgtgaccgccgaagttgaaccagtcgctgttgaaaagagaccagtcactttgtccaacgttccaggtattgctactgctga<br>attgcaagttggtttcgacgccaccttgttggaagttgcctctatcactgtcggtgacatcgttttgaacccatccgttaacttc<br>tcttctgtcgtcaacggttctaccattaagttgttgttcttggacgacacttgggtagtcaattgatctctaaggacggtgttt<br>ggctactatcaacttcaaggctaagacggttacctccaaggttaccactccagtcgctgtttctggtactccagtcttcgctg<br>atggtactttggctgaattaaaatacgaaaccgttgctggttccgttaccatcgaaccatcccaaccagttaagactgttact<br>gctactgtcggtaccgctaccggtaaggtcggtgaaactgtcggtcattctcgagactggtacggtgcttggttcctaga<br>ggatcaccaattgtcaaggctggtttcactgtcgaaatcgttggtactaccaagtccgctgttaccgactccaacggttactt<br>tgaaatcaaggatgttgctgctggtacttacactgttaagatcactaaagctaactacctaccagagaaattgctaacgtct<br>ccgttaccgctgacaaggaattgtccacttctgcttccccaattttgatgtgggctatttctcaaattactgatggtcaaattca<br>agctaccactaccgctaccactgaagctactactactgctgcccatcttccactgttgaaaccgtctccccatatctaccg<br>aaactatctctcaacaaaccgaaaacggtgctgccaaggccgctgtcggtatgggtgctggtgccttagctgccgctgct<br>atgttgtta (SEQ ID NO: 21) |
| ScfB2<br>CipA,<br>*Clostridium*<br>*thermocellum*<br>CipC,<br>*Clostridium*<br>*cellulolyticum*<br>CbpA,<br>*Clostridium*<br>*cellulovorans*<br>CipC,<br>*Clostridium*<br>*josui*<br>*Saccharomyces*<br>*cerevisiae*<br>CWP2 | atggtctctttcacttctttgttggcgggtgtcgctgctatcagtggtgtcttggctgccccagccgctgaagtcgaaccagt<br>tgccgttgaaaagagaggtgttgtttctgtccaattcaacaacggttctagcccagcttcctccaactccatctacgccagat<br>tcaaggttactaacacttctggttctcaatcaatctagagatttgaagttgagatactactacactcaagatgctgacaagc<br>cattgaccttctggtgtgaccacgctggttacatgtctggttccaactacatcgacgccacctccaaggttactggtagcttc<br>aaggccgtttctccagccgttactaacgctgatcactacttggaagtcgctttgaactccgatgccggttcttttgccagctg<br>gtggttccatcgaaattcaaacccgtttcgctagaaacgattggtccaacttttgaccaatctaacgactggtcctacactgc<br>cgctggttcttacatggactggcaaaagatttctgcttcgttggtggtaccttagcttacggttccacccccagacggtggta<br>acccaccaccacaagatccaactattaacccaacttccatctctgctaaggctggttccttcgctgatactaagattacctttg<br>actccaaacggtaacaccttcaacggcatctctgaattgcaatcttctcaatacaccaagggtactaacgaagttaccttgtt<br>ggcttcttacttgaacacttttgccagaaaacaccactaagacttttgaccttcgacttcggtgttggtaccaagaatccaaagt<br>tgactattaccgttctaccaaaggacatcccaggtgattcttttaaaggttgctgttggtaccgctgaaggcaacgtcggcga<br>caccgttaccgtcccagttaccttcgctgacgtcgcctctgctggtaacgtcggtacttgtaacttctacttggcttacgatg<br>cctccttgttggacgttgtctctgtcgctgctggtccaatcgttaagaacgctgctgtcaatttctcttcttccgcctctaacgg<br>ctccatcagttctcttattcttggataacactatcaccgacgaattgattactgctgacggtgtttttgctaacattaccttcaagtt<br>gaagtctgttactgccaagactaccactccagtcacttttcaaggacggtggtgctttcggtgacggtactatgccaaaatt<br>gctaccgttactaagactaacggttccgttactattgtcccaggtatccaaccaactaaggaagccgtcagaattaaggttg<br>acactgttaacgctaagccaggtgacactgtcagaattccagtcagattctctggtatcccatctaagggtattgccaactg<br>tgacttcgttttactcttacgatccaaacgttttagaaatcatcgaaattgaaccaggtgatatcatcgttgatccaaacccaga<br>caagtccttcgacactgctgttacccagacagaaagattatcgtcttcttgttcgctgaagactctggtaccggtgcttacg<br>ctattaccaaggatggtgtctttgccactatcgttgctaaggttaagtctggtgccccaaacggtttaagcgttatcaagttcg<br>ttgaagtcggtggtttcgctaacaacgacttggttgaacaaaagacccaattcttcgatggtggtgtcaacgttggtgtcca<br>cgtgaccgccgaagttgaaccagtcgctgttgaaaagagaccagtcactttgtccaacgttccaggtattgctactgctga<br>attgcaagttggtttcgacgccaccttgttggaagttgcctctatcactgtcggtgacatcgttttgaacccatccgttaacttc<br>tcttctgtcgtcaacggttctaccattaagttgttgttcttggacgacacttgggtagtcaattgatctctaaggacggtgttt<br>ggctactatcaacttcaaggctaagacggttacctccaaggttaccactccagtcgctgtttctggtactccagtcttcgctg<br>atggtactttggctgaattaaaatacgaaaccgttgctggttccgttaccatcgaaccatcccaaccagttaagactgttact<br>gctactgtcggtaccgctaccggtaaggtcggtgaaactgtcgtcattctcgagactaataaacctgtaataagaagga<br>tataaaactgaagacttgaacgttgctgtcggtaccgccgaaggtaacgtcggtgaaactgtcactgtcccagttaccttc<br>gccaacgtcgccaaggtcaataacgttggtacctgtaacttctacttggcttacgacgcttccttgttggatgttgtctccgtc<br>gatgctggtccaattgttaagaacgccgccgttaacttctcttcttctgcctctaacggtactatctccttcttcgttcttggacaa<br>cactattactgacgaattgatcacctccgacggtgtcttcgctaacattaccttcaagttgaagaacgttctactaagactac |

TABLE 7-continued

DNA sequences used to express a chimeric cellulosome in yeast.

| | |
|---|---|
| | caccccaatctccttcaaggacggtggtgctttcggtgatggtaacatggctaagattgctaccgttgtcaaaaccaacgg<br>ttctgtcactatcatcccaggtgacccagaaccagcggccgcattggttcctagaggatccaccaattgtcaaggctggttt<br>cactgtcgaaatcgttggtactaccaagtccgctgttaccgactccaacggttactttgaaatcaaggatgttgctgctggta<br>cttacactgttaagatcactaaagctaactaccttaccagagaaattgctaacgtctccgttaccgctgacaaggaattgtcc<br>acttctgcttccccaattttgatgtgggctattctcaaattactgatggtcaaattcaagctaccactaccgctaccactgaa<br>gctactactactgctgccccatcttccactgttgaaaccgtctccccatcttctaccgaaactatctctcaacaaaccgaaaa<br>cggtgctgccaaggccgctgtcggtatgggtgctggtgccttagctgccgctgctatgttgtta (SEQ ID<br>NO: 23) |
| *S. fibuligera* sBGLI | gcggccgctcaaggaagtaattatctacttttttacaacaaatattaattaaaatggtgtccttcacctctttgttggctggtgtc<br>gctgctattagcggtgttgttggccgctccagctgctgaagtcgaatctgttgccgttgaaaagagatcccgtgtcccaatcc<br>aaaactacacccaatcccccatctcaaagagatgaatcttcccaatgggtctctccacactactacctacccccacaaggtg<br>gtcgtttacaagacgtctggcaagaagcctacgctagagccaaggctattgtcggtcaaatgactattgttgaaaaggtca<br>atttgactaccggcaccggttggcaattggacccatgtgtcggtaacactggttctgttccaagattcggtattccaaacttg<br>tgtttacaagatggtccttttggggtgtcagattcgctgattttgtcaccggttacccatctgcttttggctaccggtgctaccttca<br>acaaggatttgttcttacaaagaggtcaagcttttgggtcacgaatttaactctaagggtgtccacatcgctttaggtccagct<br>gtcggtccattgggtgttaaggccagaggtggtagaaactttgaagctttcggttccgatccatacttgcaaggtaccgct<br>gctgctgccactatcaagggtttgcaagaaaacaacgtcatggcttgtgttaagcacttcatcggtaacgaacaagaaaa<br>gtacagacaacctgacgatatcaacccagctactaaccaaaccactaaggaagctatctccgccaacattccagacaga<br>gctatgcacgctttgtacttgtggccattcgctgactccgtccgtgccggtgttggttctgtcatgtgctcttacaacagagtc<br>aacaacacttacgcttgtgaaaactcttacatgatgaaccatttgttgaaagaagaatttgggtttccaaggtttcgtcgtctct<br>gactgggtgctcaattgtccggtgtttactctgctatttccggtttggatatgtccatgccaggtgaagtttacggtggttgg<br>aacactggtacctcttttctgggtgtcaaacttgactaaggctatctacaacgaaactgttccaattgaaagattggacgatat<br>ggccaccagaatcttggctgctttgtacgctactaactcttttccaaccgaagaccacttgccaaacttcagttcttggacta<br>ccaaggaatacgttaacaagtactacgctgacaacaccaccgaaattgtcaaagtcaactacaacgttgacccatctaat<br>gatttcaccgaagacaccgctttgaaggttgccgaagaatctattgtcttgttaaagaacgaaaacaacacttttgccaatttc<br>cccagaaaaggccaaaagattattgttgtctggtatcgctgctggtccagatccaatcggttaccaatgtgaggaccaatc<br>ttgtactaacggtgctttgttccaaggctggggttccggttctgtcggttctccaaagtaccaagttactccattcgaagaaat<br>ttcttacttggccagaaagaacaagatgcaattcgactacatcagagaatcttacgacctagctcaagttactaaggtcgct<br>tctgatgctcatttgtctatcgtcgttgtctccgctgcttctggtgaaggttacattactgttgacggtaaccaaggtgataga<br>agaacttgacccttgtgaacaacggtgataagttgatcgaaaccgtcgctgaaaactgtgctaacactgttgttgttgtca<br>cttccactggtcaaatcaacttcgaaggtttcgctgatcacccaaacgttaccgctattgtctgggctggtccattaggtgat<br>agatccggtactgctatcgctaacatcctattcggtaaggctaatccatctggtcacttaccattcactattgctaagaccga<br>cgatgactacatcccaattgaaacctactctccatcttccggtgaaccagaagacaaccatttggttgaaaacgacttgtta<br>gtcgactatagatactttgaagaaaagaacatcgaacctagatacgccttcggttacggtttgtcttacaacgaatacgaag<br>tttccaacgctaaggtttctgctgctaagaaggtcgatgaagaattgccccgaacagctacttacttgtctgaattttcttacc<br>aaaacgccaaggactctaagaacccatccgatgctttcgccccagccgattgaatagagttaacgaatacttgtacccat<br>acttggactctaacgtcaccttgaaggacggtaattacgaatacccagatggttactccactgaacaaagaactaccccaa<br>accaaccaggtggtggtttgggtggtaacgacgctttatgggaagttgcttacaactccaccgacaaatttgtcccacaag<br>gtaactctactgataagttcgttccacaattgtaatttgaagcaccctgaagatggtaagttcgaaactccaatccaattgaga<br>ggtttcgaaaaggttgaattgtctcctggtgaaaagaagactgtcgatttgagattgttgcgtagagacttgtctgtctgggaa<br>tactactcgtcaatcttggatcgttgaatctggtacttacgaagccttgattggtgtcgcagtcaacgacatcaagacatctg<br>tcctgtttactatttgaggcgcgccggatctgcgatagatcaattttttttctttttctcttgagctcgcggccgc (SEQ<br>ID NO: 25) |
| Doc 1<br>*Acetivibrio cellulolyticus* Cel9A | Tcaacgacatcaagacatctgtcctgtttactattgtcaccactcccactccaactcctgcccaatacgtttacggtgatgtc<br>aacggtgatggttccttgaactctatcgatttcggtgtcatgagaaagtacttattgggtatgatcaaggaattctcctacgaa<br>aacggtttgaaggccggtgacgttgacggtaacggtatgttcaactcttttggacttcgcttacatgagacaatacatgttgg<br>gtatcatctccaaattcccagttcaaagtaaggcgcgccggatctgcgatagatcaattttttttct (SEQ ID<br>NO: 27) |
| Doc 2<br>*Clostridium cellulolyticum* CelA | Tcaacgacatcaagacatctgtcctgtttactattgtcactacccccaaccccaactccagctcaatacgtttacccagttatt<br>gtctacggtgacgttaacggtgatggtaacgtcaactccactgacttgactatgttgaaaagatacttgttgaagtccgttac<br>taacatcaatagagaagctgctgacgtcaacagagatggtgctatcaactcctccgatatgaccattttgaagagatacttg<br>atcaagtaaggcgcgccggatctgcgatagatcaattttttttct (SEQ ID NO: 29) |
| Doc 3<br>*Clostridium cellulovorans* EngB | Tcaacgacatcaagacatctgtcctgtttactattgttaccacccccaaccccaactccagctcaatacgtttactacagcttg<br>ggtgacgtcaacaaagacggtaaagtcaacgctattgattacgccgttttgaagtccatcttgttgggtaccaacaccaac<br>gttgacttgtctgtctccgacatgaacaaggacggtaaggttaacgctttggatttggctgttttgaagaaaatgttgttgtctt<br>aaggcgcgccggatctgcgatagatcaattttttttct (SEQ ID NO: 31) |
| Doc 4<br>*Clostridium josui* Cel8A | Tcaacgacatcaagacatctgtcctgtttactattgtcactacccccaactccaactccagctcaatacgtttacggtttgaag<br>ggtgatgttaacaacgatggtgctatcgacgctttggacatcgctgctttgaagaaggccatttttgactcaatctacctccaa<br>catcaacttaactaacgctgacatgaacaacgacggtaacattgacgctatcgacttcgctcaattgaaggttaagttgttg<br>aactaaggcgcgccggatctgcgatagatcaattttttttct (SEQ ID NO: 33) |
| Doc 5<br>*Clostridium thermocellum* CelS | Tcaacgacatcaagacatctgtcctgtttactattgtcaccacccccaactccaactccagctcaatacgtttacggtgacgt<br>taacgacgacggtaaggttaactccactgacgccgttgctttgaagagatacgttttgagatccggtatctctatcaacacc<br>gacaacgctgatttgaacgaagacggtagagtcaactccaccgacttgggtatcttgaaaagatacatttgtaaggcgc<br>gccggatctgcgatagatcaattttttttct (SEQ ID NO: 35) |
| Doc 6<br>*Bacteroides cellulosolvens* Cel48A | Tcaacgacatcaagacatctgtcctgtttactattgttaagttgaagggtgatttgaacggtgacggcgttatcaacatggc<br>tgacgtcatgatcttagctcaatccttcggtaaagctattggtaacccaggtgttaacgaaaaggctgatttgaacaacgac<br>ggtgttattaacatggccgacgctatcatcttggctcaatacttcggtaagactaagtccgccgaagtggtatgttctaagg<br>cgcgccggatctgcgatagatcaattttttttct (SEQ ID NO: 37) |

TABLE 7-continued

DNA sequences used to express a chimeric cellulosome in yeast.

| | |
|---|---|
| Coh 1_CWP2<br>*Acetivibrio*<br>*cellulolyticus*<br>ScaA<br>*Saccharomyces*<br>*cerevisiae*<br>CWP2 | Aaccaagcaactgcttatcaacacacttaattaaaatggtttctttcacctctttgttagctggtgttgccgccatctctggtgt<br>cttggctgctccagctgccgaagttgaaccagtcgctgttgaaaagagaggtttcaccgtcaacgttgattccgtcaatgg<br>taacgttggtgaacaaatcgttgtcccagttagtttcgccaatgtcccatctaacggtgtttccaccgctgatatgaccattac<br>ttacgacagttctaagttggaatacgtttctggtgctgccggttccatcgtcactaacccaactgttaacttcggtatcaacaa<br>ggaagctgacggtaagttgaaggttttgttcttagactacactatgtccaccggttacatctctaccaacggtgtcttcgcca<br>acgtcacttcaaggttttgaactccgctccaaccactgttggtatcaccggtgctaccttcggtgacaagaacttaggtaa<br>catctccgccaccattaacgctggttctatcaacggtggtgtcgactacatcaaccagacttcgttactacctccaccacc<br>gccccaatcgtcaaggctggtttcactgttgaaattgtcggtaccactaagtccgccgtcaccgactctaacggttacttcg<br>aaattaaggacgttgctgctggtacctacactgttaagattactaaggctaactacttgactagagaaatcgctaacgtctcc<br>gttactgctgacaaagaattgtccacttctgcttcccaattttgatgtgggctatttctcaaattactgatggtcaaattcaag<br>ctaccaccactgccaccaccgaagctactaccaccgccgctccttcttccaccgtcgaaaccgtttctccatcttctactga<br>aactatctctcaacaaactgaaaacggtgctgctaaggctgccgtcggtatgggtgctggtgctttggctgctgctgctatg<br>ctattgtaaggcgcgccgcttttgattaagccttctagtccaaa (SEQ ID NO: 39) |
| Coh 2<br>*Clostridium*<br>*cellulolyticum*<br>CipC | Gcggccgcctgccgaagttgaaccagtcgctgttgaaaagagattgaaggttgctgtcggtactgctgaaggtaacgtc<br>ggtgacaccgttaccgttccagtcacttcgctgatgttgcctcagctggtaacgttggtacctgtaacttctacctagcttac<br>gacgcctccttgttggacgtcgtctctgttgctgctggtccaatcgtcaagaacgctgctgttaacttctcttcttctgcttcta<br>acggttctatttccttcttgttcttggataacactattaccgacgaattaattaccgctgacggtgtttcgccaacatcactttc<br>aagttgaagtcgtaccgctaagaccaactacccagttaccttcaaggacggtggtgccttcggtgatggtactatggct<br>aagatcctactgttaccaagactaacggttccgttacctacatcaacccagacttcgttactacctccaccacgcggccg<br>c (SEQ ID NO: 41) |
| Coh 3<br>*Clostridium*<br>*cellulovorans*<br>CbpA | Gcggccgcctgccgaagttgaaccagtcgctgttgaaaagagaccagtcacttgtccaacgttccaggtattgctactg<br>ctgaattgcaagttggtttcgacgccaccttgttggaagttgcctctatcactgtggtgacatcgttttgaaccatccgtta<br>acttctcttctgtcgtcaacggttctaccattaagttgttgttcttggacgacacttgggtagtcaattgatctctaaggacgg<br>tgttttggctactatcaacttcaaggctaagacggttacctccaaggttaccactccagtcgctgttcctggtactccagtctt<br>cgctgatggtactttggctgaattaaaatacgaaaccgttgctggttccgttaccatcgaaccatcccaaccagttaagact<br>gttactgctactgtcggtaccgctaccggtaaggtcggtgaaactgtcgctgtctacatcaacccagacttcgttactacct<br>ccaccacgcggccgc (SEQ ID NO: 43) |
| Coh 4<br>*Clostridium*<br>*josui* CipC | Gcggccgcctgccgaagttgaaccagtcgctgttgaaaagagaactgaagacttgaacgttgctgtcggtaccgccga<br>aggtaacgtcggtgaaactgtcactgtcccagttaccttcgccaacgtcgccaaggtcaataacgttggtacctgtaacttc<br>tacttggcttacgacgcttccttgttggatgttgtctccgtcgatgctggtccaattgttaagaacgccgccgttaacttctctt<br>cttctgcctctaacggtactatctccttcttgttcttggacaacactattactgacgaattgatcacctccgacggtgtcttcgc<br>taacattaccttcaagttgaagaacgtttctactaagactaccaccccaatctccttcaaggacggtggtgctttcggtgatg<br>gtaacatggctaagattgctaccgttgtcaaaaccaacggttctgtcactatcatcccaggtgacccagaaccatacatca<br>acccagacttcgttactacctccaccacgcggccgc (SEQ ID NO: 45) |
| Coh 5<br>*Clostridium*<br>*thermocellum*<br>CipA | Gcggccgcctgccgaagttgaaccagtcgctgttgaaaagagagctgttcgtattaaggtcgacaccgtcaacgctaag<br>ccaggtgatactgtcagaatcccagtcagattctctggtattcctcaaagggtatcgctaactgtgatttcgtttactcctac<br>gatccaaacgtttttggaaattatcgaaatcgaaccaggtgacatcatcgtcgatcaaacccagataagtccttcgacact<br>gctgtttaccagacagaaagattatcgtcttcttgttcgctgaagactccggtactggtgctactgctattaccaaggacg<br>gtgtcttcgctactattgttgccaaagtgaagtctggtgccccaaacggtttgtctgttatcaagttcgttgaagttggtggttt<br>cgctaacaacgatttagtcgaacaaaagaccccaattcttgacggtggtgttaacgtcggttacatcaacccagacttcgtt<br>actacctccaccacgcggccgc (SEQ ID NO: 47) |
| Coh 6<br>*Bacteroides*<br>*cellulosovens*<br>CipBc | Gcggccgcctgccgaagttgaaccagtcgctgttgaaaagagagttactgctactgtcgacaagactaccgcctccgtt<br>ggtgacattatcacctacactattaaggacgttgctggtttcgccggttatcaagccaacgtcaagtacgacccat<br>ctgttttgcaaccagtttacgacgacagatctgcttacgactctgctgctgtcccagaatacggtaccttgttgcaaaagag<br>atactccccaaccgacatggcttctaacgacttgtctaagggtaccttgacttttggtagaacttacatgaacttggattctta<br>caaagcttctggttctgccgaaaccaccggttctatcgctgttattagattcaaggtcttgaagaacactgctaccaccatta<br>agttgcaaaatgccgcttccttgaccaacgctgtcgacggtaccatgttgttcgactggtctggtgcccaattagctggtta<br>caaggttgctcaagctcccttacatcaacccagacttcgttactacctccaccacgcggccgc (SEQ ID NO: 49) |
| CBH1<br>*Talaromyces*<br>*emersonii* | atgctaagaagagctttactattgagctcttctgctatcttggccgttaaggctcaacaagccggtaccgctactgctgaaa<br>accaccctccattgacctggcaagaatgtaccgctccaggttcttgtaccacccaaaacggtgctgtcgtcttggacgcta<br>actggagatgggtccacgacgtcaacggttacactaactgttacaccggtaacacctgggacccaactactgtccagac<br>gacgaaacttgcgctcaaaactgtgccttggacggtgctgactacgaaggtacttacggtgttacctcctctggttcttcctt<br>gaagttgaacttcgtcactggttctaacgtcggttccagattgtatttgttgcaagatgactccacttaccaaatcttcaagttg<br>ttgaacagaaattttcttttcgacgtcgatgtgtccaacttgccttgcgttgttgaacggtgctctatacttcgttgctatggacg<br>ctgatggtggtttccaagtacccaaacaacaaggctggtgccaaatacggtactggttactgtgactctcaatgtccac<br>gtgacttgaagtttattgatggtgaagctaatgtcgaaggttggcaaccatcttctaacaactgctaacactggcatcggtga<br>ccacggttcttgctgtgccgaaatggacgtttgggaagccaactccatttccaacgccgtcactccacacccatgtgacac<br>tccaggtcaaactgttgtccggcgatgactgtggtggtacttactctaacgatagatacgctggtacctgtgatccgacac<br>ggttgcgacttcaatccatacagaatgggtaacactcctttacggtccaggcaagatcatcgacactactaagccattca<br>ctgttgtcacccaattcttgaccgacgatggtactgataccggtacttgtccgaaatcaagagattctacatccaaaactct<br>aacgtcatcccacaaccaaattccgacatctctggtgtcactggtaactccattaccaccgaattttgtaccgcccaaaagc<br>aagctttcggtgaccacgacttctacaacacggtggtttggctaagatgggtgctgctatgcaacaaggtatggtttt<br>ggtcatgtctttgtgggacgactacgctgctcaaatgtgtggttggactccgattacccaaccgatgccgacccaaccac<br>cctggtatcgctagaggtacctgtccaactgactctggtgttccatctgacgtcgaatccaatctccaaactcctacgtc<br>acttactccaacattaaattcggtccaatcaactccactttcactgcttcttaa (SEQ ID NO: 51) |
| CBH2b<br>*Chrysosporium*<br>*lucknowense* | atgggcaagaagttgttcattaccgctgccttagctgccgcagtgcttgctgcaccagtgatcgaagagagacaaaattg<br>cggagccgtctggacacagtgcggaggcaacggctggaagcccaacatgttgtgcttctggctcaacgtcgctggc<br>acagaacgagtggtattcccagtgccttccaaactcccaggtgacttcttcaacaaccccagctcaacgtctacttcaca<br>gagatccacaagtacctcttctagcacaaccagaagtggctcatcctcatctagcagtacgacccctccaccgtatcaa<br>gtcctgtcacgagtatccctggcggagcaacctcaacagccagttattccggcaatcctttctctggagtgagattatttgc |

TABLE 7-continued

DNA sequences used to express a chimeric cellulosome in yeast.

```
aaacgactattatagatcagagghtcacaaccttgcaattccttctatgacgggaaccctagccgcaaaggcttccgccgt
agcagaagtccctagtttccaatggcttgacagaaacgttacaatagatacacttatggtacagactttatctcaggttaga
gctttgaataaggccggtgccaacccaccttatgctgcccaattagtagtctatgacttgccagatagagactgtgctgcc
gcagcttctaatggtgaattttccatcgcaaatggcggagctgcaaactatagatcatacattgatgcaataagaaaacac
atcattgagtattctgatattagaataatccttgtgattgaaccagactccatggctaatatggttaccaacatgaatgtagcc
aagtgttctaacgcagcttccacataccatgagctaaccgtatatgcattaaaacaactgaatctacctaacgttgctatgta
cttagatgccggtcatgccggatggttgggctggcctgcaaatatccaacccgcagctgaattgttcgctggaatctacaa
cgacgccggaaagcccgctgccgttagaggcttagccacaaatgttgcaaattacaacgcttggtcaattgctagtgccc
cttcttataccctcaccaaatcctaactacgatgagaaacattacatagaagcattttccccattgttaaactccgctggattcc
ctgccagattcatcgtggataccggtagaaacggcaaacaaccaactggacaacaacaatggggagattggtgtaacgt
caagggaaccggcttcggcgtcaggcctacggcaaacaccggacacgagctagtcgacgcttttgtatgggttaagcc
aggtggcgaaagtgacggaacaagtgacacgagtgctgcaagatacgattaccactgtggtctgtccgacgctttacag
cccgcccccgaggctggacaatggttccaggcttattttgaacaattgttaacgaacgcaaatccaccattctaa
(SEQ ID NO: 53)
```

EG
Coptotermes
formosanus

```
atgagattcccttccatttcactgctgttttgttcgcagcctcaagtgctttagcagcctatgactacaagacagtattgaag
aactccttgttgttctacgaagctcaaagaagtggaaaattgcctgcagaccagaaggtgacctggagaaaagattccgc
attaaacgacaagggacagaaggagaggacttaactggaggttattacgacgccggagactttgtgaagttcggttttc
caatggcatacacagttaccgtgttggcctggggttagtcgattatgaatctgcttacagtactgcgggtgccttggatgat
ggtagaaaggccttgaaatggggtacagattattctttgaaagcacataccgctgccaatgagttttacggacaggtgggt
cagggagatgtggatcatgcttactggggacgtcctgaggacatgactatgtctagaccagctacaagatcgatacatc
aaaacctggtagtgacttagctgcagaaacagcagccgctttagcagcaaccgcaatagcttacaagtcagccgattcta
cctacagtaacaacttaattactcatgcaaagcagttgttcgattttgcaaacaattatagaggaaagtactctgatagtatta
ccgatgccaagaatttctatgcatccggtgattataaggacgaattagtatgggctgcagcctggttgtatagagctacaaa
tgataacacttacttaaccaaagccgaatcattgtataatgaatttggtttaggatcttggaacggtgcattcaattgggataa
caagatatccggagttcaggtcttattagccaaattgacatccaaacaagcatacaaagataaagttcagggttatgttgatt
acttagtctcctctcaaaagaaaactcaaaggggattggtctatattgaccaatgggggaaccttaagacacgcagctaata
gtgccttgatcgctttacaggccgctgatttgggtataaacgctgctagttatagacaatacgcaaagaagcaaattgattat
gccttaggtgacggaggtcgttcttacgtggtcggattcggaactaaccctccagtaagacctcatcatagatccagttcct
gtcctgacgcaccagccgcttgcgactggaatacttacaactctgccggaccaaatgcccacgtcttgaccggagcctta
gtaggtggaccagattccaacgatagttacacagattcacgttctgattatatcagtaacgaagtcgctactgattacaatg
ccggttttccaatctgcagttgctggttttgttgaaagccggagtataa (SEQ ID NO: 55)
```

EG1
Trichoderma
reesei

```
atgggtctccttcacctcccctgctggccggcgttgccgctatctctggtgtcctagcagcccctgccgcagaagttgaacct
gtcgcagttgagaaacgtgaggccgaagcagaagctcaacaaccagaaggaacatcaacaccagaagtccatccaaagtt
aacaacctataaatgtactaagagtggagggtgtgtagccgcaggacaaagtggtcttagactggaattatcgttggat
gcatgatgccaattataattcctgtactgttaacggcggtgttaacactacgttatgcccgatgaagcgacttgtggtaag
aattgttttattgaaggggttgactacgccgctagtggtgttacgacgagtgggtcatccttgacgatgaatcaatacatgc
cttcttctagtggtgggtattcctctgtgtctccaaggctgtatttattggattccgatggggaatatgttatgttaaaattaaat
gggcaagaacgtagttttgatgtggatctatctgcattacgtttcgttggagaaaatggtagtcttttatcttcacaaatggacga
aaacggcggagccaatcagtacaatacagctgctgctaattatggttcaggctattgtgatgctcaatgtccagtcgagac
ttggaggaatggcaccttaaacacatcacatcaaggatttgtgctaacgaaatggacatattagaaggtaattcaagagct
aatgcactaactccgcactcttgtactgcgaccgcatgtgattctgccggttgtggtttcaaccctatggttctggttataag
agttactacggtccgggagacaccgtggatacgtcaaagaccttcactataatcactcagtttaacacagataacggatct
ccgagtggtaatttggtgagtattactaggaaatatcagcagaacggtgttgatattccgtccgcgcagccaggcggtga
cactatatctagctgtcgttcctccgccagtgcctatggcggacttgctacaatgggtaaggcattgtcctcaggtatggtccta
gtattttctatttggaatgataattcacaatacatgaattggctggattctggtaatgcaggcccttgctcctctacagaaggta
acccaagcaatatactagctaataacccaaatactcatgttgtctttagtaatattagatggggcgatataggtagcactacg
aacagtaccgcacctcctcctccacctgctagctccacgacattttccactactagaaggtccagcactaccagacatca
ccatcttgtactcaaacccattggggacagtgtggtggtataggttacagcggttgcaaaacttgcacatctggtactacat
gccaatacagtaatgactattactcacaatgt (SEQ ID NO: 57)
```

CBH2
Trichoderma
reesei

```
atgggtctccttcacctcccctgctggccggcgttgccgctatctctggtgtcctagcagcccctgccgcagaagttgaacct
gtcgcagttgagaaacgtgaggccgaagcagaagctgtcccattagaagaaagacaagcctgctcctctgtttggggtc
aatgtggtggtcaaaactggtctggtccaacttgttgtgcttccggttctacctgtgtttactccaacgactactattcccaatg
tttgccaggtgctgcttcctcttcctcttcaactagagctgcttctacaacttctagggtctcccaaccacttccagatcctct
tctgctactccaccaccaggttctactaccactagagttccaccagtcggttccggtactgctacttactctggtaacccttc
gtcggtgttactccatgggtaacgcttactacgtctctgaagtttcttctttggctatccaatctttgactggtgctatggcta
ccgctgctgctgctgtcgccaaagttccatcatcatgtggttggacaccttggacaaaactccattaatggaacaaacctt
ggcagacataaggactgctaacaagaacggcggtaactacgctggtcaatttgttgtgtacgacttgccagacagagact
gtgctgctttggcttccaacggtgaatactccatcgctgacggtggtgtcgcaagtacaagaactacattgataccattag
acaaatcgttgtcgaatactctgacatcagaaccttgttagtcatcgaaccagattctttagccaatttagtcaccaacttggg
tactccaaagtgtgctaacgctcaatctgcctacttagaatgtatcaattatgcagttaccccaattgaacttgccaaacgttgc
tatgtacttggacgctggtcacgccggttggttgggttggccagctaaccaagacccagccgctcaattattcgccaacgt
ttacaagaatgctcttctcctacgaacgttgcgtggttttggctactaacgtcgctaactacaacgggttggaacatcacttctc
caccatcttacacccaaggtaacgctgtttacaacgaaaagttgtacattcacgctatcggtccattattggctaaccatggt
tggtctaacgcctcttcatcaccgaccaaggtagatccggtaaacaaccaactggtcaacaacaatgggtgattggtgt
aacgtcatcggtactggtttcggtatcagaccatccgctaacactggtgattccttgttggattccttcgtctgggttaagcca
ggtggtgaatgtgatggcacctctgattcctctgctccaagattcgattccactgcgccttgccagacgctttgcaaccag
ccccacaagctggtcatggttccaagcttactttgtccaattgttgaccaacgctaacccatctttcttgtaa (SEQ
ID NO: 59)
```

TABLE 7-continued

DNA sequences used to express a chimeric cellulosome in yeast.

| Gene/Species and Genes derived from | Amino acid sequence |
| --- | --- |
| ScfA<br>CipA,<br>*Clostridium thermocellum*<br>CipC,<br>*Clostridium cellulolyticum*<br>CbpA,<br>*Clostridium cellulovorans*<br>ScaA,<br>*Acetivibrio cellulolyticus*<br>*Saccharomyces cerevisiae*<br>CWP2 | Mvsftsllagvaaisgvlaapaaevepvavekr<br>gvvsvqfnngsspassnsiyarfkvtntsgspinl<br>adlklryyytqdadkpltfwcdhagymsgsnyi<br>datskvtgsfkavspavtnadhylevalnsdags<br>lpaggsieiqtrfarndwsnfdqsndwsytaags<br>ymdwqkisafvggtlaygstpdggnpppqdpt<br>inptsisakagsfadtkitltpngntfngiselqssq<br>ytkgtnevtllasylntlpentttktltfdfgvgtknp<br>kltitvlpkdipgdslkvavgtaegnvgdtvtvp<br>vtfadvasagnvgtcnfylaydaslldvvsvaag<br>pivknaavnfsssasngsisflfldntitdelitadg<br>vfanitfklksvtaktttpvtfkdggafgdgtmak<br>iatvtktngsvtivpgiqptkeavrikvdtvnakp<br>gdtvripvrfsgipskgiancdfvysydpnvleii<br>eiepgdiivdpndksfdtavypdrkiivflfaed<br>sgtgayaitkdgvfativakvksgapnglsvikf<br>vevggfanndlveqktqffdggvnvgvhvtpvt<br>lsnvpgiataelqvgfdatllevasitvgdivlnps<br>vnfssvvngstiklflflddtlgsqliskdgvlatinf<br>kaktvtskvttpvavsgtpvfadgtlaelkyetva<br>gsvtiepsqpvktvtatvgtatgkvgetvavyvk<br>kddpngftvnvdsvngnvgeqivvpvsfanvp<br>sngvstadmtitydsskleyvsgaagsivtnptv<br>nfginkeadgklkvlfldytmstgyistngvfan<br>vtfkvlnsapttvgitgatfgdknlgnisatinagsi<br>nggyyvinpdfvttsttapivkagftveivgttks<br>avtdsngyfeikdvaagtytvkitkanyltreian<br>vsvtadkelstsaspilmwaisqitdgqiqatttat<br>teatttaapsstvetvspsstetisqqtengaakaa<br>vgmgagalaaaamll (SEQ ID NO:<br>20) |
| ScfB 1<br>CipA,<br>*Clostridium thermocellum*<br>CipC,<br>*Clostridium cellulolyticum*<br>CbpA,<br>*Clostridium cellulovorans*<br>*Saccharomyces cerevisiae*<br>CWP2 | gvvsvqfnngsspassnsiyarfkvtntsgspinl<br>adlklryyytqdadkpltfwcdhagymsgsnyi<br>datskvtgsfkavspavtnadhylevalnsdags<br>lpaggsieiqtrfarndwsnfdqsndwsytaags<br>ymdwqkisafvggtlaygstpdggnpppqdpt<br>inptsisakagsfadtkitltpngntfngiselqssq<br>ytkgtnevtllasylntlpentttktltfdfgvgtknp<br>kltitvlpkdipgdslkvavgtaegnvgdtvtvp<br>vtfadvasagnvgtcnfylaydaslldvvsvaag<br>pivknaavnfsssasngsisflfldntitdelitadg<br>vfanitfklksvtaktttpvtfkdggafgdgtmak<br>iatvtktngsvtivpgiqptkeavrikvdtvnakp<br>gdtvripvrfsgipskgiancdfvysydpnvleii<br>eiepgdiivdpndksfdtavypdrkiivflfaed<br>sgtgayaitkdgvfativakvksgapnglsvikf<br>vevggfanndlveqktqffdggvnvgvhvtae<br>vepvavekrpvtlsnvpgiataelqvgfdatllev<br>asitvgdivlnpsvnfssvvngstiklflfldtlgs<br>qliskdgvlatinfkaktvtskvttpvavsgtpvfa<br>dgtlaelkyetvagsvtiepsqpvktvtatvgtatg<br>kvgetvaviletaaalvprgspivkagftveivgtt<br>ksavtdsngyfeikdvaagtytvkitkanyltrei<br>anvsvtadkelstsaspilmwaisqitdgqiqattt<br>atteatttaapsstvetvspsstetisqqtengaaka<br>avgmgagalaaaamll (SEQ ID<br>NO: 22) |
| ScfB2<br>CipA,<br>*Clostridium thermocellum*<br>CipC,<br>*Clostridium cellulolyticum*<br>CbpA,<br>*Clostridium cellulovorans*<br>CipC, | Mvsftsllagvaaisgvlaapaaevepvavekr<br>gvvsvqfnngsspassnsiyarfkvtntsgspinl<br>adlklryyytqdadkpltfwcdhagymsgsnyi<br>datskvtgsfkavspavtnadhylevalnsdags<br>lpaggsieiqtrfarndwsnfdqsndwsytaags<br>ymdwqkisafvggtlaygstpdggnpppqdpt<br>inptsisakagsfadtkitltpngntfngiselqssq<br>ytkgtnevtllasylntlpentttktltfdfgvgtknp<br>kltitvlpkdipgdslkvavgtaegnvgdtvtvp<br>vtfadvasagnvgtcnfylaydaslldvvsvaag<br>pivknaavnfsssasngsisflfldntitdelitadg |

TABLE 7-continued

DNA sequences used to express a chimeric cellulosome in yeast.

| | |
|---|---|
| Clostridium josui Saccharomyces cerevisiae CWP2 | vfanitfklksvtakttttpvtfkdggafgdgtmak iatvtktngsvtivpgiqptkeavrikvdtvnakp gdtvripvrfsgipskgiancdfvysydpnvleii eiepgdiivdpnpdksfdtavypdrkiivflfaed sgtgayaitkdgvfativakvksgapnglsvikf vevggfannddlveqktqffdggvnvgvhvtae vepvavekrpvtlsnvpgiataelqvgfdatllev asitvgdivlnpsvnfssvvngstikllflddtlgs qliskdgvlatinfkaktvtskvttpvavsgtpvfa dgtlaelkyetvagsvtiepsqpvktvtatvgtatg kvgetvavilentnkpviegyktedlnvavgtaeg nvgetvtvpvtfanvakvnnvgtcnfylaydasl ldvvsvdagpivknaavnfsssasngtisflfldn titdelitsdgyfanitfklknvstkttttpisfkdgga fgdgnmakiatvvktngsvtiipgdpepaaalv prgspivkagftveivgttksavtdsngyfeikdv aagtytvkitkanylltreianvsvtadkelstsasp ilmwaisqitdgqiqatttatteatttaapsstvetv spssstetisqqtengaakaavgmgagalaaaam ll (SEQ ID NO: 24) |
| S. fibuligera sBGLI | mvsftsllagvaaisgvlaapaaevesvavekrs rvpiqnytqspsqrdessqwvsphyyptpqggr lqdvwqeayarakaivgqmtivekvnlttgtgw qldpcvgntgsvprfgipnlclqdgplgvrfadf vtgypsglatgatfnkdlflqrgqalghefnskgv hialgpavgplgvkarggrnfeafgsdpylqgta aaatikglqennvmacvkhfigneqekyrqpd dinpatnqttkeaisanipdramhalylwpfads vragvgsmcsynrvnntyacensymmnhll keelgfqgfvvsdwgaqlsgvysaisgldmsm pgevyggwntgtsfwgqnltkaiynetvpierl ddmatrilaalyatnsfptedhlpnfssswttkeyg nkyyadntteivkvnynvdpsndftedtalkva eesivllknenntlpispekakrlllsgiaagpdpi gyqcedqsctngalfqgwgsgsvgspkyqvtp feeisylarknkmqfdyiresydlaqvtkvasda hlsivvvsaasgegyitvdgnqgdrknltlwnn gdklietvaencantvvvvtstgqinfegfadhp nvtaivwagplgdrsgtaianilfgkanpsghlpf tiaktdddyipietyspssgepednhlvendllvd yryfeekniepryafgyglsyneyevsnakvsa akkvdeelpepatylsefsyqnakdsknpsdaf apadlnrvneylypyldsnvtlkdgnyeypdgy steqrttpnqpggglggndalwevaynstdkfv pqgnstdkfvpqlylkhpedgkfetpiqlrgfek velspgekktvdlrllrrdlsvwdttrqswivesgt yealigvavndiktsvlfti* (SEQ ID NO: 26) |
| Doc 1 Acetivibrio cellulolyticus Cel9A | Ndiktsvlftivttptptpaqyvygdvngdgslns idfgvmrkyllgmikefsyenglkagdvdgng mfnsldfaymrqymlgiiskfpvqk (SEQ ID NO: 28) |
| Doc 2 Clostridium cellulolyticum CelA | Ndiktsvlftivttptptpaqyvypvivygdvng dgnvnstdltmlkryllksvtninreaadvnrdg ainssdmtilkrylik (SEQ ID NO: 30) |
| Doc 3 Clostridium cellulovorans EngB | Ndiktsvlftivttptptpaqyvyyslgdvnkdg kvnaidyavlksillgtntnvdlsvsdmnkdgk vnaldlavlkkmlls (SEQ ID NO: 32) |
| Doc 4 Clostridium josui Cel8A | Ndiktsvlftivttptptpaqyvyglkgdynndg aidaldiaalkkailtqststsninltnadmnndgni daidfaqlkvklln (SEQ ID NO: 34) |
| Doc 5 Clostridium thermocellum CelS | Ndiktsvlftivttptptpaqyvygdvnddgkvn stdavalkryvlrsgisintdnadlnedgrvnstdl gilkryil (SEQ ID NO: 36) |

TABLE 7-continued

DNA sequences used to express a chimeric cellulosome in yeast.

| | |
|---|---|
| Doc 6<br>*Bacteroides*<br>*cellulosolvens*<br>Cel48A | Ndiktsvlftivklkgdlngdgvinmadvmila<br>qsfgkaignpgvnekadlnndgvinmadaiila<br>qyfgktksaevvmf (SEQ ID NO:<br>38) |
| Coh 1_CWP2<br>*Acetivibrio*<br>*cellulolyticus*<br>ScaA<br>*Saccharomyces*<br>*cerevisiae*<br>CWP2 | Mvsftsllagvaaisgvlaapaaevepvavekr<br>gftvnvdsvngnvgeqivvpvsfanvpsngvst<br>admtitydsskleyvsgaagsivtnptvnfgink<br>eadgklkvlfldytmstgyistngvfanvtfkvln<br>sapttvgitgatfgdknlgnisatinagsinggyin<br>pdfvttsttapivkagftveivgttksavtdsngyf<br>eikdvaagtytvkitkanyltreianvsvtadkels<br>tsaspilmwaisqitdgqiqatttatteatttaapsst<br>vetvspsstetisqqtengaakaavgmgagalaa<br>aamll (SEQ ID NO: 40) |
| Coh 2<br>*Clostridium*<br>*cellulolyticum*<br>CipC | Aevepvavekrlkvavgtaegnvgdtvtvpvtf<br>advasagnvgtcnfylaydaslldvvsvaagpiv<br>knaavnfsssasngsisflfldntitdelitadgvfa<br>nitfklksvtakttttpvtfkdggafgdgtmakiat<br>vtktngsvtyinpdfvttst (SEQ ID<br>NO: 42) |
| Coh 3<br>*Clostridium*<br>*cellulovorans*<br>CbpA | Aevepvavekrpvtlsnvpgiataelqvgfdatl<br>levasitvgdivlnpsvnfssvvngstikllflddtl<br>gsqliskdgvlatinfkaktvtskvttpvavsgtp<br>vfadgtlaelkyetvagsvtiepsqpvktvtatvg<br>tatgkvgetvavyinpdfvttst (SEQ ID<br>NO: 44) |
| Coh 4<br>*Clostridium*<br>*josui* CipC | Aevepvavekrtedlnvavgtaegnvgetvtvp<br>vtfanvakvnnvgtcnfylaydaslldvvsvda<br>gpivknaavnfsssasngtisflfldntitdelitsd<br>gvfanitfklknvstkttttpisfkdggafgdgnma<br>kiatvvvktngsvtiipgdpepyinpdfvttst<br>(SEQ ID NO: 46) |
| Coh 5<br>*Clostridium*<br>*thermocellum*<br>CipA | Aevepvavekravrikvdtvnakpgdtvripvr<br>fsgipskgiancdfvysydpnvleiieiepgdiiv<br>dpnpdksfdtavypdrkiivflfaedsgtgayait<br>kdgvfativakvksgapnglsvikfvevggfan<br>ndlveqktqffdggvnvgyinpdfvttst<br>(SEQ ID NO: 48) |
| Coh 6<br>*Bacteroides*<br>*cellulosovens*<br>CipBc | Aevepvavekrvtatvdkttasvgdiitytinvk<br>dvagfagyqanvkydpsvlqpvyddrsaydsa<br>avpeygtllqkrysptdmasndlskgtltfgrty<br>mnldsykasgsaettgsiavirfkvlkntattiklq<br>naasltnavdgtmlfdwsgaqlagykvaqapyi<br>npdfvttst (SEQ ID NO: 50) |
| CBH1<br>*Talaromyces*<br>*emersonii* | Mlrralllsssailavkaqqagtataenhppltwq<br>ectapgscttqngavvldanwrwvhdvngytn<br>cytgntwdptycpddetcaqncaldgadyegty<br>gvtssgsslklnfvtgsnvgsrlyllqddstyqifk<br>llnrefsfdvdvsnlpcglngalyfvamdadgg<br>vskypnnkagakygtgycdsqcprdlkfidgea<br>nvegwqpssnnantgigdhgsccaemdvwe<br>ansisnavtphpcdtpgqtmcsgddcggtysnd<br>ryagtcdpdgcdfnpyrmgntsfygpgkiidtt<br>kpftvvtqfltddgtdtgtlseikrfyiqnsnvipq<br>pnsdisgvtgnsittefctaqkqafgdtddfsqhg<br>glakmgaamqqgmvlvmslwddyaaqml<br>wldsdyptdadpttpgiargtcptdsgvpsdves<br>qspnsyvtysnikfgpinstftas (SEQ ID<br>NO: 52) |
| CBH2b<br>*Chrysosporium*<br>*lucknowense* | Makklfitaalaaavlaapvieerqncgavwtq<br>cggngwqgptccasgstcvagnewysqclpns<br>qvtssttpsststsqrststsssttrsgsssssttppp<br>vsspvtsipggatstasysgnpfsgvrlfandyyr<br>sevhnlaipsmtgtlaakasavaevpsfqwldm<br>vtidtlmvqtlsqvralnkaganppyaaqlvvyd<br>lpdrdcaaaasngefsianggaanyrsyidairk<br>hiieysdiriilviepdsmanmvtnmnvakcsn<br>aastyheltvyalkqlnlpnvamyldaghagwl<br>gwpaniqpaaelfagiyndagkpaavrglatnv<br>anynawsiasapsytspnpnydekhyieafspl |

TABLE 7-continued

DNA sequences used to express a chimeric cellulosome in yeast.

| | |
|---|---|
| | lnsagfparfivdtgrngkqptgqqqwgdwcn vkgtgfgvrptantghelvdafvwvkpggesd gtsdtsaarydyhcglsdalqpapeagqwfqay feqlltnanppf (SEQ ID NO: 54) |
| EG<br>Coptotermes<br>formosanus | mrfpsiftavlfaassalaaydyktylknsllfyea qrsgklpadqkvtwrkdsalndkgqkgedltgg yydagdfvkfgfpmaytvtvlawglvdyesay stagalddgrkalkwgtdyflkahtaanefygqv gqgdvdhaywgrpedmtmsrpaykidtskpg sdlaaetaaalaataiayksadstysnnlithakql fdfannyrgkysdsitdaknfyasgdykdelvw aaawlyratndntyltkaeslynefglgswngaf nwdnkisgvqvllakltskqaykdkvqgyvdy lvssqkktpkglvyidqwgtlrhaansalialqaa dlginaasyrqyakkqidyalgdggrsyvvgfgt nppvrphhrssscpdapaacdwntynsagpna hvltgalvggpdsndsytdsrsdyisnevatdyn agfqsavagllkagv (SEQ ID NO: 56) |
| EG1<br>Trichoderma<br>reesei | Mvsftsllagvaaisgvlaapaaevepvavekre aeaeaqqpgtstpevhpklttykctksggcvaqd tsvvldwnyrwmhdanynsctvnggvnttlcp deatcgkncfiegvdyaasgvttsgssltmnqy mpsssggyssvsprlylldsdgeyvmlklngqe lsfdvdlsalpcgengslylsqmdengganqyn taganygsgycdaqcpvqtwrngtlntshqgfc cnemdilegnsranaltphsctatacdsagcgfn pygsgyksyygpgdtvdtsktftiitqfntdngsp sgnlvsitrkyqqngvdipsaqpggdtisscpsa saygglatmgkalssgmvlvfsiwndnsqym nwldsgnagpcsstegnpsnilannpnthvvfs nirwgdigsttnstappppassttfsttrrssttsss psctqthwgqcggigysgcktctsgttcqysndy ysqc (SEQ ID NO: 58) |
| CBH2<br>Trichoderma<br>reesei | Mvsftsllagvaaisgvlaapaaevepvavekre aeaeavpleerqacssvwgqcggqnwsgptcc asgstcvysndyysqclpgaasssssstraasttsrv spttsrsssatpppgstttrvppvgsgtatysgnpf vgvtpwanayyasevsslaipsltgamataaaa vakvpsfmwldtldktplmeqtladirtankng gnyagqfvvydlpdrdcaalasngeysiadggv akyknyidtirqivveysdirtllviepdslanlvt nlgtpkcanaqsaylecinyavtqlnlpnvamyl daghagwlgwpanqdpaaqlfanvyknassp ralrglatnvanyngwnitsppsytqgnavyne klyihaigpllanhgwsnaffitdqgrsgkqptg qqqwgdwcnvigtfgirpsantgdslldsfvw vkpggecdgtsdssaprfdshcalpdalqpapq agawfqayfvqlltnanpsfl (SEQ ID NO: 60) |

Example 4

Production of a Cellulosome from an Anaerobic Fungus in Yeast

The cellulosomes from anaerobic fungi are useful for expression in yeast. The organisms produce very active high molecular weight cellulase complexes (Wilson C. A. and Wood T. M., Appl. Microbiol. Biotechnol. 37(1):125-9 (1992)). In the cited study, the authors showed that these complexes were more active than C. thermocellum cellulosome under the conditions tested. Molecular evidence surrounding the cellulases produced by these species is mounting (e.g., Dijkatinan R., Arch. Microbiol. 167(2-3):137-42 (1997); Nagy T., et al., J. Mol. Biol. 373(3):612-22 (2007); Raghothama S., et al., Nat. Struct. Biol. 8(9):775-8 (2001); Dijkerman R., et al., Appl. Environ. Microbiol. 62(1):20-5 (1996)), although the scaffoldin in the system has still not been clearly identified.

Several approaches are taken to recreate an anaerobic fungal cellulosome in yeast. One strategy is to fuse anaerobic fungal cellulase catalytic domains to dockerin domains from bacteria that are known to function in yeast as (demonstrated in previous examples), and to use these in conjunction with a bacterial scaffoldin. A list of several known catalytic domains from the anaerobic fungus Piromyces equi is found in Table 8.

A separate strategy to create an anaerobic fungal cellulosome in yeast, is to clone large portions of DNA, or cDNA into yeast. Large portions of anaerobic fungal genomes could be cloned into yeast on YAC vectors. Strains containing these vectors are then screened for the presence of anaerobic fungal cellulases by activity assays. Similarly, cDNA libraries from a number of anaerobic fungal species are created and cloned into expression vectors for yeast expression. These libraries are be screened for activity of anaerobic fungal cellulases. The libraries are also optionally combined, combinatorially, and the resulting mixes of cDNA clones screened for activity against cellulose. If a particular mixture of strains produced high avicelase activity, for example, this mixture contains all the necessary components of the anaerobic fungal cellulosome system. Plasmids from the strains making up this mixture are then sequenced and the encoded proteins identified.

Novel cellulase genes are also identified from newly isolated anaerobic fungal species. These species are isolated from the rumens of a number of herbivores, and cDNA libraries are created. Cellulase genes isolated in this way may not have much similarity to the genes previously isolated and described in the literature.

TABLE 8

Amino acid sequences of cellulosomal components from *Piromyces equi*.

| Gene | Amino acid sequence | Accession # |
|---|---|---|
| Cel6A | Mkasialtaiaalaanasaacfserlgypccrgnevfytdndgdwgvengnwcgiggasattcwsqalgypcctstsdv ayvdgdgnwgvengnwcgiiaggnssnnnsgstinvgdvtignqythtgnpfaghkffinpyytaevdgaiaqisnas lrakaekmkefsnaiwldtiknmnewlelknlkyalaeqnetgktvltvfvvydlpgrdchalasngellandsdwaryq seyidvieeklktyksqpvvlvvepdslanmvtnldstpacrdsekyymdghaylikklgvlphvamyldighafwlg wddnrlkagkvyskviqsgapgnvrgfasnvanytpwedptlsrgpdtewnpcpdekryieamykdfksagiksvyf iddtsrnghktdrthpgewcnqtgvgigarpqanpisgmdyldafywvkplgesdgysdttavrydgycghatamkp apeagqwfqkhfeqglenanppl (SEQ ID NO: 61) | AAL92497 |
| NCP1 | Mfkqigitallvasasaacwsesqgfkccssknṫpvvytdasgdwgvenndwcgipkeeavtcfsqklcygccpkrta vsytdadgdwgyangdwcgivaeekptcwsealgykccqttskieftdndgnwgfengdwcglqkvsgrtttttrttttr rttttttrrttttttrkvsatysvvyetgkklnsgfdnwgwdskmsfkdnslvltadpdeygaislknlnsnyygkggciylgv kteteglvkvqgvrgydeteafnvgsfrsssdfteykfevddeyqfdriivqdgpasnipiymryiiystgscddfnppvd ttkvpvttttkksnvratytvifknasglpngydnwgwgctlsyyggamiinpqegkygavslkrnsgsfrggslrfdmk negkvkilvenseadekfevetispsdeyvtyildvdfdlpfdridfqdapgngdriwiknlvhstgsaddfvdpin (SEQ ID NO: 62) | AAK20910 |
| Cel3A | Mkiqnilvaltcglvsqvfatswseadekaksfmsdlsesekidivtgymnmqgtcvgnikpldrknfkglclqdgpag vrfnggtsttwqaginnaatfnkdllykigkdqgaefyakginialapsmnilrapasgrvwenfgedpylsgvcgaqitk gyqdsgvivaakhyvandiehnreasssnmddqtlmeihvepfyrtikdgdagsvmasynavnniyvvqnkkvltei lkegigfqgfvmsdwwaihdlegsfnagmdmnmpggkawgpdyvnnsfwgsnisnairsgqvsssrlddavrriir tlyrfdqmsgypnvnlkapsmhadtnrqaaiessvllknaddilpltkkyrkiaiigkdadkaqsctdtacsggniiqgwg sgttdftgisdpitaiknraskegisivssisdsaneganvakdadvavvfvratsgeeyivvdnnkgdrnnldlwhggnd lvksvaavnkntvvvihapatvnlpflnnvkaiihagmpgaesgnaiasilfgdsnpsghlpftwaaredyccdvsypa elphggnsktaydykeglfvgyrwfdkknktpifpfghglsytffdysnlsyslkksgtqvtgleatvtvantgsyegatvp mlflgfpavselgdypvrnlkafekvnlkagekktvtltvdqhglsyyntskksfvvptggeftvyvgksagdlplkkaik ntqgtnessssvgdennnnpnnnadcsvngykccsnsnaevvytdgdgnwgvengqwciikeqqqqtcfsiklgy pcckgnevaytdndgqwgfengqwcgiatatsgaggcpytskngypvcqttkveyvdsdkwgvengnwcimcn (SEQ ID NO: 63) | AAO41704 |
| Cel5A | mkflnvlsitgliivgsnaasscwseklgykccegdkvvytdndgkwgvenqkwcgiienepttivepveptivepve psttveepveptstivepeetvelepirdisskelikemmfgwnlgntldaectswmnyekdpigsetcwgnpkttedm ykilmdnqfnvfripttwtghigeapdykinekwmkrvheivdypykngafvilnihheswnhafeetveeakvelak vwaqiaeefkdydehlifegqneprkndtpvewnggdqegwdvvnamnavfmktvrssggnnakrhlmippyaa acnknsfdnfdfpedddkviasvhayspynfalnngegavdkfdatgkneldynlglikkrfvskgipvimgeygamn rdneevratwaeyymkeitalgvpqvwwdngifegegerfglidrknlkvvypsivaalqkgrglevnvlhaiepkpe pepttttvvepeettavdeptstveptgnirdisskelikemnfgwnlgntldaectswmnyekdpigsetcwgnpktted mykilmdnqfnvfripttwtghigeapdykinekwmkrvheivdypykngafvilnihheswnhafeetveeakvel akvwaqiaeefkdydehlifegqneprkndtpvewnggdqegwdvvnamnavfmktvrssggnnakrhlmippy aaacnqnsfdhfdfpedddkviasvhayspynfalnngegavdkfdatgkneldynlglikkrfvskgipvimgeyga mnrdneeeratwaeyymkeitalgipqvwwdngifegegerfglidrkrnlkvvypsivaalqkgrglevnvlhaiepe ptttvvepeettavdeptstveptgnirdisskklikemnfgwnlgntldaectswmnyekdpigsetcwgnpkttedm ykilmdnqfnvfripttwtghigeapdykinekwmkrvheivdypykngafvilnihheswnhafeetveeakvelak vwaqiaeefkdydehlifegqneprkndtpvewnggdqegwdvvnamnavfmktvrssggnnakrhlmippyaa acnknsfdnfdfpedddkviasvhayspynfalnngegavdkfdatgkneldynlglikkrfvskgipvimgeygamn rdneeeratwaeyymkeitalgipqvwwdngifegegerfglidrknlkvvypsivaalqkgrglevnvlhaiepkpep epttttvvepeettavdeptstveptgnirdisskelikemnfgwnlgntldaectswmnyekdpigsetcwgnpkttedm ykilmdnqfnyfripttwtghigeapdykinekwmkrvheivdypykngafvilnihheswnhafeetveeakvelak vwaqiaeefkdydehlifegqneprkndtpvewnggdqegwdvvnamnavfmktvrssggnnakrhlmippyaa acnknsfdnfdfpedddkviasvhayspynfalnngegavdkfdatgkneldynlglikkrfvskgipvimgeygamn rdneeeratwaeyymkeitalgipqvwwdngvfegegerfglidrknlkvvypsivaalqkgrglevnvlhaieeepae cwaeklgyqccspnntrvvvtdesgkwgvenadwcgiietkdkcwsipygykccdhcrvltkdetgkwgemngew cgidtnkck (SEQ ID NO: 64) | CAB92326 |
| Cel9A | Mkfqsiisavaalvapmavgaksqdyarhielsllfyeaqrsgklpennriywrhdsmldagadnkvdltggyydagd nvkfnfpqaaltlllawsgwyyadgykeagqweyildavrwgadyfvkchtgknelyvqvgkgatdhgfwyppeyi qydhpsykitasapgsevagdtasflaaasilfkeedpsysanllkhaieiydfadayrgeyikavpdaqgfysnwsgyn delafgalwlyratgeskymdkfskiadasygeqdtkaygtctgpiswddkrpgayilaaivtgdekrkqqaywycdn vltqprtpgglwydsnlskwasnryasnaaamlamfanylpktdskrskyvdfvkkqtdyilgdnpmkinyvvgaea nspkavhhraasgtydsqdtnarptdyniftlwgalaggpgpkdeytdsrknyemnevaldynaafqtnlaflvkegyn kpdpdsvkvhdrsfpkkadtpditvevtdktievstgsnmmcsswcveftt dykieavhdcimyqsgpdyiicnrres nfldgkgtpqvikyqgsngqgpltidesvvmcdgwhapqsshkpmykpengrkykvvgsggvgnttplfeqsecw paflcggstspkttttikkttttttkksdptnsnscfsvaqgypccgagipvsyeddsgqwgiengnwcgiapikescgdypc ctgcdvqytddkkwgvennnwclikedkcqgssgtvtctgqnlgypccdtceaiytdesgkwgikngdwcglkssc (SEQ ID NO: 65) | AAM81967 |

TABLE 8-continued

Amino acid sequences of cellulosomal components from *Piromyces equi*.

| Gene | Amino acid sequence | Accession # |
|---|---|---|
| Cel45A | Mrlaltscialaasiakvsaacwaqsqgynccnnpsstkveytdasgqwgvqngqwcgidysygqnqgnesctgngs<br>ypccntcqatytdgdgdwafengnwcgiknsckqqpqnnnqctgngayrccntcqatytdnegkwafengdwcgik<br>yscpsqqvtttttrrtttttqqqqptgsggnsnvplnppdfsgqtgkttrywdcclascswqenckndgaqgvvrscnvdg<br>itpftdlsnlwrvksgcnggsvymcndqqpwaindnvaygfvashekcctcqrlkftsgpiagkqmivqttntggdlss<br>nhfdiqmpgggfgifdgctsqfggsyqwgeryggissasqcanlppqlkagcewrfnwfknadnpavvfervqcpke<br>lteitgcvpgddasakklpw (SEQ ID NO: 66) | CAB92325 |
| Cel48A | Mpsirsslallgataafaapamrkryndeyaqrvtdlydtmtgngsysseyfspekvpyhsvetlmveapdqghesvse<br>tysfwiwleavngkitgnydgveeawsylekhiipdsknqpgnsrynpsspatyaaehdeiydypsklifqdglvged<br>piakelqqaygnwdiyimhwiidgdnwygygqqgdgtskpsfintfqrgpsestwktvphpcweamkwggrngfl<br>dlftvdnsyakqwrytaapdadaraiqaayfaymwaeedgvnlssvaskaaklgdylryaqydkyfkkigncvgydk<br>csagrgknsahyliswyfawgglqgdwawrigsshthtgyqnplaawilstqsafkpksstgakdwatsldrqlelfr<br>wlqsaegciaggatnswqgayeqpssdittfygmwydwqpvyhdppsnnwtgmqgwgmervcslyylsgneka<br>gkvcqewakwvknttrvtgeeivhattldwegnpdewnasnfnksnlnrslhgtvssegvdlgtiasimkglmwvsm<br>kdndqeginlavqvmdaiegyrdnlgyssleargdyekfggevyipsgwtgknaqqanlkngvtfidirpkykqdpd<br>wpqveeflnggnppefnyhrfwaqteiavanglisiyglkstggsspiyggdevtecpasitrqgyscckvgcqvvyqd<br>adgdwgvenndwcgcgkapapkpkcptsitnqgysccsscgpvyyqdadgdwgvengdwcgmptsc (SEQ ID NO: 67) | CAB92326 |

Example 5

Production of a "Synthetic" Cellulosome Based on Yeast Machinery

An alternative method for generating a scaffoldin for creating a cellulosome in yeast is to create a chimera of a yeast surface expressed protein with dockerin domains, or with other domains that could be used for protein binding. One particular embodiment is outlined below for CipC from *C. cellulolyticum* and FLO1 from *S. cerevisiae*.

Figure 10:
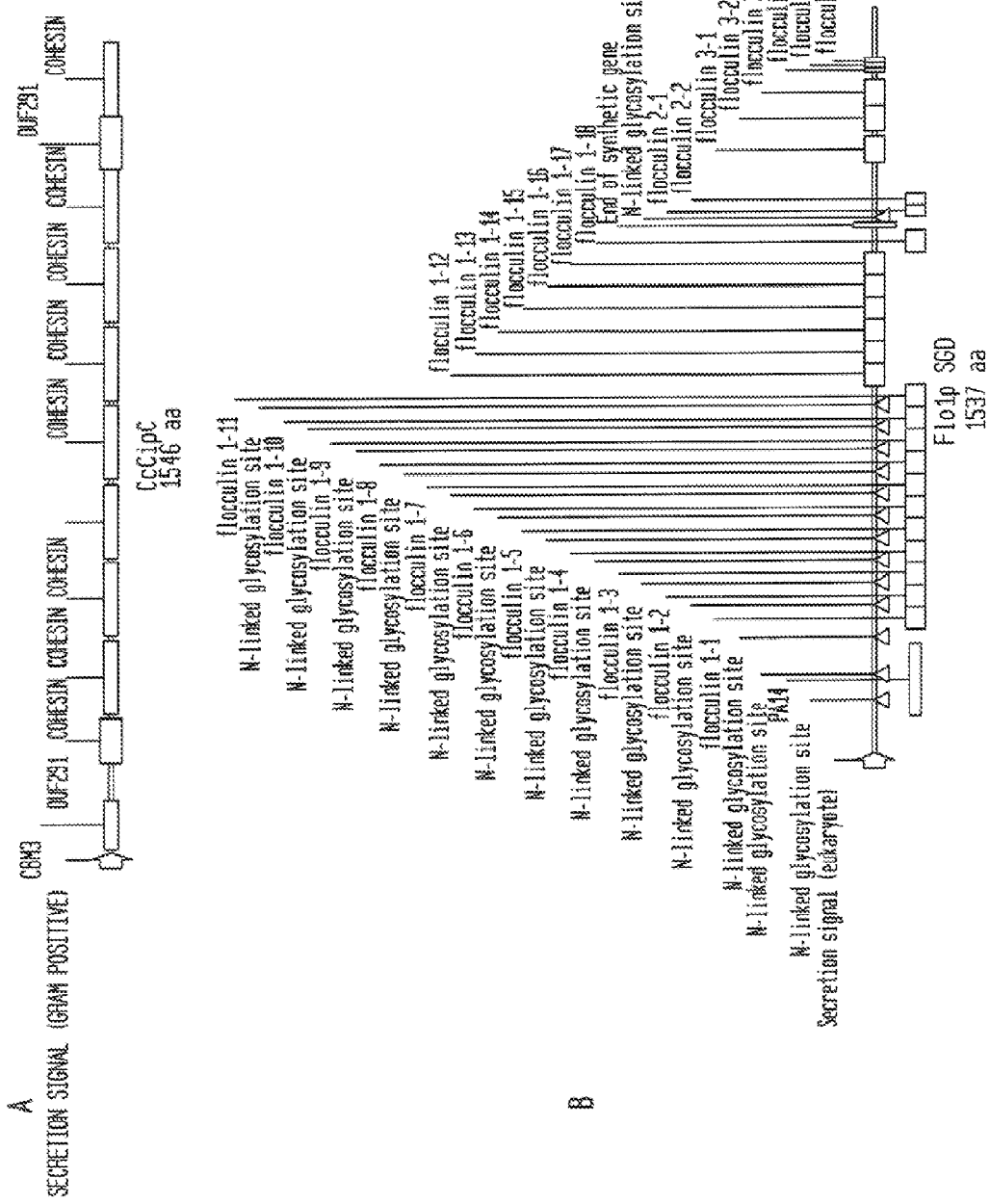
FIG. 10 depicts the linear structure of the C. cellulolyticum CipC (A) and S. cerevisiae FLO1 (B) proteins respectively.

CipC is a large (1546 AA) glycosylated protein, which serves as the scaffoldin in the *C. cellulolyticum* cellulosome. Although it is not known exactly how or where CipC is glycosylated, the glycosylation in other cellulosomes is hypothesized to help prevent proteolysis (See FIG. 10). A blast search of CipC against the *Saccharomyces* genome revealed that this protein has some limited similarity to flocculation proteins. In particular, 2 regions of FLO1, have ~25% identity and ~35% similarity with CipC. FLO1 is a large extracellular protein from *S. cerevisiae* (1537AA), which is heavily glycosylated, and contains tandem repeats of AA sequences called "flocculins." Its N-terminal end functions as a sugar-binding protein (binds the sugars in cell walls of other yeast cells), its middle is a glycosylated extension, and its C-terminal end is GPI anchored to the yeast cell wall (see FIG. 10).

Creating and Searching a Library of Chimeras for Enhanced Expression

Yeast mediated ligation is used to create a library of CipC and FLO1 chimeras. The N-terminal section of FLO1 is used to facilitate entry into the secretory pathway via it's secretion signal, and for binding of the scaffolding chimeras to the yeast cell surface via its PA14 domain, which has been shown previously to act as an N-terminal cell wall anchor for recombinant proteins in yeast. Flocculins are generated by PCR with overlapping DNA sequence for recombination in yeast. Similar portions of DNA are generated for the cohesions and DUF291 (hydrophilic) domains of CipC. The CBM of CipC is made to form the C-terminus of the proteins and contains a 6x his tag.

In addition to the constructs created for the scaffoldin, a version of GFP with a dockerin domain attached is created and expressed in yeast. The protein is purified via a HIS tag, and saved for assays via flow cytometry. These flow cytometry assays are useful for quantifying binding as described further below.

After transformation of these fractions into yeast for recombination with a 2 micron vector, the transformants are subjected to flow cytometry after probing with GFP-dockerin fusion protein, and an anti-HIS antibody. The intensity amount of the anti-HIS antibody bound to the cell surface is used to assess the amount of scaffoldin expressed, and the relative amount of GFP to anti-HIS antibody is used as an indicator of the length of the scaffoldins (how many cohesins they contain per scaffoldin).

FLO1 is modified to contain other types of protein binding domains, whose partners could be placed on the catalytic cellulase domains of interest. There are a very large number of protein-protein interaction partners known in yeast because of large scale two hybrid screens (Schwikowski B., et al, *Nat. Biotechnol.* 18(12): 1257-61 (2000)). The results of these and similar screens are useful to determine candidate protein domains for use in cellulosome production to induce protein-protein interaction. Additional data on protein interacting pairs in yeast is available at the website of Saccharomyces Genome Database.

Example 5

Demonstration of Binding of *C. Cellulolyticum* Cellulosome Components

*C. cellulolyticum* cellulosome components were purified by standard methods and used with a Biacore instrument to show binding of yeast expressed Cel5A and Cel5D to CipC. Aggregation of purified CipC was eliminated by the addition of EDTA.

Concentrated CipC was biotinylated using the EZ-link biotinylation kit from Pierce, after exchanging the buffer for 50 mM MES, pH 6.0, 10 mM $CaCl_2$, and adjusting the pH to ~8.0. Biotinylated CipC was buffer exchanged with 50 mM MES, pH 6.0, 10 mM $CaCl_2$, 0.005% P20. Additionally, concentrated and partially purified cellulase components were also buffer exchanged with this buffer. A Biacore system at Dartmouth College was used to evaluate the binding of cellulase components. The data from the run with a chip coated with Streptavidin can be found in FIG. 11. The running buffer was 50 mM MES, pH 7.0, 10 mM$CaCl_2$, with 0.005%

P20, and the flow rate was 10 uL/min for 30 uL injections, and 30 uL/min for 100 uL injections.

Figure 11:
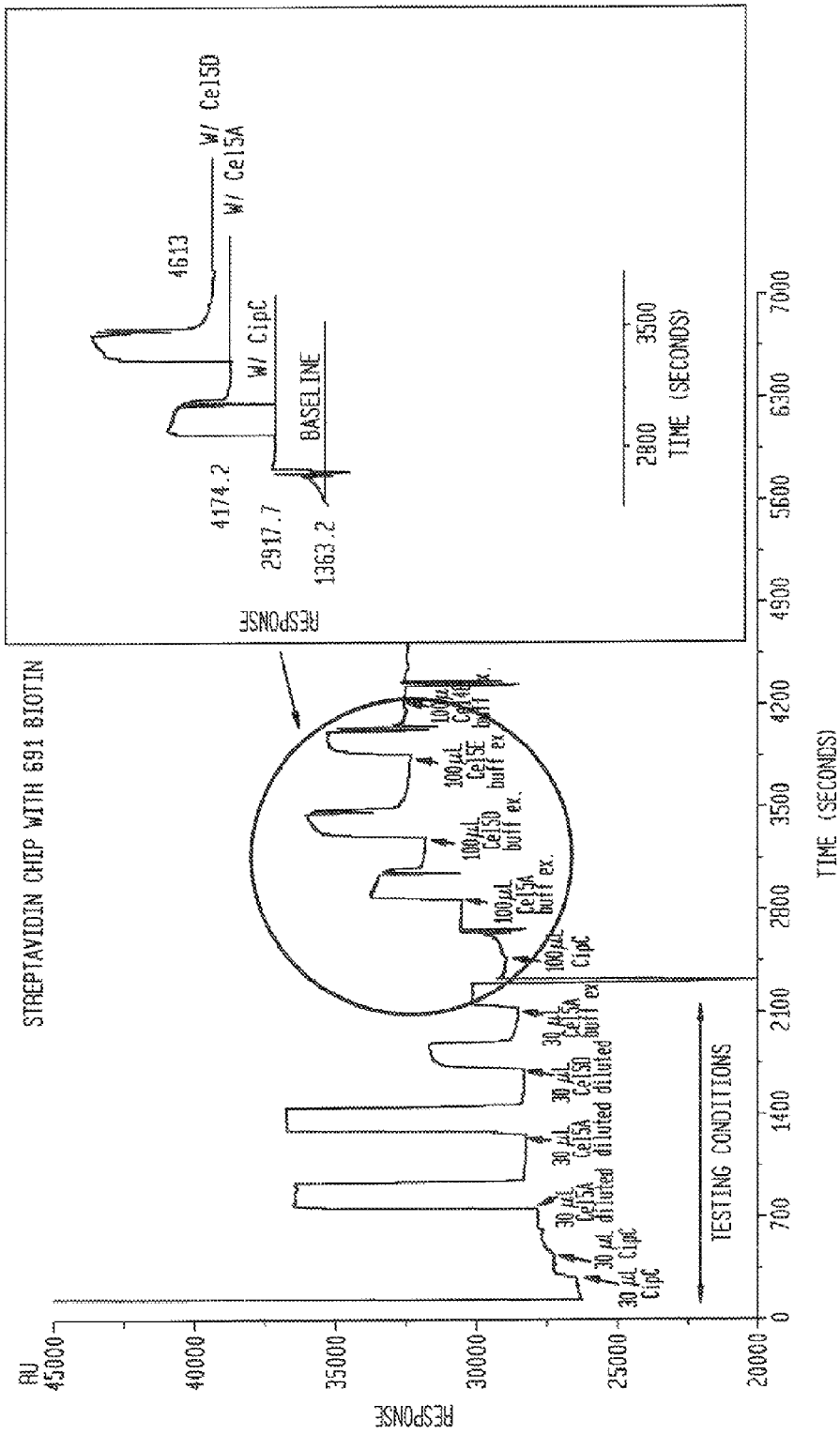
FIG. 11 depicts Trace of Response Units (measure of mass accumulated on chip surface) as a function of time for a Biacore experiment with partially purified cellulosome components made in yeast. The data is corrected using a control channel on the chip that does not have CipC bound to it. The box at right is an enlargement of a portion of the graph and shows the new increased baseline measurements achieved after the addition of Cel5D and Cel5A to the scaffoldin, CipC.

FIG. 11 shows the readout from the Biacore device (Response Units), which is a measure of light deflection caused by the accumulation of mass on chip. The signal is corrected by subtracting the signal from a control channel that was not treated with CipC, but was treated with the subsequent samples. The inset of the figure shows an enlarged portion of the graph. The first increase from 1363 to 2918 units is characteristic of binding to the streptavidin chip, as signal increases and reaches a new steady state, without any decrease in signal. The two subsequent increases after addition of the cellulosome components, Cel5A and Cel5D, show rapid increases in signal (fast on), followed a rapid decrease in signal (fast off), and a new increased baseline (slow off), indicating that some amount of the Cel5A and Cel5D bound to the CipC and did not detach.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, Tables, figures, and text presented in the cited documents.

What is claimed is:

1. A transformed yeast host cell comprising:
    a) at least one heterologous polynucleotide comprising a nucleic acid which encodes an endogluconase;
    b) at least one heterologous polynucleotide comprising a nucleic acid which encodes a (β-glucosidase;
    c) at least one heterologous polynucleotide comprising a nucleic acid which encodes a first cellobiohydrolase; and,
    d) at least one heterologous polynucleotide comprising a nucleic acid which encodes a second cellobiohydrolase different from the first cellobiohydrolase;
    wherein at least one of the endoglucanase, (β-glucosidase, first or second cellobiohydrolase is fused to a dockerin domain; and
    said transformed yeast host cell further comprising:
    e) a nucleic acid which encodes an exogenous scaffoldin polypeptide; wherein the scaffoldin polypeptide contains at least one cohesin domain.

2. The transformed yeast host cell of claim 1, wherein the scaffoldin polypeptide comprises a carbohydrate binding module.

3. The transformed yeast host cell of claim 1 wherein the scaffoldin polypeptide comprises a cell wall anchoring domain.

4. The transformed yeast host cell of claim 3 wherein the cell wall anchoring domain is from cell wall protein 2 (CWP2) or FLO1 of S. cerevisiae.

5. The transformed yeast host cell of claim 1 wherein the scaffoldin polypeptide includes a secretion signal.

6. The transformed yeast host cell of claim 1 wherein the dockerin domain is fused to a biomass-degrading enzyme.

7. The transformed yeast host cell of claim 1 wherein the scaffoldin polypeptide is a chimeric polypeptide.

8. The transformed yeast host cell of claim 1 wherein the scaffoldin polypeptide is a *C. cellulolyticum* CipC.

9. The transformed yeast host cell of claim 1 wherein the scaffoldin polypeptide contains at least eight cohesion domains.

10. The transformed yeast host cell of claim 1 wherein the transformed host further comprise a dockerin domain fused to , a xylanase, a β-xylosidase, an arabinoxylan esterase, a pectinase, a laccase, an amylase, or a serine protease inhibitor.

11. The transformed yeast host cell of claim 7 wherein the dockerin is fused to a β-glucosidase.

12. The transformed yeast host cell of claim 11 wherein the β-glucosidase is from *S. fibuligera*.

13. The transformed yeast host cell of claim 7 wherein the dockerin is fused to an endoglucanase.

14. The transformed yeast host cell of claim 13 wherein the endoglucanase is from *C. formoanus*.

15. The transformed yeast host cell of claim 1 wherein the first cellobiohydrolase is a cellobiohydrolase I.

16. The transformed yeast host cell of claim 15 wherein the cellobiohydrolase I is from *T. emersonii*.

17. The transformed yeast host cell of claim 1 wherein the second cellobiohydrolase is a cellobiohydrolase II.

18. The transformed yeast host cell of claim 17 wherein the cellobiohydrolase II is from a *C. lucknowense*.

19. The transformed yeast host cell of claim 1 wherein the cell expresses:
   a) the endogluconase is from *C. formosanus* fused to a dockerin domain;
   b) the β-glucosidase is from *S. fibuligera* fused to a dockerin domain;
   c) the first cellobiohydrolase is a cellobiohydrolase I from *T. emersonii* fused to a dockerin domain; and,
   d) the second cellobiohydrolase is a cellobiohydrolase II from *C. lucknowense* fused to a dockerin domain.

20. The transformed yeast host cell of claim 1 wherein the dockerin domain is from an organism selected from the group consisting of *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosponum, Coptotermes formosanus, Nasutitermes takasagoensis, Coptotermes acinaciformis, Mastotermes darwinensis, Reticulitermes speratus, Reticulitermes .beta.avipes, Nasutitermes walken, Panesthia cnbrata, Arabidopsis thahana, Ruminococcus flavefaciens, Ruminococcus albus, Fibrobacter succinogenes, Clostridium acetobutylicum, Clostridium thermocellum, Clostridium cellulolyticum, Acetivibno cellulolyticus, Anaerocellum thermophdum, Caldicellulosiruptor saccharolyticum, Eubacterium cellulosolvens*, and *Fervidobacterium islandicum*.

21. The transformed yeast host cell of claim 20 wherein the dockerin domain is from a *C. cellulolyticum*.

22. The transformed yeast host cell of claim 21 wherein the dockerin domain is selected from the group consisting of Cel48, Cel5A, Cel9E, Cel5D, Cel9G, Cel8C, Cel8C, Cel9H, Cel9J, Cel9M, Cel5N, Cel9P, and Cel9Q.

23. A cellulosome composition comprising the transformed yeast host cell of claim 1.

24. A composition comprising the transformed yeast host cell of claim 1 and a cellulosic material.

25. The composition of claim 24 wherein the cellulosic material comprises a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

26. A method of fermenting cellulose using the cell of claim 1, the method comprising culturing the transformed yeast host cell of claim 1 in medium that contains insoluble cellulose under suitable conditions for a period sufficient to allow saccharification and fermentation of the cellulose.

27. The method of claim 26 wherein the fermentation produces ethanol.

28. A co-culture comprising at least two eukaryotic host cells wherein:
   (a) a first host cell expresses a polypeptide comprising an exogenous scaffoldin polypeptide is the transformed yeast host cell of claim 1; and,
   (b) a second host cell expresses one or more polypeptides comprising a dockerin domain.

29. The co-culture of claim 28 wherein the exogenous scaffoldin polypeptide further comprises a carbohydrate binding module.

30. The co-culture of claim 28 wherein the exogenous scaffoldin polypeptide further comprises a cell wall anchoring domain.

31. The co-culture of claim 30 wherein the cell wall anchoring domain is from CWP or FLO1 of *S. cerevisiae*.

32. The co-culture of claim 28 wherein the exogenous scaffoldin polypeptide is fused to a secretion signal.

33. The co-culture of claim 28 wherein the dockerin domain is fused to a biomass-degrading enzyme.

34. The co-culture of claim 33 wherein the dockerin domain is fused to a β-glucosidase.

35. The co-culture of claim 34 wherein the β-glucosidase is from *S. fibuligera*.

36. The co-culture of claim 33 wherein the dockerin domain is fused to an endoglucanase.

37. The co-culture of claim 36 wherein the endoglucanase is from *C. formoanus*.

38. The co-culture of claim 33 wherein the dockerin domain is fused to a cellobiohydrolase.

39. The co-culture of claim 38 wherein the dockerin domain is fused to a cellobiohydrolase I.

40. The co-culture of claim 39 wherein the cellobiohydrolase I is from *T. emersonii*.

41. The co-culture of claim 38 wherein the dockerin domain is fused to a cellobiohydrolase II.

42. The co-culture of claim 41 wherein the cellobiohydrolase II is from *C. lucknowense*.

43. The co-culture of claim 28, wherein at least one cell of the co-culture expresses:
   a) the endogluconase I from *C. formosanus* fused to a dockerin domain;
   b) the β-glucosidase from *S. fouligera* fused to a dockerin domain;
   c) the cellobiohydrolase I from *Z emersonii* fused to a dockerin domain; and,
   d) the cellobiohydrolase from *C. lucknowense* fused to a dockerin domain.

44. The co-culture of claim 28 wherein the one or more polypeptides comprising a dockerin domain is from an organism selected from the group consisting of *Orpinomyces joynii, Piromyces equi, Neocallimastix frontalis, Anaeromyces mucronatus, Anaeromyces elegans, Trichoderma reesei, Chrysosporium lucknowense, Talaromyces emersonii, Humicola grisea, Humicola insolens, Thermoascus aurantiacus, Acremonium thermophilum, Aspergillus nidulans, Aspergillus niger, Aspergillus oryzae, Chaetomium thermophilum, Emericella nidulans, Fusarium oxysporum, Neurospora crassa, Penicillium janthinellum, Phanerochaete chrysosporium, Coptotermes formosanus, Nasutitermes takasagoensis, Coptotermes acinaciformis, Mastotermes darwinensis, Reticulitermes speratus, Reticulitermes flavipes, Nasutitermes walkeri, Panesthia cribrata, Arabidopsis thaliana, Ruminococcus flavefaciens, Ruminococcus albus, Fibrobacter succinogenes, Clostridium acetobutylicum, Clostridium thermocellum, Clostridium cellulolyticum, Acetivibrio cellulolyticus, Anaerocellum thermophilum, Caldicellulosiruptor saccharolyticum, Eubacterium cellulosolvens,* and *Fervidobacterium islandicum*.

45. The co-culture of claim 44 wherein the one or more polypeptides containing a dockerin domain is from C. cellulolyticum.

46. The co-culture of claim 45 wherein the one or more polypeptides containing a dockerin domain is selected from the group consisting of Cel48, Cel5A, Cel9E, Cel5D, Cel9G, Cel8C, Cel8C, Cel9H, Cel9J, Cel9M, Cel5N, Cel9P, and Cel9Q.

47. A cellulosome composition comprising the co-culture of claim 28.

48. A composition comprising the co-culture of claim 28 and a cellulosic material.

49. The composition of claim 48 wherein the cellulosic material comprises a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

50. A method of fermenting cellulose using the co-culture of claim 28, said method comprising culturing said co-culture of claim 28 in medium that contains insoluble cellulose under suitable conditions for a period sufficient to allow saccharification and fermentation of the cellulose.

51. The method of claim 50 wherein the fermentation produces ethanol.

* * * * *